(12) United States Patent
Wagner et al.

(10) Patent No.: US 9,707,417 B2
(45) Date of Patent: Jul. 18, 2017

(54) USE OF BENZOTROPOLONE DERIVATIVES AS UV ABSORBERS AND ANTIOXIDANTS AND THEIR USE IN SUNSCREENS AND/OR COSMETIC COMPOSITIONS

(75) Inventors: Barbara Wagner, Lörrach (DE); Reinhold Öhrlein, Rheinfelden-Herten (DE); Bernd Herzog, Grenzach-Wyhlen (DE); Kai Eichin, Kandern (DE); Gabriele Baisch, Binzen (DE); Stephanie Portmann, Basel (CH)

(73) Assignee: BASF SE, Ludwigshafen (DE)

( * ) Notice: Subject to any disclaimer, the term of this patent is extended or adjusted under 35 U.S.C. 154(b) by 746 days.

(21) Appl. No.: 13/000,163

(22) PCT Filed: Jun. 18, 2009

(86) PCT No.: PCT/EP2009/057587
§ 371 (c)(1),
(2), (4) Date: Jan. 28, 2011

(87) PCT Pub. No.: WO2009/156324
PCT Pub. Date: Dec. 30, 2009

(65) Prior Publication Data
US 2011/0123468 A1  May 26, 2011

(30) Foreign Application Priority Data

Jun. 25, 2008 (EP) .................................. 08158977
Oct. 10, 2008 (EP) .................................. 08166349
Mar. 19, 2009 (EP) .................................. 09155560

(51) Int. Cl.
*A61K 8/49* (2006.01)
*A61Q 17/04* (2006.01)
(Continued)

(52) U.S. Cl.
CPC ................ *A61Q 17/04* (2013.01); *A61K 8/35* (2013.01); *A61Q 19/08* (2013.01); *C07C 49/747* (2013.01);
(Continued)

(58) Field of Classification Search
CPC .......... A61Q 17/04; A61Q 19/08; A61K 8/35; C07C 49/747; C07C 62/38; C07C 69/712;
(Continued)

(56) References Cited

U.S. PATENT DOCUMENTS 2,770,545 A    11/1956   Thompson
5,135,957 A    8/1992    Shimamura
(Continued)

OTHER PUBLICATIONS

R.M. Silverstein, Spectrometric Identification of Organic Compounds 289-302 (John Wiley & Sons 1991) (1963).*
(Continued)

*Primary Examiner* — Sean Basquill
(74) *Attorney, Agent, or Firm* — Marshall, Gerstein & Borun LLP

(57) ABSTRACT

Described is the use of benzotropolone and their derivatives, especially the compounds of formula (1); wherein $R_2$, $R_3$, $R_4$, $R_5$ and $R_6$ independently of one another are hydrogen; OH; $C_1$-$C_{30}$alkyl, $C_2$-$C_{30}$al-kenyl, $C_1$-$C_{30}$alkoxy, $C_3$-$C_{12}$cycloalkyl or $C_1C_{30}$hydroxyalkyl, which may be substituted by one or more E and/or interrupted by one or more D; $C_6$-$C_{20}$aryl, which may be substituted by one or more G; $C_4$-$C_{20}$heteroaryl, which may be substituted by one or more G, $C_2$-$C_{18}$alkenyl, $C_2$-$C_{18}$alkynyl, $C_7$-$C_{25}$aralkyl, CN, or —CO—$R_{17}$; $C_1$-$C_{30}$mono- or dialkylamino; $COR_9$; $COOR_9$; $CONR_9R_{10}$; CN; $SO_2R_9$; $OCOOR_9$; $OCOR_9$; $NHCOOR_9$; $NR_9COR_{10}$; $NH_2$; *—(CO)—NH—$(CH_2)_{n1}$—(PO)—$(OR_{11})_2$; —(CO)—O—$(CH_2)_{n1}$—(PO)—$(OR_{11})_2$; sulphate; sulphonate; phosphate; phosphonate; —$(CH_2)_{n2}$—[O—$(SO_2)]_{n3}$—$OR_{11}$; —O—$(CH_2)_{n4}(CO)_{n5}$—$R_{11}$; —$(O)_{n6}$—$(CH_2)_{n7}$—(PO)—$(OR_9)_2$; —$(O)_{n6}$—$(CH_2)_{n7}$—$SO_2$—$OR_9$; halogen; organosilanyl; organo-siloxanyl; or a sugar residue linked directly in an α- or β-mode via the anomeric oxygen to the benzotropolone system or via a linear or branched alkylene, alkenylene, alkadiene or alkatriene spacer (sugar-$(CH_2)_n$—$(X_1)_{1\ or\ 0}$-benzotropolone system, wherein n=1-10 and $X_1$═—O—; —(CO)—; —O—CO—; —COO—, —NH—; —S—; —$SO_2$—); $R_1$, $R_7$ and $R_8$ independently of one another are hydrogen; $C_1C_{12}$alkyl or $C_3$-$C_{12}$-cycloalkyl, which may be substituted by one or more E and/or interrupted by one or more D; $C_6$-$C_{20}$aryl, which may be substituted by one or more G; $C_4$-$C_{20}$heteroaryl, which may be substituted by one or more G, $C_2$-$C_{18}$alkenyl, $C_2$-$C_{18}$alkynyl, $C_7$-$C_{25}$aralkyl, or $COOR_9$; $COR_9$; $CONR_9R_{10}$; $SO_3R_9$; $SO_2R_9$; $PO_3(R_9)_2$; $PO_2(R_9)_2$; organosilanyl; organosiloxanyl; or a sugar residue linked directly in an α- or β-mode via the anomeric oxygen to the benzotropolone system or via a linear or branched alkylene, alkenylene, alkadiene or alkatriene spacer (sugar-$(CH_2)_n$—$(X_2)_{1\ or\ 0}$—*, wherein n=1-10 and $X_2$═—C(═O)—; —O—CO—*); $R_9$ and $R_{10}$ independently from each other are hydrogen; $C_1C_{18}$alkyl or $C_3$-$C_{12}$-cycloalkyl which may be substituted by one or more E and/or interrupted by one or more D; $C_6$-$C_{20}$aryl, which may be substituted by one or more G; $C_4$-$C_{20}$heteroaryl, which may be substituted by one or more G; organosilanyl; organosiloxanyl; or a sugar residue linked directly in an α- or β-mode via the anomeric oxygen or via a linear or branched alkylene, alkenylene, alkadiene or alkatriene spacer (sugar-$(CH_2)_n$—*, wherein n=1-10); or $R_9$ and $R_{10}$ together form a five or six membered ring, $R_{11}$ is hydrogen; or $C_1$-$C_5$alkyl; $n_1$, $n_2$, $n_4$ and $n_7$ independently from each other are a number from 1 to 5; $n_3$, $n_5$ and $n_6$ independently from each other are a 0; or 1; D is —CO—; —COO—; —S—; —SO—; —SO2-; —O—; —$NR_{14}$—; —$S_1R_{19}R_{20}$—; —$POR_{11}$—; —$CR_{12}$═$CR_{13}$—; or —C≡C—; and E is —$OR_{18}$; —$SR_{18}$; —$NR_{14}R_{15}$; —$NR_{14}COR_{15}$; —$COR_{17}$; —$COOR_{16}$; —$CONR_{14}R_{15}$; —CN; halogen; Or $SO_3R_{18}$; $SO_2R_{18}$; $PO_3(R_{18})_2$; $PO_2(R_{18})$ (Continued)

$_2$; organosilanyl; organosiloxanyl; or a sugar residue linked directly in an α- or β-mode via the anomeric oxygen or via a linear or branched alkylene, alkenylene, alkadiene or alkatriene spacer (sugar-$(CH_2)n$-$(X_1)_{1\ or\ 0}$—*, wherein n=1-10 and X1=—O—; —C(=O)—; —O—CO—; —COO—; —NH—; —S—; —SO$_2$—); G is E; $C_1$-$C_{18}$alkyl, which is optionally interrupted by D; $C_1$-$C_{18}$perfluoroalkyl; $C_1$-$C_{18}$alkoxy, which is optionally substituted by E and/or interrupted by D; wherein $R_{12}$, $R_{13}$, $R_{14}$ and $R_{15}$ independently of each other are hydrogen; $C_6$-$C_{18}$aryl which is optionally substituted by OH, $C_1$-$C_{18}$alkyl or $C_1$-$C_{18}$alkoxy; $C_1$-$C_{18}$alkyl, which is optionally interrupted by —O—; or Ri4 and Ri5 together form a five or six membered ring, Ri6 is hydrogen; C6-Ci8aryl which is optionally substituted by OH, $C_1$-$C_{18}$alkyl or d-$C_{18}$alkoxy; $C_1$-$C_{18}$alkyl which is optionally interrupted by —O—; $R_{17}$ is H; $C_6$-$C_{18}$aryl which is optionally substituted by OH, $C_1$-$C_{18}$alkyl or $C_1$-$C_{18}$alkoxy; or d-$C_{18}$alkyl which is optionally interrupted by —O—; $R_{18}$ is hydrogen; $C_6$-$C_{18}$aryl, which is optionally substituted by OH, $C_1$-$C_{18}$alkyl or d-$C_{18}$alkoxy; $C_1$-$C_{18}$alkyl, which is optionally interrupted by —O—; $R_{19}$ and $R_{20}$ independently of each other are hydrogen; $C_1$-$C_{18}$alkyl; $C_6$-$C_{18}$aryl which is optionally substituted by $C_1$-$C_{18}$alkyl; and $R_{21}$ is $C_1$-$C_{18}$alkyl; or $C_6$-$C_{18}$aryl, which is substituted by $C_1$-$C_{18}$alkyl; * means, that this radical is directed to the benzotropolone moiety; for the protection of human and animal hair and skin against UV radiation.

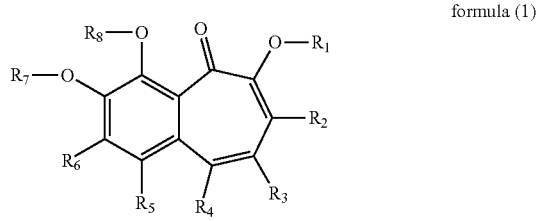

formula (1)

10 Claims, 1 Drawing Sheet

(51) Int. Cl.
| | | |
|---|---|---|
| *A61K 8/35* | (2006.01) |
| *A61Q 19/08* | (2006.01) |
| *C07C 49/747* | (2006.01) |
| *C07C 62/38* | (2006.01) |
| *C07C 69/712* | (2006.01) |
| *C07C 69/757* | (2006.01) |
| *C07C 305/18* | (2006.01) |
| *C07F 9/40* | (2006.01) |
| *C07H 15/18* | (2006.01) |
| *C07H 15/203* | (2006.01) |
| *C07H 15/26* | (2006.01) |

(52) U.S. Cl.
CPC ............ *C07C 62/38* (2013.01); *C07C 69/712* (2013.01); *C07C 69/757* (2013.01); *C07C 305/18* (2013.01); *C07F 9/4006* (2013.01); *C07H 15/18* (2013.01); *C07H 15/203* (2013.01); *C07H 15/26* (2013.01); *C07C 2102/12* (2013.01)

(58) Field of Classification Search
CPC . C07C 69/757; C07C 305/18; C07C 2102/12; C07F 9/4006; C07H 15/18; C07H 15/203; C07H 15/26
See application file for complete search history.

(56) References Cited

U.S. PATENT DOCUMENTS

| 7,087,790 B2 * | 8/2006 | Ho et al. .................. 568/311 |
| 2003/0157035 A1 | 8/2003 | Chaudhuri |
| 2005/0049284 A1 | 3/2005 | Ho |
| 2005/0058709 A1 * | 3/2005 | Fisher et al. .................. 424/468 |
| 2006/0241154 A1 * | 10/2006 | Ho et al. .................. 514/355 |
| 2007/0219275 A1 | 9/2007 | Baschong |

OTHER PUBLICATIONS

Jhoo et al., Journal of Agricultural and Food Chemistry, vol. 53 (15), (2005) pp. 6146-6150.

* cited by examiner

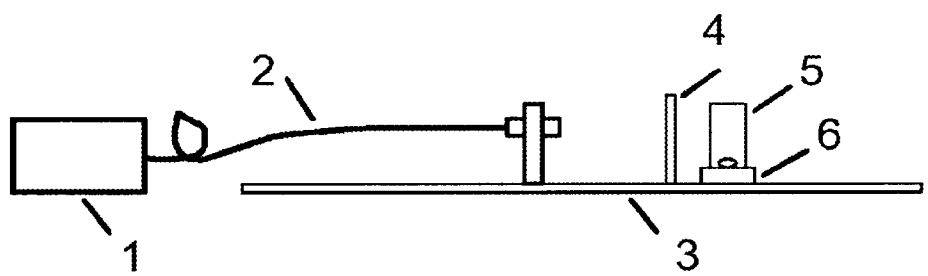

USE OF BENZOTROPOLONE DERIVATIVES AS UV ABSORBERS AND ANTIOXIDANTS AND THEIR USE IN SUNSCREENS AND/OR COSMETIC COMPOSITIONS

The present invention relates to the use of one or more benzotropolone and their derivatives as antioxidants and UV absorbers and their use in sunscreens and/or cosmetic compositions.

Oxidative damage of biological systems is caused by many different intrinsic and extrinsic factors. Reactive oxygen species (ROS) and radicals play a pivotal role in inducing oxidative damage and aging processes in skin cells. The aging processes are characterized by wrinkles and loss of skin tone and resilience. Therefore natural and synthetic antioxidants are used in many different cosmetic and/or topical pharmaceutical products in order to prevent or mitigate the adverse effects of oxidants and/or radicals.

Phenolic compounds are the most intensively studied and widely used natural and synthetic antioxidants. Examples for various types of natural phenolic antioxidants are alpha-tocopherol, quercetin, morin, 3,4-dihydroxybenzoic acid, thymol and carvacrol among others. The vitamin alpha-tocopherol is the major lipid-soluble, chain-breaking antioxidant in human blood plasma and in low-density lipoprotein associates. Its mechanism of action as an antioxidant, and that of phenolic compounds in general, is believed to be the transfer of its phenolic H-atom to a chain-carrying peroxyl radical at a rate much faster than that at which the chain-propagating step of lipid peroxidation proceeds.

Many phenolic compounds used as antioxidants in food, cosmetics, personal care and household products are not always photochemically stable, which limits their utility.

It is also well known that ultraviolet (UV) light is another important source of radical generation as well as of a number of biological adverse effects. Therefore photostable antioxidants with UV absorbing properties would be expedient in two aspects:
firstly they would be able to prevent free radical initiated damage to biological and chemical molecules and
secondly they would serve as a second defence line by absorbing UV light.

It is well known that ultraviolet radiation (light) is harmful to human skin. Depending on the wavelength the UV radiation causes different types of skin damage. UV-B radiation (about 290 nm to about 320 nm) is responsible for sunburn and can cause skin cancer. UV-A radiation (about 320 nm to about 400 nm) while producing tanning of the skin, contributes also to sunburn and the induction of skin cancer. Moreover, UVA mainly produces free radicals/reactive oxygen species through interaction with endogenous photosensitizers. These free radicals will cause indirect damage to DNA, proteins and membranes. Therefore free radical reactions in the skin are one of the most interesting subjects of skin research because they are involved in various skin diseases, including skin tumors, skin wrinkling and skin aging.

The purpose of sun care products is the reduction of skin damage produced by single and repeated exposure to solar ultraviolet (UV) radiation. Multiple lines of defence have been developed, aimed to protect skin against UV light and from oxidative stress. Sun care products therefore contain UV absorbers as a first defence line. Their purpose is to attenuate the UV radiation of the sun. Antioxidants are used in sun care products as a secondary line of defence. Their purpose is to neutralize reactive radicals.

Surprisingly it was found that the benzotropolone moiety is able to provide UV light shielding and antioxidative properties in one molecule.

In addition their metal ion chelating properties might also contribute to their potent capability to inhibit oxidative processes. Trace metals can significantly contribute to the free-radical formation by e.g. decomposing lipid hydroperoxides into free radicals. Metal chelators like benzotropolones, which convert metal pro-oxidants especially iron or copper derivatives, into stable products inhibit free-radical formation initiated through metal ions. The ability of benzotropolones to chelate metal ions is obvious when a metal salt is added into a benzotropolone containing solution. Upon addition of metal salts the solution often immediately changes its color.

The benzotropolone moiety is the characteristic structural feature of some natural occurring compounds among which the theaflavins are best known. Theaflavins are found in black tea and exhibit a wide range of biological activities among which the antioxidative properties are best recognized. The theaflavins represent a group of dark orange-red colored pigments what makes them unsuitable for topical applications where low discolorations are desired.

In addition they are tedious to prepare, highly unstable, difficult to handle or tedious to be isolated from natural resources in large scale amounts.

It was now found that compounds consisting of the benzotropolone moiety are effective and photostable UV absorbers with strong antioxidant properties and therefore suitable to be used for the protection of human and animal hair and skin against UV radiation in sunscreen applications.

The present invention relates to benzotropolone and their derivatives which are partly only moderately colored and therefore suitable for use in personal care applications.

BRIEF DESCRIPTION OF THE DRAWING

FIG. 1 illustrates the experimental set-up for irradiation using a metal halide lamp.

Novel synthetic protocols for natural identical derivatives, apt for large scale preparation are also given.

Preferably, the benzotropolone moiety is 3,4,6-trihydroxy-5H-benzocyclohepten-5-one.

Preferably, the instant invention relates to the use of benzotropolone moieties of formula

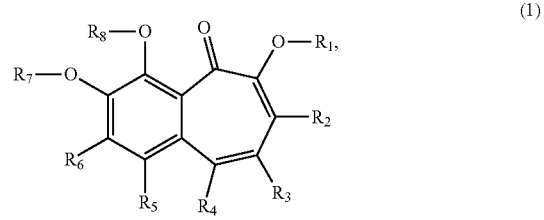

(1)

wherein
$R_2$, $R_3$, $R_4$, $R_5$ and $R_6$ independently of one another are hydrogen; OH; $C_1$-$C_{30}$alkyl, $C_2$-$C_{30}$alkenyl, $C_1$-$C_{30}$alkoxy, $C_3$-$C_{12}$cycloalkyl or $C_1$-$C_{30}$hydroxyalkyl, which may be substituted by one or more E and/or interrupted by one or more D; $C_6$-$C_{20}$aryl, which may be substituted by one or more G; $C_4$-$C_{20}$heteroaryl, which may be substituted by one or more G, $C_2$-$C_{18}$alkenyl, $C_2$-$C_{18}$alkynyl, $C_7$-$C_{25}$aralkyl, CN, or —CO—$R_{17}$; $C_1$-$C_{30}$mono- or dialkylamino; $COR_9$; $COOR_9$;

CONR$_9$R$_{10}$; CN; SO$_2$R$_9$; OCOOR$_9$; OCOR$_9$; NHCOOR$_9$; NR$_9$COR$_{10}$; NH$_2$; *—(CO)—NH—(CH$_2$)$_{n1}$—(PO)—(OR$_{11}$)$_2$; —(CO)—O—(CH$_2$)$_{n1}$—(PO)—(OR$_{11}$)$_2$; sulphate; sulphonate; phosphate; phosphonate; —(CH$_2$)$_{n2}$—[O—(SO$_2$)]$_{n3}$—OR$_{11}$; —O—(CH$_2$)$_{n4}$(CO)$_{n5}$—R$_{11}$; —(O)$_{n6}$—(CH$_2$)$_{n7}$—(PO)—(OR$_9$)$_2$; —(O)$_{n6}$—(CH$_2$)$_{n7}$—SO$_2$—OR$_9$; halogen; organosilanyl; organosiloxanyl; or a sugar residue linked directly in an α- or β-mode via the anomeric oxygen to the benzotropolone system or via a linear or branched alkylene, alkenylene, alkadiene or alkatriene spacer (sugar-(CH$_2$)$_n$—(X$_1$)$_{1\ or\ 0}$-benzotropolone system, wherein n=1-10 and X$_1$=—O—; —(CO)—; —O—CO—; —COO—, —NH—; —S—; —SO$_2$—);

R$_1$, R$_7$ and R$_8$ independently of one another are hydrogen; C$_1$-C$_{12}$alkyl or C$_3$-C$_{12}$-cycloalkyl, which may be substituted by one or more E and/or interrupted by one or more D; C$_6$-C$_{20}$aryl, which may be substituted by one or more G; C$_4$-C$_{20}$heteroaryl, which may be substituted by one or more G; C$_2$-C$_{18}$alkenyl, C$_2$-C$_{18}$alkynyl, C$_7$-C$_{25}$aralkyl, or COOR$_9$; COR$_9$; CONR$_9$R$_{10}$; SO$_3$R$_9$; SO$_2$R$_9$; PO$_3$(R$_9$)$_2$; PO$_2$(R$_9$)$_2$; organosilanyl; organosiloxanyl; or a sugar residue linked directly in an α- or β-mode via the anomeric oxygen to the benzotropolone system or via a linear or branched alkylene, alkenylene, alkadiene or alkatriene spacer (sugar-(CH$_2$)$_n$—(X$_2$)$_{1\ or\ 0}$—*, wherein n=1-10 and X$_2$=—C(=O)—; —O—CO—*);

R$_9$ and R$_{10}$ independently from each other are hydrogen; C$_1$-C$_{18}$alkyl or C$_3$-C$_{12}$-cycloalkyl which may be substituted by one or more E and/or interrupted by one or more D; C$_6$-C$_{20}$aryl, which may be substituted by one or more G; C$_4$-C$_{20}$heteroaryl, which may be substituted by one or more G; organosilanyl; organosiloxanyl; or a sugar residue linked directly in an α- or β-mode via the anomeric oxygen or via a linear or branched alkylene, alkenylene, alkadiene or alkatriene spacer (sugar-(CH$_2$)$_n$—*, wherein n=1-10); or R$_9$ and R$_{10}$ together form a five or six membered ring, R$_{11}$ is hydrogen; or C$_1$-C$_5$alkyl;

n$_1$, n$_2$, n$_4$ and n$_7$ independently from each other are a number from 1 to 5;

n$_3$, n$_5$ and n$_6$ independently from each other are a 0; or 1;

D is —CO—; —COO—; —S—; —SO—; —SO$_2$—; —O—; —NR$_{14}$—; —SiR$_{19}$R$_{20}$—; —POR$_{11}$—; —CR$_{12}$=CR$_{13}$—; or —C≡C—; and E is —OR$_{18}$; —SR$_{18}$; —NR$_{14}$R$_{15}$; —NR$_{14}$COR$_{15}$; —COR$_{17}$; —COOR$_{16}$; —CONR$_{14}$R$_{15}$; —CN; halogen; or SO$_3$R$_{18}$; SO$_2$R$_{18}$; PO$_3$(R$_{18}$)$_2$; PO$_2$(R$_{18}$)$_2$; organosilanyl; organosiloxanyl; or a sugar residue linked directly in an α- or β-mode via the anomeric oxygen or via a linear or branched alkylene, alkenylene, alkadiene or alkatriene spacer (sugar-(CH$_2$)$_n$—(X$_1$)$_{1\ or\ 0}$—*, wherein n=1-10 and X$_1$=—O—; —C(=O)—; —O—CO—; —COO—; —NH—; —S—; —SO$_2$—);

G is E; C$_1$-C$_{18}$alkyl, which is optionally interrupted by D; C$_1$-C$_{18}$perfluoroalkyl; C$_1$-C$_{18}$alkoxy, which is optionally substituted by E and/or interrupted by D; wherein R$_{12}$, R$_{13}$, R$_{14}$ and R$_{15}$ independently of each other are hydrogen; C$_6$-C$_{18}$aryl which is optionally substituted by OH, C$_1$-C$_{18}$alkyl or C$_1$-C$_{18}$alkoxy; C$_1$-C$_{18}$alkyl, which is optionally interrupted by —O—; or R$_{14}$ and R$_{15}$ together form a five or six membered ring, R$_{16}$ is hydrogen; C$_6$-C$_{18}$aryl which is optionally substituted by OH, C$_1$-C$_{18}$alkyl or C$_1$-C$_{18}$alkoxy; C$_1$-C$_{18}$alkyl which is optionally interrupted by —O—;

R$_{17}$ is H; C$_6$-C$_{18}$aryl which is optionally substituted by OH, C$_1$-C$_{18}$alkyl or C$_1$-C$_{18}$alkoxy; or C$_1$-C$_{18}$alkyl which is optionally interrupted by —O—;

R$_{18}$ is hydrogen; C$_6$-C$_{18}$aryl, which is optionally substituted by OH, C$_1$-C$_{18}$alkyl or C$_1$-C$_{18}$alkoxy; C$_1$-C$_{18}$alkyl, which is optionally interrupted by —O—;

R$_{19}$ and R$_{20}$ independently of each other are hydrogen; C$_1$-C$_{18}$alkyl; C$_6$-C$_{18}$aryl which is optionally substituted by C$_1$-C$_{18}$alkyl; and R$_{21}$ is C$_1$-C$_{18}$alkyl; or C$_6$-C$_{18}$aryl, which is substituted by C$_1$-C$_{18}$alkyl;

* means, that this radical is directed to the benzotropolone moiety;

for the protection of human and animal hair and skin against UV radiation.

C$_1$-C$_{30}$alkyl are straight chain or branched radicals like methyl, ethyl, n-propyl, isopropyl, n-butyl, sec.butyl, tert..butyl, amyl, isoamyl or tert.amyl, hexyl, 2-ethylhexyl, heptyl, octyl, isooctyl, nonyl, decyl, undecyl, dodecyl, tetradecyl, undecyl, eicosyl, tetracosyl, pentacosyl, heptacosyl, octacosyl or triacontyl.

C$_1$-C$_{30}$alkoxy are straight chain or branched radicals like methoxy, ethoxy, n-propoxy, isopropoxy, n-butyloxy, sec.butyloxy, tert.butyloxy, amyloxy, isoamyloxy, tert.amyloxy, hexyloxy, 2-ethylhexyloxy, heptyloxy, octyloxy, isooctyloxy, nonyloxy, decyloxy, undecyloxy, dodecyloxy, tetradecyloxy, undecyloxy eicosyloxy tetracosyloxy, pentacosyloxy, heptacosyloxy, octacosyloxy or triacontyloxy.

C$_2$-C$_{30}$alkenyl are straight chain or branched radicals like allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl, n-octadec-4-enyl, eicosenyl, tetracosenyl, pentacoensyl, heptacosenyl, octacosenyl or triacontenyl.

C$_3$-C$_{12}$cycloalkyl is for example cyclopropyl, cyclobutyl, cyclopentyl, cycloheptyl, cyclooctyl, cyclononyl, cyclodecyl, cycloundecyl, cyclododecyl and preferably cyclohexyl.

Each alkyl or cycloalkyl can be saturated or unsaturated.

Each alkyl, cycloalkyl or alkoxy can preferably be substituted by one or more E and/or interrupted by one or more D.

Each aryl can be preferably substituted by G.

Each heteroaryl can be preferably substituted by G, C$_2$-C$_{18}$alkenyl, C$_2$-C$_{18}$alkynyl, C$_7$-C$_{25}$aralkyl, CN, or —CO—R$^{28}$.

The compounds of formula (1) can be present in their protonised or deprotonised form.

Preference is given to compounds wherein

R$_1$, R$_7$ and R$_8$ are hydrogen; and

R$_2$, R$_3$, R$_4$, R$_5$ and R$_6$ are defined as in formula (1).

Preference is given to compounds of formula (1), wherein

R$_2$, R$_3$, R$_4$, R$_5$ and R$_6$ independently of one another are hydrogen; OH; C$_1$-C$_{30}$alkyl, C$_2$-C$_{30}$alkenyl, C$_1$-C$_{30}$alkoxy, C$_3$-C$_{12}$cycloalkyl or C$_1$-C$_{30}$hydroxyalkyl, which may be substituted by one or more E and/or interrupted by one or more D; C$_6$-C$_{20}$aryl, which may be substituted by one or more G; C$_6$-C$_{20}$heteroaryl, which may be substituted by one or more G, C$_2$-C$_{18}$alkenyl, C$_2$-C$_{18}$alkynyl, C$_7$-C$_{25}$aralkyl, CN, or —CO—R$_{17}$; C$_1$-C$_{30}$mono- or dialkylamino; COR$_9$; COOR$_9$; CONR$_9$R$_{10}$; CN; SO$_2$R$_9$; OCOOR$_9$; NHCOOR$_9$; NR$_9$COR$_{10}$; NH$_2$; *—(CO)—NH—(CH$_2$)$_{n1}$—(PO)—(OR$_{11}$)$_2$; —(CO)—O—(CH$_2$)$_{n1}$—(PO)—(OR$_{11}$)$_2$; sulphate; sulphonate; phosphate; phosphonate; —(CH$_2$)$_{n2}$—

[O—($SO_2$)]$_{n3}$—$OR_{11}$; —O—($CH_2$)$_{n4}$(CO)$_{n5}$—$R_{11}$; —(O)$_{n6}$—($CH_2$)$_{n7}$—(PO)—($OR_9$)$_2$; —(O)$_{n6}$—($CH_2$)$_{n7}$—$SO_2$—$OR_9$; halogen; organosilanyl; organosiloxanyl; or a sugar residue linked directly in an α- or β-mode via the anomeric oxygen to the benzotropolone system or via a linear or branched alkylene, alkenylene, alkadiene or alkatriene spacer (sugar-($CH_2$)$_n$—($X_1$)$_{1\ or\ 0}$-benzotropolone system, wherein n=1-10 and $X_1$=—O—; —(CO)—; —O—CO—; —COO—, —NH—; —S—; —$SO_2$—);

$R_1$, $R_7$ and $R_8$ independently of one another are hydrogen; $C_1$-$C_{12}$alkyl or $C_3$-$C_{12}$-cycloalkyl, which may be substituted by one or more E and/or interrupted by one or more D; $C_6$-$C_{20}$aryl, which may be substituted by one or more G; $C_6$-$C_{20}$heteroaryl, which may be substituted by one or more G, $C_2$-$C_{18}$alkenyl, $C_2$-$C_{18}$alkynyl, $C_7$-$C_{25}$aralkyl, CN, or $COOR_9$; $COR_9$; $CONR_9R_{10}$; $SO_3R_9$; $SO_2R_9$; $PO_3(R_9)_2$; $PO_2(R_9)_2$; organosilanyl; organosiloxanyl; or a sugar residue linked directly in an α- or β-mode via the anomeric oxygen to the benzotropolone system or via a linear or branched alkylene, alkenylene, alkadiene or alkatriene spacer (sugar-($CH_2$)$_n$—($X_2$)$_{1\ or\ 0}$—*, wherein n=1-10 and $X_2$=—C(=O)—; —O—CO—);

$R_9$ and $R_{10}$ independently from each other are hydrogen; $C_1$-$C_{18}$alkyl or $C_3$-$C_{12}$-cycloalkyl which may be substituted by one or more E and/or interrupted by one or more D; $C_6$-$C_{20}$aryl, which may be substituted by one or more G; organosilanyl; organosiloxanyl; or a sugar residue linked directly in an α- or β-mode via the anomeric oxygen or via a linear or branched alkylene, alkenylene, alkadiene or alkatriene spacer (sugar-($CH_2$)$_n$—*, wherein n=1-10); or $R_9$ and $R_{10}$ together form a five or six membered ring, $R_{11}$ is hydrogen; or $C_1$-$C_5$alkyl;

$n_1$, $n_2$, $n_4$ and $n_7$ independently from each other are a number from 1 to 5;

$n_3$ and $n_5$ independently from each other are a 0; or 1;

D is —CO—; —COO—; —S—; —SO—; —$SO_2$—; —O—; —$NR_{14}$—; —$SiR_{19}R_{20}$—; —$POR_{11}$; —$CR_{12}$=$CR_{13}$—; or —C≡C—; and E is —$OR_{18}$; —$SR_{18}$; —$NR_{14}R_{15}$; —$NR_{14}COR_{15}$; —$COR_{17}$; —$COOR_{16}$; —$CONR_{14}R_{15}$; —CN; halogen; or $SO_3R_{18}$; $SO_2R_{18}$; $PO_3(R_{18})_2$; $PO_2(R_{18})_2$; organosilanyl; organosiloxanyl; or a sugar residue linked directly in an α- or β-mode via the anomeric oxygen or via a linear or branched alkylene, alkenylene, alkadiene or alkatriene spacer (sugar-($CH_2$)$_n$—($X_1$)$_{1\ or\ 0}$—*, wherein n=1-10 and $X_1$=—O—; —C(=O)—; —O—CO—; —NH—; —S—; —$SO_2$—);

G is E; $C_1$-$C_{18}$alkyl, which is optionally interrupted by D; $C_1$-$C_{18}$ perfluoroalkyl; $C_1$-$C_{18}$alkoxy, which is optionally substituted by E and/or interrupted by D; wherein $R_{12}$, $R_{13}$, $R_{14}$ and $R_{15}$ independently of each other are hydrogen; $C_6$-$C_{18}$aryl which is optionally substituted by $C_1$-$C_{18}$alkyl or $C_1$-$C_{18}$alkoxy; $C_1$-$C_{18}$alkyl, which is optionally interrupted by —O—; or $R_{14}$ and $R_{15}$ together form a five or six membered ring, $R_{16}$ is hydrogen; $C_6$-$C_{18}$aryl which is optionally substituted by $C_1$-$C_{18}$alkyl or $C_1$-$C_{18}$alkoxy; $C_1$-$C_{18}$alkyl which is optionally interrupted by —O—;

$R_{17}$ is H; $C_6$-$C_{18}$aryl which is optionally substituted by $C_1$-$C_{18}$alkyl or $C_1$-$C_{18}$alkoxy; or $C_1$-$C_{18}$alkyl which is optionally interrupted by —O—;

$R_{18}$ is hydrogen; $C_6$-$C_{18}$aryl, which is optionally substituted by $C_1$-$C_{18}$alkyl or $C_1$-$C_{18}$alkoxy; $C_1$-$C_{18}$alkyl, which is optionally interrupted by —O—;

$R_{19}$ and $R_{20}$ independently of each other are hydrogen; $C_1$-$C_{18}$alkyl; $C_6$-$C_{18}$aryl which is optionally substituted by $C_1$-$C_{18}$alkyl; and $R_{21}$ is $C_1$-$C_{18}$alkyl; or $C_6$-$C_{18}$aryl, which is substituted by $C_1$-$C_{18}$alkyl;

* means, that this radical is directed to the benzotropolone moiety.

Preferred are compounds of formula (1), wherein
$R_1$, $R_7$ and $R_8$ are hydrogen; and
$R_2$, $R_3$, $R_4$, $R_5$ and $R_6$ are defined as formula (1).

Further preferred are compounds of formula (1), wherein
$R_6$ is hydrogen; OH; $C_1$-$C_{30}$alkyl or $C_1$-$C_{30}$alkoxy, which may be substituted by one or more E and/or interrupted by one or more D; phosphate; phosphonate or a sugar residue linked directly in an α- or β-mode via the anomeric oxygen to the aromatic benzotropolone system or via a linear or branched linear or branched alkylene, alkenylene, alkadiene or alkatriene spacer (sugar-($CH_2$)$_n$—($X_1$)$_{1\ or\ 0}$-benzotropolone system, wherein n=1-10 and $X_1$=—O—; —C(=O)—; —O—CO—; —COO—; —NH—; —S—; —$SO_2$—);

$R_5$ is hydrogen; substituted or unsubstituted $C_1$-$C_{18}$alkyl; or a sugar residue linked directly in an α- or β-mode via the anomeric oxygen to the benzotropolone system or via a linear or branched alkylene, alkenylene, alkadiene or alkatriene spacer (sugar-($CH_2$)$_n$—($X_1$)$_{1\ or\ 0}$-benzotropolone system, wherein n=1-10 and $X_1$=—O—; —C(=O)—; —O—CO—; —COO—; —NH—; —S—; —$SO_2$—);

$R_2$ and $R_4$ independently from each other are hydrogen; or substituted or unsubstituted $C_1$-$C_{18}$alkyl;

$R_3$ is hydrogen; or carboxylate COOX; wherein
X is Na, K or $NH_4$; and
D and E are defined as in formula (1).

Further preferred are compounds of formula (1), wherein
$R_2$, $R_3$, $R_4$, $R_5$ and $R_6$, independently of one another are a mono-, di- or oligosaccharide residue alpha- or beta-linked to the benzotropolone ring system, wherein said residue consists of hexose or pentose subunits.

Further preferred are compounds of formula (1), wherein
$R_3$ and $R_6$, independently of one another are a mono-, di- or oligosaccharide residue alpha- or beta-linked to the benzotropolone ring system, wherein said residue consists of hexose or pentose subunits; and
$R_2$, $R_4$, $R_5$ are defined as in formula (1).

Preference is given to compounds wherein
$R_2$, $R_3$, $R_4$, $R_5$ and $R_6$, independently of one another are hydrogen; $C_1$-$C_{12}$alkyl, $C_1$-$C_{30}$alkoxy or $C_1$-$C_{12}$alkenyl substituted by E;
E is carboxylate; $OCOR_9$; sulphate; sulphonate; phosphonate; or phosphate; and
$R_9$ is defined as in formula (1).

Further preferred are compounds of formula (1), wherein
$R_3$ is a radical of formula

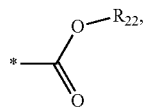

wherein
$R_{22}$ is hydrogen; $C_1$-$C_{12}$alkyl, which may be substituted by one or more E and/or interrupted by one or more D; $C_6$-$C_{20}$aryl, which may be substituted by one or more G; $C_4$-$C_{20}$heteroaryl, which may be substituted by one or more G, $C_2$-$C_{18}$alkenyl, $C_2$-$C_{18}$alkynyl, $C_7$-$C_{25}$aralkyl, or —CO—$R_{17}$; organosilanyl; organosiloxanyl; or a sugar residue linked directly in an α- or β-mode via the anomeric oxygen to the carboxylic group or via a linear or branched alkylene, alkenylene, alkadiene or alkatriene spacer (sugar-$(CH_2)_n$-carboxylic group, wherein n=1-10);

$R_{17}$ is H; $C_6$-$C_{18}$aryl which is optionally substituted by $C_1$-$C_{18}$alkyl or $C_1$-$C_{18}$alkoxy; or $C_1$-$C_{18}$alkyl which is optionally interrupted by —O—; and $R_1$, $R_2$, $R_4$, $R_5$, $R_6$, $R_7$ and $R_8$, D, G and E are defined as in formula (1).

Further preferred are compounds of formula (1), wherein at least one of $R_2$, $R_3$, $R_4$, $R_5$, $R_6$, $R_9$, $R_{10}$, $R_{11}$, and $R_{12}$ independently of one another are sulphate; sulphonate; phosphate; or phosphonate and/or $R_1$, $R_7$ and $R_8$ together with the adjacent oxygen independently of one another form a sulphate, sulphonate, phosphate or phosphonate group.

The compounds of formula (1), wherein $R_1$, $R_2$, $R_3$, $R_4$, $R_5$, $R_6$, $R_7$ or $R_8$ are defined as in formula (1) with the proviso that if $R_6$ is hydroxy and at least one of $R_1$, $R_2$, $R_3$, $R_4$, $R_5$, $R_7$ or $R_9$ is not hydrogen, as antioxidants and/or radical scavengers.

The compounds of formula (1), wherein $R_3$ is OH; $C_1$-$C_{30}$alkyl, $C_2$-$C_{30}$alkenyl, $C_1$-$C_{30}$alkoxy, $C_3$-$C_{12}$-cycloalkyl or $C_1$-$C_{30}$hydroxyalkyl, which may be substituted by one or more E and/or interrupted by one or more D; $C_6$-$C_{20}$aryl, which may be substituted by one or more G; $C_4$-$C_{20}$heteroaryl, which may be substituted by one or more G, $C_2$-$C_{18}$alkenyl, $C_2$-$C_{18}$alkynyl, $C_7$-$C_{14}$aralkyl, CN, or —CO—$R_{17}$; $C_1$-$C_{30}$mono- or dialkylamino; $COR_6$; $COOR_6$; —OC(=O)$R_6$; $CONR_9R_{10}$; CN; $SO_2R_9$; $OCOOR_6$; $NHCOOR_6$; $NR_6COR_{10}$; $NH_2$; —(CO)—NH—$(CH_2)_{n1}$—(PO)—$(OR_{11})_2$; sulphate; sulphonate; phosphate; phosphonate; —$(CH_2)_{n2}$—[O—$(SO_2)]_{n3}$—$OR_{11}$; —O—$(CH_2)_{n4}$(CO)$_{n5}$—$R_{11}$; —(O)$_{n6}$—$(CH_2)_{n7}$—(PO)—$(OR'_9)_2$; —(O)$_{n6}$—$(CH_2)_{n7}$—$(SO_2)$—$OR'_9$; halogen; organosilanyl; organosiloxanyl; or a sugar residue linked directly in an α- or β-mode via the anomeric oxygen to the benzotropolone system or via a linear or branched alkylene, alkenylene, alkadiene or alkatriene spacer (sugar-$(CH_2)_n$—$(X_1)_{1 \ or \ 0}$-benzotropolone system, wherein n=1-10 and $X_1$=—O—; —C(=O)—; —O—CO—; —COO—; —NH—; —S—; —SO_2$—);

are more preferred as antioxidants and/or radical scavengers, wherein $R_1$, $R_2$, $R_4$, $R_5$, $R_6$, $R_7$, $R_8$, $R_9$, $R_{10}$, $R_{11}$, $R_{17}$, B, E, D, G, $n_1$, $n_2$, $n_3$, $n_4$, $n_5$, $n_6$, and $n_7$ are defined as in formula (1).

Further preferred are compounds of formula (1), wherein $R_6$ is OH; $C_1$-$C_{30}$alkyl, $C_2$-$C_{30}$alkenyl, $C_1$-$C_{30}$alkoxy, $C_3$-$C_{12}$-cycloalkyl or $C_1$-$C_{30}$hydroxyalkyl, which may be substituted by one or more E and/or interrupted by one or more D; $C_6$-$C_{20}$aryl, which may be substituted by one or more G; $C_4$-$C_{20}$heteroaryl, which may be substituted by one or more G, $C_2$-$C_{18}$alkenyl, $C_2$-$C_{18}$alkynyl, $C_7$-$C_{14}$aralkyl, CN, or —CO—$R_{17}$; $C_1$-$C_{30}$mono- or dialkylamino; $COR_9$; $COOR_9$; —OC(=O)$R_9$; $CONR_9R_{10}$; CN; $SO_2R_9$; $OCOOR_9$; $NHCOOR_9$; $NR_9COR_{10}$; $NH_2$; —(CO)—NH—$(CH_2)_{n1}$—(PO)—$(OR_{11})_2$; sulphate; sulphonate; phosphate; phosphonate; —$(CH_2)_{n2}$—[O—$(SO_2)]_{n3}$—$OR_{11}$; —O—$(CH_2)_{n4}$(CO)$_{n5}$—$R_{11}$; —(O)$_{n6}$—$(CH_2)_{n7}$—(PO)—$(OR'_9)_2$; —(O)$_{n6}$—$(CH_2)_{n7}$—$(SO_2)$—$OR'_9$; halogen; organosilanyl; organosiloxanyl; or a sugar residue linked directly in an α- or β-mode via the anomeric oxygen to the benzotropolone system or via a linear or branched alkylene, alkenylene, alkadiene or alkatriene spacer (sugar-$(CH_2)_n$—$(X_1)_{1 \ or \ 0}$-benzotropolone system, wherein n=1-10 and $X_1$=—O—; —C(=O)—; —O—CO—; —COO—; —NH—; —S—; —SO_2$—);

$R_1$, $R_2$, $R_3$, $R_4$, $R_5$, $R_7$, $R_8$, $R_9$, $R_{10}$, $R_{11}$, $R_{17}$, B, E, D, G, $n_1$, $n_2$, $n_3$, $n_4$, $n_5$, $n_6$, and $n_7$ are defined as in formula (1).

Further preference is given to compounds of formula (1) with one or more sugar residues.

Examples of benzotropolone compounds according to the present invention are listed in Table 1 below:

TABLE 1

Representatives of benzotropolones according to the present invention

B-1

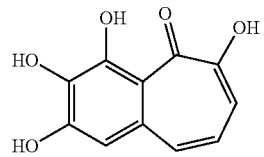 [SMILES: O=c1c(O)cccc2cc(O)c(O)c(O)c12]

B-2

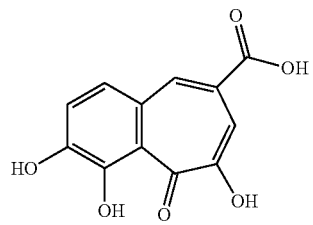 [SMILES: O=C(O)c1cc(O)c(=O)c2c(O)c(O)ccc2c1]

TABLE 1-continued
Representatives of benzotropolones according to the present invention
B-3 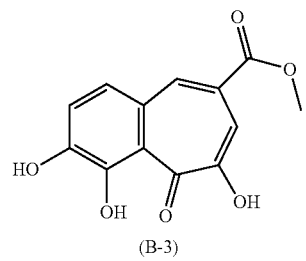
(B-3)
B-4 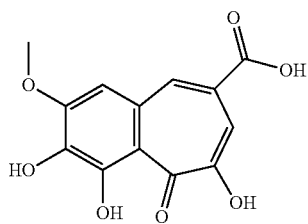 [SMILES: COc1cc2cc(C(=O)O)cc(O)c(=O)c2c(O)c1O]
B-5 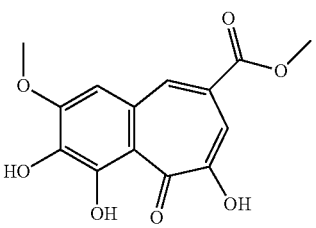 [SMILES: COC(=O)c1cc(O)c(=O)c2c(O)c(O)c(OC)cc2c1]
B-6 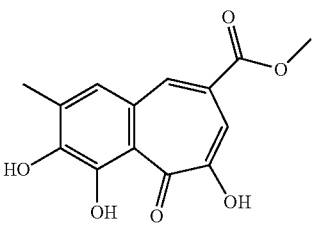 [SMILES: COC(=O)c1cc(O)c(=O)c2c(O)c(O)c(C)cc2c1]
B-7 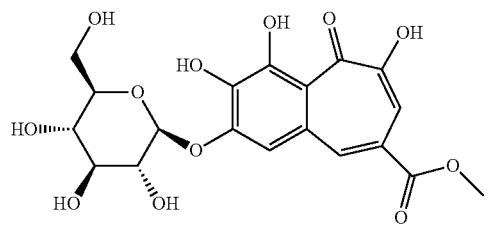 [SMILES: COC(=O)c1cc(O)c(=O)c2c(O)c(O)c(O[C@@H]3O[C@H](CO)[C@@H](O)[C@H](O)[C@H]3O)cc2c1]
B-8 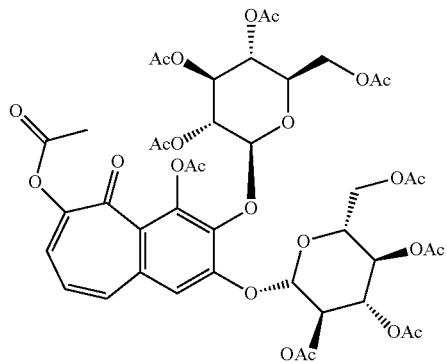

TABLE 1-continued
Representatives of benzotropolones according to the present invention
B-9
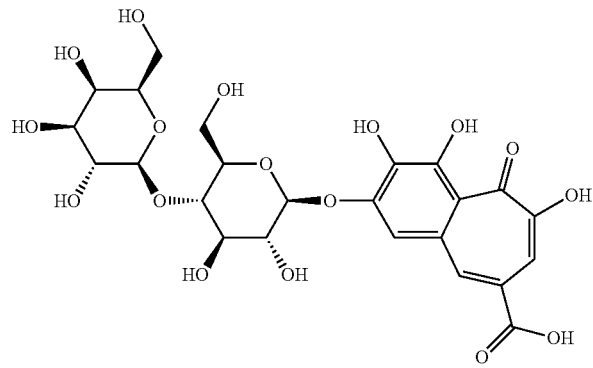 [SMILES: O=C(O)c1cc(O)c(=O)c2c(O)c(O)c(O[C@@H]3O[C@H](CO)[C@@H](O[C@@H]4O[C@H](CO)[C@H](O)[C@H](O)[C@H]4O)[C@H](O)[C@H]3O)cc2c1]
B-10
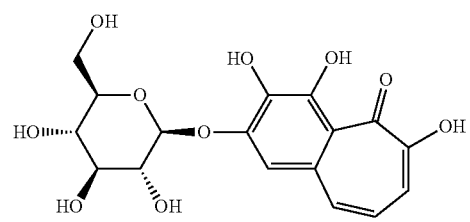 [SMILES: O=c1c(O)cccc2cc(O[C@@H]3O[C@H](CO)[C@@H](O)[C@H](O)[C@H]3O)c(O)c(O)c12]
B-11
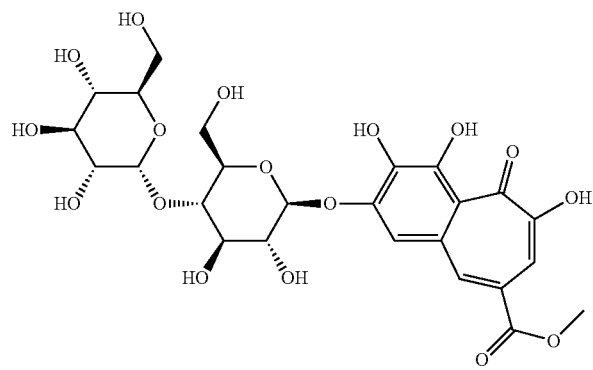 [SMILES: COC(=O)c1cc(O)c(=O)c2c(O)c(O)c(O[C@@H]3O[C@H](CO)[C@@H](O[C@H]4O[C@H](CO)[C@@H](O)[C@H](O)[C@H]4O)[C@H](O)[C@H]3O)cc2c1]
B-12
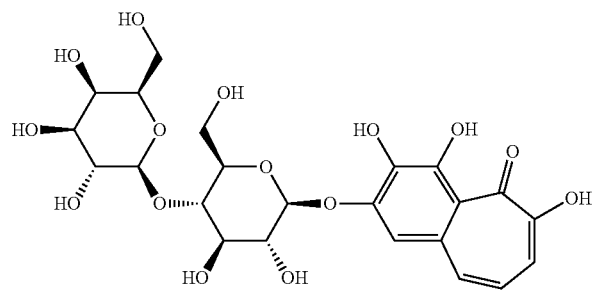 [SMILES: O=c1c(O)cccc2cc(O[C@@H]3O[C@H](CO)[C@@H](O[C@@H]4O[C@H](CO)[C@H](O)[C@H](O)[C@H]4O)[C@H](O)[C@H]3O)c(O)c(O)c12]
B-13
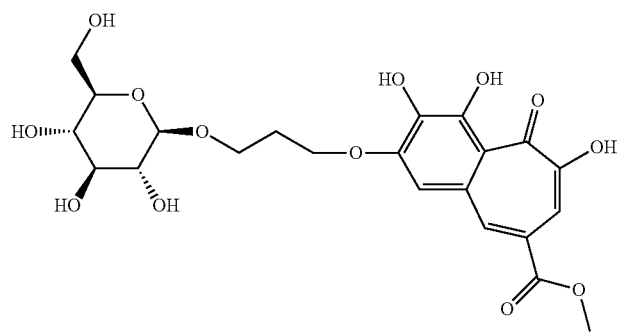 [SMILES: COC(=O)c1cc(O)c(=O)c2c(O)c(O)c(OCCCO[C@@H]3O[C@H](CO)[C@@H](O)[C@H](O)[C@H]3O)cc2c1]

TABLE 1-continued
Representatives of benzotropolones according to the present invention
B-14 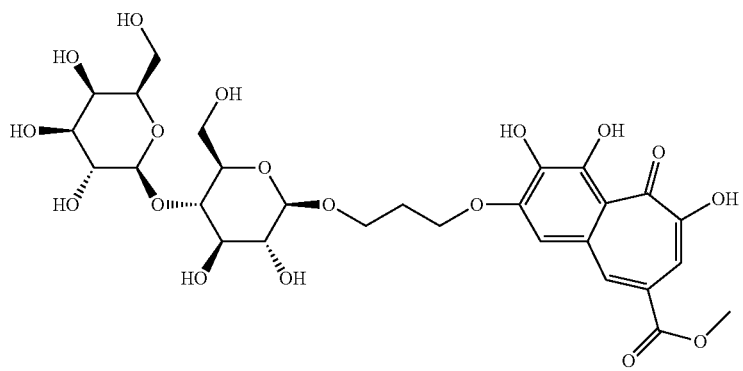 [SMILES: COC(=O)c1cc(O)c(=O)c2c(O)c(O)c(OCCCO[C@@H]3O[C@H](CO)[C@@H](O[C@@H]4O[C@H](CO)[C@H](O)[C@H](O)[C@H]4O)[C@H](O)[C@H]3O)cc2c1]
B-15 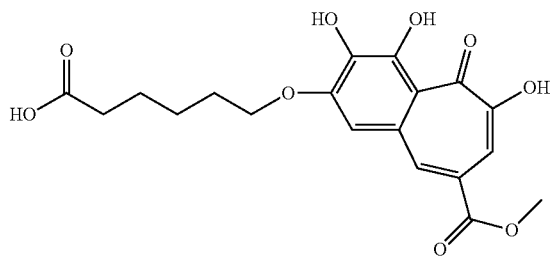 [SMILES: COC(=O)c1cc(O)c(=O)c2c(O)c(O)c(OCCCCCC(=O)O)cc2c1]
B-16 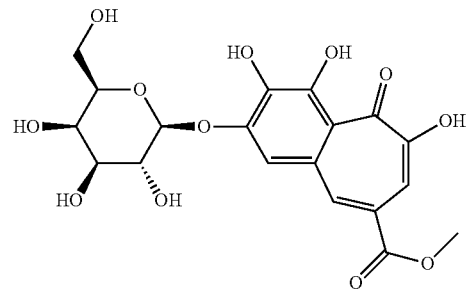 [SMILES: COC(=O)c1cc(O)c(=O)c2c(O)c(O)c(O[C@@H]3O[C@H](CO)[C@H](O)[C@H](O)[C@H]3O)cc2c1]
B-17 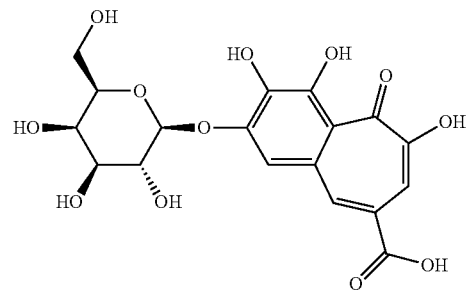 [SMILES: O=C(O)c1cc(O)c(=O)c2c(O)c(O)c(O[C@@H]3O[C@H](CO)[C@H](O)[C@H](O)[C@H]3O)cc2c1]
B-18 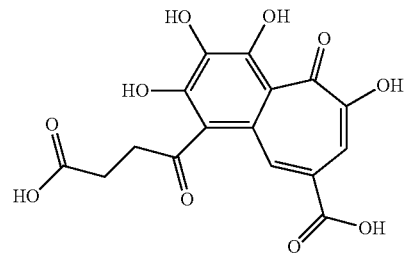 [SMILES: O=C(O)CCC(=O)c1c(O)c(O)c(O)c2c(=O)c(O)cc(C(=O)O)cc12]

TABLE 1-continued
Representatives of benzotropolones according to the present invention
B-19 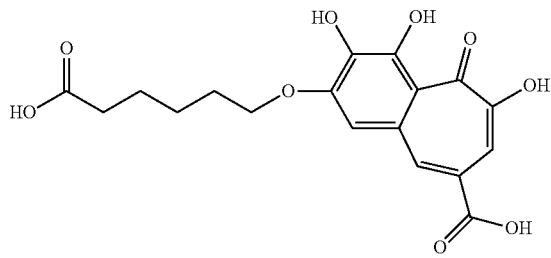 [SMILES: O=C(O)CCCCCOc1cc2cc(C(=O)O)cc(O)c(=O)c2c(O)c1O]
B-20 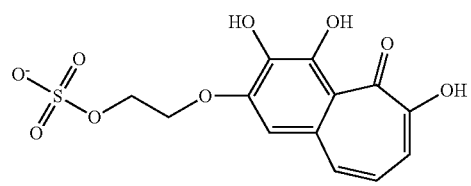 [SMILES: O=c1c(O)cccc2cc(OCCOS(=O)(=O)[O-])c(O)c(O)c12]
B-21 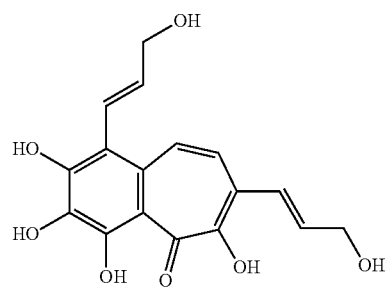 [SMILES: O=c1c(O)c(/C=C/CO)ccc2c(/C=C/CO)c(O)c(O)c(O)c12]
B-22 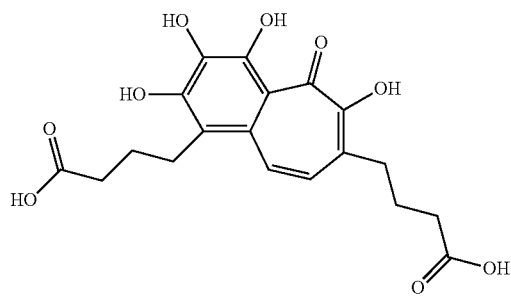 [SMILES: O=C(O)CCCc1ccc2c(CCCC(=O)O)c(O)c(O)c(O)c2c(=O)c1O]
B-23 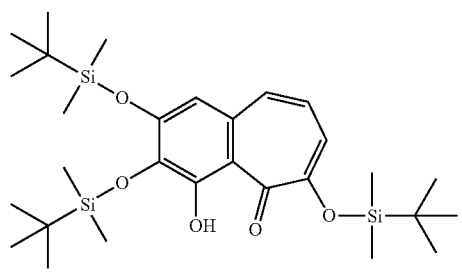 [SMILES: CC(C)(C)[Si](C)(C)Oc1cc2cccc(O[Si](C)(C)C(C)(C)C)c(=O)c2c(O)c1O[Si](C)(C)C(C)(C)C]
B-24 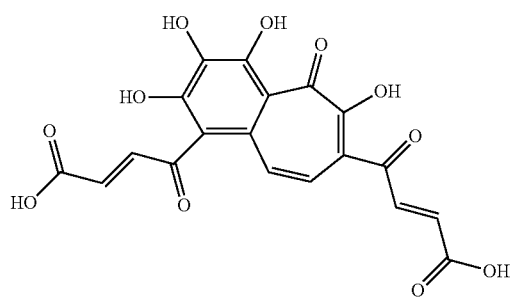 [SMILES: O=C(O)/C=C/C(=O)c1ccc2c(C(=O)/C=C/C(=O)O)c(O)c(O)c(O)c2c(=O)c1O]

TABLE 1-continued
Representatives of benzotropolones according to the present invention
B-25 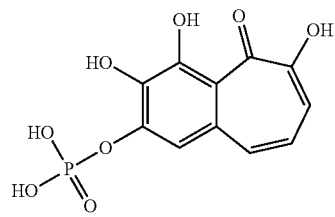 [SMILES: O=c1c(O)cccc2cc(OP(=O)(O)O)c(O)c(O)c12]
B-26 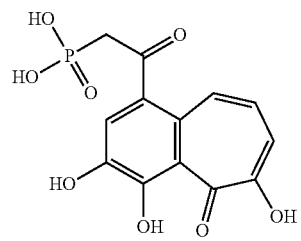 [SMILES: O=C(CP(=O)(O)O)c1cc(O)c(O)c2c(=O)c(O)cccc12]
B-27 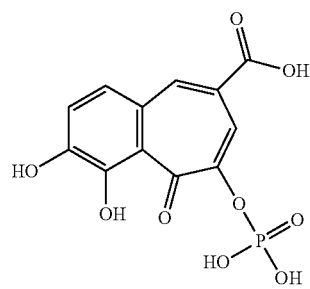 [SMILES: O=C(O)c1cc(OP(=O)(O)O)c(=O)c2c(O)c(O)ccc2c1]
B-28 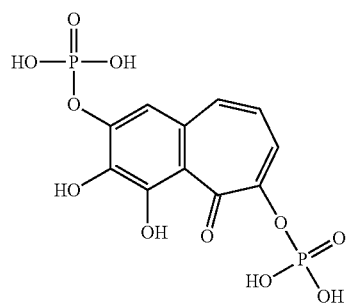 [SMILES: O=c1c(OP(=O)(O)O)cccc2cc(OP(=O)(O)O)c(O)c(O)c12]
B-29 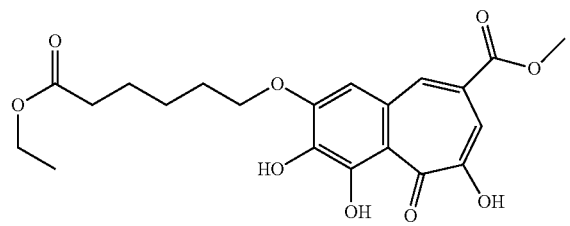 [SMILES: CCOC(=O)CCCCCOc1cc2cc(C(=O)OC)cc(O)c(=O)c2c(O)c1O]
B-30 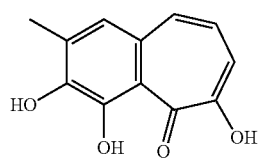 [SMILES: Cc1cc2cccc(O)c(=O)c2c(O)c1O]

TABLE 1-continued
Representatives of benzotropolones according to the present invention
B-31
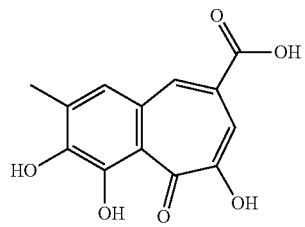 [SMILES: Cc1cc2cc(C(=O)O)cc(O)c(=O)c2c(O)c1O]
B-32
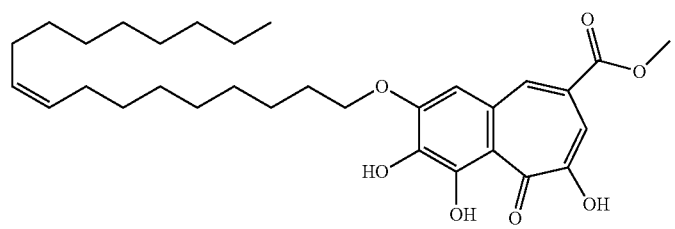 [SMILES: CCCCCCCC/C=C\CCCCCCCCOc1cc2cc(C(=O)OC)cc(O)c(=O)c2c(O)c1O]
B-33
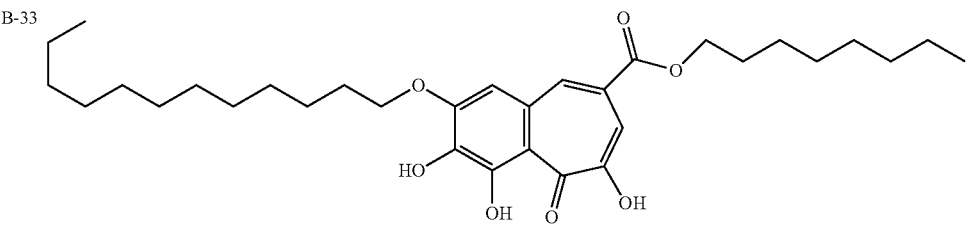
B-34
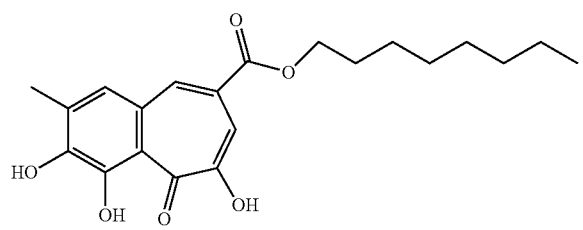 [SMILES: CCCCCCCCOC(=O)c1cc(O)c(=O)c2c(O)c(O)c(C)cc2c1]
B-35
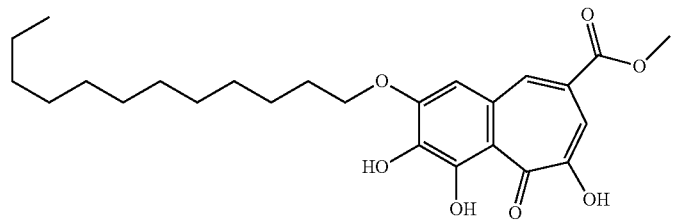 [SMILES: CCCCCCCCCCCCOc1cc2cc(C(=O)OC)cc(O)c(=O)c2c(O)c1O]
B-36
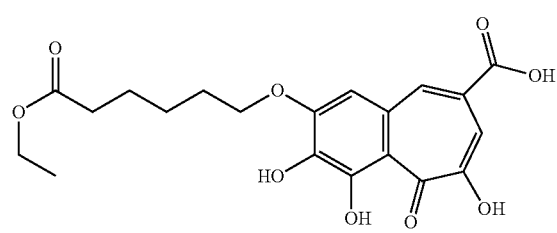 [SMILES: CCOC(=O)CCCCCOc1cc2cc(C(=O)O)cc(O)c(=O)c2c(O)c1O]

TABLE 1-continued
Representatives of benzotropolones according to the present invention
B-37 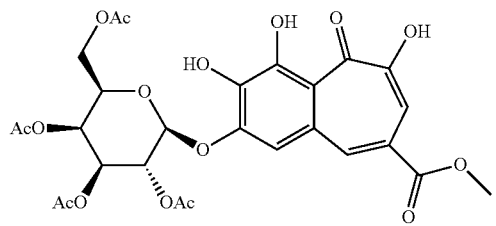
(B-37)
B-38 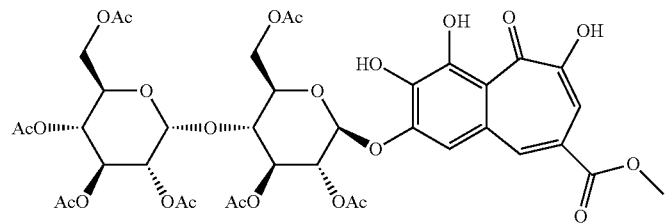 [SMILES: COC(=O)c1cc(O)c(=O)c2c(O)c(O)c(O[C@@H]3O[C@H](COC(C)=O)[C@@H](O[C@H]4O[C@H](COC(C)=O)[C@@H](OC(C)=O)[C@H](OC(C)=O)[C@H]4OC(C)=O)[C@H](OC(C)=O)[C@H]3OC(C)=O)cc2c1]
B-39 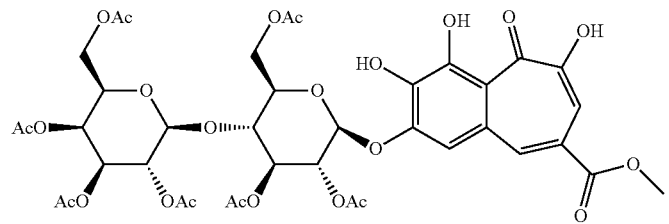 [SMILES: COC(=O)c1cc(O)c(=O)c2c(O)c(O)c(O[C@@H]3O[C@H](COC(C)=O)[C@@H](O[C@@H]4O[C@H](COC(C)=O)[C@H](OC(C)=O)[C@H](OC(C)=O)[C@H]4OC(C)=O)[C@H](OC(C)=O)[C@H]3OC(C)=O)cc2c1]
B-40 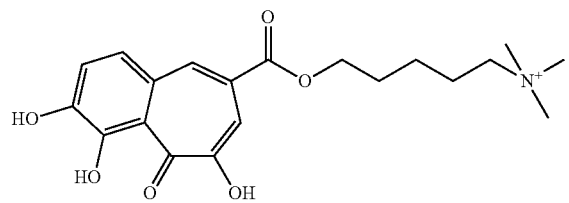 [SMILES: C[N+](C)(C)CCCCCOC(=O)c1cc(O)c(=O)c2c(O)c(O)ccc2c1]
B-41 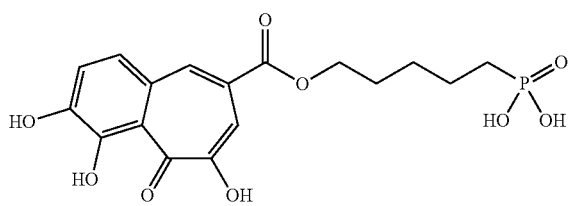 [SMILES: O=C(OCCCCCP(=O)(O)O)c1cc(O)c(=O)c2c(O)c(O)ccc2c1]
B-42 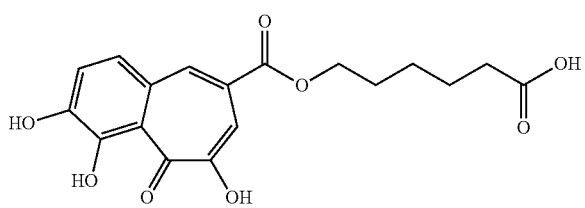 [SMILES: O=C(O)CCCCCOC(=O)c1cc(O)c(=O)c2c(O)c(O)ccc2c1]
B-43 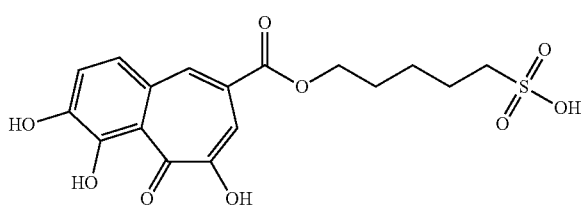 [SMILES: O=C(OCCCCCS(=O)(=O)O)c1cc(O)c(=O)c2c(O)c(O)ccc2c1]

TABLE 1-continued
Representatives of benzotropolones according to the present invention
B-44
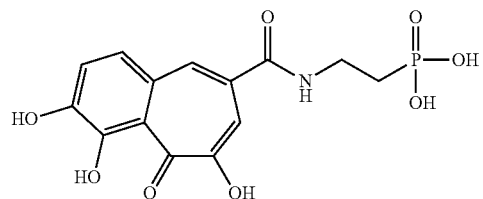 [SMILES: O=C(NCCP(=O)(O)O)c1cc(O)c(=O)c2c(O)c(O)ccc2c1]
B-45
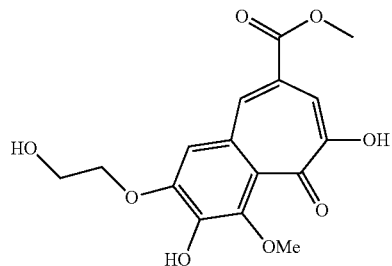 [SMILES: COC(=O)c1cc(O)c(=O)c2c(OC)c(O)c(OCCO)cc2c1]
B-46
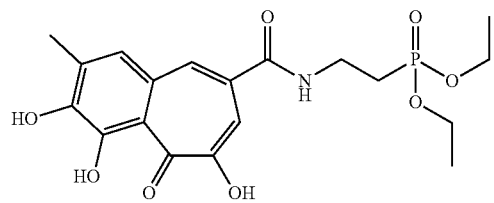 [SMILES: CCOP(=O)(CCNC(=O)c1cc(O)c(=O)c2c(O)c(O)c(C)cc2c1)OCC]
B-47
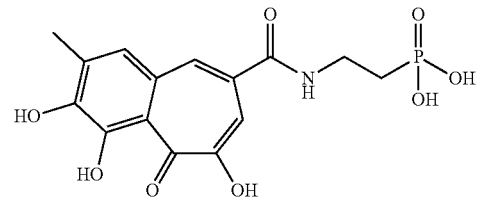 [SMILES: Cc1cc2cc(C(=O)NCCP(=O)(O)O)cc(O)c(=O)c2c(O)c1O]
B-48
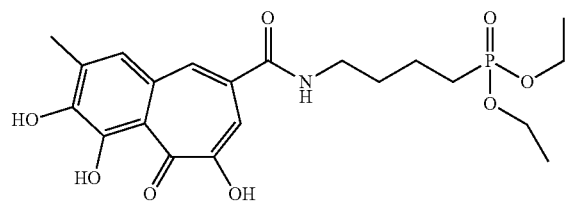 [SMILES: CCOP(=O)(CCCCNC(=O)c1cc(O)c(=O)c2c(O)c(O)c(C)cc2c1)OCC]
B-49
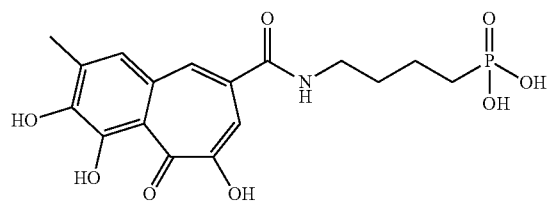 [SMILES: Cc1cc2cc(C(=O)NCCCCP(=O)(O)O)cc(O)c(=O)c2c(O)c1O]
B-50
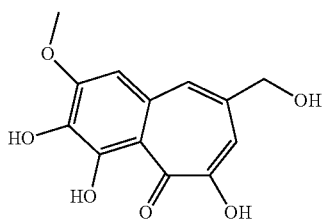 [SMILES: COc1cc2cc(CO)cc(O)c(=O)c2c(O)c1O]

TABLE 1-continued
Representatives of benzotropolones according to the present invention
B-51 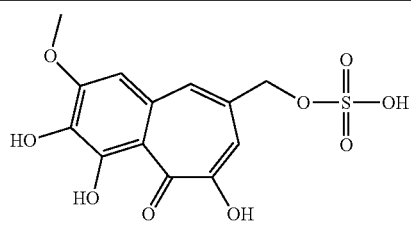
B-52 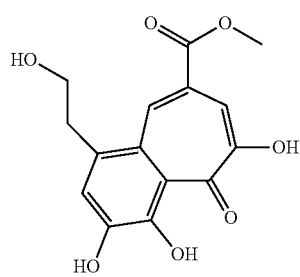 [SMILES: COC(=O)c1cc(O)c(=O)c2c(O)c(O)cc(CCO)c2c1]
B-53 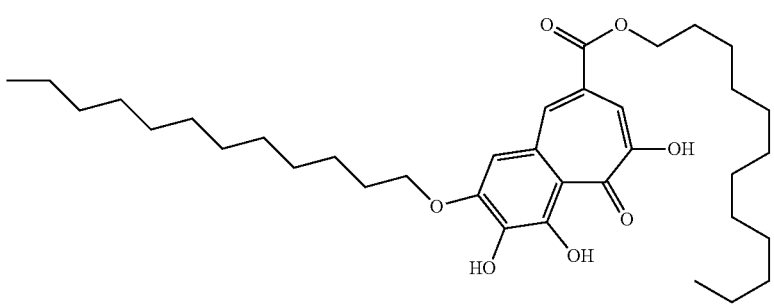 [SMILES: CCCCCCCCCCCCOC(=O)c1cc(O)c(=O)c2c(O)c(O)c(OCCCCCCCCCCCC)cc2c1]
B-54 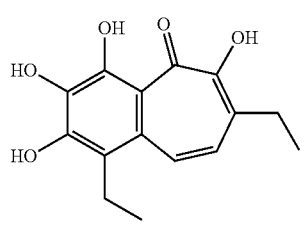 [SMILES: CCc1ccc2c(CC)c(O)c(O)c(O)c2c(=O)c1O]
B-55 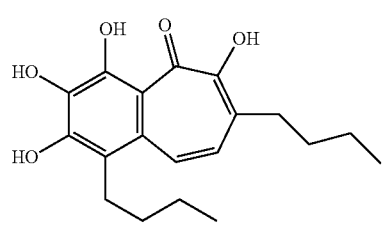 [SMILES: CCCCc1ccc2c(CCCC)c(O)c(O)c(O)c2c(=O)c1O]
B-56 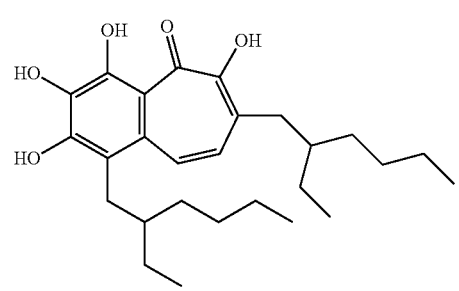 [SMILES: CCCCC(CC)Cc1ccc2c(CC(CC)CCCC)c(O)c(O)c(O)c2c(=O)c1O]

TABLE 1-continued
Representatives of benzotropolones according to the present invention
B-57 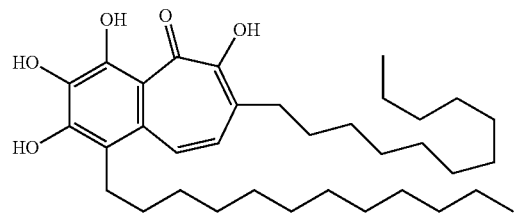 [SMILES: CCCCCCCCCCCCc1ccc2c(CCCCCCCCCCCC)c(O)c(O)c(O)c2c(=O)c1O]
B-58 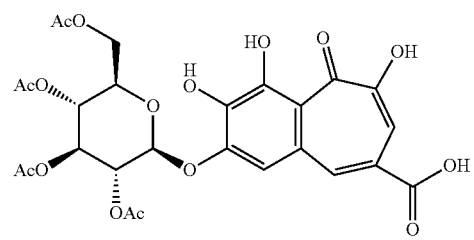 [SMILES: CC(=O)OC[C@H]1O[C@@H](Oc2cc3cc(C(=O)O)cc(O)c(=O)c3c(O)c2O)[C@H](OC(C)=O)[C@@H](OC(C)=O)[C@@H]1OC(C)=O]
B-59 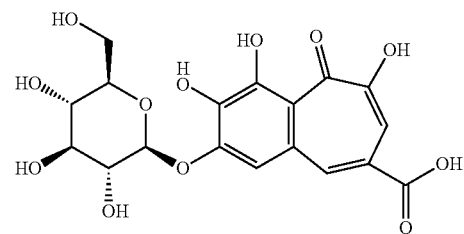 [SMILES: O=C(O)c1cc(O)c(=O)c2c(O)c(O)c(O[C@@H]3O[C@H](CO)[C@@H](O)[C@H](O)[C@H]3O)cc2c1]
B-60 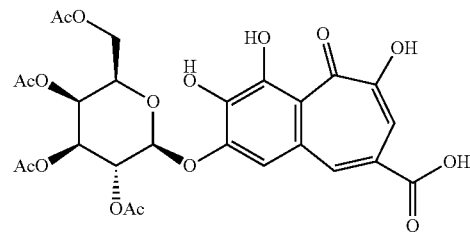 [SMILES: CC(=O)OC[C@H]1O[C@@H](Oc2cc3cc(C(=O)O)cc(O)c(=O)c3c(O)c2O)[C@H](OC(C)=O)[C@@H](OC(C)=O)[C@H]1OC(C)=O]
B-61 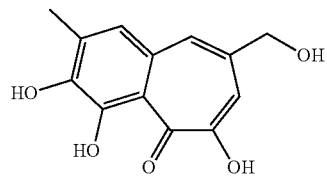 [SMILES: Cc1cc2cc(CO)cc(O)c(=O)c2c(O)c1O]
B-62 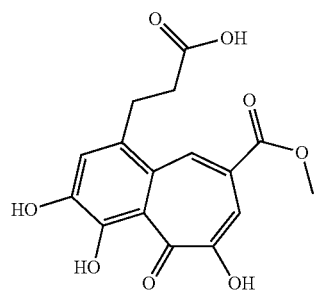 [SMILES: COC(=O)c1cc(O)c(=O)c2c(O)c(O)cc(CCC(=O)O)c2c1]

The benzotropolone derivatives as used in the present invention are partially known from the prior art, partially they represent novel compounds.

The novel compounds correspond to the formula

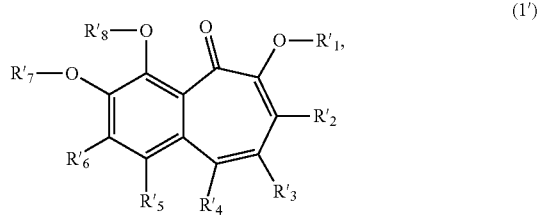

(1')

wherein $R'_2$, $R'_4$, $R'_5$ and $R'_6$ independently of one another are hydrogen; OH; $C_1$-$C_{30}$alkyl, $C_2$-$C_{30}$alkenyl, $C_1$-$C_{30}$alkoxy, $C_3$-$C_{12}$-cycloalkyl or $C_1$-$C_{30}$hydroxyalkyl, which may be substituted by one or more E and/or interrupted by one or more D; $C_6$-$C_{20}$aryl, which may be substituted by one or more G; $C_4$-$C_{20}$heteroaryl, which may be substituted by one or more G, $C_2$-$C_{18}$alkenyl, $C_2$-$C_{18}$alkynyl, $C_7$-$C_{25}$aralkyl, CN, or —CO—$R'_{17}$; $C_1$-$C_{30}$mono- or dialkylamino; COR'$_9$; COOR'$_9$; OCOR'$_9$; CONR'$_9$R'$_{10}$; CN; SO$_2$R'$_9$; OCOOR'$_9$; NHCOOR'$_9$; NR'$_9$COR'$_{10}$; NH$_2$; —(CO)—NH—(CH$_2$)$_{n1}$—(PO)—(OR'$_{11}$)$_2$; sulphate; sulphonate; phosphate; phosphonate; —(CH$_2$)$_{n2}$—[O—(SO$_2$)]$_{n3}$—OR'$_{11}$; —O—(CH$_2$)$_{n4}$(CO)$_{n5}$—R'$_{11}$; —(O)$_{n6}$—(CH$_2$)$_{n7}$—(PO)—(OR'$_9$)$_2$; —(O)$_{n6}$—(CH$_2$)$_{n7}$—(SO$_2$)—OR'$_9$; halogen; organosilanyl; organosiloxanyl; or a sugar residue linked directly in an α- or β-mode via the anomeric oxygen to the aromatic benzotropolone system or via a linear or branched alkylene, alkenylene, alkadiene or alkatriene spacer (sugar-(CH$_2$)$_n$—(X$_1$)$_{1\ or\ 0}$-benzotropolone system, wherein n=1-10 and X$_1$=—O—; —C(=O)—; —O—CO—; —COO—; —NH—; —S—; —SO$_2$—);

$R'_1$, $R'_7$ and $R'_8$ independently of one another are hydrogen; $C_1$-$C_{12}$alkyl or $C_3$-$C_{12}$-cycloalkyl, which may be substituted by one or more E and/or interrupted by one or more D; $C_6$-$C_{20}$aryl, which may be substituted by one or more G; $C_4$-$C_{20}$heteroaryl, which may be substituted by G, $C_2$-$C_{18}$alkenyl, $C_2$-$C_{18}$alkynyl, $C_7$-$C_{25}$aralkyl, or —CO—R'$_{17}$; COOR'$_9$; COR'$_9$; CONR'$_9$R'$_{10}$; SO$_3$R'$_9$; SO$_2$R'$_9$; PO$_3$(R'$_9$)$_2$; PO$_2$(R'$_9$)$_2$; organosilanyl; organosiloxanyl; or a sugar residue linked directly in an α- or β-mode via the anomeric oxygen to the benzotropolone system or via a linear or branched alkylene, alkenylene, alkadiene or alkatriene spacer (sugar-(CH$_2$)$_n$—(X$_1$)$_{1\ or\ 0}$-benzotropolone system, wherein n=1-10 and X$_1$=—O—; —C(=O)—; —O—CO—; —SO$_2$—);

$R'_3$ is OH; $C_1$-$C_{30}$alkyl, $C_2$-$C_{30}$alkenyl, $C_1$-$C_{30}$alkoxy, $C_3$-$C_{12}$-cycloalkyl or $C_1$-$C_{30}$hydroxyalkyl, which may be substituted by one or more E and/or interrupted by one or more D; $C_6$-$C_{20}$aryl, which may be substituted by one or more G; $C_4$-$C_{20}$heteroaryl, which may be substituted by one or more G, $C_2$-$C_{18}$alkenyl, $C_2$-$C_{18}$alkynyl, $C_7$-$C_{25}$aralkyl, CN, or —CO—R'$_{17}$; $C_1$-$C_{30}$mono- or dialkylamino; COR'$_9$; COOR'$_9$; CONR'$_9$R'$_{10}$; CN; SO$_2$R'$_9$; OCOOR'$_9$; NHCOOR'$_9$; NH$_2$; —(CO)—NH—(CH$_2$)$_{n1}$—(PO)—(OR'$_{11}$)$_2$; sulphate; sulphonate; phosphate; phosphonate; —(CH$_2$)$_{n2}$—[O—(SO$_2$)]$_{n3}$—OR'$_{11}$; —O—(CH$_2$)$_{n4}$(CO)$_{n5}$—R'$_{11}$; —(O)$_{n6}$—(CH$_2$)$_{n7}$—(PO)—(OR'$_9$)$_2$; —(O)$_{n6}$—(CH$_2$)$_{n7}$—(SO$_2$)—OR'$_9$; halogen; organosilanyl; organosiloxanyl; or a sugar residue linked directly in an α- or β-mode via the anomeric oxygen to the benzotropolone system or via a linear or branched alkylene, alkenylene, alkadiene or alkatriene spacer (sugar-(CH$_2$)$_n$—(X$_1$)$_{1\ or\ 0}$-benzotropolone system, wherein n=1-10 and X$_1$=—O—; —C(=O)—; —O—CO—; —COO—; —NH—; —S—; —SO$_2$—);

$R'_9$ and $R'_{10}$ independently from each other are hydrogen; $C_1$-$C_{12}$alkyl or $C_3$-$C_{12}$cycloalkyl, which may be substituted by one or more E and/or interrupted by one or more D; $C_6$-$C_{20}$-aryl, which may be substituted by one or more G; organosilanyl; organosiloxanyl; or a sugar residue linked directly in an α- or β-mode via the anomeric oxygen or via a linear or branched alkylene, alkenylene, alkadiene or alkatriene spacer (sugar-(CH$_2$)$_n$—(X$_1$)$_{1\ or\ 0}$—*, wherein n=1-10 and X$_1$=; —C(=O)—; —O—CO—); or $R'_9$ and $R'_{10}$ together form a five or six membered ring, $R'_{11}$ is hydrogen; or $C_1$-$C_5$alkyl;

$n_1$, $n_2$, $n_4$ and $n_7$ independently from each other are a number from 1 to 5;

$n_3$, $n_5$ and $n_5$ independently from each other are a 0; or 1;

D is —CO—; —COO—; —S—; —SO—; —SO$_2$—; —O—; —NR'$_{14}$—; —SiR'$_{19}$R'$_{20}$—; —POR'$_{11}$—; —CR'$_{12}$=CR'$_{13}$—; or —C≡C—; and E is —OR'$_{18}$; —SR'$_{18}$; —NR'$_{14}$R'$_{15}$; —NR'$_{14}$COR'$_{15}$; —COR'$_{17}$; —COOR'$_{16}$; —CONR'$_{14}$R'$_{15}$; —CN; halogen; or SO$_3$R'$_{18}$; SO$_2$R'$_{18}$; PO$_3$(R'$_{18}$)$_2$; PO$_2$(R'$_{18}$)$_2$; organosilanyl; organosiloxanyl; or a sugar residue linked directly in an α- or β-mode via the anomeric oxygen to the aromatic benzotropolone system or via a linear or branched alkylene, alkenylene, alkadiene or alkatriene spacer (sugar-(CH$_2$)$_n$—(X$_1$)$_{1\ or\ 0}$-benzotropolone system, wherein n=1-10 and X$_1$=—O—; —C(=O)—; —O—CO—; —COO—; —NH—; —S—; —SO$_2$—);

G is E; $C_1$-$C_{18}$alkyl, which is optionally interrupted by D; $C_1$-$C_{18}$ perfluoroalkyl; $C_1$-$C_{18}$alkoxy, which is optionally substituted by E and/or interrupted by D; wherein $R'_{12}$, $R'_{13}$, $R'_{14}$ and $R'_{15}$ independently of each other are hydrogen; $C_6$-$C_{18}$aryl which is optionally substituted by $C_1$-$C_{18}$alkyl or $C_1$-$C_{18}$alkoxy; $C_1$-$C_{18}$alkyl, which is optionally interrupted by —O—; or $R'_{14}$ and $R'_{15}$ together form a five or six membered ring, $R'_{16}$ is hydrogen; $C_6$-$C_{18}$aryl which is optionally substituted by $C_1$-$C_{18}$alkyl or $C_1$-$C_{18}$alkoxy; $C_1$-$C_{18}$alkyl which is optionally interrupted by —O—;

$R'_{17}$ is H; $C_6$-$C_{18}$aryl which is optionally substituted by $C_1$-$C_{18}$alkyl or $C_1$-$C_{18}$alkoxy; or $C_1$-$C_{18}$alkyl which is optionally interrupted by —O—;

$R'_{18}$ is hydrogen; $C_6$-$C_{18}$aryl, which is optionally substituted by $C_1$-$C_{18}$alkyl or $C_1$-$C_{18}$alkoxy; $C_1$-$C_{18}$alkyl, which is optionally interrupted by —O—;

$R'_{19}$ and $R'_{20}$ independently of each other are hydrogen; $C_1$-$C_{18}$alkyl; $C_6$-$C_{18}$aryl which is optionally substituted by $C_1$-$C_{18}$alkyl; and wherein at least one of $R'_1$, $R'_2$, $R'_3$, $R'_4$, $R'_5$, $R'_6$, $R'_7$ or $R'_8$ is a sugar residue linked directly in an α- or β-mode via the anomeric oxygen to the benzotropolone system or via a linear or branched alkylene, alkenylene, alkadiene or alkatriene spacer (sugar-(CH$_2$)$_n$—(X$_1$)$_{1\ or\ 0}$-benzotropolone system, wherein n=1-10 and X$_1$=—O—; —C(=O)—; —O—CO—; —COO—; —NH—; —S—; or —SO$_2$—).

Preferred are compounds of formula (1'), wherein
$R'_1$, $R'_3$, $R'_4$, $R'_7$ and $R'_8$ are hydrogen;
$R'_6$ is OH; and
$R'_2$ and $R'_5$ are independently of each other —C(=O)—$C_1$-$C_{30}$alkyl, $C_4$-$C_{30}$alkyl or $C_4$-$C_{30}$alkenyl, which may be substituted by one or more E and/or interrupted by one or more D; and D and E are defined as in formula (1').

Preferred are also compounds of formula (1'), wherein
$R'_2$, $R'_3$, $R'_4$ and $R'_6$ independently of one another are hydrogen; OH; $C_1$-$C_{30}$alkyl, $C_2$-$C_{30}$alkenyl, $C_1$-$C_{30}$alkoxy, $C_3$-$C_{12}$-cycloalkyl or $C_1$-$C_{30}$hydroxyalkyl, which may be substituted by one or more E and/or interrupted by one or more D; $C_6$-$C_{20}$aryl, which may be substituted by one or more G; $C_4$-$C_{20}$heteroaryl, which may be substituted by one or more G, $C_2$-$C_{18}$alkenyl, $C_2$-$C_{18}$alkynyl, $C_7$-$C_{25}$aralkyl, CN, or —CO—$R'_{17}$; $C_1$-$C_{30}$mono- or dialkylamino; $COR'_9$; $COOR'_9$; $OCOR'_9$; $CONR'_9R'_{10}$; CN; $SO_2R'_9$; $OCOOR'_9$; $NHCOOR'_9$; $NR'_9COR'_{10}$; $NH_2$; —(CO)—NH—$(CH_2)_{n1}$—(PO)—$(OR'_{11})_2$; sulphate; sulphonate; phosphate; phosphonate; —$(CH_2)_{n2}$—[O—$(SO_2)]_{n3}$—$OR'_{11}$; —O—$(CH_2)_{n4}$ $(CO)_{n5}$—$R'_{11}$; —$(O)_{n6}$—$(CH_2)_{n7}$—(PO)—$(OR'_9)_2$; —$(O)_{n6}$—$(CH_2)_{n7}$—$(SO_2)$—$OR'_9$; halogen; organosilanyl; organosiloxanyl; or a sugar residue linked directly in an α- or β-mode via the anomeric oxygen to the aromatic benzotropolone system or via a linear or branched alkylene, alkenylene, alkadiene or alkatriene spacer (sugar-$(CH_2)_n$—$(X_1)_{1\ or\ 0}$-benzotropolone system, wherein n=1-10 and $X_1$=—O—; —C(=O)—; —O—CO—; —COO—; —NH—; —S—; —$SO_2$—);

$R'_1$, $R'_7$ and $R'_8$ independently of one another are hydrogen; $C_1$-$C_{12}$alkyl or $C_3$-$C_{12}$-cycloalkyl, which may be substituted by one or more E and/or interrupted by one or more D; $C_6$-$C_{20}$aryl, which may be substituted by one or more G; $C_4$-$C_{20}$heteroaryl, which may be substituted by G, $C_2$-$C_{18}$alkenyl, $C_2$-$C_{18}$alkynyl, $C_7$-$C_{25}$aralkyl, or —CO—$R'_{17}$; $COOR'_9$; $COR'_9$; $CONR'_9R'_{10}$; $SO_3R'_9$; $SO_2R'_9$; $PO_3(R'_9)_2$; $PO_2(R'_9)_2$; organosilanyl; organosiloxanyl; or a sugar residue linked directly in an α- or β-mode via the anomeric oxygen to the benzotropolone system or via a linear or branched alkylene, alkenylene, alkadiene or alkatriene spacer (sugar-$(CH_2)_n$—$(X_1)_{1\ or\ 0}$-benzotropolone system, wherein n=1-10 and $X_1$=—O—; —C(=O)—; —O—CO—; —$SO_2$—);

$R'_9$ and $R'_{10}$ independently from each other are hydrogen; $C_1$-$C_{12}$alkyl or $C_3$-$C_{12}$cycloalkyl, which may be substituted by one or more E and/or interrupted by one or more D; $C_6$-$C_{20}$-aryl, which may be substituted by one or more G; organosilanyl; organosiloxanyl; or a sugar residue linked directly in an α- or β-mode via the anomeric oxygen or via a linear or branched alkylene, alkenylene, alkadiene or alkatriene spacer (sugar-$(CH_2)_n$—$(X_1)_{1\ or\ 0}$—*, wherein n=1-10 and $X_1$=; —C(=O)—; —O—CO—); or $R'_9$ and $R'_{10}$ together form a five or six membered ring,
$R'_{11}$ is hydrogen; or $C_1$-$C_5$alkyl;
$n_1$, $n_2$, $n_4$ and $n_7$ independently from each other are a number from 1 to 5;
$n_3$, $n_5$ and $n_5$ independently from each other are a 0; or 1;

D is —CO—; —COO—; —S—; —SO—; —$SO_2$—; —O—; —$NR'_{14}$—; —$SiR'_{19}R'_{20}$—; —$POR'_{11}$—; —$CR'_{12}$=$CR'_{13}$—; or —C≡C—; and E is —$OR'_{18}$; —$SR'_{18}$; —$NR'_{14}R'_{15}$; —$NR'_{14}COR'_{15}$; —$COR'_{17}$; —$COOR'_{16}$; —$CONR'_{14}R'_{15}$; —CN; halogen; or $SO_3R'_{18}$; $SO_2R'_{18}$; $PO_3(R'_{18})_2$; $PO_2(R'_{18})_2$; organosilanyl; or a sugar residue linked directly in an α- or β-mode via the anomeric oxygen to the aromatic benzotropolone system or via a linear or branched alkylene, alkenylene, alkadiene or alkatriene spacer (sugar-$(CH_2)_n$—$(X_1)_{1\ or\ 0}$-benzotropolone system, wherein n=1-10 and $X_1$=—O—; —C(=O)—; —O—CO—; —COO—; —NH—; —S—; —$SO_2$—);

G is E; $C_1$-$C_{18}$alkyl, which is optionally interrupted by D; $C_1$-$C_{18}$ perfluoroalkyl; $C_1$-$C_{18}$alkoxy, which is optionally substituted by E and/or interrupted by D; wherein $R'_{12}$, $R'_{13}$, $R'_{14}$ and $R'_{15}$ independently of each other are hydrogen; $C_6$-$C_{18}$aryl which is optionally substituted by $C_1$-$C_{18}$alkyl or $C_1$-$C_{18}$alkoxy; $C_1$-$C_{18}$alkyl, which is optionally interrupted by —O—; or $R'_{14}$ and $R'_{15}$ together form a five or six membered ring, $R'_{16}$ is hydrogen; $C_6$-$C_{18}$aryl which is optionally substituted by $C_1$-$C_{18}$alkyl or $C_1$-$C_{18}$alkoxy; $C_1$-$C_{18}$alkyl which is optionally interrupted by —O—;

$R'_{17}$ is H; $C_6$-$C_{18}$aryl which is optionally substituted by $C_1$-$C_{18}$alkyl or $C_1$-$C_{18}$alkoxy; or $C_1$-$C_{18}$alkyl which is optionally interrupted by —O—;

$R'_{18}$ is hydrogen; $C_6$-$C_{18}$aryl, which is optionally substituted by $C_1$-$C_{18}$alkyl or $C_1$-$C_{18}$alkoxy; $C_1$-$C_{18}$alkyl, which is optionally interrupted by —O—;

$R'_{19}$ and $R'_{20}$ independently of each other are hydrogen; $C_1$-$C_{18}$alkyl; $C_6$-$C_{18}$aryl which is optionally substituted by $C_1$-$C_{18}$alkyl; and $R'_5$ is *—$(CH_2)$—$(CH_2)$—(CO)O—$R'_{15}$; or *—$(CH_2)$—$(CH_2)$—OH;

$R'_{15}$ is hydrogen or $C_3$-$C_{30}$alkyl, which may be substituted by one or more E and/or interrupted by one or more D.

Preferred are also compounds of formula

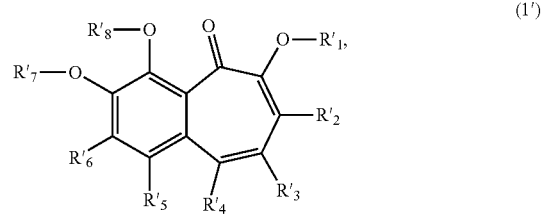

(1')

wherein
$R'_2$, $R'_3$, $R'_4$, $R'_5$ and $R'_6$ independently of one another are hydrogen; OH; $C_1$-$C_{30}$alkyl, $C_2$-$C_{30}$alkenyl, $C_1$-$C_{30}$alkoxy, $C_3$-$C_{12}$-cycloalkyl or $C_1$-$C_{30}$hydroxyalkyl, which may be substituted by one or more E and/or interrupted by one or more D; $C_6$-$C_{20}$aryl, which may be substituted by one or more G; $C_4$-$C_{20}$heteroaryl, which may be substituted by one or more G, $C_2$-$C_{18}$alkenyl, $C_2$-$C_{18}$alkynyl, $C_7$-$C_{25}$aralkyl, CN, or —CO—$R'_{17}$; $C_1$-$C_{30}$mono- or dialkylamino; $COR'_9$; $COOR'_9$; $OCOR'_9$; $CONR'_9R'_{10}$; CN; $SO_2R'_9$; $OCOOR'_9$; $NHCOOR'_9$; $NR'_9COR'_{10}$; $NH_2$; —(CO)—NH—$(CH_2)_{n1}$—(PO)—$(OR'_{11})_2$; sulphate; sulphonate; phosphate; phosphonate; —$(CH_2)_{n2}$—[O—$(SO_2)]_{n3}$—$OR'_{11}$; —O—$(CH_2)_{n4}$ $(CO)_{n5}$—$R'_{11}$; —$(O)_{n6}$—$(CH_2)_{n7}$—(PO)—$(OR'_9)_2$, —$(O)_{n6}$—$(CH_2)_{n7}$—$(SO_2)$—$OR'_9$, halogen; organosilanyl; organosiloxanyl; or a sugar residue linked directly in an α- or β-mode via the anomeric oxygen to the aromatic benzotropolone system or via a linear or branched alkylene, alkenylene, alkadiene or alkatriene spacer (sugar-$(CH_2)_n$—$(X_1)_{1\ or\ 0}$-benzotropolone system, wherein n=1-10 and $X_1$=—O—; —C(=O)—; —O—CO—; —COO—; —NH—; —S—; —$SO_2$—);

R'$_1$, R'$_7$ and R'$_8$ independently of one another are hydrogen; C$_1$-C$_{12}$alkyl or C$_3$-C$_{12}$-cycloalkyl, which may be substituted by one or more E and/or interrupted by one or more D; C$_6$-C$_{20}$aryl, which may be substituted by one or more G; C$_4$-C$_{20}$heteroaryl, which may be substituted by G, C$_2$-C$_{18}$alkenyl, C$_2$-C$_{18}$alkynyl, C$_7$-C$_{25}$aralkyl, or —CO—R'$_{17}$; COOR'$_9$; COR'$_9$; CONR'$_9$R'$_{10}$; SO$_3$R'$_9$; SO$_2$R'$_9$; PO$_3$(R'$_9$)$_2$; PO$_2$(R'$_9$)$_2$; organosilanyl; organosiloxanyl; or a sugar residue linked directly in an α- or β-mode via the anomeric oxygen to the benzotropolone system or via a linear or branched alkylene, alkenylene, alkadiene or alkatriene spacer (sugar-(CH$_2$)$_n$—(X$_1$)$_{1\ or\ 0}$-benzotropolone system, wherein n=1-10 and X$_1$=—O—; —C(=O)—; —O—CO—; —SO$_2$—);

R'$_9$ and R'$_{10}$ independently from each other are hydrogen; C$_1$-C$_{12}$alkyl or C$_3$-C$_{12}$-cycloalkyl, which may be substituted by one or more E and/or interrupted by one or more D: C$_6$-C$_{20}$aryl, which may be substituted by one or more G; organosilanyl; organosiloxanyl; or a sugar residue linked directly in an α- or β-mode via the anomeric oxygen or via a linear or branched alkylene, alkenylene, alkadiene or alkatriene spacer (sugar-(CH$_2$)$_n$—(X$_1$)$_{1\ or\ 0}$—*, wherein n=1-10 and X$_1$=; —C(=O)—; —O—CO—); or R'$_9$ and R'$_{10}$ together form a five or six membered ring, R'$_{11}$ is hydrogen; or C$_1$-C$_5$alkyl;

n$_1$, n$_2$, n$_4$ and n$_7$ independently from each other are a number from 1 to 5;

n$_3$ and n$_5$ independently from each other are a 0; or 1;

D is —CO—; —COO—; —S—; —SO—; —SO$_2$—; —O—; —NR'$_{14}$—; —SiR'$_{19}$R'$_{20}$—; —POR'$_{11}$—; —CR'$_{12}$=CR'$_{13}$—; or —C≡C—; and E is —OR'$_{18}$; —SR'$_{18}$; —NR'$_{14}$R'$_{15}$; —NR'$_{14}$COR'$_{15}$; —COR'$_{17}$; —COOR'$_{16}$; —CONR'$_{14}$R'$_{15}$; —CN; halogen; or SO$_3$R'$_{18}$; SO$_2$R'$_{18}$; PO$_3$(R'$_{18}$)$_2$; PO$_2$(R'$_{18}$)$_2$; organosilanyl; organosiloxanyl; or a sugar residue linked directly in an α- or β-mode via the anomeric oxygen to the aromatic benzotropolone system or via a linear or branched alkylene, alkenylene, alkadiene or alkatriene spacer (sugar-(CH$_2$)$_n$—(X$_1$)$_{1\ or\ 0}$-benzotropolone system, wherein n=1-10 and X$_1$=—O—; —C(=O)—; —O—CO—; —COO—; —NH—; —S—; —SO$_2$—);

G is E; C$_1$-C$_{18}$alkyl, which is optionally interrupted by D; C$_1$-C$_{18}$ perfluoroalkyl; C$_1$-C$_{18}$alkoxy, which is optionally substituted by E and/or interrupted by D; wherein R'$_{12}$, R'$_{13}$, R'$_{14}$ and R'$_{15}$ independently of each other are hydrogen; C$_6$-C$_{18}$aryl which is optionally substituted by C$_1$-C$_{18}$alkyl or C$_1$-C$_{18}$alkoxy; C$_1$-C$_{18}$alkyl, which is optionally interrupted by —O—; or R'$_{14}$ and R'$_{15}$ together form a five or six membered ring, R'$_{16}$ is hydrogen; C$_6$-C$_{18}$aryl which is optionally substituted by C$_1$-C$_{18}$alkyl or C$_1$-C$_{18}$alkoxy; C$_1$-C$_{18}$alkyl which is optionally interrupted by —O—;

R'$_{17}$ is H; C$_6$-C$_{18}$aryl which is optionally substituted by C$_1$-C$_{18}$alkyl or C$_1$-C$_{18}$alkoxy; or C$_1$-C$_{18}$alkyl which is optionally interrupted by —O—;

R'$_{18}$ is hydrogen; C$_6$-C$_{18}$aryl, which is optionally substituted by C$_1$-C$_{18}$alkyl or C$_1$-C$_{18}$alkoxy; C$_1$-C$_{18}$alkyl, which is optionally interrupted by —O—;

R'$_{19}$ and R'$_{20}$ independently of each other are hydrogen; C$_1$-C$_{18}$alkyl; C$_6$-C$_{18}$aryl which is optionally substituted by C$_1$-C$_{18}$alkyl; and R'$_{21}$ is C$_1$-C$_{18}$alkyl; or C$_6$-C$_{18}$aryl, which is substituted by C$_1$-C$_{18}$alkyl; wherein the compound contains at least one group selected from sulphate, phosphate, and phosphonate.

Most preferred are also compounds of formula

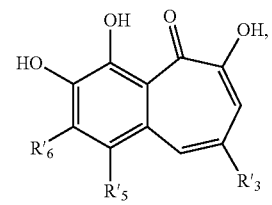

(2')

wherein

R'$_3$ is hydroxy; *—(CO)—O—R'$_{15}$; —(CO)—NH—(CH$_2$)$_{n1}$—(PO)—(OR'$_{16}$)$_2$; or —(SO$_2$)—OR'$_{17}$ R'$_5$ is —(CH$_2$)$_{n2}$—[O—(SO)$_2$]$_{n3}$—OR'$_{18}$;

R'$_6$ is C$_1$-C$_{18}$alkyl, C$_1$-C$_{18}$alkoxy or C$_1$-C$_{18}$hydroxyalkyl, which may be interrupted by one or more than one C$_2$-C$_4$alkenylene; —O—(CH$_2$)$_{n4}$(CO)$_{n5}$—R'$_{19}$; —(O)$_{n6}$—(CH$_2$)$_{n7}$—(PO)—(OR'$_{20}$)$_2$; —(O)$_{n6}$—(CH$_2$)$_{n7}$—(SO$_2$)—OR'$_{20}$; or a radical of formula

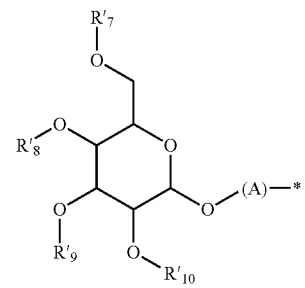

(1a)

R'$_7$, R'$_8$, and R'$_{10}$ independently from each other are hydrogen; —CO—C$_1$-C$_{20}$alkyl; —COOH; —COO—C$_1$-C$_6$alkyl;

R'$_9$ is hydrogen; —CO—C$_1$-C$_{20}$alkyl; —COOH; —COO—C$_1$-C$_6$alkyl; or a radical of formula

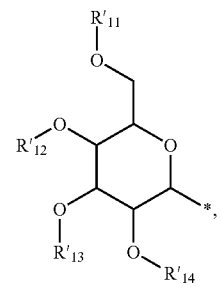

(1'b)

wherein

R'$_{11}$, R'$_{12}$, R'$_{13}$ and R'$_{14}$ independently from each other are hydrogen; or —CO—C$_1$-C$_{20}$alkyl;

A is *—(CH$_2$)$_{n6}$—(O)$_{n7}$—**;

R'$_{15}$, R'$_{16}$, R'$_{17}$, R'$_{18}$, R'$_{19}$ and R'$_{20}$ independently form each other are hydrogen; or C$_1$-C$_5$alkyl;

n$_1$, n$_2$, n$_4$ and n$_6$ independently form each other are a number from 1 to 5; and n$_3$, n$_5$ and n$_7$ independently form each other are 0; or 1.

Very preferred are also compounds of formula

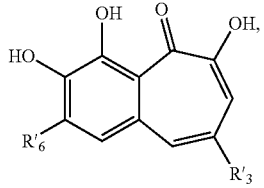
(3′)

wherein

R′$_3$ is *—(CO)O—R′$_{15}$, or *—(CO)—NH—R′$_{15}$;

R′$_6$ is C$_1$-C$_{30}$alkyl, which may be substituted by one or more E and/or interrupted by one or more D;

R′$_{15}$ is C$_3$-C$_{30}$alkyl, which may be substituted by one or more E and/or interrupted by one or more D; and D and E are defined as in formula (1′).

The benzotropolones according to the present invention are isolated from natural sources like from a plant extract and/or those synthesized by chemical oxidation of specific precursor compounds such as pyrogallol derivatives and 1,2-dihydroxy-benzene derivatives.

Another embodiment of the instant invention relates to a process for preparing the compounds of general formula (1) described hereinbefore, wherein said process comprises the step of reacting a compound of general formula (1a) with a compound of general formula (1b):

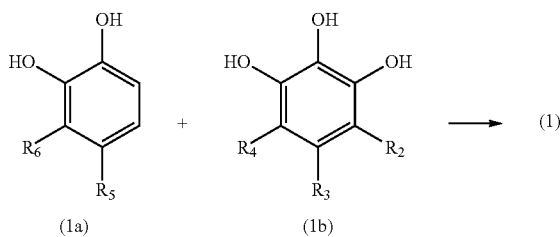

The conversion can be mediated by a variety of oxidising agents. The oxidising agent can also be molecular oxygen.

Preferably said reacting step is catalyzed for example by a catecholase. Examples are laccase-catalyzed or tyrosinase-catalyzed transformations, or peroxidase-catalyzed oxidations in the presence of hydrogen peroxide of (1a) to (1c) followed by subsequent reaction with (1b).

1,2,3-trihydroxybenzene derivatives with substituents in the 4-, 5- and/or 6-position can be transformed to benzotropolone derivatives of formula (1) by the reaction with o-benzoquinones of general formula (1c) as described in DE 1 091 114.

The conversion of compounds of the general formula (1b) to benzotropolones of formula (1) can also be achieved by the oxidative coupling of in-situ generated o-benzoquinones.

In the following reaction scheme the conversion of the compound of general formula (1a) with a compound of general formula (1b) via the formation of intermediate and unstable o-benzoquinone of general formula (1c) is illustrated. The o-benzoquinone is generated from the 1,2-dihydroxybenzene of formula (1a).

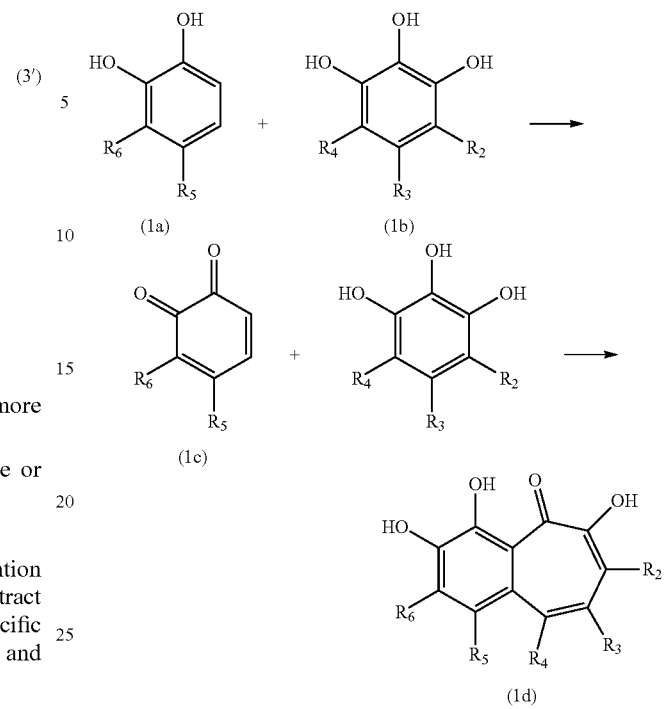

The enzymatic transformation is preferably carried out in an aqueous buffer system or a mixture with organic solvents or in sole organic solvents.

The reaction temperature is between −20 and 100° C., more preferably between 0 and 40° C. and most preferably between 10 and 30° C.

Suitable enzymes which can be used according to the present invention are any polyphenoloxidases which are selected from the group of laccases E.C.[1.10.3.2], catecholoxidases E.C. [1.10.3.1], tyrosinases E.C.[1.14.18.1] and combinations thereof.

Preferably laccases and/or tyrosinases are used. Even more preferably laccases are used.

Most preferably laccases from *Trametes versicolor* are applied.

Another preferred embodiment encompasses the application of the above mentioned polyphenoloxidases in form of cross-linked enzyme crystals (CLEC), preferably of laccase.

The enzymatic formation can be promoted by using an additional oxidant like hydrogen peroxide or N-oxides like 2,2,6,6-tetramethyl-4-hydroxy-1-piperidinyloxy (CAS No. 2226-96-2) or TEMPO (CAS No. 2564-83-2).

A further class of enzymes which are able to perform the desired reaction are peroxidases [E.C. 1.11.1.7]. They use hydrogen peroxide instead of molecular oxygen as oxidant.

Besides molecular oxygen also inorganic or organic oxidants can be used for the said oxidative coupling reaction. Typical inorganic oxidants are such as K$_3$[Fe(CN)$_6$], periodates such as potassium periodate, permanganates such as potassium permanganate, oxides like silver oxide or lead oxide, hydrogen peroxide. The synthesis of benzotropolone derivatives by using inorganic oxidants is for example described by L. Horner et al. (Monatshefte für Chemie, 1967, 98 (3), pages 852-73 and Zeitschrift für Naturforschung, 1959, 14b, pages 741-746) or by A. Critchlow et al. (Journal of the Chemical Society, 1951, pages 1318-25).

However, these methods suffer from the production of noxious heavy metal waste. In addition, trace amounts of heavy metal impurities can hardly be removed from the final compounds, which is highly undesirable for the intended use.

This method can be applied to a variety of different catechol structures of formula (1a) and different trihydroxybenzene structures of formula (1b) leading to the corresponding phenols of formula (1).

The compounds of general formula (1d) can be further converted to the benzotropolone of general formula (1) by any synthetic means which transfer unsubstituted into substituted hydroxyl groups. Such methods and techniques are well known to any person skilled in the art.

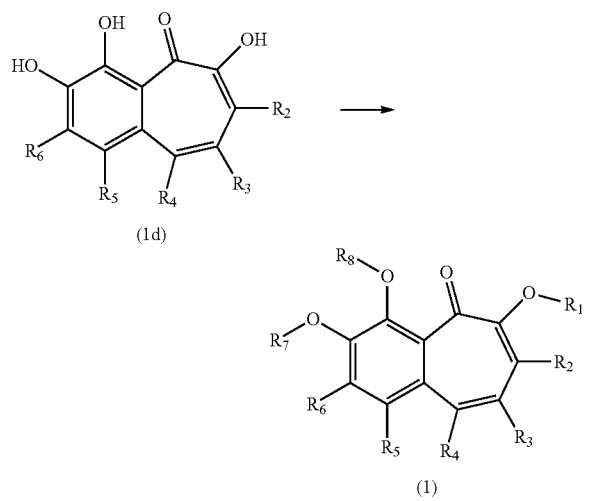

The benzotropolones according to the present invention are preferably used in cosmetic or pharmaceutical preparations.

The cosmetic or pharmaceutical preparations can be prepared by physically mixing the benzotropolones of formula (1) with the adjuvant using customary methods, for example by simply stirring together the individual components, especially by making use of the dissolution properties of already known cosmetic UV absorbers, for example octyl methoxycinnamate, salicylic acid isooctyl ester etc.

Cosmetic or pharmaceutical preparations contain from 0.001% to 20% by weight, preferably from 0.01 to 3% by weight, based on the total weight of the composition, of at least one benzotropolone of formula (1).

Preference is given to the use of mixing ratios of the benzotropolones of formula (1) according to the present invention and optional further light-protective agents (as described in Tables 2-4) and/or further antioxidants as described below of from 1:99 to 99:1, especially from 1:95 to 95:1 and preferably from 10:90 to 90:10, based on weight. Of special interest are mixing ratios of from 20:80 to 80:20, especially from 40:60 to 60:40 and preferably approximately 50:50. Such mixtures can be used, inter alia, to improve solubility or increase UV absorption.

In order to optimize the anti-oxidizing effect, the topical application could contain at least one further hydrophilic or lipophilic antioxidant within the concentration range from 0.001% to 10% of the total weight of the cosmetic preparation. Those additional antioxidants are preferably selected from the group containing:
  tocopherol ($\alpha$, $\beta$, $\gamma$, $\delta$ isomers, in particular vitamin E) and its derivatives (in particular vitamin E derivatives such as vitamin E acetate, vitamin E linoleate, vitamin E nicotinate and vitamin E succinate)
  tocotrienol ($\alpha$, $\beta$, $\gamma$, $\delta$ isomers), containing one unsaturated fatty chain, and its esters of acids
  ascorbic acid and its esters of acids such as phosphoric acid and also sodium, potassium, lithium and magnesium salts, Ascorbyl Tetraisopalmitate, further ester with pyrrolidoncarboxylic acid and esters of acids with general formulas,
  (3) $H(CH_2)_n(CHR)COOH$ and (4) $CH_3(CH_2)_mCH=CH(CH_2)_nCOOH$, wherein R is hydrogen atom or OH group, m, n are integral numbers from 0 to 20 where m+n sum is maximally 21.
Retinoids include all natural and/or synthetic analogs of vitamin A or retinal-like compounds which possess the biological activity of vitamin A in the skin as well as the geometric isomers and stereoisomers of these compounds. Preferred compounds are retinol, retinol esters (e.g., $C_2$-$C_{22}$ alkyl esters (saturated or unsaturated alkyl chains) of retinal, including retinyl palmitate, retinyl acetate, retinyl propionate), retinal, and/or retinoic acid (including all trans retinoic acid and/or 13-cis-retinoic acid) or derivatives. Other retinoids which are useful herein are described in U.S. Pat. No. 4,677,120, issued Jun. 30, 1987 to Parish et al; U.S. Pat. No. 4,885,311, issued Dec. 5, 1989 to Parish et al; U.S. Pat. No. 5,049,584, issued Sep. 17, 1991 to Purcell et al., U.S. Pat. No. 5,124,356, issued Jun. 23, 1992 to Purcell et al. Other suitable retinoids are tocopheryl-retinoate [tocopherol ester of retinoic acid (trans or cis)], adapalene [6-(3-(1-adamantyl)-4-methoxyphenyl)-2-naphtoic acid] and tazarotene (ethyl 6-[2-(4,4-dimethylthiochroman-6-yl)-ethynyl]nicotinate)
carotenoids such as $\alpha$-, $\beta$-, $\gamma$-, and $\delta$-carotene, lutein, xanthophylls, zeaxanthine, violaxanthine, cryptoxanthine, fukoxanthine, antheraxanthine, lycopene, didehydrolycopene and tetradehydrolycopene carotenoids
enzymatic antioxidants such as Glutathione peroxidase, Catalase, Superoxide dismutase.
Ubiquinone and Idebenone (hydroxydecyl Ubiquinone), as well as ubiquinol and its derivatives
Lipoic acid and its derivatives such as alpha-lipoic acid . . . .
Rutinic acid and its derivatives such as $\alpha$-glucosylrutin, a water soluble flavonoid, rutin hydrate (vitamin P)
Botanical extracts such as white and green tea extracts, black tea extracts, chicory leaf extract (*Cichorium intubybus*), Passionflower extract (*Passiflora incarnata*), *Aspalathus linearis* extract, rosmary extract, red leaf extract of Aceraceae Maple tree or of Rosaceae Cherry tree, *Curcuma longa* L (curcuminoids active ingredients), *Leontopodium alpinum* extract, *Emblica officinalis (phyllanthus emblica)* tree extract . . . .
Phenolic acids such as caffeic acid, 3,4-dihydroxyphenyl acetic acid, 3,4-dihydroxybenzoic acid.
Flavonoids and polyphenols such as flavanones selected from the group consisting of unsubstituted flavanones, mono-substituted flavanones and mixtures thereof; chalcones selected from the group consisting of unsubstituted Chalcones, mono-substituted chalcones, di-substituted chalcones, tri-substituted chalcones, and mixtures thereof; flavones selected from the group consisting of unsubstituted flavones, mono-substituted flavones, di-substituted flavones, and mixtures thereof; one or more isoflavones; coumarins selected from the group consisting of unsubstituted coumarins, mono-substituted coumarins, di-substituted coumarins, and mixtures thereof; flavonols, anthocyanins, catechins such as green tea catechins like (−)-epigallocatechin-3-gallate, (−)-epicatechin, (−)-epigallocatechin and mixtures thereof, theaflavin, proanthocyanidins (Grape seed extract). Flavonoids which are broadly disclosed in U.S. Pat. Nos. 5,686,082 and 5,686,367 can also be used.

chlorogenic acid and ferulic acid and their derivatives.

Tropolone derivatives such as tropolone (CAS No. 533-75-5) itself, hinokitiol, nootkatin, stipitatic acid, puberulic acid, stipitatonic acid, puberulonic acid, gamma-thujaplicin, beta-thujaplicin, colchiceine or tropolone derivatives as described in patent application WO 2008/003529 A1 and mixtures thereof.

It is also possible to use a third kind of antioxidants that interrupt the photochemical reaction chain triggered when UV radiation penetrates the skin or hair. Typical examples of such antioxidants are amino acids and their derivatives (e.g. glycine, histidine, acetyl histidine, tyrosine, caproyl tyrosine, tryptophan), imidazoles (e.g. urocanic acid) and derivatives thereof, peptides, such as D,L-carnosine, D-carnosine, L-carnosine and derivatives thereof (e.g. anserine), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine).

But also (metal) chelating agents (in particular α-hydroxy fatty acids, palmitic acid, phytin acid, lactoferrin) and preferably those disclosed in U.S. Pat. No. 5,487,884, issued Jan. 30, 1996 to Bisset et al; International publications No. 91/16035 & No. 91/16034 from Bush et al., published Oct. 31, 1995. Hydroxy acids (e.g. citric acid, lactic acid, malic acid, hydroxyl succinic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, coniferyl benzoate of benzoin resin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, N-[3-(3,5-di-tert-butyl-4-hydroxyphenyl)propionyl]-sulfanilic acid (and salts thereof, for example the disodium salts), zinc and derivatives thereof (e.g. ZnO, $ZnSO_4$), selenium and derivatives thereof (e.g. seleno methionine), stilbene and derivatives thereof (in particular hydroxystilbenes, resveratrol and pinosylvin) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned.

Further synthetic and natural antioxidants are listed e.g. in patent WO 0025731: Structures 1-3 (page 2), structure 4 (page 6), structures 5-6 (page 7) and compounds 7-33 (page 8-14).

The topical application can additionally contain at least one component with anti-inflammatory effect, preferably from 0.1% to 10% more preferably about 0.5% to about 5%, of the composition, from following groups:

Steroidal anti-inflammatory agents, including but not limited to, corticosteroids such as hydrocortisone and their derivatives . . . .

Non-steroidal anti-inflammatory agents, including but not limited to, oxicams, salicylates, acetic acid derivatives, fenamates, propionic acid derivatives, pyrazoles . . . .

Natural anti-inflammatory agents including but not limited to:
  α-bisabolol, allantoin, lyophilized extract of aloe vera, panthenol, betulin, compounds of the Licorice (*Glycyrrhiza glabra*) including glycyrrhetic acid, glycyrrhizic acid, and derivatives thereof (salts and esters) such as sodium glycyrrhizinate, potassium glycyrrhizinate, ammonium glycyrrhizinate
  botulinic acid, alkaline salts thereof and salts of alkaline-earth metals, boswellic acid, alkaline salts thereof and salts of alkaline-earth metals, rosemaric acid, alkaline salts thereof and salts of alkaline-earth metals
  poly-no saturated fatty acids, as linoleic (18:2n6), α-linolenic (18:3n3), γ-linolenic (18:3n6), octadecanetetraenic (18:4n3), dihomo-γ-linolenic (20:3n6), eicosantetraenic (20:4n3), arachidonic (20:4n6), eicosanpentaenic (20:5n3) acids and esters thereof with alcohols of the general formula (5) $R_1$ $(CH_2)_m$—(CHOH)—$(CH2)_nR_2$, wherein $R_1$ and $R_2$ are hydrogen atoms or OH group, m, n are integral numbers from 0 to 17 where m+n sum is maximally 21.
  phytosterols and their polyethoxylate derivatives of the general formulas (6) and (7) below, where R is isoalkyl or isoalkenyl group with 8-10 carbon atoms, where n is integral number from 0 to 50, especially campesterol, β-sitosterol, stigmasterol, cholesterol, Δ-5-avenasterol, Δ-7-avenasterol, brassicasterol, spinasterol and
  fukosterol

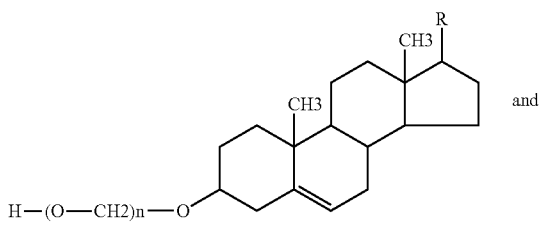

(6)

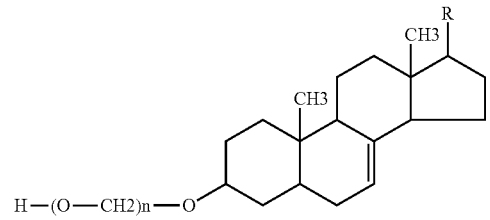

(7)

The cosmetic or pharmaceutical preparations according to the present invention may contain additional antioxidants.

Examples of suitable antioxidants include but are not limited to p-hydroxybenzoic acid and its derivatives (ethylisobutyl, glyceryl esters of p-hydroxybenzoic acid), salicylates (octylamyl, phenyl, benzyl menthyl, glycerol and dipropyleneglycol esters), benzylidene malonates, phenylmethyl propanoic acid derivatives like [(4-hydroxy-3,5- dimethoxyphenyl)methyl]-propanedioic acid, bis(2-ethylhexyl) ester (CAS No. 872182-46-2), hydroxyl or methoxy substituted benzophenones, uric or tannic acid and its derivatives.

Further additional antioxidants which can be used in the cosmetic compositions according to the present invention are chosen from the group consisting of acetylcysteine, 3-tert-butyl-4-hydroxyanisole, 2,6-di-tert-butyl-p-cresol, caffeic acid, chlorogenic acid, decylmercaptomethylimidazole, diacetyl thiodipropionate, digalloyl trioleate, dilauryl thiodipropionate, dimyristyl thiodipropionate, dioleyl tocopheryl methylsilanol, disodium rutinyl disulphate, distearyl thiodipropionate, ditridecyl thiodipropionate, dodecyl gallate, erythorbic acid, ethyl ferulate, hydroquinone and alkylated hydroquinones (e.g. tert-butylhydroquinone, diamylhydroquinone, di-tert-butylhydroquinone), p-hydroxyanisole, hydroxylamine hydrochloride, hydroxylamine sulphate, isooctyl thioglycolate, kojic acid, madecassicoside, methoxy-PEG-7-rutinyl succinate, octyl gallate, phenylthioglycolic acid, phloroglucinol, propyl gallate, rosmarinic acid and its derivatives, rutin, sodium erythorbate, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocophersolan, o-tolylbiguanide, tris(nonylphenyl) phosphite, dexpanthenol, alpha-hydroxycarboxylic acids (in particular glycolic acid, lactic acid, mandelic acid) and salts thereof, di-methyloldimethylhydantoin, N-acylamino acids and salts thereof (in particular N-octanoylglycine) and hinokitol, and mixtures thereof for the long-term stabilization of a glycerol monoalkyl ether of the general formula R—O—CH$_2$—CHOH—CH$_2$—OH, in which R is a branched or unbranched $C_3$-$C_{18}$alkyl group, where the alkyl group can be substituted by one or more hydroxyl and/or $C_1$-$C_4$alkoxy group(s) and/or the alkyl chain can be interrupted by up to four oxygen atoms.

Further additional antioxidants which can be used in the cosmetic compositions according to the present invention are chosen from the group consisting of as well as alanine diacetic acid, quercetin, morin, 3,4-dihydroxybenzoic acid, thymol, carvacrol, catechins, as well as derivatives of gum benzoin resin, rutin and its derivatives, and benzylphosphonates such as, for example, dimethyl 2,5-di-tert-butyl-4-hydroxybenzylphosphonate, diethyl 3,5-di-tert-butyl-4-hydroxybenzylphosphonate and the calcium salt of monoethyl 3,5-di-tert-butyl-4-hydroxybenzylphosphonate.

Further additional antioxidants which can be used in the cosmetic compositions according to the present invention correspond to compounds of formula

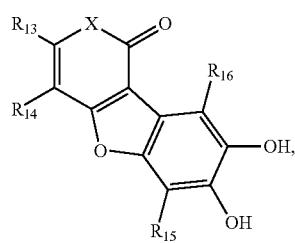

(I)

wherein

X is O, NH or $NR_{27}$, $R_{13}$, $R_{14}$, $R_{15}$ and $R_{16}$ are independently of each other H; halogen; hydroxy; $C_1$-$C_{24}$alkyl; $C_1$-$C_{24}$alkyl which is substituted by at least one E and/or interrupted by at least one D; $C_1$-$C_{24}$perfluoroalkyl; $C_6$-$C_{14}$ perfluoroaryl; $C_5$-$C_{12}$cycloalkyl; $C_5$-$C_{12}$cycloalkyl which is substituted by G and/or interrupted by S—, —O—, or —$NR_{27}$—; —$NR_{27}R_{28}$; $C_1$-$C_{24}$alkylthio; —$PR_{29}R_{30}$; $C_5$-$C_{12}$cycloalkoxy; $C_5$-$C_{12}$cycloalkoxy which is substituted by G; $C_6$-$C_{24}$aryl; $C_6$-$C_{24}$aryl which is substituted by G, $C_1$-$C_{24}$alkyl, $C_5$-$C_{12}$cycloalkyl, $C_7$-$C_{25}$aralkyl, $C_{24}$ perfluoroalkyl, $C_6$-$C_{14}$ perfluoroaryl or $C_1$-$C_{24}$haloalkyl; $C_4$-$C_{20}$heteroaryl; $C_4$-$C_{20}$heteroaryl which is substituted by G, fluorine, $C_1$-$C_{24}$alkyl, $C_5$-$C_{12}$cycloalkyl, $C_7$-$C_{25}$aralkyl, $C_1$-$C_{24}$ perfluoroalkyl, $C_6$-$C_{14}$ perfluoroaryl or $C_1$-$C_{24}$haloalkyl; $C_2$-$C_{24}$alkenyl; $C_2$-$C_{24}$alkynyl; $C_1$-$C_{24}$alkoxy; $C_1$-$C_{24}$alkoxy which is substituted by at least one E and/or interrupted by at least one D; $C_7$-$C_{25}$aralkyl; $C_7$-$C_{25}$aralkyl, which is substituted by G; $C_7$-$C_{25}$aralkoxy; $C_7$-$C_{25}$aralkoxy which is substituted by G, or —CO—$R_{31}$; or $R_{13}$ and $R_{14}$ are a group

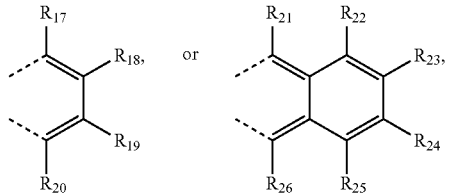

wherein $R_{17}$, $R_{18}$, $R_{19}$, $R_{20}$, $R_{21}$, $R_{22}$, $R_{23}$, $R_{24}$, $R_{25}$ and $R_{26}$ independently of each other are H; halogen; hydroxy; $C_1$-$C_{24}$alkyl; $C_1$-$C_{24}$alkyl which is substituted by at least one E and/or interrupted by at least one D; $C_1$-$C_{24}$ perfluoroalkyl; $C_6$-$C_{14}$ perfluoroaryl; $C_5$-$C_{12}$cycloalkyl; $C_5$-$C_{12}$cycloalkyl which is substituted by at least one G and/or interrupted by at least one S—, —O—, or —$NR_{27}$—; $C_5$-$C_{12}$cycloalkoxy; $C_5$-$C_{12}$cycloalkoxy which is substituted by G; $C_6$-$C_{24}$aryl; $C_6$-$C_{24}$aryl which is substituted by at least one G; $C_2$-$C_{20}$heteroaryl; $C_2$-$C_{20}$heteroaryl which is substituted by at least one G; $C_2$-$C_{24}$alkenyl; $C_2$-$C_{24}$alkynyl; $C_1$-$C_{24}$alkoxy; $C_1$-$C_{24}$alkoxy which is substituted by at least one E and/or interrupted by at least one D; $C_7$-$C_{25}$aralkyl; $C_7$-$C_{25}$aralkyl, which is substituted by at least one G; $C_7$-$C_{25}$aralkoxy; $C_7$-$C_{25}$aralkoxy which is substituted by at least one G, or at least —CO—$R_{31}$;

D is —CO—; —COO—; —S—; —SO—; —$SO_2$—; —O—; —$NR_{27}$—; —$POR_{29}$—; —$CR_{32}$=$CR_{33}$—; or —C≡C—;

E is —$OR_{34}$; —$SR_{34}$; —$NR_{27}R_{28}$; —[$NR_{27}R_{28}R_{36}$]$^+$$Z^-$; —$COR_{31}$; —$COOR_{35}$; —$CONR_{27}R_{28}$; —CN; —$N_3$; —$OCOOR_{35}$; or halogen;

G is E; or $C_1$-$C_{24}$alkyl;

$R_{32}$, $R_{33}$, $R_{27}$, $R_{28}$ and $R_{36}$ independently of each other are H; $C_6$-$C_{18}$aryl; $C_6$-$C_{18}$aryl which is substituted by $C_1$-$C_{24}$alkyl; or $C_1$-$C_{24}$alkoxy; $C_1$-$C_{24}$alkyl; or $C_1$-$C_{24}$alkyl which is interrupted by at least one —O—;

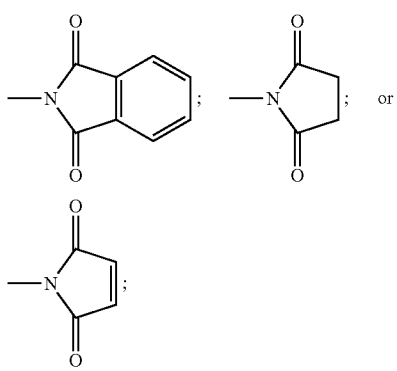

or

R$_{27}$ and R$_{28}$ together form a five or six membered ring, in particular

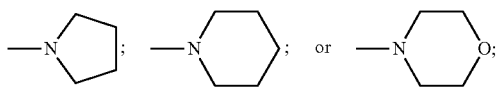

Z is halogen;

R$_{31}$ and R$_{25}$ independently of each other are H; C$_6$-C$_{18}$aryl; C$_6$-C$_{18}$aryl which is substituted by C$_1$-C$_{24}$alkyl, or C$_1$-C$_{24}$alkoxy; C$_1$-C$_{24}$alkyl; or C$_1$-C$_{24}$alkyl which is interrupted by at least one —O—;

R$_{34}$ is hydrogen; C$_6$-C$_{18}$aryl; C$_6$-C$_{18}$aryl, which is substituted by C$_1$-C$_{24}$alkyl or C$_1$-C$_{24}$alkoxy; C$_1$-C$_{24}$alkyl; or C$_1$-C$_{24}$alkyl which is interrupted by at least one —O—; and R$_{29}$ and R$_{30}$ independently of each other are C$_1$-C$_{24}$alkyl; C$_6$-C$_{18}$aryl; or C$_6$-C$_{18}$aryl, which is substituted by C$_1$-C$_{24}$alkyl;

R$_{15}$ and R$_{16}$ may further be a mono-, di- or oligosaccharide residue alpha- or beta-linked to the phenolic ring system either directly or via the phenolic oxygen.

Beside the compounds of formula (1) the cosmetic compositions according to the present invention may also contain phenolic or lactone-type antioxidants as disclosed for example in WO00/25731 and/or hindered amine light stabilizers as disclosed in WO 03/103622, e.g. hindered nitroxyl, hydroxylamine and hydroxylamine salt compounds.

Further components additionally useful in the present compositions are listed further below, and in the publications referred to.

Examples of organic UV filters that can be used in admixture with the compounds of formula (1) are listed in the Tables 2-4:

TABLE 2

Suitable UV filter substances which can be additionally used with the compounds of formula (1)

p-aminobenzoic acid derivatives, for example 4-dimethylaminobenzoic acid 2-ethylhexyl ester;
salicylic acid derivatives, for example salicylic acid 2-ethylhexyl ester;
benzophenone derivatives, for example 2-hydroxy-4-methoxybenzophenone and its 5-sulfonic acid derivative;
diphenylacrylates, for example 2-ethylhexyl 2-cyano-3,3-diphenylacrylate, and 3-(benzofuranyl) 2-cyanoacrylate;
3-imidazol-4-ylacrylic acid and esters;
benzofuran derivatives, especially 2-(p-aminophenyl)benzofuran derivatives, described in EP-A-582 189, U.S. Pat. No. 5,338,539, U.S. Pat. No. 5,518,713 and EP-A-613 893;
polymeric UV absorbers, for example the benzylidene malonate derivatives described in EP-A-709 080;
camphor derivatives, for example 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylenedimethine)-bis(7,7-dimethyl-2-oxo-bicyclo[2.2.1]heptane-1-methanesulfonic acid) and salts, 3-(4'-sulfo)benzylidene-bornan-2-one and salts; Camphor Benzalkonium methosulfate;
hydroxyphenyltriazine compounds, for example 2-(4'-methoxyphenyl)-4,6-bis(2'-hydroxy-4'-n-octyloxyphenyl)-1,3,5-triazine; 2,4-bis{[4-(3-(2-propyloxy)-2-hydroxy-propyloxy)-2-hydroxy]-phenyl}-6-(4-methoxyphenyl)-1,3,5-triazine; 2,4-bis{[4-(2-ethyl-hexyloxy)-2-hydroxy]-phenyl}-6-[4-(2-methoxyethyl-carboxyl)-phenylamino]-1,3,5-triazine; 2,4-bis{[4-(tris-(trimethylsilyloxy-silylpropyloxy)-2-hydroxy]-phenyl}-6-(4-methoxyphenyl)-1,3,5-triazine; 2,4-bis{[4-(2''-methylpropenyloxy)-2-hydroxy]-phenyl}-6-(4-methoxyphenyl)-1,3,5-triazine; 2,4-bis{[4-(1',1',1',3',5',5',5'-heptamethyltrisilyl-2''-methyl-propyloxy)-2-hydroxy]-phenyl}-6-(4-methoxyphenyl)-1,3,5-triazine; 2,4-bis{[4-(3-(2-propyloxy)-2-hydroxy-propyloxy)-2-hydroxy]-phenyl}-6-[4-ethylcarboxy)-phenylamino]-1,3,5-triazine;
benzotriazole compounds, for example 2,2'-methylene-bis(6-(2H-benzotriazol-2-yl)-4-(1,1,3,3-tetramethylbutyl)-phenol;
trianilino-s-triazine derivatives, for example 2,4,6-trianiline-(p-carbo-2'-ethyl-1'-oxy)-1,3,5-triazine and the UV absorbers disclosed in U.S. Pat. No. 5,332,568, EP-A-517 104, EP-A-507 691, WO 93/17002 and EP-A-570 838;
2-phenylbenzimidazole-5-sulfonic acid and salts thereof;
menthyl o-aminobenzoates;
physical sunscreens coated or not as titanium dioxide, zinc oxide, iron oxides, mica, MnO, Fe$_2$O$_3$, Ce$_2$O$_3$, Al$_2$O$_3$, ZrO$_2$. (surface coatings: polymethylmethacrylate, methicone (methylhydrogenpolysiloxane as described in CAS 9004-73-3), dimethicone, isopropyl titanium triisostearate (as described in CAS 61417-49-0), metal soaps as magnesium stearate (as described in CAS 4086-70-8), perfluoroalcohol phosphate as C9-15 fluoroalcohol phosphate (as described in CAS 74499-44-8; JP 5-86984, JP 4-330007)).
The primary particle size is an average of 15 nm-35 nm and the particle size in dispersion is in the range of 100 nm-300 nm.

TABLE 2-continued

Suitable UV filter substances which can be additionally used with the compounds of formula (1)

aminohydroxy-benzophenone derivatives disclosed in DE 10011317, EP 1133980 and EP 1046391
phenyl-benzimidazole derivatives as disclosed in EP 1167358
the UV absorbers described in "Sunscreens", Eds. N. J. Lowe, N. A. Shaath, Marcel Dekker, Inc., New York and Basle or in Cosmetics & Toiletries (107), 50ff (1992) also can be used as additional UV protective substances.

TABLE 3

Suitable UV filter substances which can be additionally used with the UV absorbers according to the present invention

| | |
|---|---|
| DE 10013318 | T 1 pp 8-9, all Examples pp 10-13, T 2 pp 13-14, all Examples p 14, Ex A, B, C, D, E, F pp 19-20 |
| DE102004038485A1 | Formula 1 on p 2; Ex 1-4 on p 13; |
| DE102004039281A1 | Formulas I-II on p 1; Ex Ia-Iae on pp 7-12; Ex IIa-IIm on pp 14-15; Ex 1-25 on pp 42-56; |
| DE 10206562 A1 | Ex 1-3 p 10, Ex 4-7 p 11, Ex 8-15 pp 12-14 |
| DE 10238144 A1 | Ex on p 3-5; |
| DE 10331804 | T 1 p 4, T 2 + 3 p 5 |
| DE 19704990 A1 | Ex 1-2 on pp 6-7; |
| EP 613 893 | Ex 1-5 + 15, T 1, pp 6-8 |
| EP 0 998 900 A1 | Ex on pp 4-11 |
| EP 1 000 950 | Comp. In Table 1, pp 18-21 |
| EP 1 005 855 | T 3, p 13 |
| EP 1 008 586 | Ex 1-3, pp 13-15 |
| EP 1 008 593 | Ex 1-8, pp 4-5 |
| EP 1 027 883 | Compound VII, p 3 |
| EP 1 027 883 | Comp I-VI, p 3 |
| EP 1 028 120 | Ex 1-5, pp 5-13 |
| EP 1 059 082 | Ex 1; T 1, pp 9-11 |
| EP 1 060 734 | T 1-3, pp 11-14 |
| EP 1 064 922 | Compounds 1-34, pp 6-14 |
| EP 1 077 246 A2 | Ex 1-16 on pp 5-11; |
| EP 1 081 140 | Ex 1-9, pp 11-16 |
| EP 1 103 549 | Compounds 1-76, pp 39-51 |
| EP 1 108 712 | 4,5-Dimorpholino-3-hydroxypyridazine |
| EP 1 123 934 | T 3, p 10 |
| EP 1 129 695 | Ex 1-7, pp 13-14 |
| EP 1 167 359 | Ex 1, p 11 and Ex 2, p 12 |
| EP 1 232 148 B1 | Ex 4-17 on pp 3-5; |
| EP 1 258 481 | Ex 1, pp 7, 8 |
| EP 1 310 492 A1 | Ex 1-16 on pp 22-30 |
| EP 1 371 654 A1 | Ex on pp 5-7 |
| EP 1 380 583 A2 | Ex 1, p 6; |
| EP 1 423 351 A2 | Ex 1-16 on pp 31-37; |
| EP 1 423 371 A1 | T 1 on pp 4-8, Ex on p 9, Ex 1-9 on pp 36-42; |
| EP 1 454 896 A1 | Ex 1-5 on pp 10-13, Examples on pp 4-5; |
| EP 1 471 059 A1 | Ex 1-5 on pp 4-5; |
| EP 1 484051 A2 | Formula III-VII on pp18-19, Ex 7-14 on pp 7-9, Ex 18-23 on pp 11-12, Ex 24-40 on pp 14-17; |
| EP 1648849 A2 | Formula 1 on p 4; Ex 1-2 on pp 13-17; Ex C10 and O10 on pp15-16; |
| EP 420 707 B1 | Ex 3, p 13 (CAS Reg. No 80142-49-0) |
| EP 503 338 | T 1, pp 9-10 |
| EP 517 103 | Ex 3, 4, 9, 10 pp 6-7 |
| EP 517 104 | Ex 1, T 1, pp 4-5; Ex 8, T 2, pp 6-8 |
| EP 626 950 | all compounds |
| EP 669 323 | Ex 1-3, p 5 |
| EP 743 309 A1 | Ex 1-12 on pp 18-24; |
| EP 780 382 | Ex 1-11, pp 5-7 |
| EP 823 418 | Ex 1-4, pp 7-8 |
| EP 826 361 | T 1, pp 5-6 |
| EP 832 641 | Ex 5 + 6 p 7; T 2, p 8 |
| EP 832 642 | Ex 22, T 3, pp 10-15; T 4, p 16 |
| EP 848944 A2 | Formulas I and II on p 1; Ex on p 8; Examples on p 10; |
| EP 852 137 | T 2, pp 41-46 |
| EP 858 318 | T 1, p 6 |
| EP 863 145 | Ex 1-11, pp 12-18 |
| EP 878 469 A1 | T 1, pp 5-7; |
| EP 895 776 | Comp. In rows 48-58, p 3; R 25 + 33, p 5 |
| EP 911 020 | T 2, pp 11-12 |
| EP 916 335 | T 2-4, pp 19-41 |
| EP 924 246 | T 2, p 9 |
| EP 933 376 | Ex 1-15, pp 10-21 |

TABLE 3-continued

Suitable UV filter substances which can be additionally used with the UV absorbers according to the present invention

| | |
|---|---|
| EP 944 624 | Ex 1 + 2, pp 13-15 |
| EP 945 125 | T 3 a + b, pp 14-15 |
| EP 95 097 | Ex 1, p 4 |
| EP 967 200 | Ex 2; T 3-5, pp 17-20 |
| EP 969 004 | Ex 5, T 1, pp 6-8 |
| FR 2842806 A1 | Ex I p 10, Ex II p 12 |
| FR 2861075 A1 | Ex 1-3 on pp 12-14; |
| FR 2862641 | Formula 3 on p4; Ex A-J on pp 7-9; |
| FR 2869907 A1 | Formula 1 on p 6; T 1 on p 7-8; Ex 4-39 on pp 12-35; |
| KR 2004025954 | all kojyl benzoate derivatives |
| JP 06135985 A2 | Formula 1 on p 2; Ex 1-8 on pp 7-8; |
| JP 2000319629 | CAS Reg Nos. 80142-49-0, 137215-83-9, 307947-82-6 |
| JP 2003081910 A | Ex on p 1; |
| JP 2005289916 A | Formula I on p 1; Ex Ia-Id on pp 2-3; |
| JP 2005290240 A | Formulas I on p 2, Ex II on p 2; |
| US 2003/0053966A1 | Ex on pp 3-6 |
| US 2004057912 A1 | Ex on p 7-9, Ex 1 on p 10; |
| US 2004057914 A1 | Ex on p 8-12, Ex 1 on p 12; |
| US 2004/0057911A1 | Formula I and II on p 1; formula III and IV on p3; Ex 1-3 on pp 5-6; |
| US 2004/0071640A1 | Ex 1-12 on pp 4-7; |
| US 2004/0091433A1 | Ex 1-6 on pp 14-16; |
| US 2004/0136931A1 | Ex 1-3 on p 7; |
| US 2004/0258636A1 | Ex 1-11 on pp 9-15; |
| US 2005/0019278A1 | Ex 1-9 on pp 6-8; |
| US 2005/0136012A1 | Formula 1 on p 2; |
| US 2005/0136014A1 | Formula a-c on p 2; Examples on p 3; |
| US 2005/0201957A1 | Formula 1 on p1; Ex A, B, C, D, E, F, G on pp 2-3; |
| US 2005/0249681A1 | all compounds on pp 2-3, Ex 1 on p 6; |
| US 2005186157A1 | Formula 1 on p 1; Ex 1-6 on pp 2-4; |
| US 2005260144A1 | Formula I on p1; Formula II on p 3; Ex 1-10 on pp 8-11; |
| US 2006018848A1 | Ex a-p on pp 3-4; |
| US 2006045859A1 | Formula 1 on p 1; Ex 1-10 on pp 2-4; |
| U.S. Pat. No. 5,635,343 | all compounds on pp 5-10 |
| U.S. Pat. No. 5,332,568 | Ex 1, p 5, T 1 + 2, pp 6-8 |
| U.S. Pat. No. 5,338,539 | Ex 1-9, pp 3 + 4 |
| U.S. Pat. No. 5,346,691 | Ex 40, p 7; T 5, p 8 |
| U.S. Pat. No. 5,801,244 | Ex 1-5, pp 6-7 |
| U.S. Pat. No. 6,613,340 | Ex I, II pp 9-11, Examples on rows 28-53 p 6 |
| U.S. Pat. No. 6,800,274 B2 | Formulas I-VI and IX-XII on pp 14-18; |
| U.S. Pat. No. 6,890,520 B2 | Ex 1-10 on pp 6-9; |
| U.S. Pat. No. 6,926,887 B2 | Ex A on pp5/6; Formulas I-VIII on pp 27-29; |
| U.S. Pat. No. 6,936,735 B2 | Formulas 1-2 on p 2; formula 3-4 on p 6; |
| U.S. Pat. No. 6,962,692 B2 | Formulas VII and VIII on p 6; Formulas I, II, IV-VI, IX, X on pp 14-16; Formula III on p 19; |
| WO 0149686 | Ex 1-5, pp 16-21 |
| WO 0168047 | Tables on pp 85-96 |
| WO 0181297 | Ex 1-3, pp 9-11 |
| WO 0191695 | Formula I on p 4, T on p 8 |
| WO 0202501 A1 | Ex Ia-c, p 5 |
| WO 02069926 A1 | Ex on p 9, Ex on pp 17-23 |
| WO 02072583 | T on pp 68-70 |
| WO 02080876 | Ex 1 on pp 7-9 |
| WO 0238537 | All compounds p 3, compounds on rows 1-10 p 4 |
| WO 03004557 A1 | Ex A1-A29 on pp 36-57; |
| WO 03007906 | Ex I-XXIII, pp 42-48 |
| WO 03086341 A2 | Formula 2-21, pp 4-6; |
| WO 03092643 A1 | T on pp 34-35, compounds listed on p 16 |
| WO 03097577 A1 | Ex on pp 6-8; Ex 1-3 on pp 15-18; |
| WO 03104183 A1 | Formula I-IV on p 1; Ex 1-5 on pp 27-28; |
| WO 04000256 A1 | Ex 1-10 on pp 18-24 |
| WO 04020398 A1 | Ex 1-3 on pp 14-17 |
| WO 04020398 A1 | Formulas I-VI on pp 21-24, Formula IX on p 25; |
| WO 04075871 | Ex 1-3 on pp 17-18; Ex 7-9 on pp 21-22; |
| WO 05009938 A2 | Formula I on p 1; Ex 1-2 on pp 14-15; |
| WO 05065154 A2 | Formula a-c on pp 5-6; |
| WO 05080341 A1 | Formula 1 on p 3; Examples on pp 9-13; |
| WO 05107692 A1 | Formula 1 on p 2; Ex 1-9 on pp 27-29; |
| WO 05118562 A1 | Formula I on p 4; Ex Ia-Ig on p 5; |
| WO 05121108 A1 | Formula I on p 3; Formula Ia on p 5; T 1 on p 7; Ex 3-22 on pp 11-23; |
| WO 06009451 | T 1 on pp 5-8; Formulas III and UV0 on p 9; |
| WO 06016806 | T 1 on pp 6-7; T 2 on p 10; T 3 on p 11; T 4 on p 15; |
| WO 06032741 | Formulas 1-3 on p 1; Ex a-k on pp 5-7; Ex 1-4 on pp 18-20; |
| WO 9217461 | Ex 1-22, pp 10-20 |

TABLE 3-continued

Suitable UV filter substances which can be additionally used with the UV absorbers according to the present invention

| | |
|---|---|
| WO 9220690 | Polymeric Comp in Examples 3-6 |
| WO 9301164 | T 1 + 2, pp 13-22 |
| WO 9714680 | Ex 1-3, p 10 |

(Abbreviations T: Table, R: row, Comp: compound, Ex: compound(s) of Patent Example, p: page; the generic scope of the UV absorbers is described in the left-hand column; specific compounds are indicated in the right-hand column)

TABLE 4

Suitable UV filter substances and adjuvants which can be additionally used with the compounds of formula (1)

| No. | Chemical Name | CAS No. |
|---|---|---|
| 1 | (+/−)-1,7,7-trimethyl-3-[(4-methylphenyl)methylene]bicyclo[2.2.1]-heptan-2-one; p-methyl benzylidene camphor | 36861-47-9 |
| 2 | 1,7,7-trimethyl-3-(phenylmethylene)bicyclo[2.2.1]heptan-2-one; benzylidene camphor | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone | 131-57-7 |
| 7 | 2-Hydroxy-4-methoxy benzophenone-5-sulfonic acid | 4065-45-6 |
| 8 | 2,2'-dihydroxy-4,4'-dimethoxybenzophenone | 131-54-4 |
| 9 | 2,2'-Dihydroxy-4-methoxybenzophenone | 131-53-3 |
| 10 | Alpha-(2-oxoborn-3-ylidene)toluene-4-sulphonic acid and its salts; Mexoryl SL | 56039-58-8 |
| 11 | 1-[4-(1,1-dimethylethyl)phenyl]-3-(4-methoxyphenyl)propane-1,3-dione; avobenzone | 70356-09-1 |
| 12 | Methyl N,N,N-trimethyl-4-[(4,7,7-trimethyl-3-oxobicyclo[2,2,1]hept-2-ylidene)methyl]anilinium sulphate; Mexoryl SO | 52793-97-2 |
| 22 | 3,3,5-Trimethyl cyclohexyl-2-hydroxy benzoate; homosalate | 118-56-9 |
| 27 | Menthyl-o-aminobenzoate | 134-09-8 |
| 28 | Menthyl salicylate | 89-46-3 |
| 29 | 2-Ethylhexyl 2-cyano,3,3-diphenylacrylate; Octocrylene | 6197-30-4 |
| 30 | 2-ethylhexyl 4-(dimethylamino)benzoate | 21245-02-3 |
| 32 | 2-ethylhexyl salicylate | 118-60-5 |
| 33 | Benzoic acid, 4,4',4''-(1,3,5-triazine-2,4,6-triyltriimino)tris-, tris(2-ethylhexyl)ester; 2,4,6-Trianilino-(p-carbo-2'-ethylhexyl-1'-oxi)-1,3,5-triazine; octyl triazone | 88122-99-0 |
| 34 | 4-aminobenzoic acid | 150-13-0 |
| 35 | Benzoic acid, 4-amino-, ethyl ester, polymer with oxirane | 113010-52-9 |
| 38 | 2-phenyl-1H-benzimidazole-5-sulphonic acid; phenylbenzimidazolsulfonic acid | 27503-81-7 |
| 39 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 40 | Triethanolamine salicylate | 2174-16-5 |
| 41 | 3,3'-(1,4-phenylenedimethylene)bis[7,7-dimethyl-2-oxo-bicyclo[2.2.1]heptane-1 methanesulfonic acid]; Cibafast H | 90457-82-2 |
| 42 | Titanium dioxide | 13463-67-7 |
| 44 | Zinc oxide | 1314-13-2 |
| 45 | 2,2'-Methylene-bis-[6-(2H-benzotriazol-2-yl)-4-(1,1,3,3-tetramethyl-butyl)-phenol]; Tinosorb M | 103597-45-1 |
| 46 | 2,4-bis{[4-(2-ethylhexyloxy)-2-hydroxy]-phenyl}-6-(4-methoxyphenyl)-(1,3,5)-triazine; Tinosorb S | 187393-00-6 |
| 47 | 1H-Benzimidazole-4,6-disulfonic acid, 2,2'-(1,4-phenylene)bis-, disodium salt | 180898-37-7 |
| 48 | Benzoic acid, 4,4'-[[6-[[4-[[[(1,1-dimethylethyl)amino]carbonyl]phenyl]-amino]1,3,5-triazine-2,4-diyl]diimino]bis-, bis(2-ethylhexyl)ester; di-ethylhexyl butamido triazone; Uvasorb HEB | 154702-15-5 |
| 49 | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane; Mexoryl XL | 155633-54-8 |
| 50 | Dimethicodiethylbenzalmalonate; Polysilicone 15; Parsol SLX | 207574-74-1 |
| 51 | Benzenesulfonic acid, 3-(2H-benzotriazol-2-yl)-4-hydroxy-5-(1-methylpropyl)-, monosodium salt; Tinogard HS | 92484-48-5 |
| 53 | 1-Dodecanaminium, N-[3-[[4-(dimethylamino)benzoyl]amino]propyl]-N,N-dimethyl-, salt with 4-methylbenzenesulfonic acid (1:1); Escalol HP610 | 156679-41-3 |
| 54 | 1-Propanaminium, N,N,N-trimethyl-3-[(1-oxo-3-phenyl-2-propenyl)-amino]-, chloride | 177190-98-6 |
| 55 | 1H-Benzimidazole-4,6-disulfonic acid, 2,2'-(1,4-phenylene)bis- | 170864-82-1 |
| 56 | 1,3,5-Triazine, 2,4,6-tris(4-methoxyphenyl)- | 7753-12-0 |
| 57 | 1,3,5-Triazine, 2,4,6-tris[4-[(2-ethylhexyl)oxy]phenyl]- | 208114-14-1 |

TABLE 4-continued

Suitable UV filter substances and adjuvants which can be additionally used with the compounds of formula (1)

| No. | Chemical Name | CAS No. |
|---|---|---|
| 58 | 1-Propanaminium, 3-[[3-[3-(2H-benzotriazol-2-yl)-5-(1,1-dimethyl-ethyl)-4-hydroxyphenyl]-1-oxopropyl]amino]-N,N-diethyl-N-methyl-, methyl sulfate (salt) | 340964-15-0 |
| 59 | 2-Propenoic acid, 3-(1H-imidazol-4-yl)- | 104-98-3 |
| 60 | Benzoic acid, 2-hydroxy-, [4-(1-methylethyl)phenyl]methyl ester | 94134-93-7 |
| 61 | 1,2,3-Propanetriol, 1-(4-aminobenzoate); glyceryl PABA | 136-44-7 |
| 62 | Benzeneacetic acid, 3,4-dimethoxy-α-oxo- | 4732-70-1 |
| 63 | 2-Propenoic acid, 2-cyano-3,3-diphenyl-, ethyl ester | 5232-99-5 |
| 64 | Anthralinic acid, p-menth-3-yl ester | 134-09-8 |
| 65 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, |
| 66 | 1,3,5-Triazine-2,4,6-triamine, N,N'-bis[4-[5-(1,1-dimethylpropyl)-2-benzoxazolyl]phenyl]-N''-(2-ethylhexyl)- or Uvasorb K2A | 288254-16-0 |
| 68 | sterols (cholesterol, lanosterol, phytosterols), as described in WO0341675 | |
| 69 | mycosporines and/or mycosporine-like amino acids as described in WO2002039974, e.g. Helioguard 365 from Milbelle AG, isolated mycosporine like amino acids from the red alga porphyra umbilicalis (INCI: Porphyra Umbilicalis) that are encapsulated into liposomes,) | |
| 70 | alpha-lipoic-acid as described in DE 10229995 | |
| 71 | synthetic organic polymers as described in EP 1371358, [0033]-[0041] | |
| 72 | phyllosilicates as described in EP 1371357 [0034]-[0037] | |
| 73 | silica compounds as described in EP1371356, [0033]-[0041] | |
| 74 | inorganic particles as described in DE10138496 [0043]-[0055] | |
| 75 | latex particles as described in DE10138496 [0027]-[0040] | |
| 76 | 1H-Benzimidazole-4,6-disulfonic acid, 2,2'-(1,4-phenylene)bis-, disodium salt; Bisimidazylate; Neo Heliopan APC | 180898-37-7 |
| 77 | Pentanenitrile, 2-[2,3-dihydro-5-methoxy-3,3-dimethyl-6-[(2-methyl-2-propenyl)oxy]-1H-inden-1-ylidene]-4,4-dimethyl-3-oxo- | 425371-15-9 |
| 78 | Pentanenitrile, 2-(2,3-dihydro-6-hydroxy-5-methoxy-3,3-dimethyl-1H-inden-1-ylidene)-4,4-dimethyl-3-oxo- | 425371-14-8 |
| 79 | Benzenepropanenitrile, α-(2,3-dihydro-3,3,5-trimethyl-1H-inden-1-ylidene)-β-oxo- | 425371-11-5 |
| 80 | Cyclohexanepropanenitrile, α-[5-(1,1-dimethylethyl)-2,3-dihydro-3,3-dimethyl-1H-inden-1-ylidene]-1-methyl-β-oxo- | 425371-10-4 |
| 81 | Pentanenitrile, 2-[6-(acetyloxy)-2,3-dihydro-5-methoxy-3,3-dimethyl-1H-inden-1-ylidene]-4,4-dimethyl-3-oxo- | 425371-09-1 |
| 82 | Pentanenitrile, 2-[2,3-dihydro-5-methoxy-3,3-dimethyl-6-[2-methyl-3-[1,3,3,3-tetramethyl-1-[(trimethylsilyl)oxy]disiloxanyl]propoxy]-1H-inden-1-ylidene]-4,4-dimethyl-3-oxo- | 425371-08-0 |
| 83 | Pentanenitrile, 2-(2,3-dihydro-5-methoxy-3,3,6-trimethyl-1H-inden-1-ylidene)-4,4-dimethyl-3-oxo- | 425371-07-9 |
| 84 | Pentanenitrile, 4,4-dimethyl-3-oxo-2-(2,3,7,8-tetrahydro-8,8-dimethyl-6H-indeno[5,6-b]-1,4-dioxin-6-ylidene)- | 425371-06-8 |
| 85 | Pentanenitrile, 2-(2,3-dihydro-3,3,6-trimethyl-1H-inden-1-ylidene)-4,4-dimethyl-3-oxo- | 425371-05-7 |
| 86 | Pentanenitrile, 2-(2,3-dihydro-3,3,5,6-tetramethyl-1H-inden-1-ylidene)-4,4-dimethyl-3-oxo- | 425371-04-6 |
| 87 | Pentanenitrile, 2-(2,3-dihydro-5-methoxy-3,3,4,6-tetramethyl-1H-inden-1-ylidene)-4,4-dimethyl-3-oxo- | 425371-03-5 |
| 88 | Pentanenitrile, 2-(2,3-dihydro-5,6-dimethoxy-3,3-dimethyl-1H-inden-1-ylidene)-4,4-dimethyl-3-oxo- | 261356-13-2 |

Personal Care Uses

The benzotropolones of formula (1) may be used as single component or in mixture with other stabilizers or UV absorbers in particular for skin-care products, bath and shower additives, preparations containing fragrances and odoriferous substances, hair-care products, dentifrices, deodorizing and antiperspirant preparations, decorative preparations, light protection formulations and preparations containing active ingredients.

Skin-care products are, in particular, body oils, body lotions, body gels, treatment creams, skin protection ointments, shaving preparations, such as shaving foams or gels, skin powders, such as baby powder, moisturizing gels, moisturizing sprays, revitalizing body sprays, cellulite gels and peeling preparations.

Suitable bath and shower additives are shower gels, bath-salts, bubble baths and soaps.

Preparations containing fragrances and odoriferous substances are in particular scents, perfumes, toilet waters and shaving lotions (aftershave preparations).

Suitable hair-care products are, for example, shampoos for humans and animals, in particular dogs, hair conditioners, products for styling and treating hair, perming agents, hair sprays and lacquers, hair gels, hair fixatives and hair dyeing or bleaching agents.

Suitable dentifrices are in particular tooth creams, toothpastes, mouth-washes, mouth rinses, anti-plaque preparations and cleaning agents for dentures.

Suitable decorative preparations are in particular lipsticks, nail varnishes, eye shadows, mascaras, dry and moist make-up, rouge, powders, depilatory agents and suntan lotions.

Suitable cosmetic formulations containing active ingredients are in particular hormone preparations, vitamin preparations, vegetable extract preparations and antibacterial preparations.

The mentioned body-care products may be in the form of creams, ointments, pastes, foams, gels, lotions, powders, make-ups, sprays, sticks or aerosols.

These products preferably contain the benzotropolones of formulae (1) and, optionally, other UV absorbers, sterically hindered amines, complexing agents and phenolic or non-phenolic antioxidants.

The present invention therefore also relates to a body-care product comprising at least one compound of formula (1).

The compounds of formula (1) are present in the body care and household products in a concentration of about 5 to about 50000 ppm, based on the total formulation, preferably from about 10 to about 10000 ppm, and most preferably from about 500 to about 5000 ppm.

The cosmetic compositions according to the present invention may also contain one or one more additional compounds as described below.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of C12-C15 alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_{13}$ carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butylstearate, n-hexyllaurate, n-decyloleate, iso-octylstearate, iso-nonylstearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Natural or Synthetic Triglycerides Including Glyceryl Esters and Derivatives

Di- or tri-glycerides, based on C6-C18 fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, *macadamia* nut oil, olive oil, hydrogenated tallow, apricot kernel oil, hazelnut oil, borago oil, etc.

Waxes

Including esters of long-chain acids and alcohols as well as compounds having wax-like properties, e.g., carnauba wax, beeswax (white or yellow), lanolin wax, candellila wax, ozokerite, Japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes

Alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Fluorinated or Perfluorinated Oils

Perfluorhexane, dimethylcyclohexane, ethylcyclopentane, polyperfluoromethylisopropyl ether.

Emulsifiers

Any conventionally usable emulsifier can be used for the compositions. Emulsifier systems may comprise for example: carbocyclic acids and their salts: alkaline soap of sodium, potassium and ammonium, metallic soap of calcium or magnesium, organic basis soap such as Lauric, palmitic, stearic and oleic acid etc. Alkyl phosphates or phosphoric acid esters, acid phosphate, diethanolamine phosphate, potassium cetyl phosphate. Ethoxylated carboxylic acids or polyethyleneglycol esters, PEG-n acylates. Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group. Fatty alcohol polyglycolether such as laureth-n, ceteareth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan, glucose derivatives, $C_8$-$C_{22}$ alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated paraffins, sulfonated tetraproplyne sulfonate, sodium lauryl sulfates, ammonium and ethanolamine lauryl sulfates, lauryl ether sulfates, sodium laureth sulfates, sulfosuccinates, acyl isothionates, alkanolamide sulfates, taurines, methyl taurines, imidazole sulfates. Amine derivatives, amine salts, ethoxylated amines, oxide amine with chains containing an heterocycle such as alkyl imidazolines, pyridine derivatives, isoquinoteines, cetyl pyridinium chlorure, cetyl pyridinium bromide, quaternary ammonium such as cetyltrimethylbroide ammonium bromide (CTBA), stearylalkonium. Amide derivatives, alkanolamides such as acylamide DEA, ethoxylated amides such as PEG-n acylamide, oxydeamide. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly-(oxyethylene)m-block-poly(oxypropylene)n-block(oxyethylene). Zwitterionic surfactants that carry at least one quaternary ammonium group and at least one carboxylate and/or sulfonate group in the molecule. Zwitterionic surfactants that are especially suitable are betaines, such as N-alkyl-N, N_dimethylammonium glycinates, cocoalkyldimethylammonium glycinate, N-acylaminopropyl-N,N-dimethylammonium glycinates, cocoacylaminopropyldimethylammonium glycinate and 2_alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkylbetaine, N-alkylaminobetaines. Alkylimidazolines, alkylopeptides, lipoaminoacides, self emulsifying bases and the compounds as described in K. F. DePolo, A short textbook of cosmetology, Chapter 8, Table 8-7, p 250-251.

Non ionic emulsifiers such as PEG-6 beeswax (and) PEG-6 stearate (and) polyglyceryl-2-isostearate [Apifac], glyceryl stearate (and) PEG-100 stearate. [Arlacel 165], PEG-5 glyceryl stearate [arlatone 983 S], sorbitan oleate (and) polyglyceryl-3 ricinoleate.[Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20 [Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and szeareth-7 and steareth-10 [Emulsifying wax U.S.N.F], glyceryl stearate and PEG-75 steparate [Gelot 64], propylene glycol ceteth-3 acetate. [Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Anionic emulsifiers such as PEG-2 stearate SE, glyceryl stearate SE [Monelgine, Cutina KD], propylene glycol stearate [Tegin P], cetearyl Alcohol and Sodium cetearyl sulfate [Lanette N, Cutina LE, Crodacol GP], cetearyl alcohol and sodium lauryl sulfate [Lanette W], trilaneth-4 phopshate and glycol stearate and PEG-2 stearate [Sedefos 75], glyceryl stearate and sodium lauryl Sulfate [Teginacid Special]. Cationic acid bases such as cetearyl alcohol and cetrimonium bromide.

The emulsifiers may be used in an amount of, for example, from 1 to 30% by weight, especially from 4 to 20% by weight and preferably from 5 to 10% by weight, based on the total weight of the composition.

When formulated in O/W emulsions, the preferably amount of such emulsifier system could represent 5% to 20% of the oil phase.

Super-Fatting Agents

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Surfactants

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers silicon dioxide, magnesium silicates, aluminium silicates, polysaccharides or derivatives thereof for example hyaluronic acid, xanthan gum, guar-guar, agar-agar, alginates, carraghenan, gellan, pectines, or modified cellulose such as hydroxycellulose, hydroxypropylmethylcellulose. In addition polyacrylates or homopolymer of reticulated acrylic acids and polyacrylamides, carbomer (carbopol types 980, 981, 1382, ETD 2001, ETD2020, Ultrez 10) or Salcare range such as Salcare SC80 (steareth-10 alkyl ether/acrylates copolymer), Salcare SC81 (acrylates copolymer), Salcare SC91 and Salcare AST (sodium acrylates copolymer/PPG-1 trideceth-6), sepigel 305 (polyacrylamide/laureth-7), Simulgel NS and Simulgel EG (hydroxyethyl acrylate/sodium acryloyldimethyl taurate copolymer), Stabilen 30 (acrylates/vinyl isodecanoate crosspolymer), Pemulen TR-1 (acrylates/C10-30 alkyl acrylate crosspolymer), Luvigel EM (sodium acrylates copolymer), Aculyn 28 (acrylates/beheneth-25 methacrylate copolymer), etc.

Polymers

Suitable cationic polymers are, for example, cationic cellulose derivatives, for example a quaternised hydroxymethyl cellulose obtainable under the name Polymer JR 400 from Amerchol, cationic starches, copolymers of diallylammonium salts and acrylamides, quaternised vinylpyrrolidone/vinyl imidazole polymers, for example Luviquatâ (BASF), condensation products of polyglycols and amines, quaternised collagen polypeptides, for example lauryldimonium hydroxypropyl hydrolyzed collagen (Lamequatâ L/Grünau), quaternised wheat polypeptides, polyethyleneimine, cationic silicone polymers, for example amidomethicones, copolymers of adipic acid and dimethylaminohydroxypropyldiethylenetriamine (Cartaretin/Sandoz), copolymers of acrylic acid with dimethyldiallylammonium chloride (Merquat 550/Chemviron), polyaminopolyamides, as described, for example, in FR-A-2 252 840, and the crosslinked water-soluble polymers thereof, cationic chitin derivatives, for example of quaternised chitosan, optionally distributed as microcrystals; condensation products of dihaloalkyls, for example dibromobutane, with bisdialkylamines, for example bisdi-methylamino-1,3-propane, cationic guar gum, for example Jaguar C-17, Jaguar C-16 from Celanese, quaternised ammonium salt polymers, for example Mirapol A-15, Mirapol AD-1, Mirapol AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylatetert. butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones. Furthermore the polymers as described in EP 1093796 (pages 3-8, paragraphs 17-68) may be used.

Cationic Surfactants cetyl trimethyl ammonium bromide (CTAB), dimethicone copolyols, amidomethicones, acrylamidepropyltrimonium chloride/Acrylamide copolymer, guar hydroxypropyl trimonium chloride, hydroxycetyl hydroxyethyl dimonium chloride quaternium compounds as listed in International Cosmetic Ingredient Dictionary and Handbook, 7$^{th}$ Edition 1997, for example Quaternium-80, polyquaternium compounds, as listed in International Cosmetic Ingredient Dictionary and Handbook, 7$^{th}$ Edition 1997, for example polyquaternium-5, polyquaternium-6, polyquaternium-7, polyquaternium-10, polyquaternium-11, polyquaternium-17, polyquaternium-18, polyquaternium-24 or polyquaternium-27, polyquaternium-28, polyquaternium-32, polyquaternium-37.

Biogenic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising Active Ingredients

As deodorising active ingredients are for example, antiperspirants, for example aluminium chlorohydrates (see J. Soc. Cosm. Chem. 24, 281 (1973)). Under the trade mark Locronâ of Hoechst A G, Frankfurt (FRG), there is available commercially, for example, an aluminium chlorohydrate corresponding to formula Al2(OH)5Cl×2.5 H2O, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlorhexidine gluconate. 5-chloro-2-(2,4-dichlorophenoxy)-phenol (Triclosan, Irgasan, Ciba Specialty Chemicals Inc.) has also proved especially effective.

Anti-Dandruff Agents

As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Hydrotropic Agents

For improvement of the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propyleneglycol, glycerine, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols for that purpose comprise preferably 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives

Suitable preservatives include, for example methyl-, ethyl-, propyl-, butyl-parabens, benzalkonium chloride, 2-bromo-2-nitro-propane-1,3-diol, dihydroacetic acid, diazolidinyl urea, 2-dichloro-benzyl alcohol, dmdm hydantoin, formaldehyde solution, methyldibromoglutanitrile, phenoxyethanol, sodium hydroxymethylglycinate, imidazolidinyl urea, Triclosan and further substance classes listed in the following reference: K. F. Depolo—A Short Textbook Of Cosmetology, Chapter 7, Table 7-2, 7-3, 7-4 and 7-5, P 210-219.

Bacteria-Inhibiting Agents

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils

Mixtures of natural and/or synthetic aromatic substances. Natural aromatic substances are, for example, extracts from blossom (lilies, lavender, roses, jasmine, neroli, ylangylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Other Adjuvants

It is furthermore possible for the cosmetic preparations to contain, as adjuvants, anti-foams, such as silicones, structurants, such as maleic acid, solubilizers, such as ethylene glycol, propylene glycol, glycerol or diethylene glycol, opacifiers, such as latex, styrene/PVP or styrene/acrylamide copolymers, propellants, such as propane/butane mixtures, $N_2O$, dimethyl ether, CO2, N2 or air, so-called coupler and developer components as oxidation dye precursors, reducing agents, such as thioglycolic acid and derivatives thereof, thiolactic acid, cysteamine, thiomalic acid or mercaptoethanesulfonic acid, or oxidising agents, such as hydrogen peroxide, potassium bromate or sodium bromate.

Suitable insect repellents are, for example, N,N-diethyl-m-toluamide, 1,2-pentanediol or insect repellent 3535; suitable self-tanning agents are, for example, dihydroxyacetone and/or erythrulose or dihydroxy acetone and/or dihydroxy acetone precursors as described in WO 01/85124 and/or erythrulose.

The compounds of formula (1) as well as mixtures of these compounds with other UV absorbers as listed in Tables 2-4, phenolic or non-phenolic antioxidants or with complex formers are particularly suitable for protecting body-care and household products against photolytic degradation.

The present stabilizer systems are particularly suitable for stabilizing body care products, in particular:
  skin-care preparations, e.g. skin-washing and cleansing preparations in the form of tablet-form or liquid soaps, soapless detergents or washing pastes,
  bath preparations, e.g. liquid (foam baths, milks, shower preparations) or solid bath preparations, e.g. bath cubes and bath salts;

skin-care preparations, e.g. skin emulsions, multi-emulsions or skin oils; body oils, body lotions, body gels; skin protection ointments;

cosmetic personal care preparations, e.g. facial make-up in the form of day creams or powder creams, face powder (loose or pressed), rouge or cream make-up, eye-care preparations, e.g. eye shadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and anti-perspirants or callus-removing preparations;

light-protective preparations, such as sun milks, lotions, creams or oils, sun blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances and odoriferous substances containing preparations (scents, eau de Cologne, eau de toilette, eau de perfume, perfume de toilette, perfume), perfume oils or perfume creams;

cosmetic hair-treatment preparations, e.g. hair-washing preparations in the form of shampoos and conditioners, hair-care preparations, e.g. pre-treatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidising dyes, or natural hair colorants, such as henna or camomile;

dentifrices, in particular tooth creams, toothpastes, mouth-washes, mouth rinses, anti-plaque preparations and cleaning agents for dentures;

decorative preparations, in particular lipsticks, nail varnishes, eye shadows, mascaras, dry and moist make-up, rouge, powders, depilatory agents and suntan lotions cosmetic formulations containing active ingredients, in particular hormone preparations, vitamin preparations, vegetable extract preparations and antibacterial preparations.

Suitable cosmetic formulations containing active ingredients are in particular hormone preparations, vitamin preparations, vegetable extract preparations and antibacterial preparations.

Presentation Forms

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a stick, in the form of a spray (spray with propellant gas or pump-action spray) or an aerosol, in the form of a foam, or in the form of a paste.

Of special importance as cosmetic preparations for the skin are light-protective preparations, such as sun milks, lotions, creams, oils, sun blocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pre-treatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition:
0.01 to 5% by weight of the compound of formula (1),
12.0% by weight of sodium laureth-2-sulfate,
4.0% by weight of cocamidopropyl betaine,
3.0% by weight of sodium chloride,
and water ad 100%.

For example, especially the following hair-cosmetic formulations may be used:

$a_1$) spontaneously emulsifying stock formulation, comprising the compound of formula (1) according to the invention, optionally another stabilizer, PEG-6-C10oxoalcohol and sorbitan sesquioleate, to which water and any desired quaternary ammonium compound, for example 4% minkamidopropyl dimethyl-2-hydroxyethylammonium chloride or Quaternium 80 is added;

$a_2$) spontaneously emulsifying stock formulation comprising the compound of formula (1) according to the invention, optionally another stabilizer, tributyl citrate and PEG-20-sorbitan monooleate, to which water and any desired quaternary ammonium compound, for example 4% minkamidopropyl dimethyl-2-hydroxyethylammonium chloride or Quaternium 80 is added;

b) quat-doped solutions comprising the compound of formula (1) according to the invention in butyl triglycol and tributyl citrate; and optionally another stabilizer;

c) mixtures or solutions comprising the compound of formula (1) according to the invention with alkylpyrrolidone; and optionally another stabilizer.

Examples of body care products of the present invention are listed in the Table below:

| Body care product | Ingredients |
|---|---|
| moisturizing cream | vegetable oil, emulsifier, thickener, perfume, water, antioxidant, UV absorbers |
| shampoo | surfactant, emulsifier, preservatives, perfume, antioxidant, UV absorbers |
| Toothpaste | cleaning agent, thickener, sweetener, flavour, colorant, antioxidant, water, UV absorbers |
| lip-care stick | vegetable oil, wax, $TiO_2$, antioxidant, UV absorbers |

Household Products

The stabilizer systems of the present invention are also used in household cleaning and treatment agents, for example in laundry products and fabric softeners, liquid cleansing and scouring agents, glass detergents, neutral cleaners (all-purpose cleaners), acid household cleaners (bath), bathroom cleaners, WC cleaners, for instance in washing, rinsing and dishwashing agents, kitchen and oven cleaners, clear rinsing agents, dishwasher detergents, shoe polishes, polishing waxes, floor detergents and polishes, metal, glass and ceramic cleaners, textile-care products, rug cleaners and carpet shampoos, agents for removing rust, color and stains (stain remover salt), furniture and multi-purpose polishes and leather and vinyl dressing agents (leather and vinyl sprays) and air fresheners.

Household cleaning agents are aqueous or alcoholic (ethanol or isopropyl alcohol) solutions of one or more of the following components:
- anionic, nonionic, amphoteric and/or cationic surfactants
- soaps, prepared by saponification of animal and vegetable greases
- organic acids, like hydrochloric acid, phosphoric acid, or sulphuric acid,
- for basic products inorganic (NaOH or KOH) or organic bases;
- abrasives for improved cleaning of surfaces,
- waxes and/or silicones for maintenance and protection of surfaces,
- polyphosphates,
- substances which eliminate hypochlorite or halogens;
- peroxides comprising bleaching activators like TAED, for example sodium perborate or $H_2O_2$;
- enzymes;
- in washing detergents discoloration inhibitors, soil-release compounds, grey scale inhibitors, foam inhibitors, fluorescent whitening agents;
- cleaning agents based on wax may comprise solvents selected from benzine, turpentine and/or paraffins and emulsifiers based on wax;
- filling agents like silicates, polyphosphates, Zeolithes for powdery cleaning agents;
- pigments, lakes or soluble dyes;
- perfumes; and
- light stabilizers, antioxidants and chelating agents.

Colored cleaning agents and decorative cosmetic products can comprise the following dyes:
- inorganic pigments, for example iron oxide (Iron Oxide Red, Iron Oxide Yellow, Iron Oxide Black, etc.), Ultramarines, Chromium Oxide Green or Carbon Black;
- natural or synthetic organic pigments;
- disperse dyes which may be solubilized in solvents like direct hair dyes of the HC type, for example HC Red No. 3, HC Blue No. 2 and all other hair dyes listed in International Cosmetic Ingredient Dictionary and Handbook, 7th edition 19997) or the dispersion dyes listed in Color Index International or Society of Dyers and Colourists;
- color varnishes (insoluble salts of soluble dyes, like many Ca-, Ba- or Al-salts of anionic dyes);
- soluble anionic or cationic dyes, like acid dyes (anionic), basic dyes (cationic), direct dyes, reactive dyes or solvent dyes.

Generally, for the coloration of household- and body care products all substances are suitable which have an absorption in the visible light of electromagnetic radiation (wave length of ca. 4000 to 700 nm). The absorption is often caused by the following chromophores: azo-(mono-, di, tris-, or poly-)stilbene-, carotenoide-, diarylmethane-, triarylmethan-, xanthene-, acridine-, quinoline, methine-(also polymethine-), thiazol-, indamine-, indophenol-, azine-, oxazine, thiazine-, anthraquinone-, indigoid-, phtalocyanine- and further synthetic, natural and/or inorganic chromophores.

The present invention also relates to home care and fabric care products such as drain cleaners, disinfectant solutions, upholstery cleaners, automotive care products (e.g., to clean and/or polish and protect paint, tires, chrome, vinyl, leather, fabric, rubber, plastic and fabric), degreasers, polishes (glass, wood, leather, plastic, marble, granite, and tile, etc.), and metal polishes and cleaners. Antioxidants are suitable to protect fragrances in above products as well as in dryer sheets. The present invention also relates to home care products such as candles, gel candles, air fresheners and fragrance oils (for the home).

Typical examples of household cleaning and treating agents are listed in the table below:

| Household cleaners/ household treating agents | Ingredients |
|---|---|
| detergent concentrate | surfactant mixture, ethanol, antioxidant, water, UV absorbers, antioxidants |
| shoe polishwax | wax emulsifier, antioxidant, water, preservative, UV absorbers, antioxidants |
| wax-containing floor cleaning agent | emulsifier, wax, sodium chloride, compound of formula (1), water, preservative UV absorbers, antioxidant |

The compounds of formula (1) according to the present invention are for example incorporated by dissolution in an oil phase or alcoholic or water phase, where required at elevated temperature.

The present body care products and household products have high stability towards color changes and chemical degradation of the ingredients present in these products. For example, present compositions that comprise a dye are found to have excellent color stability.

A. PREPARATION EXAMPLES

Example A1—Laccase-Catalysed Synthesis of the Compound (B-2)

(B-2)

1.12 g of 1,2-dihydroxybenzene are dissolved in 100 ml sodium acetate buffer (0.025 mM; pH 4.65) and 30 ml ethanol.

1.74 g of gallic acid and subsequently 1 mL of the enzyme stock solution are added.

The enzyme stock solution is prepared by dissolution of 10 mg of the lyophilized enzyme (laccase from *Trametes versicolor*, Fluka) in 10 ml sodium acetate buffer (0.025 mM; pH 4.65).

The reaction mixture is vigorously stirred for several hours until the end of the reaction is indicated by missing gallic acid in TLC.

The reaction mixture is filtered off and the residue is washed with water and dried in vacuum at 60° C.

0.21 g of a solid is obtained which corresponds to compound (B-2).

UV-Vis (MeOH): $\lambda_{max}$=400 nm ($\epsilon$=11413), $\lambda_{max}$=276 nm, $\epsilon$=23972.

Example A2—Laccase-Catalysed Synthesis of the Compound (B-3)

(B-3)

1.12 g of 1,2-dihydroxybenzene and 1.88 g of gallic acid methyl ester are dissolved in 80 ml sodium acetate buffer (0.025 mM; pH 4.65) and 20 ml ethanol.

After adding 1 ml of the enzyme stock solution the reaction mixture is vigorously stirred for several hours.

The enzyme stock solution is prepared by dissolution of 10 mg of the lyophilized enzyme (laccase from *Trametes versicolor*, Fluka) in 10 ml sodium acetate buffer (0.025 mM; pH 4.65).

The reaction mixture is vigorously stirred for several hours until the end of the reaction is indicated by missing gallic acid methyl ester in TLC.

The reaction mixture is filtered off and the residue washed with water and dried in vacuum at 60° C.

0.15 g of a solid is obtained corresponding to compound (B-3).

UV-Vis (MeOH): $\lambda_{max}$=395 nm ($\epsilon$=13523), $\lambda_{max}$=277 nm, $\epsilon$=26379.

Example A3—Laccase-Catalysed Synthesis of the Compound (B-4)

(B-4)

1.43 g of 3-methoxycatechol and 1.74 g of gallic acid are dissolved in 100 ml sodium acetate buffer (0.025 mM; pH 4.65) and 30 ml ethanol.

Subsequently 1 ml of the enzyme stock solution is added to the reaction mixture.

The enzyme stock solution is prepared by dissolution of 10 mg of the lyophilized enzyme (laccase from *Trametes versicolor*, Fluka) in 10 ml sodium acetate buffer (0.025 mM; pH 4.65).

The reaction mixture is vigorously stirred for several hours until the end of the reaction is indicated by missing gallic acid in TLC.

The reaction mixture is filtered off and the residue washed with water and dried in vacuum at 30° C.

0.49 g of a solid is obtained corresponding to compound (B-4).

UV-Vis (MeOH): $\lambda_{max}$=396 nm ($\epsilon$=8489), $\lambda_{max}$=307 nm, $\epsilon$=24015.

Example A4—Laccase-Catalysed Synthesis of the Compound B-5

(B-5)

43 g of 3-methoxycatechol and 1.88 g of Gallic acid methyl ester are dissolved in 80 ml sodium acetate buffer (0.025 mM; pH 4.65) and 20 ml ethanol.

Subsequently 1 ml of the enzyme stock solution is added to the reaction mixture.

The enzyme stock solution is prepared by dissolution of 10 mg of the lyophilized enzyme (laccase from *Trametes versicolor*, Fluka) in 10 ml sodium acetate buffer (0.025 mM; pH 4.65).

The reaction mixture is vigorously stirred for several hours until the end of the reaction is indicated by missing Gallic acid methyl ester in TLC.

The reaction mixture is filtered off, the residue washed with 20 ml water and dried in vacuum at 45° C.

0.52 g of a beige solid is obtained corresponding to compound (B-5).

UV-Vis (MeOH): $\lambda_{max}$=403 nm ($\epsilon$=11667), $\lambda_{max}$=308 nm ($\epsilon$=29426).

Example A5—Laccase-Catalysed Synthesis of the Compound B-6

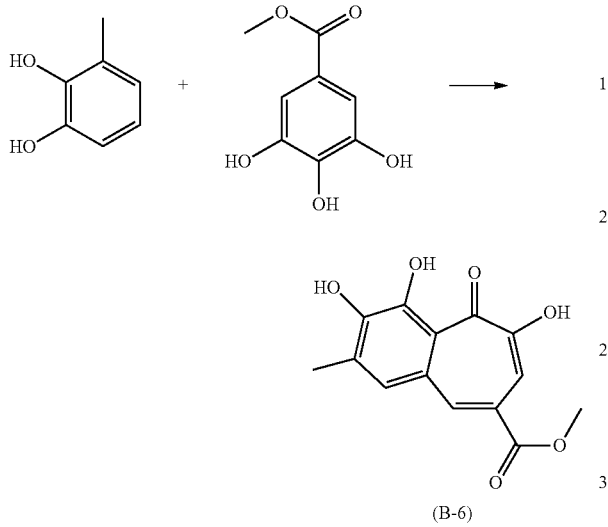

(B-6)

1.24 g of 3-methylcatechol and 1.84 g of Gallic acid methyl ester (both commercial from FLUKA) are dissolved in a mixture of 80 ml phosphate buffer (pH=5, 0.05 M) and 20 ml ethanol and are treated with 2 ml of a laccase solution (T. versicolor, 46 U) at room temperature in an open beaker for 24 h.

The resulting solid is filtered off, washed with water and dried.

0.64 g of the compound (B-6) are obtained.

$^1$H-NMR (DMSOD$_6$, 300 MHz): 10.00 (broad, 1H); 9.60 (broad, 1H); 8.22 (d, 1H); 7.55 (d, 1H); 7.51 (s, 1H); 2.33 (s, 3H).

$^{13}$C-NMR (DMSOD$_6$, 75 MHz): 17.1; 53.7; 115.6; 1213.2; 128.6; 130.0; 133.1; 139.2; 147.7; 150.8; 153.8; 167.2; 184.8.

UV-Vis (MeOH): $\lambda_{max}$=396 nm ($\epsilon$=12328), $\lambda_{max}$=280 nm ($\epsilon$=27527).

Example A6—Laccase-Catalysed Synthesis of the Compound (B-7)

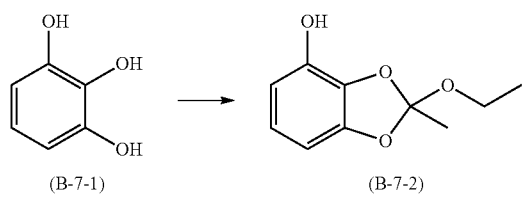

(B-7-1)        (B-7-2)

92.5 g of triethyl orthoacetate are added to 72.5 g of pyrogallol (both commercial from FLUKA) in 375 ml xylene and heated at about 120° C.

The formed ethanol is distilled off (theoretically about 66.5 mL) during 5 h.

A reddish-brown but clear solution is formed.

After cooling, the solution is washed with water (3×) and the organic phase is dried over sodium sulfate.

After removal of the xylene, a residue remains, which is recrystallized from ethyl acetate/hexane.

85.7 g (77%) of product are obtained.

Alternatively, purification of the crude product on a column of silica gel (eluent hexane-ethyl acetate/1-1) yields 85 g of compound (B-7-2) as a white powder.

$^1$H-NMR (CDCl$_3$, 300 MHz): 6.71 (dd, 1H); 6.48 (dd, 1H); 6.45 (dd, 1H); 3.61 (q, 2H); 1.82 (s, 3H); 1.21 (t, 3H).

$^{13}$C-NMR (CDCl$_3$, 75 MHz): 15.2; 24.9; 58.6; 101.3; 110.5; 121.7; 128.5; 133.64; 138.6; 147.8.

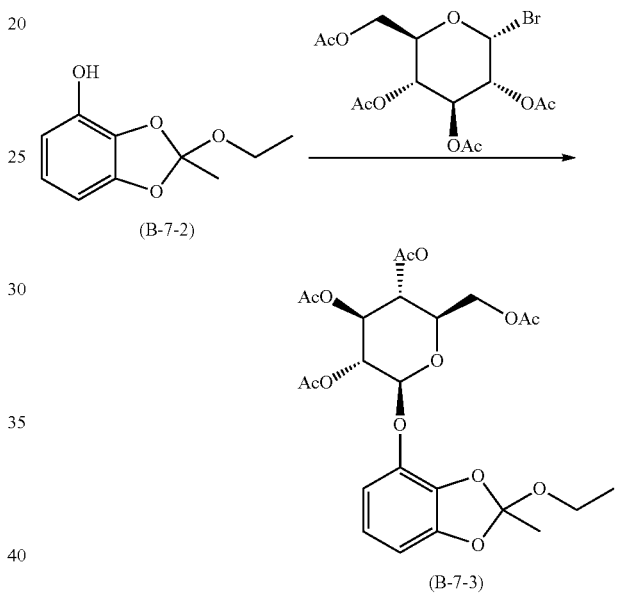

(B-7-3)

50.0 g of peracetylated α-D-glucosyl bromide (which is itself prepared from glucose penta-acetate and 48% HBr solution) and 12.0 g of protected pyrogallol (B-7-2) are dissolved at room temperature in 100 ml chloroform and 1.7 ml water.

42.0 g of potassium carbonate and 3.8 g of benzyltributylammonium chloride are added.

The mixture is stirred for two days.

The solid is filtered off and the organic phase is successively extracted with 0.1 N hydrogen chloride, sat. sodium hydrogen carbonate solution and brine.

Desiccation over sodium sulphate, filtration and evaporation of solvent renders a syrup which is crystallized from diethyl ether:

28.5 g of solid glucoside (B-7-3) are obtained.

$^1$H-NMR (CDCl$_3$, 300 MHz): 6.74 (t, 1H); 6.63 (d, 1H); 6.58 (d, 1H); 5.14-5.34 (m, 4H); 4.30 (dd, 1H); 4.12 (dt, 1H); 3.58 (q, 2H); 2.03-2.07 (4×s, 4×3H each); 1.80 (s, 3H); 1.20 (t, 3H).

$^{13}$C-NMR (CDCl$_3$, 75 MHz): 15.2; 21.0 (4×C); 24.9; 58.4; 62.1; 68.5; 71.5; 72.4; 73.0; 100.4; 103.9; 113.1; 121.6; 128.5; 136.0; 139.3; 148.4; 169.4; 170.4; 170.6.

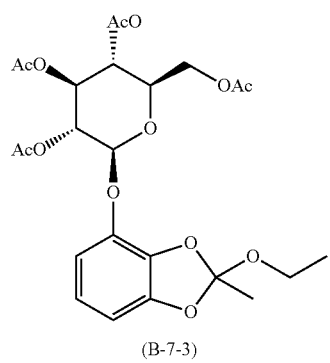

(B-7-3)

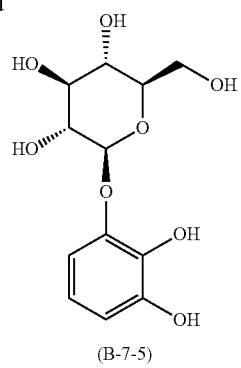

(B-7-5)

Deprotection of the compound (B-7-4) is achieved as described for compound B-9-3 with sodium methanolate in 85% yield.

$^1$H-NMR (CD$_3$OD, 300 MHz): 6.61 (d, 1H); 6.52 (t, 1H); 6.44 (d, 1H); 4.65 (d, 1H); 3.77 (d, 1H); 3.63 (dd, 1H); 3.27-3.44 (m, 4H).

$^{13}$C-NMR (CD$_3$OD, 75 MHz): 61.3; 70.2; 73.8; 76.5; 77.1; 103.2; 109.1; 110.8; 119.0; 135.4; 145.9; 146.3.

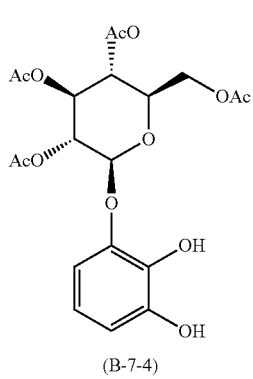

(B-7-4)

20.0 g of compound (B-7-3) and 25 mg of para-toluene sulfonic acid are dissolved in 100 ml chloroform containing 0.5 ml water and are stirred at room temperature for 4 h until all starting material is consumed.

The mixture is then dried over sodium sulfate and evaporated.

The resulting residue is passed over a column of silica gel (eluent: ethyl acetate) to remove the acid to give 14.4 g of the compound (B-7-4) as a white foamy material.

$^1$H-NMR (CDCl$_3$, 300 MHz): 6.71 (d, 2H); 6.50 (dd, 1H); 6.17 (broad, OH); 5.61 (broad, OH); 5.27 (quint., 2H); 5.14 (t, 1H); 4.93 (d, 1H); 4.27 (dd, 1H); 4.18 (dd, 1H); 3.85 (ddd, 1H); 2.10 (s, 3H); 2.08 (s, 3H); 2.04 (s, 3H); 2.03 (s, 3H).

$^{13}$C-NMR (CDCl$_3$, 75 MHz): 20.8; 20.9; 21.0; 21.1; 62.0; 86.4; 71.6; 72.5; 72.6; 102.0; 109.9; 112.0; 120.2; 135.1; 144.7; 145.6; 169.5; 170.1; 170.2; 170.7.

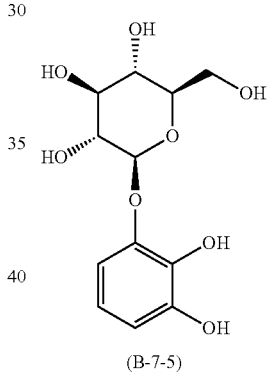

(B-7-5)

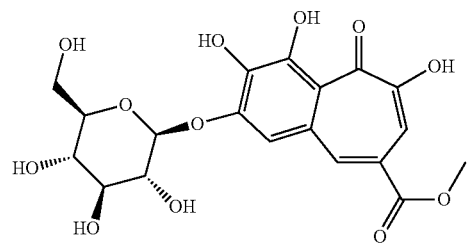

(B-7)

0.60 g of the compound (B-7-5) are dissolved at room temperature in 20 ml phosphate buffer (0.05 M, pH=5).

Under vigorous stirring 0.38 g gallic acid methyl ester, dissolved in 2 ml ethanol are added and subsequently 2 ml of a laccase solution (*T. versicolor* 1 mg per 1 ml buffer (26 U per mg)) are added.

This mixture is stirred over night, filtered off and the filtrate washed with water.

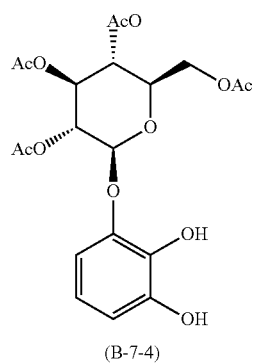

(B-7-4)

0.37 g (40%) of a slightly orange powder is obtained:

$^1$H-NMR (DMSOD$_6$, 300 MHz): 8.27 (d, 1H); 7.52 (d, 1H); 7.51 (s, 1H); 5.23 (d, 1H); 5.06 (broad 2H); 4.56 (broad 1H); 3.86 (s, 3H); 3.70 (d, 1H); 3.20-3.40 (m, 5H).

$^{13}$C-NMR (DMSOD$_6$, 75 MHz): 53.7; 61.4; 70.5; 74.0; 77.0; 100.7; 113.6; 114.9; 117.2; 124.1; 130.0; 138.7; 138.9; 150.2; 152.8; 154.2; 167.2; 184.1.

UV-Vis (MeOH): $\lambda_{max}$=399 nm ($\epsilon$=10816), $\lambda_{max}$=287 nm ($\epsilon$=26118).

Example A7—Laccase-Catalysed Synthesis of the Compound (B-9)

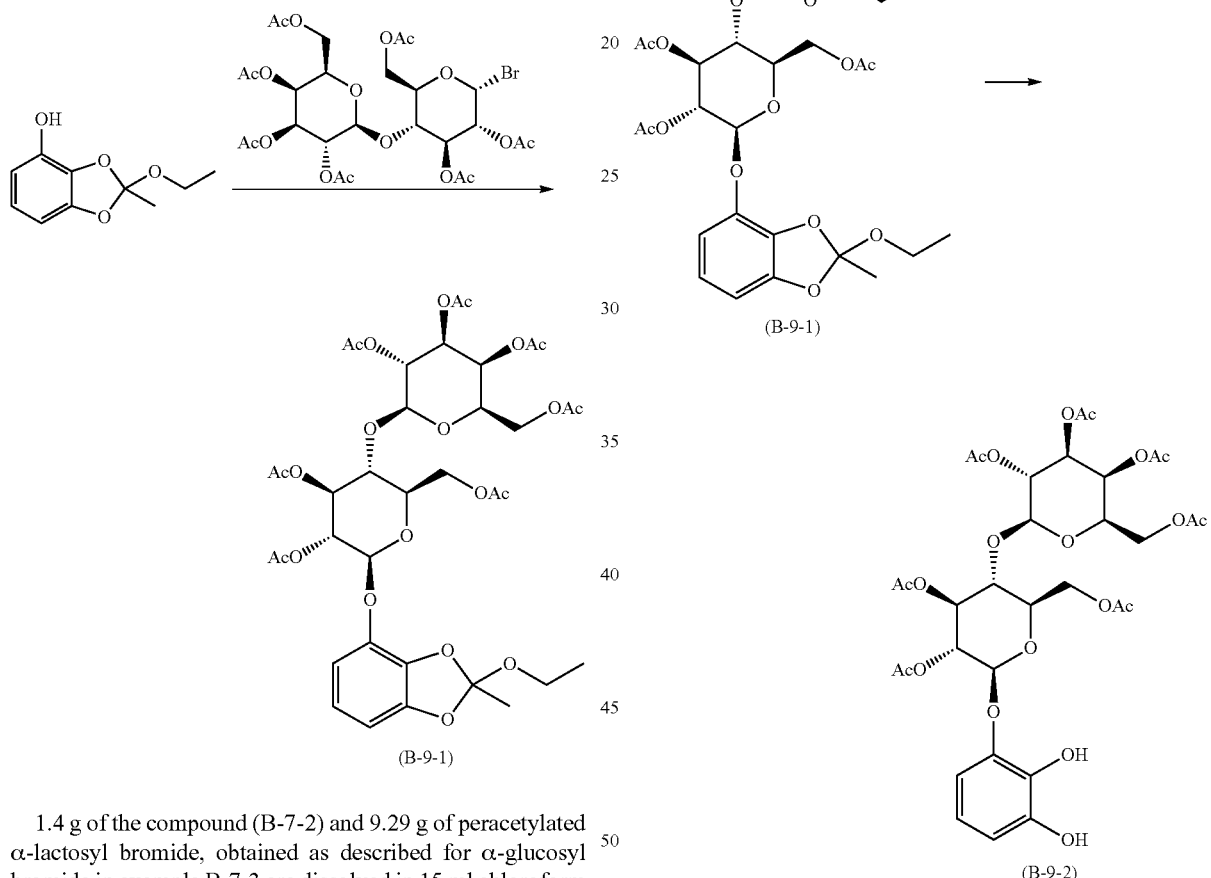

1H), 4.52 (dd, 1H), 4.48 (ddd, 1H), 4.06-4.18 (m, 4H), 3.86-3.95 (m, 2H), 3.72 (m, 1H), 3.52-3.62 (m, 2H), 2.04-2.16 (7×s, 3H each), 1.80 (s, 3H), 1.26 (t, 3H).

$^{13}$C-NMR (CDCl$_3$, 75 MHz): 14.6; 15.2; 20.8; 20.97 (2×C); 21.1; 21.2; 21.4; 24.9; 58.4; 60.7; 61.1; 61.5; 62.1; 66.9; 69.4; 71.0; 71.2; 71.8; 73.0; 73.2; 76.3; 100.2; 101.3; 103.8; 112.8; 121.5; 128.5; 135.9; 139.4; 148.3; 169.1; 169.7; 169.8; 170.1; 170.2; 170.3, 170.4.

1.4 g of the compound (B-7-2) and 9.29 g of peracetylated α-lactosyl bromide, obtained as described for α-glucosyl bromide in example B-7-3 are dissolved in 15 ml chloroform containing 0.2 ml water at room temperature.

0.45 g of benzyl tributyl ammonium chloride (Fluke) and 4.90 g of finely ground potassium carbonate (technical grade) are added to this mixture successively.

The mixture is vigorously stirred for 30 h until all starting material has been consumed.

The mixture is then filtered over celite to remove fines and evaporated.

The resulting residue is then purified over a short column of silica gel (eluent hexane-ethyl acetate/6-1 to 1-1).

4.64 g of the compound (B-9-1) are obtained as a colourless syrupy mass.

$^1$H-NMR (CDCl$_3$, 300 MHz): 6.73 (t, 1H); 6.58 (t, 2H); 5.36 (dd, 1H), 5.27 (m, 1H), 5.08-5.16 (m, 2H), 4.97 (dd, 4.32 g of the compound (B-9-1) are dissolved in 20 ml chloroform containing 0.2 ml water and 55 mg of toluene sulfonic acid.

The mixture is stirred for one hour at room temperature until all starting material is consumed.

Evaporation of the solvent and filtration of the residue over a silica gel pad (eluent hexane-ethyl acetate/1-1) gives 3.36 g of the compound (B-9-2).

$^1$H-NMR (CDCl$_3$, 300 MHz): 6.73 (dd, 2H); 6.51 (dd, 2H), 6.19 (broad OH); 5.45 (broad OH); 5.27 (dd, 1H), 5.17 (d, 1H), 5.14 (dd, 1H); 5.10 (d, 1H), 4.97 (dd, 1H), 4.88 (d, 1H); 4.52 (dd, 1H), 4.08-4.19 (m, 3H), 3.86-3.95 (m, 2H), 3.72 (ddd, 1H), 1.98-2.16 (7×s, 3H each).

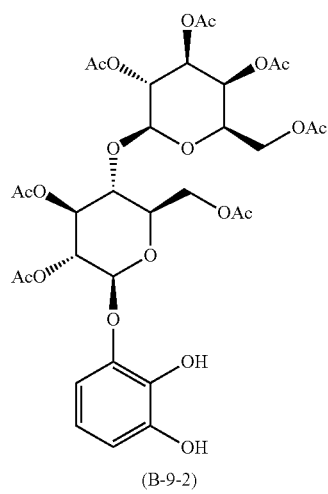

(B-9-2)

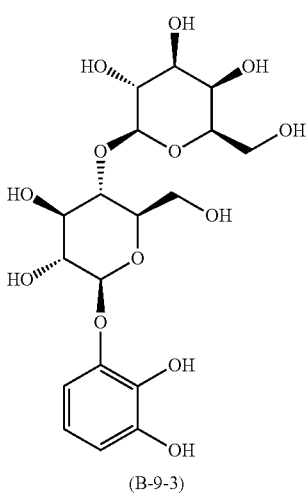

(B-9-3)

In an argon atmosphere at room temperature 3.08 g of the compound (B-9-2) are dissolved in a mixture of 20 ml methanol and 7 ml dichloromethane containing 0.27 g of sodium methanolate.

The mixture is stirred for 2.5 h and treated with 4.0 g of a mixed bed ion exchanger resin (Amberlite MB-30).

Filtration and evaporation renders 1.84 g of the compound (B-9-3) as a grey powder.

$^1$H-NMR (CD$_3$OD, 300 MHz): 6.56 (dd, 1H), 6.45 (dd, 1H), 6.30 (t, 1H), 4.73 (d, 1H); 4.38 (d, 1H); 3.90 (t, 1H); 3.46-3.82 (m, 11H).

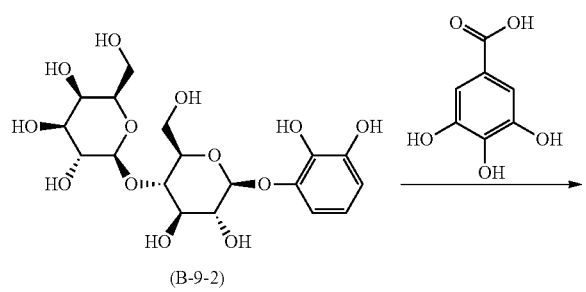

(B-9-2)

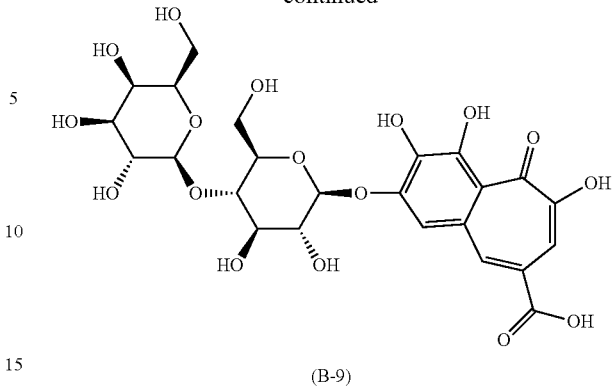

(B-9)

0.10 g of the compound (B-9-2), 0.025 g of gallic acid and 2 mg of laccase (*T. versicolor*, Fluka, 26 U/mg) are dissolved at room temperature in 10 ml of a phosphate buffer (pH=4.8, 0.1 M) and 2 ml of acetone and are stirred vigorously in an open beaker until all starting material is consumed. 90 mg of brownish solid B-9 is obtained.

$^1$H-NMR (OC(CD$_3$)$_2$, 300 MHz): 8.45 (d, 1H); 7.84 (d, 1H); 7.58 (s, 1H); 5.82 (d, 1H); 5.47 (dd, 1H); 5.43 (d, 1H); 5.40 (dd, 1H); 5.21 (dd, 1H); 5.07 (t, 1H); 4.92 (dd, 1H); 4.10-4.42 (m, 6H); 2.06 (s, 3H); 2.02 (s, 3H); 2.01 (s, 3H); 2.00 (s, 3H); 1.99 (s 3H); 1.98 (s, 3H); 1.97 (s, 3H).

Example A8—Laccase-Catalysed Synthesis of the Compound (B-13)

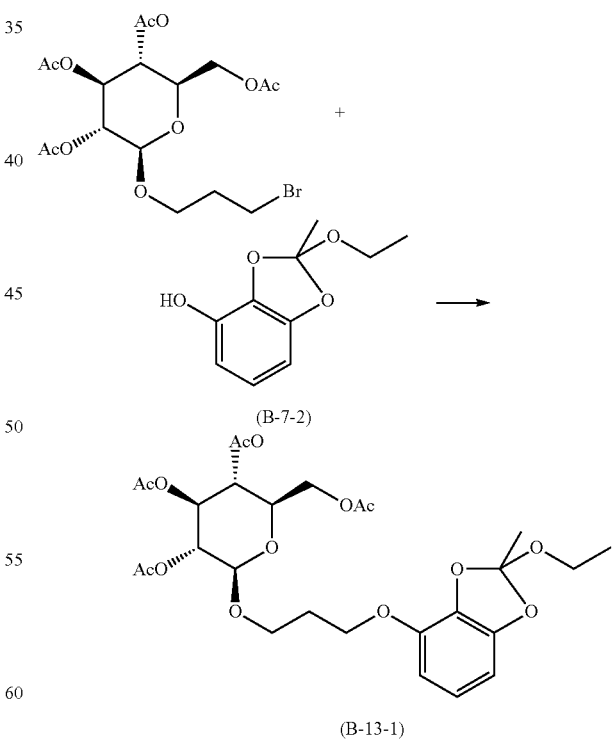

(B-13-1)

23.8 g of the protected sugar (B-7-0), obtained according U.S. Pat. No. 4,675,392 (1987), and 10.9 g of compound (B-7-2) are dissolved in 500 ml acetone and treated with 35.0 g of potassium carbonate and 230 mg of sodium iodide.

This mixture is vigorously stirred at 50° C. over night until the starting material is consumed. After cooling down the solids are filtered off and the solvent is evaporated.

The residue is purified over a silica gel pad (eluent hexane-ethyl acetate/10-4).

28.2 g of the compound (B-13-1) are obtained.

¹H-NMR (CDCl₃, 300 MHz): 6.72 (dd, 1H); 6.49 (d, 1H); 6.41 (d, 1H); 5.16 (dd, 1H); 5.06 (t 1H); 4.97 (dd, 1H); 4.52 (dd, 1H); 4.25 (dd, 1H); 4.08-4.14 (m, 3H); 4.02 (dt, 1H); 3.64-3.77 (m, 2H); 3.59 (q, 2H); 1.91-2.07 (4×s, 3H each and 2H); 1.80 (s; 3H); 1.20 (t, 3H).

¹³C-NMR (CD₃OD, 75 MHz): 15.2, 20.8; 20.9; 21.1; 24.9; 25.0; 29.9; 58.3; 62.2; 66.1; 66.8; 68.7; 71.6; 72.1; 73.1; 101.2; 101.8; 108.6; 121.6; 128.2; 134.9; 142.3; 147.9; 169.3; 169.5; 170.3; 170.7.

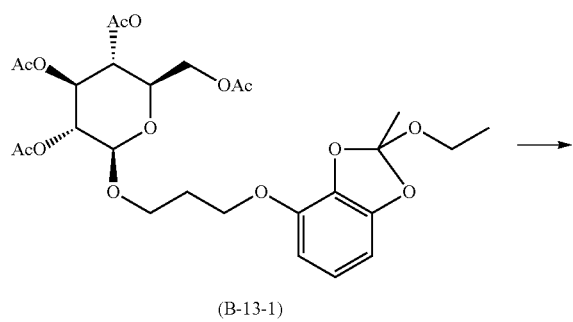

(B-13-1)

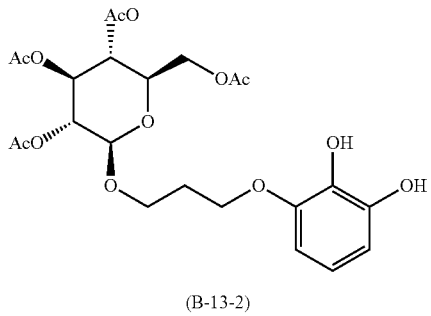

(B-13-2)

28.0 g of the compound (B-13-1) and 35 mg of para-toluene sulfonic acid are dissolved in 150 ml chloroform containing 0.9 ml water and are stirred at room temperature for two hours. The mixture is then filtered over sodium sulfate, evaporated and the residue passed over a short column of silica gel (eluent hexane-ethyl acetate/10-5) to remove the acid. Evaporation of solvent leaves 20.8 g of the compound (B-13-2) as a white solid.

¹H-NMR (CDCl₃, 300 MHz): 6.70 (t, 1H); 6.57 (dd, 1H); 6.43 (dd, 1H); 5.84 (OH); 5.52 (OH); 5.20 (t, 1H); 5.02 (t, 1H); 5.00 (dd, 1H); 4.23 (DDD, 1H); 3.99-4.15 (m, 4H); 3.72 (m, 2H); 1.95-2.05 (4×s, 3H each and 2H).

¹³C-NMR (CDCl₃, 75 MHz): 20.9; 21.0 (2×C); 21.1; 29.6; 62.2; 66.1; 66.3; 68.7; 71.5; 72.2; 73.1; 100.9; 104.9; 109.2; 119.9; 133.2; 144.7; 146.4; 169.5; 169.7; 170.3; 170.9.

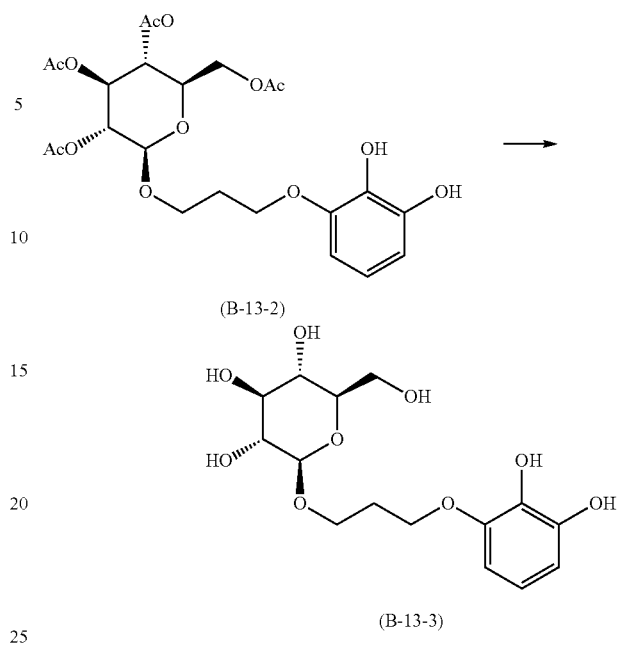

3.0 g of the compound (B-13-2) are dissolved in 25 ml methanol containing 2.1 equivalents of sodium methanolate.

The mixture is stirred in an ice-bath for ten minutes and then neutralized with Amberlite IRC 50 with additional 20 ml methanol.

The slightly brown solution is filtered off, evaporated and lyophilized from water to give 1.8 g of slightly fluffy compound (B-13-3).

¹H-NMR (CD₃OD, 300 MHz): 6.60 (t, 1H); 6.46 (d, 1H); 6.41 (d, 1H); 4.32 (d, 1H); 4.15-4.23 (m, 2H); 3.60-3.85 (m, 4H); 3.18-3.38 (m, 4H); 2.13 (t, 2H).

¹³C-NMR (CD₃ OD, 75 MHz): 29.7; 61.7; 66.3; 66.7; 70.5; 74.0; 76.7; 77.0; 103.2; 105.1; 108.9; 118.9; 134.4; 145.5; 147.7.

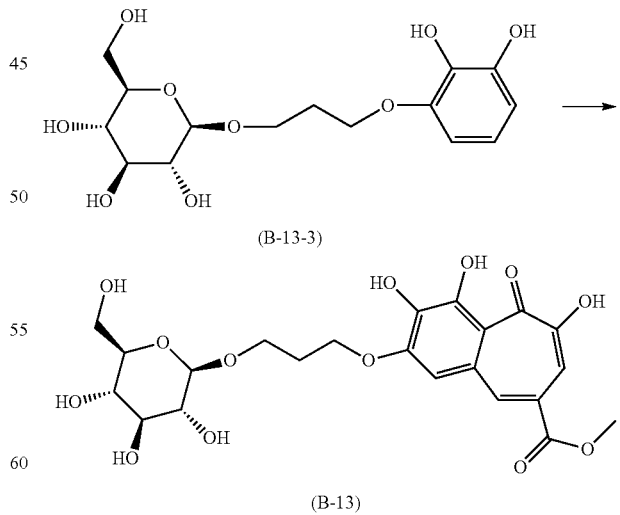

1.20 g of the compound (B-13-1) and 0.70 g of commercial gallic acid methyl ester are dissolved in 60 ml phosphate buffer (50 mmol, pH=5) at room temperature containing 6 ml ethanol.

The reaction is started by addition of a solution of 4 ml of laccase stock solution (10 mg/10 ml (23 U/mg)).

After incubation over night in an open beaker additional 46 U of laccase are added and incubation is continued.

After further 24 h the reaction mixture is centrifuged and the clear supernatant lyophilized. The resulting brown powder is stirred in 60 ml methanol and again centrifuged. This procedure is repeated twice and the methanol is then evaporated and the residue purified over a silica gel pad (eluent dichloromethane-methanol-water/10-4-0.4). 0.44 g of the benzotropolone compound (B-13) is obtained.

$^1$H-NMR (CD$_3$OD, 300 MHz): 8.24 (s 1H); 7.64 (s, 1H); 7.18 (s, +H); 4.32 (d, 1H); 4.09-4.17 (m, 2H); 3.96 (s, 1H); 3.81-3.89 (m, 3H); 3.68 (dd, 1H); 3.17-3.33 (m, 4H); 2.22 (t, 2H).

$^{13}$C-NMR (CD$_3$ OD, 75 MHz): 29.5; 52.4; 61.7; 66.3 (2×C); 70.6; 74.0; 76.9; 77.0; 103.3; 110.3; 113.6; 116.2; 124.1; 130.2; 137.8; 138.3; 150.8; 151.8; 153.9; 167.5; 183.0.

UV-Vis (MeOH): $\lambda_{max}$=404 nm ($\epsilon$=10478), $\lambda_{max}$=306 nm ($\epsilon$=28087). Solubility in water: 10.467%.

Example A9—Laccase-Catalysed Synthesis of the Compound (B-16)

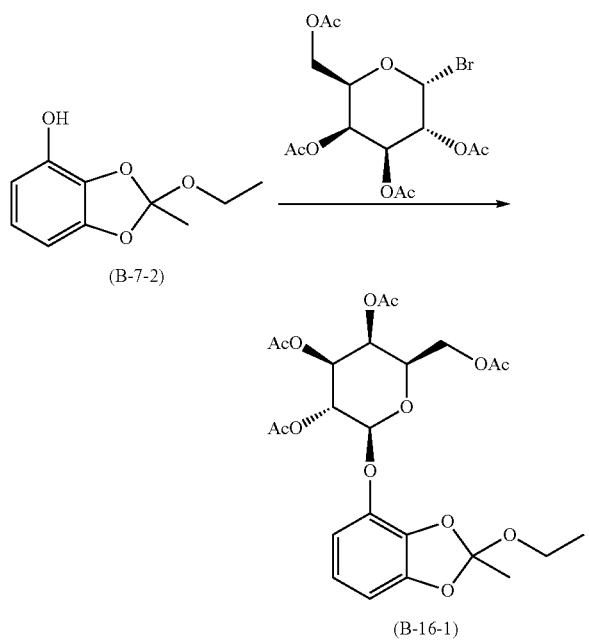

(B-7-2)

(B-16-1)

5.0 g of peracetylated α-D-galacctosyl bromide (commercial from FLUKA) and 1.3 g of protected pyrogallol (B-7-2) are dissolved at RT in 15 ml chloroform and 0.2 ml water. 4.5 g of potassium carbonate and 0.4 g of benzyltributylammonium chloride are added. The mixture is stirred vigorously until complete consumption of the starting material at room temperature (about 19 h).

The solid is filtered off over Celite and the organic phase is evaporated to leave a brown syrup which is purified over a silica gel column (eluent ethyl acetate-hexane/1-1). 2.48 g of the compound (B-16-1) are obtained.

$^1$H-NMR (CDCl$_3$, 300 MHz): 6.68 (t, 1H); 6.58 (dd, 1H); 6.52 (dd, 1H); 5.38 (dd; 1H); 5.36 (dd, 1H); 5.00-5.01 (m, 2H); 4.05-4.17 (m, 2H); 3.93 (dt, 1H); 3.51 (q, 2H); 1.95-2.11 (4×s, 4×3H each); 1.74 (s, 3H); 1.14 (t, 3H).

$^{13}$C-NMR (CDCl$_3$, 75 MHz): 15.2; 20.9; (2×C); 21.0 (2×C); 25.0; 58.4; 61.4; 67.1; 69.0; 71.1; 71.3; 101.2; 104.0; 113.1; 121.5; 128.5; 136.1; 139.5; 148.3; 169.5; 170.2; 170.3: 170.4.

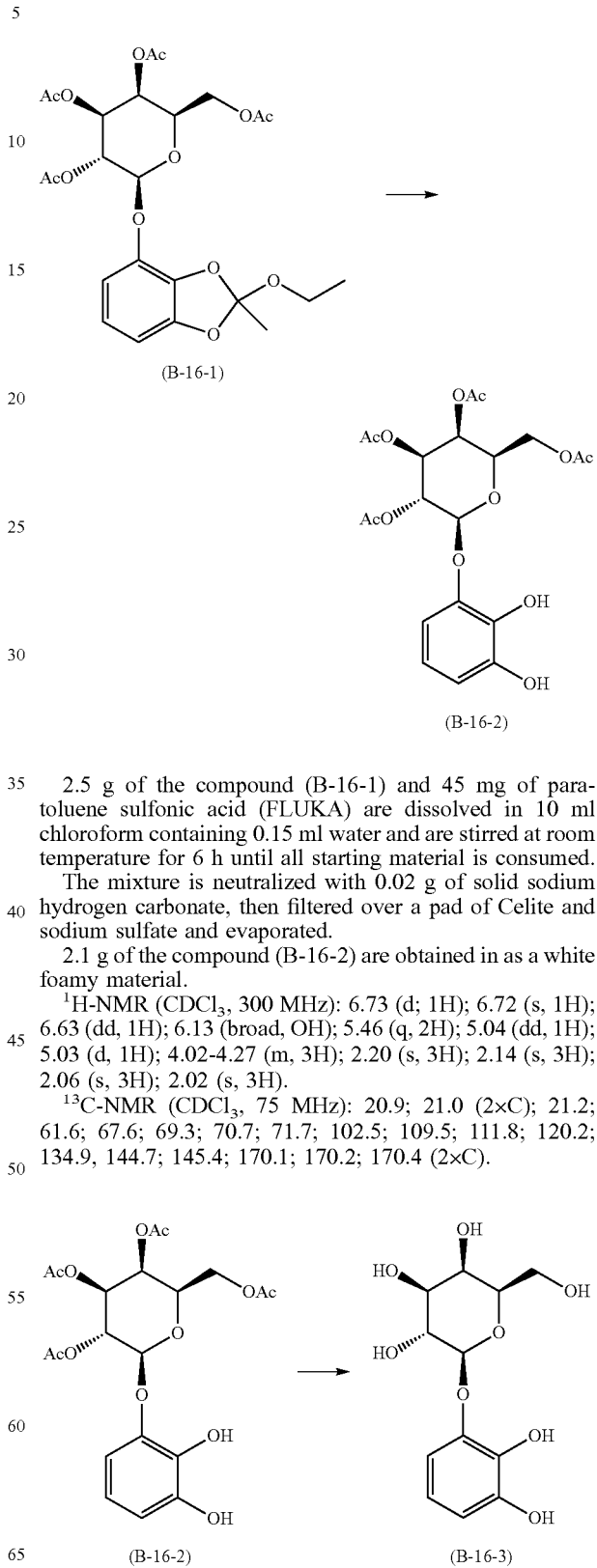

(B-16-1)

(B-16-2)

2.5 g of the compound (B-16-1) and 45 mg of paratoluene sulfonic acid (FLUKA) are dissolved in 10 ml chloroform containing 0.15 ml water and are stirred at room temperature for 6 h until all starting material is consumed.

The mixture is neutralized with 0.02 g of solid sodium hydrogen carbonate, then filtered over a pad of Celite and sodium sulfate and evaporated.

2.1 g of the compound (B-16-2) are obtained in as a white foamy material.

$^1$H-NMR (CDCl$_3$, 300 MHz): 6.73 (d; 1H); 6.72 (s, 1H); 6.63 (dd, 1H); 6.13 (broad, OH); 5.46 (q, 2H); 5.04 (dd, 1H); 5.03 (d, 1H); 4.02-4.27 (m, 3H); 2.20 (s, 3H); 2.14 (s, 3H); 2.06 (s, 3H); 2.02 (s, 3H).

$^{13}$C-NMR (CDCl$_3$, 75 MHz): 20.9; 21.0 (2×C); 21.2; 61.6; 67.6; 69.3; 70.7; 71.7; 102.5; 109.5; 111.8; 120.2; 134.9, 144.7; 145.4; 170.1; 170.2; 170.4 (2×C).

(B-16-2)

(B-16-3)

Deprotection of the compound (B-16-2) (2.0 g) is achieved as described for compound (B-9-3) with sodium methanolate.

1.3 g of the fully deprotected sugar B-16-3 are obtained.

¹H-NMR (CD₃OD, 300 MHz): 6.68 (dd, 1H); 6.50-6.54 (m, 2H); 4.68 (d, 1H); 3.75-3.90 (m, 4H); 3.53-3.65 (m, 2H).

¹³C-NMR (CD₃OD, 75 MHz): 61.30; 69.12; 71.35; 73.57; 76.00; 104.51; 109.21; 110.59; 118.32; 124.32; 145.17; 148.05.

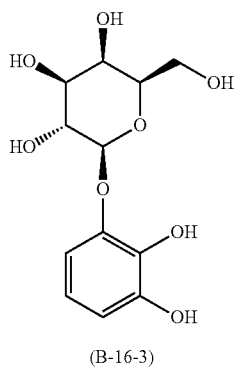

(B-16-3)

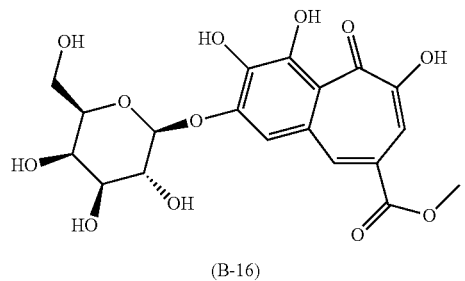

(B-16)

0.10 g of the compound (B-16-3) is dissolved at room temperature in 4 ml phosphate buffer (0.05 M, pH=5).

Under vigorous stirring 0.80 g of gallic acid methyl ester and 1 mg of laccase (*T. versicolor*: 26 U per mg) are added.

This mixture is stirred over night in an open beaker, filtered off and the filtrate washed with water.

0.07 g of a slightly orange powder corresponding to the benzotropolone compound of formula (B-16) is obtained.

¹H-NMR (DMSOD₆, 300 MHz): 8.26 (d, 1H); 7.56 (d, 1H); 7.51 (s, 1H); 5.16 (d, 1H); 3.88 (s, 3H); 3.40-3.70 (m, 6H).

Example A10—Laccase-Catalysed Synthesis of the Compound (B-15), (B-29)

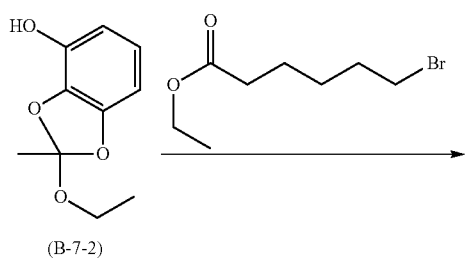

(B-7-2)

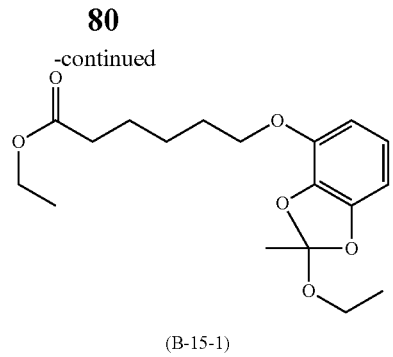

(B-15-1)

Starting phenol (B-7-2) (23.4 g) and commercial (6-bromo) ethyl hexanoate (28.0 g) are dissolved at room temperature in 200 ml dimethylformamide.

The mixture is treated with 82.6 g of potassium carbonate and vigorously stirred for 24 h.

For completion of the reaction the slurry is heated to 60° C. for 2 h.

After cooling down the mixture is filtered and the residue washed with ethyl acetate.

The washings and the filtrate are combined and successively extracted with 1 N hydrogen chloride, water and brine.

Usual work-up leaves a residue which is purified over a short silica pad (eluent: ethyl acetate-hexane/2-8).

37.2 g of the compound (B-15-1) are obtained as a colourless oil.

¹H-NMR (CDCl₃, 300 MHz): 6.69 (dd, 1H); 6.46 (ddd, 2H); 4.08 (q, 2H); 4.07 (t, 2H); 3.57 (dq, 1H); 2.30 (t, 2H); 1.78 (m, 5H); 1.68 (m, 2H); 1.50 (m, 2H); 1.24 (t, 3H); 1.70 (t, 3H).

¹³C-NMR (CDCl₃, 75 MHz): 14.60; 15.19; 24.93; 25.04; 25.84; 29.41; 34.54; 58.26; 60.46; 69.54; 101.58; 108.76; 121.45; 128.11; 135.00; 142.36; 147.96; 173.58.

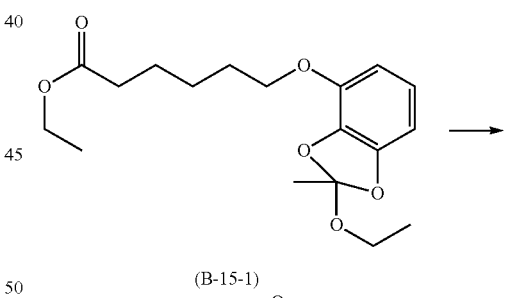

(B-15-1)

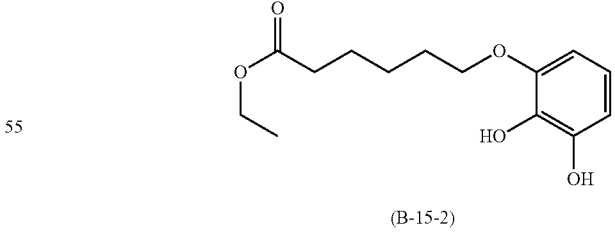

(B-15-2)

37.0 g of the compound (B-15-1) and 100 mg of para-toluene sulfonic acid (FLUKA) are dissolved in 200 ml chloroform containing 1.0 ml water and are stirred at room temperature until all starting material is consumed.

The mixture is neutralized with solid sodium hydrogen carbonate, then filtered over a pad of Celite and sodium sulfate and evaporated.

19.3 g of the compound (B-15-2) are obtained as a colourless oil.

¹H-NMR (CDCl₃, 300 MHz): 6.67 (t, 1H); 6.55 (dd, 1H); 6.40 (dd, 1H); 5.91 (broad, 2H); 4.12 (q, 2H); 3.97 (t, 2H); 2.31 (t, 2H); 1.77 (m, 2H); 1.67 (m, 2H); 1.46 (m, 2H); 1.22 (t, 3H).

¹³C-NMR (CDCl₃, 75 MHz): 14.58; 24.92; 25.84; 29.10; 34.46; 60.77; 69.09; 104.52; 109.02; 119.84; 133.14; 144.59; 146.78; 174.10.

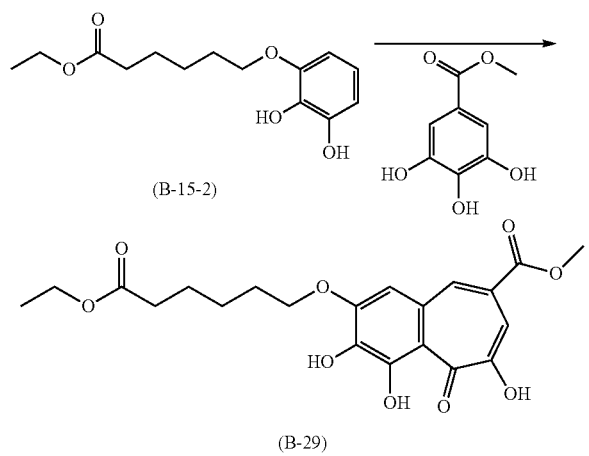

2.80 g of the compound (B-15-2) are dissolved in 40 ml phosphate buffer (0.05 M, pH=5) and 8.00 ml acetone at room temperature.

Under vigorous stirring 2.10 g of gallic acid methyl ester and 10 mg of horse radish peroxidase (FLUKA: ca. 200 U/mg) are added.

5 ml of a 3% hydrogen peroxide solution are then dropped to this mixture within 30 min. 16 ml acetone are added after 4 h and the mixture is stirred for 18 h, then additional 5 ml hydrogen peroxide solution are added and the mixture is stirred for 12 h.

The mixture is then centrifuged and the pellet repeatedly dissolved in water and centrifuged. Finally the pellet is centrifuged from water/aceton (vol/vol: 1-1) and then dried.

1.56 g of the compound (B-29) are obtained.

¹H-NMR (CDCl₃, 300 MHz): 8.33 (d, 2H); 7.89 (d, 1H); 7.02 (s, 1H); 6.33 (broad, 1H); 4.25 (t, 2H); 4.15 (t, 2H); 3.97 (s, 3H); 2.37 (t, 2H); 1.97 (m, 2H); 1.75 (m, 2H); 1.59 (m, 2H); 1.26 (t, 3H).

¹³C-NMR (CDCl₃, 75 MHz): 14.63; 24.94; 25.83; 29.01; 34.48; 53.41; 60.69; 69.34; 110.26; 114.71; 125.04; 131.26; 137.17; 138.96; 150.98; 153.47; 167.06; 173.74; 182.39.

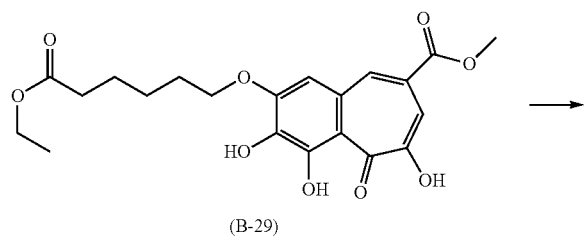

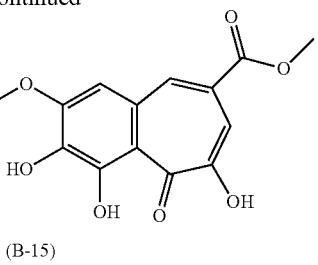

1.0 g of the compound (B-29) is dissolved at room temperature in 100 ml toluene containing 1.00 ml water and 0.5 g of the lipase NOVO 435 (Novozymes).

The reaction is stirred at 50° C. until complete ethylester cleavage.

The mixture is then filtered off, washed with acetone and evaporated to yield 0.88 g of acid (B-15).

¹H-NMR (DMSO₆, 300 MHz): 8.26 (d, 2H); 7.52 (d, 1H); 7.36 (s, 1H); 4.19 (t, 2H); 3.83 (s, 3H); 2.24 (t, 2H); 1.80 (m, 2H); 1.59 (m, 2H); 1.47 (m, 2H); 1.26 (t, 3H).

¹³C-NMR (DMSO₆, 75 MHz): 25.12; 25.88; 29.17; 34.51; 53.67; 69.26; 111.37; 114.61; 116.67; 123.95; 130.38; 138.52; 138.71; 152.08; 154.14; 167.16; 174.98; 183.47.

Example A11—Laccase-Catalysed Synthesis of the Compound (B-36)

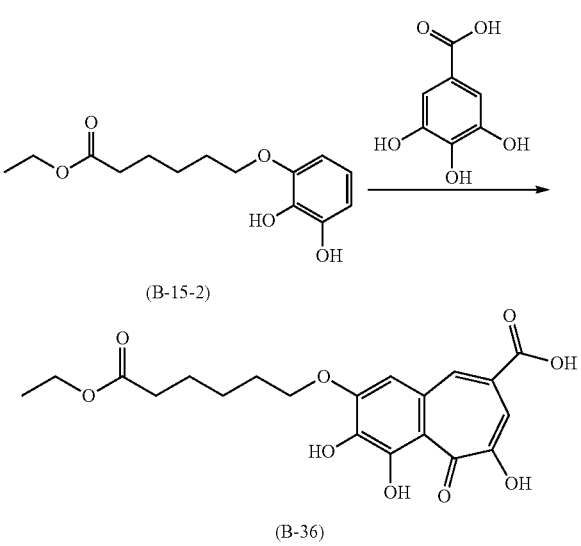

3.75 g of the compound (B-15-2) and 2.80 g of gallic acid (FLUKA) are dissolved at room temperature in a mixture of 18 ml acetone and phosphate-citric acid buffer (pH=5, 0.05 M). Under vigorous stirring 7 mg of commercial (FLUKA) horse radish peroxidise (ca. 200 U/mg) are added.

This mixture is treated over 1 h with 9 ml of a 3% solution of hydrogen peroxide.

After 6 h the mixture is filtered off and the residue extracted with a minimum of dichloromethane to yield 1.67 of acid (B-36).

¹H-NMR (DMSO₆, 300 MHz): 13.20 (OH); 9.60 (OH); 9.53 (OH); 8.30 (d, 1H); 7.60 (d, 1H); 7.42 (s, 1H); 4.20 (t, 2H); 4.02 (q, 2H); 2.29 (t, 3H), 1.79 (quint. 2H); 1.60 (m, 2H); 1.45 (m, 2H); 1.44 (t, 3H).

$^{13}$C-NMR (DMSO$_6$, 75 MHz): 14.97 25.04; 25.77; 29.07; 34.32; 60.43; 69.27; 111.17; 115.28; 116.79; 125.08; 130.72; 138.25; 138.74; 152.04; 152.09; 154.06; 168.27; 173.37; 183.51.

Example A12—Laccase-Catalysed Synthesis of the Compound (B-31)

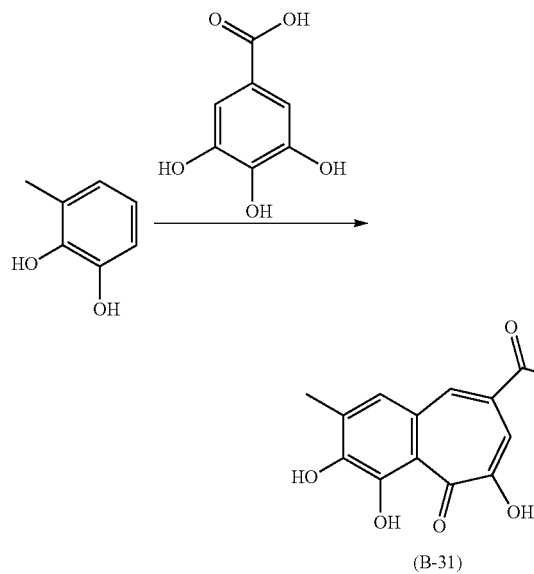

(B-31)

2.0 g of commercial (FLUKA) methylcatechol and 5.4 g of gallic acid are dissolved at room temperature in 100 ml phosphate buffer (0.05 M, pH=5) and 20 ml acetone. 7.0 mg of commercial (FLUKA) horse radish peroxidise (ca. 200 U/mg) are added and the mixture is subsequently treated with 10 ml hydrogen peroxide solution (3%) for one hour. After stirring for additional two hours at room temperature the resulting precipitate is filtered off, extensively washed with water and dried to yield 0.69 g of compound (B-31).

$^1$H-NMR (DMSO$_6$, 300 MHz): 8.24 (d, 1H); 7.63 (d, 1H); 7.51 (s, 1H); 2.35 (s, 3H).

$^{13}$C-NMR (DMSO$_6$, 75 MHz): 17.15; 116.27; 119.26; 124.27; 128.85; 129.70; 133.12; 139.16; 147.38; 150.75; 153.66; 168.18; 186.52.

Example A13—Laccase-Catalysed Synthesis of the Compound (B-34)

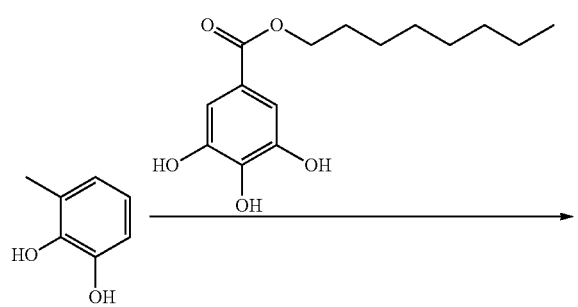

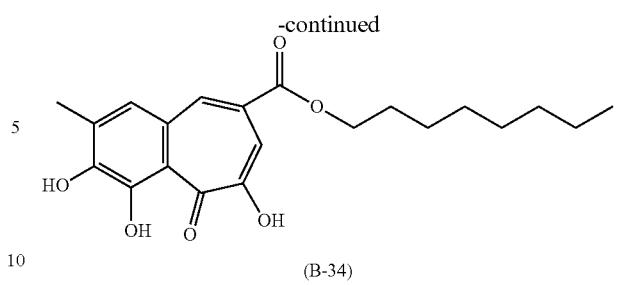

(B-34)

2.0 g of commercial (FLUKA) methylcatechol and 3.0 g of gallic acid octyl ester (FLUKA) are dissolved in 35 ml of phosphate buffer (0.05 M, pH=5) and 30 ml acetone at room temperature.

5.0 mg of commercial (FLUKA) laccase from *T. versicolor* are added and the mixture is stirred for 24 h at room temperature.

The resulting precipitate is filtered off, extensively washed with water and tried to yield 2.10 g of compound (B-34).

$^1$H-NMR (CDCl$_3$, 300 MHz): 8.30 (d, 1H); 8.17 (OH); 7.90 (d, 1H); 7.31 (s, 1H); 6.61 (OH); 4.45 (t, 2H); 2.46 (s, 3H), 1.80 (quint. 2H); 1.30-1.50 (m, 10H); 0.89 (t, 3H).

$^{13}$C-NMR (CDCl$_3$, 75 MHz): 14.46; 16.55; 23.02; 26.40; 29.05; 29.55; 29.62; 32.16; 66.69; 115.98; 118.36; 124.43; 129.55; 129.59; 132.21; 139.88; 146.25; 149.39; 152.79; 168.68; 183.42.

UV-Vis (MeOH): $\lambda_{max}$=282 nm ($\epsilon$=27979), $\lambda_{max}$=398 nm ($\epsilon$=12446).

Example A14—Laccase-Catalysed Synthesis of the Compound (B-33)

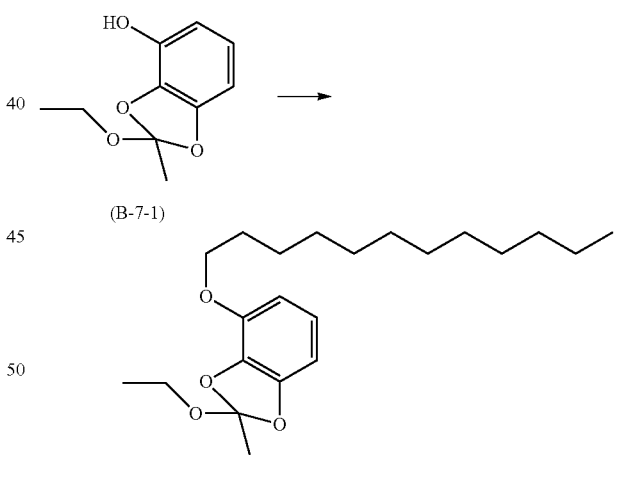

30.0 g of the compound (B-7-1), 37.5 ml commercial (FLUKA) 1-bromo-dodecane, 105 g of potassium carbonate and 22.9 g of sodium iodide are refluxed in 300 ml acetone for 2 h. Filtration and removal of the solvent leaves a residue which is purified over a short silica pad (eluent: ethyl acetate-hexane/1-10).

33.1 g of the compound (B-33-1) is obtained as a colourless oil.

$^1$H-NMR (CDCl$_3$, 300 MHz): 6.74 (t, 1H); 6.49 (t, 2H); 4.08 (t, 2H); 3.63 (dq, 2H); 1.82 (s, 3H); 1.77 (quint. 2H); 1.28-1.50 (m, 10H); 1.20 (t, 3H); 0.89 (t, 3H).

¹³C-NMR (CDCl₃, 75 MHz): 14.48; 15.23; 24.99; 26.28; 29.71; 29.75 (2×C); 29.94; 29.96; 30.00; 30.02; 32.23; 58.30; 69.95; 101.51; 108.72; 121.43; 128.14; 135.05; 142.53; 147.96.

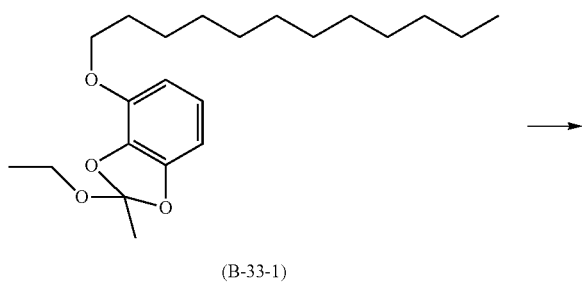

(B-33-1)

24.3 g of the compound (B-33-1) and 115 mg para-toluene sulfonic acid (FLUKA) are dissolved in 150 ml chloroform containing 0.95 ml water and are stirred at room temperature until all starting material is consumed.

The mixture is then extracted with brine and water, dried over sodium sulfate and evaporated.

19.3 g of the compound (B-33-2) are obtained as a colourless oil.

¹H-NMR (CDCl₃, 300 MHz): 6.74 (t, 1H); 6.60 (dd, 1H); 6.46 (dd, 1H); 5.45 (broad, 2H); 4.03 (t, 2H); 1.81 (quint. 2H); 1.27-1.49 (m, 18H); 0.90 (t, 3H).

¹³C-NMR (CDCl₃, 75 MHz): 14.45; 23.07; 26.38; 29.66; 29.71; 29.76; 29.94; 29.97; 30.00; 30.03; 32.29; 69.51; 104.33; 108.90; 119.95; 132.88; 144.26; 146.61.

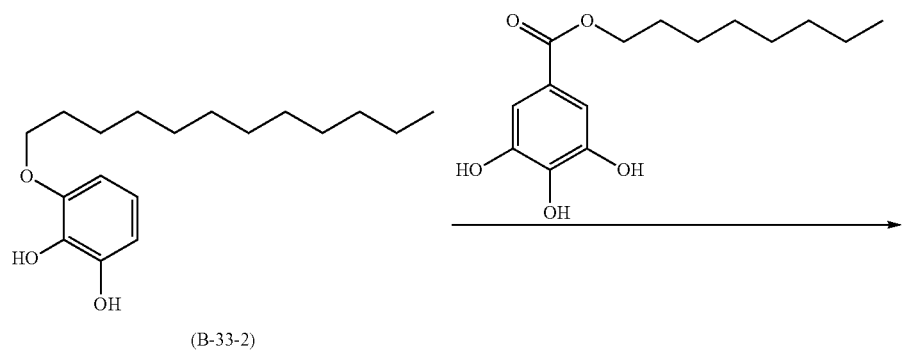

(B-33-2)

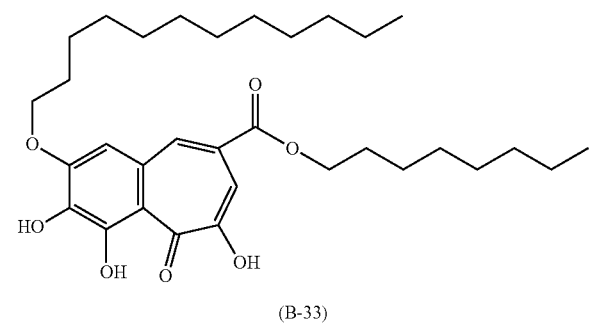

(B-33)

-continued

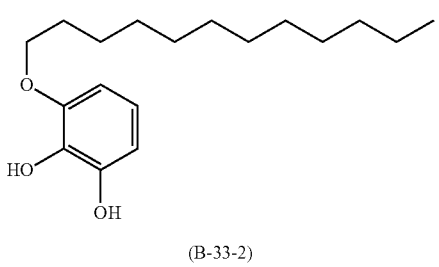

(B-33-2)

0.80 g of the compound (B-33-2) and 1.15 g of gallic acid octyl ester (FLUKA) are dissolved in 30 ml acetone and then 9 ml of phosphate buffer (0.05 M, pH=5) are added.

10.0 mg of commercial (FLUKA) laccase from *T. versicolor* are added and the mixture is stirred for 48 h at room temperature.

The resulting precipitate is centrifuged off, extensively washed with water-acetone (vol/vol 1-1) and lyophilized from dioxane/water to give 0.42 g of the compound (B-33).

¹H-NMR (CDCl₃, 300 MHz): 8.34 (OH); 8.33 (d, 1H); 7.89 (d, 1H); 7.02 (s, 1H); 6.28 (OH); 4.36 (t, 2H); 4.24 (t, 2H); 1.94 (quint. 2H); 1.81 (quint. 2H); 1.15-1.56 (m, 28H); 0.89 (t, 6H).

¹³C-NMR (CDCl₃, 75 MHz): 14.49 (2×C); 23.02; 23.06; 26.29; 26.38; 29.06; 29.39; 29.55; 29.62; 29.71 (2×C); 29.95

(2×C); 29.99 (2×C); 32.15; 32.28; 66.78; 69.79; 110.28; 114.79; 116.20; 125.48; 131.44; 137.08; 138.99; 150.90; 151.12; 153.49; 166.66; 182.41.

Example A15—Laccase-Catalysed Synthesis of the Compound B-35

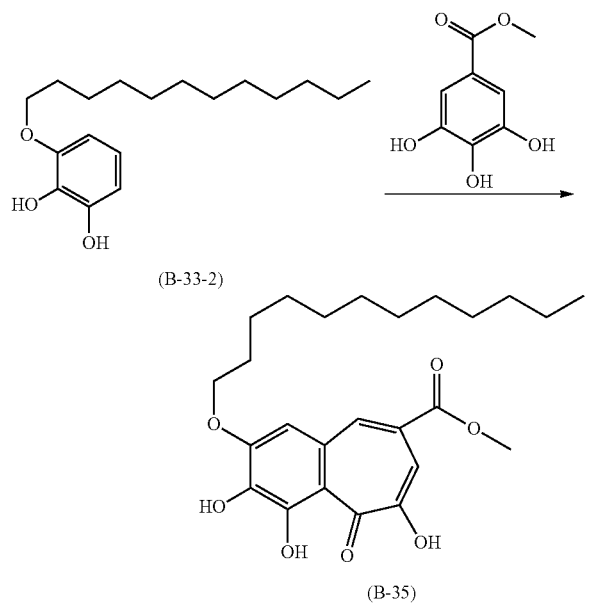

0.50 g of the compound (B-33-2) and 0.63 g of gallic acid methyl ester (FLUKA) are dissolved in 20 ml acetone.

12 ml phosphate buffer (0.05 M, pH=5) are added.

5.0 mg of commercial (FLUKA) laccase from *T. versicolor* are added and the mixture is stirred for 24 h at room temperature.

The resulting precipitate is centrifuged off, extensively washed with water and lyophilized from dioxane/water to give 0.62 g of the compound (B-35).

$^1$H-NMR (CDCl$_3$, 300 MHz): 8.34 (d, 1H); 8.33 (OH); 7.89 (d, 1H); 7.04 (s, 1H); 6.27 (OH); 4.25 (t, 2H); 3.97 (s, 3H); 1.94 (quint. 2H); 1.52 (quint. 2H); 1.25-1.50 (m, 12H); 0.88 (t, 6H).

$^{13}$C-NMR (CDCl$_3$, 75 MHz): 14.49; 23.05; 26.27; 29.37; 29.70; (2×C); 29.89; 29.95; 29.99; 30.01; 32.27; 54.41; 69.79; 110.28; 114.70; 116.19; 125.09; 131.36; 137.12; 139.02; 150.93; 151.11; 153.52; 167.10; 182.42.

Example A16—Laccase-Catalysed Synthesis of the Compound B-32

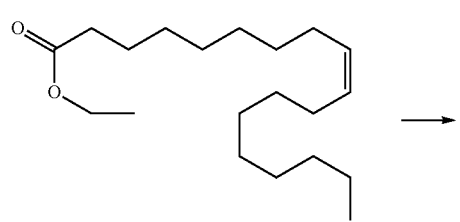

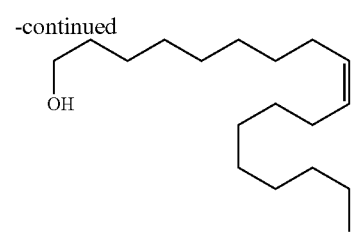

25.0 g of commercial ethyl oleate (FLUKA), dissolved in 100 ml dry tetrahydrofuran are dropped at 0° C. to a slurry of 3.05 g lithium aluminium hydride in 50 ml dry tetrahydrofurane in an argon atmosphere within 70 min.

After complete consumption of starting ester, excess hydride is quenched by successive addition of 10 ml ice-water and 10 ml 1 N sodium hydroxide solution.

The resulting precipitate is filtered over a Celite pad.

The filtrate is dried over sodium sulphate and evaporated to give 21.5 g of alcohol (B-32-1).

$^1$H-NMR (CDCl$_3$, 300 MHz): 5.34 (dt, 2H); 3.63 (t, 2H); 2.04 (m, 4H); 1.56 (quint. 2H); 1.24-1.40 (m, 26H); 0.88 (t, 6H).

$^{13}$C-NMR (CDCl$_3$, 75 MHz): 14.47; 23.05; 26.12; 27.56; 27.580; 29.60; 29.68; 29.77; 29.86; 29.88; 30.02; 30.11; 30.13; 32.26; 33.17; 63.34; 129.99; 130.12.

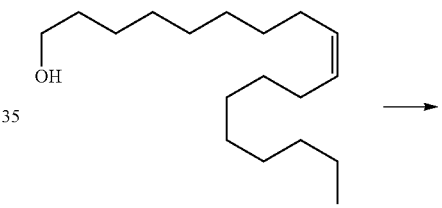

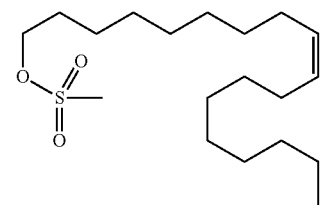

21.5 g of the compound (B-32-1) are dissolved together with 11 ml of pyridine in 120 ml dichloromethane and cooled to 0° C.

10 ml mesylchloride are added to this mixture and stirring is continued until complete consumption of the starting alcohol.

The mixture is then successively extracted with 1N hydrogen chloride, sat. sodium hydrogen carbonate and brine.

Usual product recovery gives 26.7 g of the compound (B-32-2).

$^1$H-NMR (CDCl$_3$, 300 MHz): 5.33 (dt, 2H); 4.20 (t, 2H); 2.98 (s, 3H); 2.01 (m, 4H); 1.71 (quint. 2H); 1.24-1.42 (m, 26H); 0.87 (t, 3H).

$^{13}$C-NMR (CDCl$_3$, 75 MHz): 14.47; 23.04; 25.78; 27.53; 27.58; 29.37; 29.50 (2×C); 29.68 (2×C); 29.87; 30.05; 30.12; 32.25; 37.71; 70.44; 129.89; 130.19.

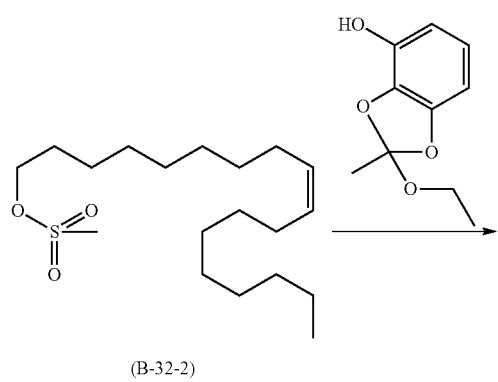

(B-32-2)

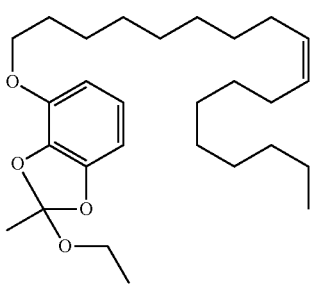

(B-32-3)

13.5 g of the compound (B-32-2), 23.9 g of the compound (B-7-2), 0.7 g of sodium iodide and 47.6 g of potassium carbonate are added to 500 ml acetone and heated to 50° C. for two days. After consumption of the starting material the mixture is filtered off, the solvent evaporated and the residue passed over a short silica pad (eluent: hexane ethyl acetate vol/vol 2-1).

29.2 g of the compound (B-32-3) are obtained.

¹H-NMR (CDCl₃, 300 MHz): 6.74 (t, 1H); 6.50 (dt, 2H); 5.35 (dt, 2H); 4.08 (t, 2H); 3.63 (dq, 2H); 2.03 (m, 4H); 1.83 (s, 3H); 1.80 (quint. 2H); 1.26-1.40 (m, 26H); 1.20 (t, 3H); 0.89 (t, 3H).

¹³C-NMR (CDCl₃, 75 MHz): 14.49; 15.23; 23.06; 24.99; 26.29; 27.58; 29.60; 29.61; 29.70; 29.74; 29.84; 29.89; 30.03; 30.07; 30.14; 32.28; 58.31; 69.94; 101.52; 108.72; 121.44; 128.14; 129.98; 130.14; 135.04; 142.53; 147.96.

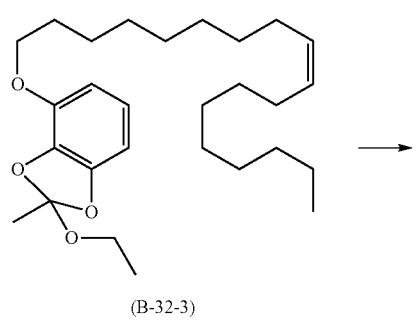

(B-32-3)

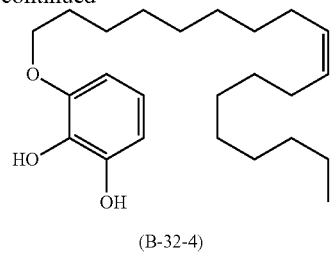

(B-32-4)

21.3 g of the compound (B-32-3) and 50 mg of para-toluene sulfonic acid (FLUKA) are dissolved in 80 ml chloroform containing 1 ml water and are stirred at room temperature until all starting material is consumed.

The mixture is dried over sodium sulfate and evaporated.

Compound (B-32-4) is obtained in yields of 16.7 g as colourless oil from passage over a short silica pad (eluent: hexane ethyl acetate vol/vol 5-2).

¹H-NMR (CDCl₃, 300 MHz): 6.74 (t, 1H); 6.50 (dt, 2H); 5.35 (dt, 2H); 4.08 (t, 2H); 3.63 (dq, 2H); 2.03 (m, 4H); 1.80 (quint. 2H); 1.26-1.40 (m, 26H); 0.89 (t, 3H).

¹³C-NMR (CDCl₃, 75 MHz): 14.49; 23.06; 24.99; 26.29; 27.58; 29.60; 29.61; 29.70; 29.74; 29.84; 29.89; 30.03; 30.07; 30.14; 32.28; 58.31; 69.94; 101.52; 108.72; 121.44; 128.14; 129.98; 130.14; 135.04; 142.53; 147.96.

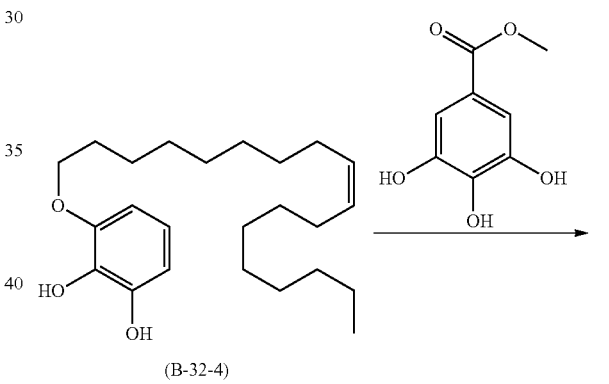

(B-32-4)

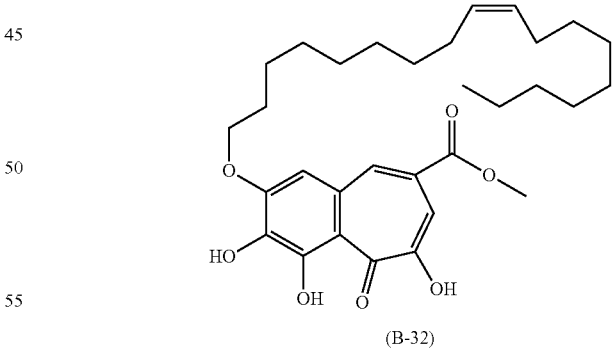

(B-32)

0.80 g of the compound (B-32-4) and 0.78 g of gallic acid methyl ester (FLUKA) are dissolved in 25 ml acetone and then 8 ml of phosphate buffer (0.05 M, pH=5) are added. 5.0 mg of commercial (FLUKA) laccase from *T. versicolor* are added and the mixture is stirred for 24 h at room temperature.

The mixture is then extracted with dichloromethane and the organic phase repeatedly washed with water to give 0.23 g of the compound (B-32).

¹H-NMR (DMSO₆, 300 MHz): 8.33 (s, 1H); 7.56 (s, 1H); 7.44 (s, 1H); 5.35 (dt, 2H); 4.21 (t, 2H); 3.88 (s, 3H); 3.63 (dq, 2H); 2.03 (m, 4H); 1.80 (quint. 2H); 1.17-1.35 (m, 26H); 0.89 (t, 3H).

¹³C-NMR (DMSO₆, 75 MHz): 14.75; 22.92; 26.19; 27.42; 29.42 (3×C); 29.51 (3×C); 29.66; 29.92 (2×C); 32.10; 53.69; 69.44; 111.43; 114.65; 116.73; 124.04; 130.27 (2×C); 130.45 (2×C); 138.56; 138.75; 152.11; 154.24; 167.23; 183.57.

Example A17—Laccase-Catalysed Synthesis of the Compound (B-37)

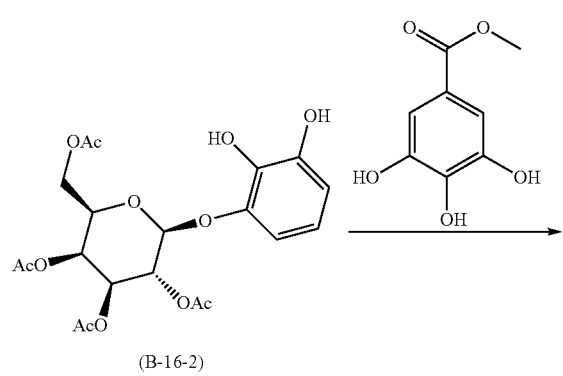

1.50 g of the compound (B-16-2) and 3.0 g of gallic acid methyl ester (FLUKA) are dissolved in 330 ml phosphate buffer (0.05 M, pH=5) at room temperature.

8.0 mg (28.6 U/g) of commercial (FLUKA) laccase from *T. versicolor* are added and the mixture is stirred for 24 h at room temperature.

The mixture is then filtered off and the residue dried to yield 1.02 g of compound (B-37).

¹H-NMR (CD₃OD, 300 MHz): 8.25 (d, 1H); 7.75 (d, 1H); 7.33 (s, 1H); 5.45-5.57 (m, 4H); 5.29 (dd, 1H); 4.38 (t, 1H); 4.25 (d, 1H); 3.90 (s, 3H); 2.03-2.18 (4×s, 3H each).

¹³C-NMR (CD₃OD, 75 MHz): 20.00 (2×C); 20.22; 20.58; 52.93; 62.12; 67.74; 69.12; 71.05; 71.97; 99.53; 112.89; 113.72; 118.05; 124.61; 129.67; 138.24; 139.16; 148.75; 152.89; 154.18; 167.83; 170.13; 170.34; 170.59; 171.05; 183.50.

Example A18—Laccase-Catalysed Synthesis of the Compound (B-38)

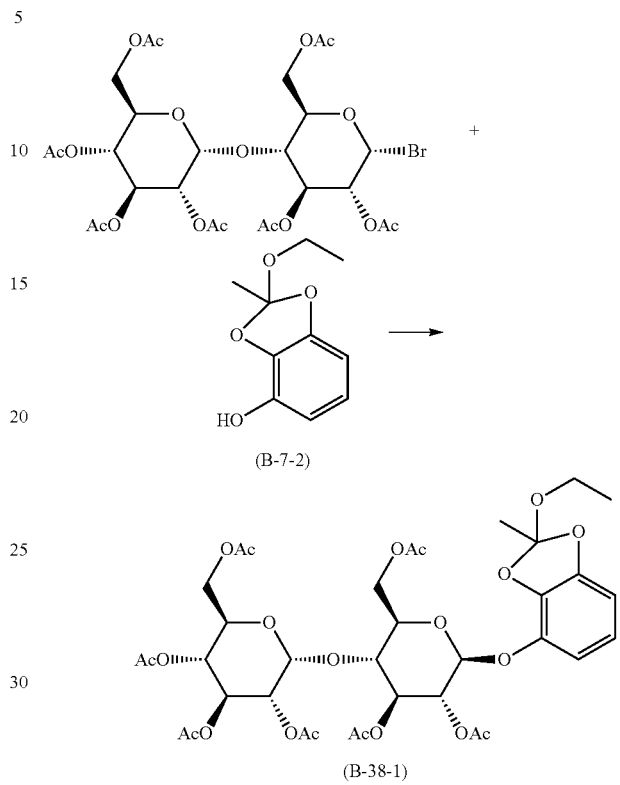

5.0 g of peracetylated maltosyl bromide (obtained according lit.: K. P. Ravindranathan et al. J. Carbohydr. Chem. 1990, 9(5), 777), 1.40 g of compound (B-7-2) and 2.50 g of potassium carbonate are vigorously stirred at room temperature in 15 ml chloroform, containing 0.23 g tributyl benzyl ammonium bromide for 2 days.

The mixture is filtered over Celite and the solvent evaporated.

The residue is purified over a silica gel column (eluent: hexane ethyl acetate vol/vol 1-1) to yield 3.4 g of a colourless foam (B-38-1).

¹H-NMR (CDCl₃, 300 MHz): 6.68 (dt, 1H); 6.52 (dt, 2H); 5.37 (dd, 1H); 5.30 (t, 1H), 5.26 (dt, 1H); 5.16 (dd, 1H); 4.95-5.04 (m, 2H); 4.82 (dd, 1H); 4.36 (m, 1H); 4.20 (m, 2H); 4.04 (m, 1H); 3.98 (dd, 1H); 3.95 (m 1H); 3.78 (m, 1H); 3.51 (dq, 2H); 1.93-2.10 (7×s, 3H each); 1.74 (d, 3H); 1.18 (dt, 3H).

¹³C-NMR (CDCl₃, 75 MHz):

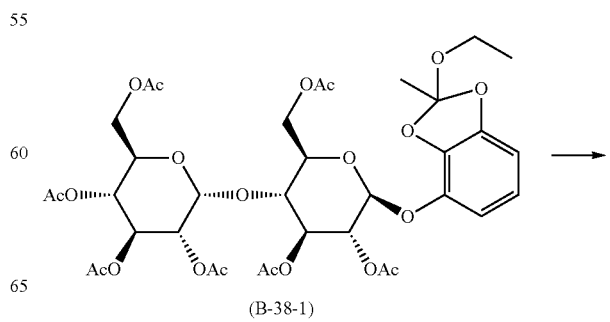

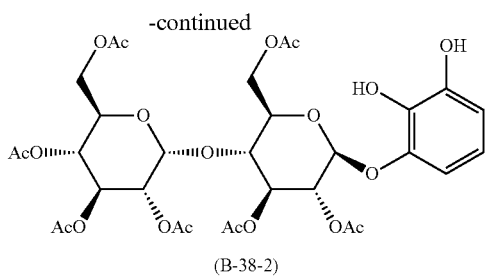

(B-38-2)

1.30 g of the compound (B-38-1) and 13 mg of para-toluene sulfonic acid (FLUKA) are dissolved in 10 ml chloroform containing 0.06 ml water and are stirred at room temperature until all starting material is consumed.

The mixture is dried over sodium sulfate and evaporated.

Compound B-38-2 is obtained in yields of 1.19 g as a foam.

$^1$H-NMR (CDCl$_3$, 300 MHz): 6.66 (d, 2H); 6.43 (m, 1H); 6.06 (OH); 5.37 (dd, 1H); 5.28 (dd, 1H); 5.26 (dd, 1H); 5.03 (dd, 1H), 4.97 (dd, 1H); 4.87 (d, 1H); 4.80 (dd, 1H); 4.49 (dd, 1H); 4.19 (ddd, 1H); 4.02 (dd, 1H); 4.00 (t, 1H); 3.90 (ddd, 1H); 3.7 (ddd, 1H); 1.93-2.08 (7×s, 3H each).

$^{13}$C-NMR (CDCl$_3$, 75 MHz): 20.94 (2×C); 21.05 (2×C); 22.00 (2×C); 21.25; 61.86; 62.58; 68.34; 69.00; 69.56; 70.32; 72.27; 72.70; 73.18; 74.97; 95.96; 101.97; 110.76; 112.18; 120.40; 135.38; 144.59; 145.71; 169.49; 170.00; 170.08; 170.14; 170.53; 170.61 (2×C).

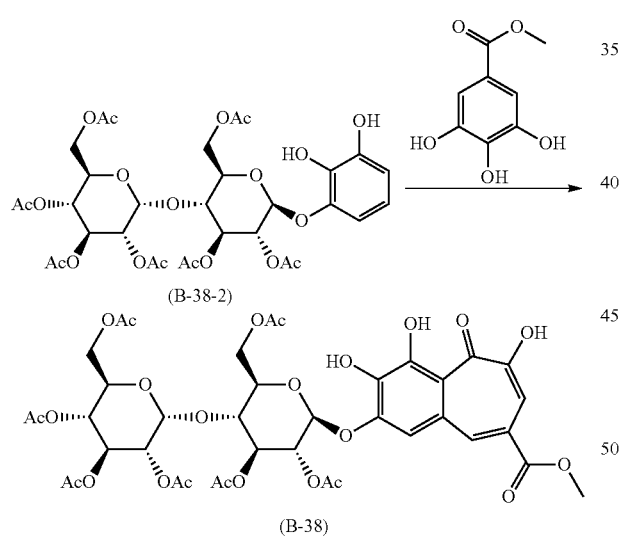

0.37 g of the compound (B-38-2) and 0.49 g of gallic acid methyl ester (FLUKA) are dissolved in 20 ml phosphate buffer (0.05 M, pH=5) at room temperature.

2.0 mg (28.6 U/g) of commercial (FLUKA) laccase from *T. versicolor* are added and the mixture is stirred for 24 h at room temperature.

The mixture is then extracted with ethyl acetate, dried over sodium sulphate evaporated to yield 0.34 g of the compound (B-38).

$^1$H-NMR (CD$_3$OD, 300 MHz): 7.84 (d, 1H); 7.45 (d, 1H); 7.02 (s, 1H); 5.35-5.50 (m, 4H); 5.16 (t, 1H); 5.07 (tt, 1H), 4.92 (dd, 1H); 4.67 (d, 1H); 4.23-4.34 (m, 2H); 4.04-4.21 (m, 4H); 3.87 (s, 3H); 1.99-2.14 (7×s, 3H each).

$^{13}$C-NMR (CD$_3$OD, 75 MHz): 19.62; 19.66; 19.78; 19.88; 19.96; 20.10; 20.23; 52.59; 60.47; 62.12; 68.65; 68.94; 69.77; 70.57; 72.19; 73.03; 74.35; 75.14; 96.48; 98.93; 107.90; 114.92; 116.78; 123.96; 129.48; 138.97; 148.61; 152.02; 153.61; 166.72; 169.97; 170.32; 170.43; 170.61; 170.70; 171.09; 171.25; 171.29; 182.98.

Example A19—Laccase-Catalysed Synthesis of the Compound (B-39)

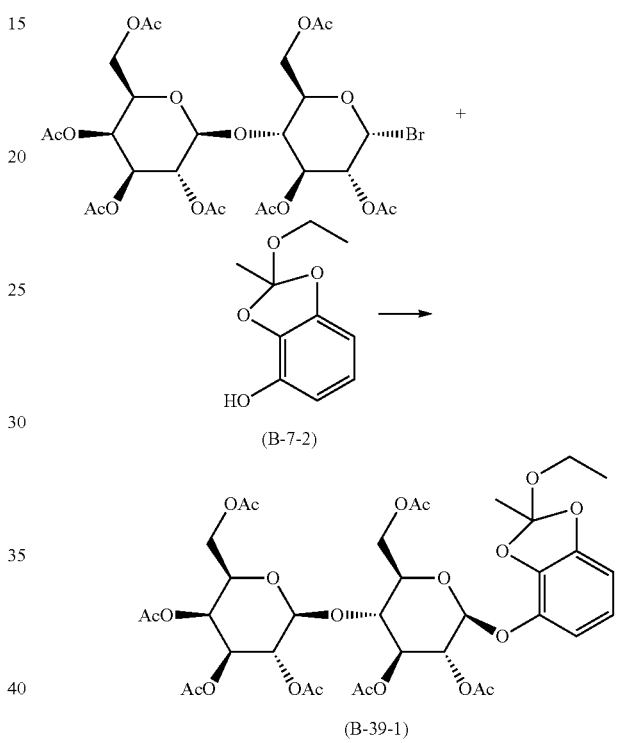

10.0 g of peracetylated lactosyl bromide (obtained according lit.: K. P. Ravindranathan et al. J. Carbohydr. Chem. 1990, 9 (5), 777), 2.80 g of the compound (B-7-2) and 5.20 g of potassium carbonate are vigorously stirred at room temperature for 3 days in 33 ml chloroform containing 0.23 g of tributyl benzyl ammonium bromide and 0.20 ml water. The mixture is filtered over Celite and the solvent evaporated.

The residue is purified over a silica gel column (eluent: hexane ethyl acetate vol/vol 1-1) to yield 5.7 g of a colourless foam (B-39-1).

$^1$H-NMR (CDCl$_3$, 300 MHz): 6.74 (t, 1H); 6.59 (dt, 2H); 5.43 (dd, 1H); 5.36 (t, 1H); 5.33 (dt, 1H), 5.23 (dd, 1H); 5.06 (m, 2H); 4.86 (dd, 1H); 4.45 (m, 1H); 4.25 (m, 2H); 4.10 (dd, 1H); 4.04 (dd, 1H); 3.95 (m 1H); 3.80 (m, 1H); 3.58 (dq, 2H); 1.99-2.10 (7×s, 3H each); 1.81 (d, 3H); 1.21 (dt, 3H).

$^{13}$C-NMR (CDCl$_3$, 75 MHz): 15.16; 20.88; 20.97; 21.03; 21.08; 21.17; 21.23; 21.32; 24.92; 58.40; 61.84; 62.26; 68.35; 68.83; 69.59; 70.31; 72.30; 72.66; 72.87; 73.00; 99.62; 99.69; 103.78; 112.86; 121.56; 128.48; 135.82; 139.16; 148.32; 169.45; 169.69; 169.98; 170.16; 170.31; 170.41; 170.56.

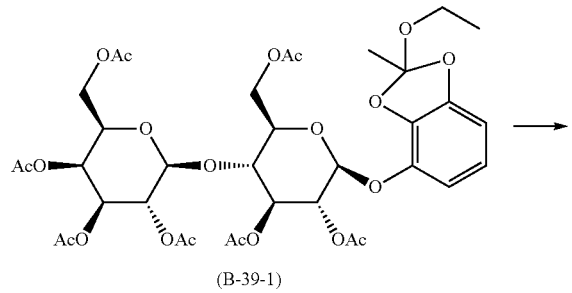

(B-39-1)

(B-39-2)

4.32 g of the compound (B-39-1) and 55 mg of para-toluene sulfonic acid (FLUKA) are dissolved in 20 ml chloroform containing 0.20 ml water and are stirred at room temperature until all starting material is consumed.

The mixture is dried over sodium sulfate and evaporated.

The compound (B-39-2) is obtained in yields of 3.36 g as colourless oil from passage over a short silica pad (eluent: hexane ethyl acetate vol/vol 1-1).

$^1$H-NMR (CDCl$_3$, 300 MHz): 6.73 (d, 2H); 6.51 (dd, 1H); 6.19 (OH); 5.45 (OH); 5.36 (dd, 1H); 5.28 (t, 1H); 5.16 (dd, 1H), 5.11 (dd, 1H); 4.98 (dd, 1H); 4.88 (d, 1H); 4.56 (dd, 1H); 4.54 (d, 1H); 4.05-4.18 (m, 3H); 3.84-3.93 (m, 2H); 3.74 (ddd, 1H); 1.98-2.16 (7×s, 3H each).

$^{13}$C-NMR (CDCl$_3$, 75 MHz): 20.90 (2×C); 21.03 (2×C); 21.08 (2×C); 21.24; 61.86; 62.60; 68.34; 68.99; 69.56; 70.33; 72.27; 72.73; 73.15; 74.99; 95.96; 101.90; 110.69; 112.18; 120.37; 135.37; 144.61; 145.69; 169.50; 170.01; 170.10; 170.14; 170.55; 170.61 (2×C).

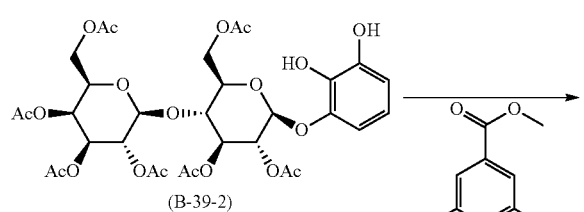

(B-39-2)

(B-39)

1.0 g of the compound (B-39-2) and 2.40 g of gallic acid methyl ester (FLUKA) are dissolved in 150 ml phosphate buffer (0.05 M, pH=5) at room temperature.

10.0 mg (286 U) of commercial (FLUKA) laccase from *T. versicolor* are added and the mixture is stirred for 24 h at room temperature.

The mixture is then filtered off and the residue washed with water.

The residue is subsequently evaporated from ethyl acetate, repeatedly.

0.81 g of the compound (B-39) is obtained.

$^1$H-NMR (DMSO$_6$, 300 MHz): 10.01 (OH); 9.79 (OH); 8.25 (d, 1H); 7.59 (d, 1H); 7.41 (s, 1H); 5.82 (d, 1H); 5.40 (t, 1H); 5.31 (d, 1H); 5.25 (dd, 1H); 5.05 (dd, 1H), 4.99 (t, 1H); 4.90 (dd, 1H); 4.46 (dd, 1H); 4.00-4.21 (m, 6H); 3.89 (s, 3H); 1.94-1.99 (7×s, 3H each).

$^{13}$C-NMR (CD$_3$OD, 75 MHz): 19.70; 19.75; 19.88; 19.96; 20.05; 20.22; 20.35; 52.67; 60.49; 62.15; 68.67; 68.84; 68.96; 69.78; 70.55; 72.18; 73.06; 75.10; 95.53; 100.10; 108.94; 114.70; 116.64; 123.87; 129.37; 138.95; 148.56; 151.88; 153.06; 166.60; 169.99; 170.34; 170.47; 170.63; 170.73; 171.06; 171.11; 171.29; 182.76.

Example A20—Laccase-Catalysed Synthesis of the Compound (B-45)

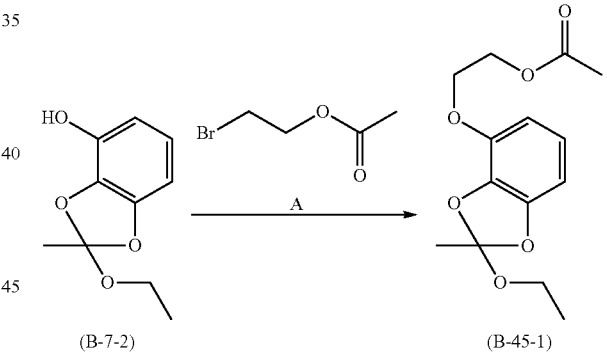

(B-7-2)                                                          (B-45-1)

4.26 g of bromoacetate A, obtained from acetylation of commercial bromoethanol with acetyl chloride applying standard conditions, 5.00 g of phenol (B-7-2), 2.86 g of commercial potassium tert. butoxide and 15 mg of sodium iodide are dissolved in 50 ml of dry dimethylformamide in an argon atmosphere and heated to 75° C. for 18 h. After cooling down to room temperature the red solution is successively extracted with 1 N hydrogen chloride, saturated sodium hydrogen carbonate, water and brine. The solution is dried over magnesium sulfate, filtered and evaporated to give an oily residue, which is purified on a silica gel column (eluent: hexane ethyl acetate vol/vol 4-1). 3.33 g of pure white B-45-1 are obtained.

$^1$H-NMR (CDCl$_3$, 300 MHz): 6.75 (dd, 1H); 6.52 (dd, 2H); 4.38-4.43 (m, 2H); 4.29-4.35 (m, 2H); 3.60 (dq, 2H); 2.09 (s, 3H); 1.82 (s, 3H); 1.21 (t, 3H).

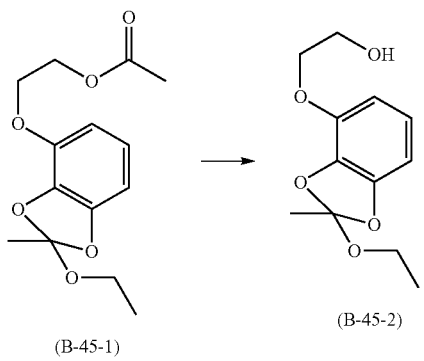 [SMILES: CCOC1(C)Oc2cccc(OCCOC(C)=O)c2O1 ; CCOC1(C)Oc2cccc(OCCO)c2O1]

2.45 g of acetate B-45-1 are dissolved at room temperature in 6 ml dry methanol containing 0.05 g of sodium methanolate. The mixture is stirred until consumption of starting ester, neutralized with weakly acidic ion exchanger, filtered and evaporated to leave a brown syrup. Purification over a silica gel column (eluent: hexane ethyl acetate vol/vol 4-1) gives 1.92 g of alcohol B-45-2 as a colorless oil.

$^1$H-NMR (CDCl$_3$, 300 MHz): 6.75 (dd, 1H); 6.54 (ddd, 2H); 4.21 (dt, 2H); 3.92-3.98 (m. 2H); 3.60 (q, 2H); 2.22 (t, OH); 1.82 (s, 3H); 1.21 (t, 3H).

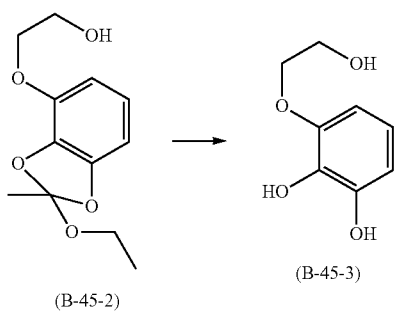 [SMILES: CCOC1(C)Oc2cccc(OCCO)c2O1 ; OCCOc1cccc(O)c1O]

2.59 g of acetal B-45-2 and 50 mg of para-toluene sulfonic acid are dissolved in 20 ml of chloroform containing 0.40 ml of water and are stirred at room temperature until complete consumption of starting material. The resulting white precipitate is filtered off and rinsed with chloroform to give 1.30 g of phenodiol B-45-3. An additional crop of product can be recovered by work-up of the mother liquors.

$^1$H-NMR (CD$_3$OD, 300 MHz): 6.59 (ddd, 1H); 6.44 (dd, 2H); 4.01 (q, 2H); 3.86 (t. 2H).

$^{13}$C-NMR (CD$_3$OD, 75 MHz): 60.72; 70.47; 104.80; 109.17; 1118.78; 134.54; 145.62; 147.51.

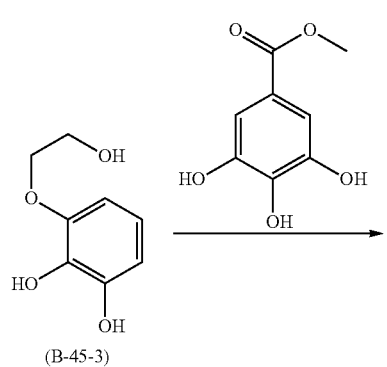

1.00 g of the compound (B-45-3) and 1.089 g of gallic acid methyl ester (FLUKA) are dissolved in 20 ml phosphate buffer and 6 ml acetone (0.05 M, pH=5) at room temperature. 4.0 mg (28.6 U/g) of commercial (FLUKA) laccase from *T. versicolor* are added and the mixture is stirred for 24 h at room temperature.

The resulting precipitate is filtered off (first filtrate) and thoroughly rinsed with deionized water. After drying and recrystallization from ethyl acetate 0.42 g of the compound B-45 are obtained. Renewed incubation of the first filtrate and filtration gives an additional crop of 0.43 g of product.

$^1$H-NMR (DMSO$_6$, 300 MHz): 9.60 (broad, OH); 8.30 (d, 1H); 7.54 (d, 1H); 7.42 (s, 1H); 5.00 (broad, OH); 4.24 (t, 2H); 3.87 (s, 3H); 3.80 (t, 2H).

$^{13}$C-NMR (DMSO$_6$, 75 MHz): 53.72; 60.25; 71.40; 111.31; 114.61; 116.89; 124.08; 130.41; 138.46; 138.69; 151.95; 152.16; 154.23; 167.22; 183.66.

Example A21—Lipase-Catalysed Synthesis of the Compound (B-19)

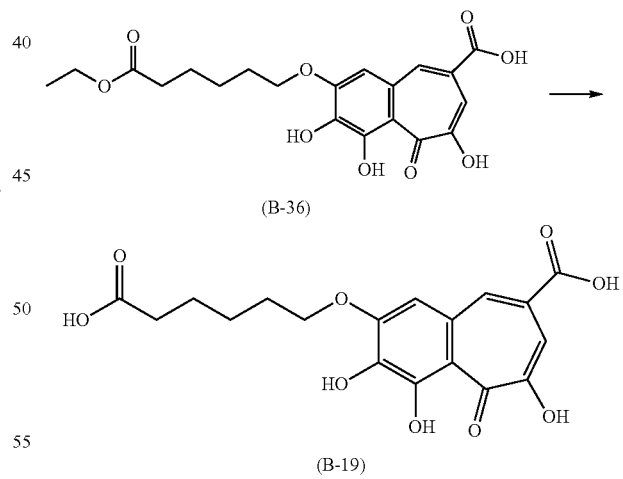

0.72 g of compound B-36 are dissolved in 20 ml of dioxane and 1 ml water. The mixture is heated to 60° C. and treated with 0.40 g of commercial lipase (NOVO 435 from Novozymes) under a slight vacuum (500 mmbar). After consumption of starting material (TLC-control), the mixture is filtered and lyophilized to give 0.60 g of the diacid B-19.

$^1$H-NMR (CD$_3$OD, 300 MHz): 8.37 (d, 1H); 7.75 (d, 1H); 7.18 (s, 1H); 4.25 (t, 2H); 2.35 (t, 2H); 1.93 (quint., 2H); 1.73 (quint., 2H); 1.60 (quint., 2H).

$^{13}$C-NMR (DMSO$_6$, 75 MHz): 25.10; 25.88; 29.16; 34.50; 69.34; 111.19; 115.28; 116.82 125.09; 130.74; 138.24; 138.75; 152.05; 152.13; 154.08; 168.28; 174.98; 183.55.

Example A22—Synthesis of the Compound (B-46)

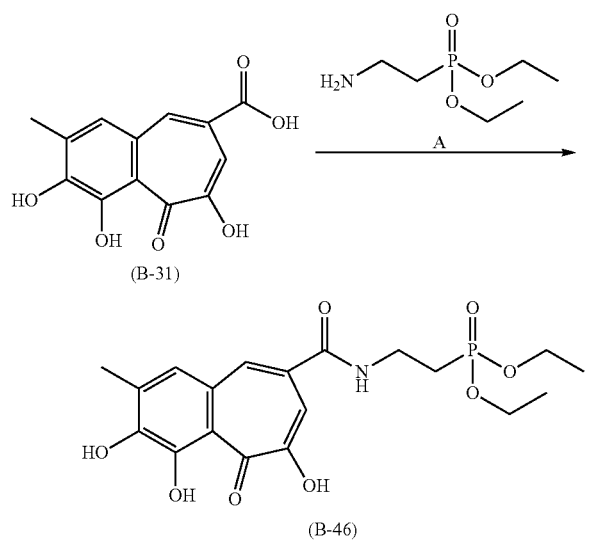

2.00 g of compound B-31 are dissolved in 10 ml dry DMF at 0° C. in an argon atmosphere. To this mixture are added subsequently 1.60 g N-3 dimethylaminopropyl N-ethyl carbodiimide hydrogen chloride salt (Aldrich), 2.60 ml of di-isopropyl ethyl amine and 15 mg 4-N,N-dimethyl amino pyridine (DMAP). Under vigouress stirring 1.45 g of amine A, dissolved in 2 ml DMF are added. The mixture then warms up to room temperature. Stirring is continued until complete consumption of tropolone B-31. The reaction mixture is then diluted with ethyl acetate and successively extracted with 1 N hydrogen chloride, saturated sodium hydrogen carbonate and brine. Usual work-up gives 0.34 g of amide B-46.

$^1$H-NMR (DMSO$_6$, 300 MHz): 9.82 (broad OH); 9.60 (broad, OH); 8.69 (t broad, NH); 7.96 (d, 1H); 7.43 (d, 1H); 7.40 (s, 1H); 3.95-4.08 (m, 4H); 3.31-3.49 (m, 2H); 2.36 (s, 3H); 2.07 (ddd, 2H); 1.24 (t, 6H).

$^{31}$P-NMR (DMSO$_6$, 121 MHz): 29.05.

Example A23—Synthesis of the Compound (B-47)

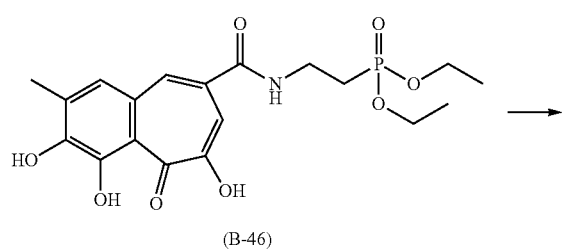

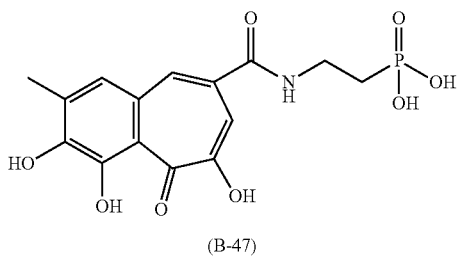

1.00 g of compound B-46 are dissolved in 20 ml acetonitrile at 0° C. The resulting suspension is then treated with 0.66 ml trimethylbromosilane (Fluka). The clear mixture is stirred for additional 3 h at room temperature with further additions of the bromosilane (3×0.66 ml) until disappearance of the starting material. The precipitate is filtered off and lyphilized from water to give 0.74 g of acid B-47.

$^1$H-NMR (CD$_3$OD, 300 MHz): 7.83 (d, 1H); 7.45 (d, 1H); 7.31 (s, 1H); 3.54-3.66 (m, 2H); 2.35 (s, 3H); 2.06 (ddd, 2H).

$^{31}$P-NMR (DMSO$_6$, 121 MHz): 27.22.

Example A24—Synthesis of the Compound (B-48)

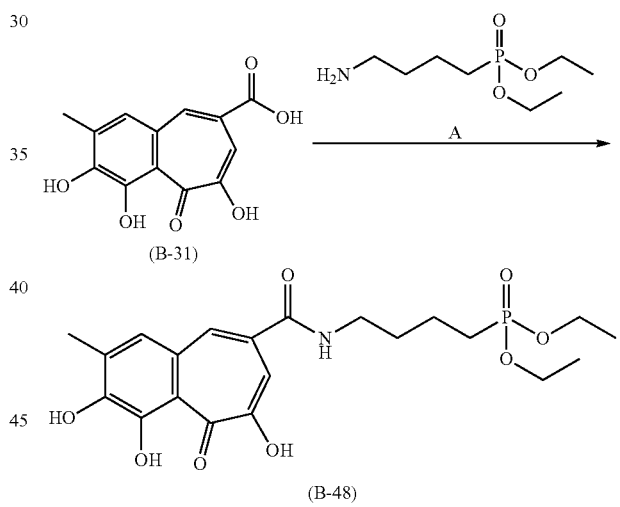

2.00 g of compound B-31 are dissolved in 15 ml dry DMF at 0° C. in an argon atmosphere. To this mixture are added subsequently 3.60 g BOP (Aldrich) and 2.60 ml of di-isopropyl ethyl amine. Under vigouress stirring 1.60 g of amine A, dissolved in 4 ml DMF are added. The mixture then warms up to room temperature. Stirring is continued until complete consumption of tropolone B-31. The reaction mixture is then diluted with ethyl acetate and successively extracted with 1 N hydrogen chloride, saturated sodium hydrogen carbonate and brine. Usual work-up gives 1.20 g of amide B-48.

$^1$H-NMR (DMSO$_6$, 300 MHz): 9.82 (broad OH); 9.60 (broad, OH); 8.60 (t broad, NH); 7.93 (d, 1H); 7.42 (d, 1H); 7.40 (s, 1H); 3.89-4.03 (m, 4H); 3.29 (broad q, 2H); 2.36 (s, 3H); 1.75 (ddd, 2H); 1.46-1.66 (m, 4H); 1.20 (t, 6H).

$^{31}$P-NMR (DMSO$_6$, 121 MHz): 32.71.

Example A25—Synthesis of the Compound (B-49)

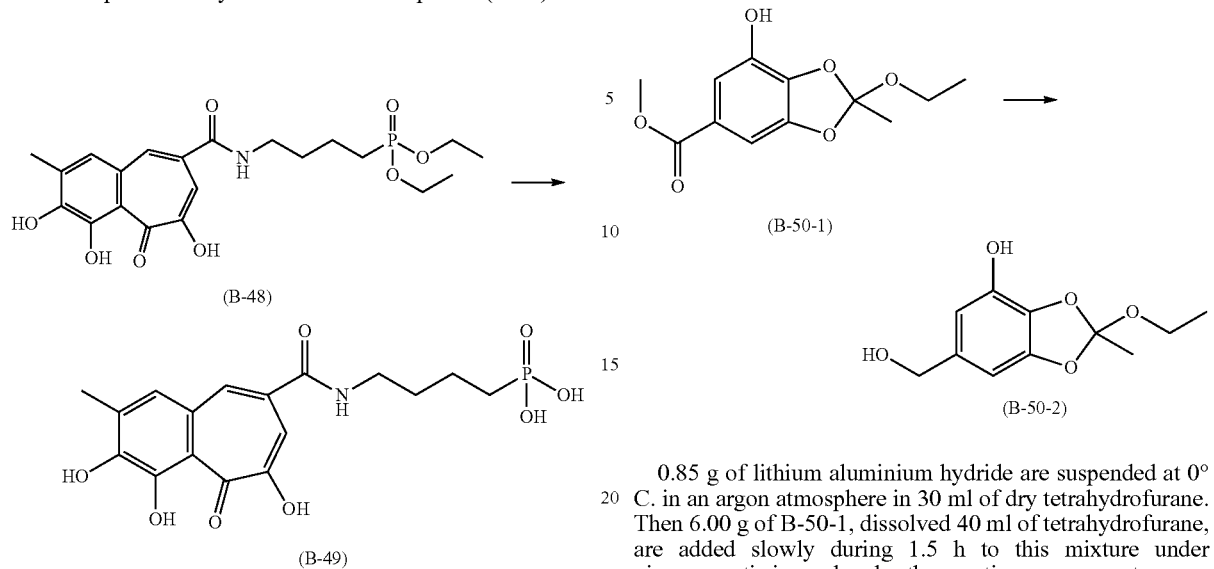

1.00 g of compound B-48 are treated as described for compound B-46 giving 0.54 g of acid B-49.

$^1$H-NMR (CD$_3$OD, 300 MHz): 7.88 (d, 1H); 7.50 (d, 1H); 7.39 (s, 1H); 3.31 (broad t, 2H); 2.42 (s, 3H); 1.74 (m, 6H).

$^{31}$P-NMR (DMSO$_6$, 121 MHz): 30.97.

Example A26—Laccase-Catalysed Synthesis of the Compound (B-50)

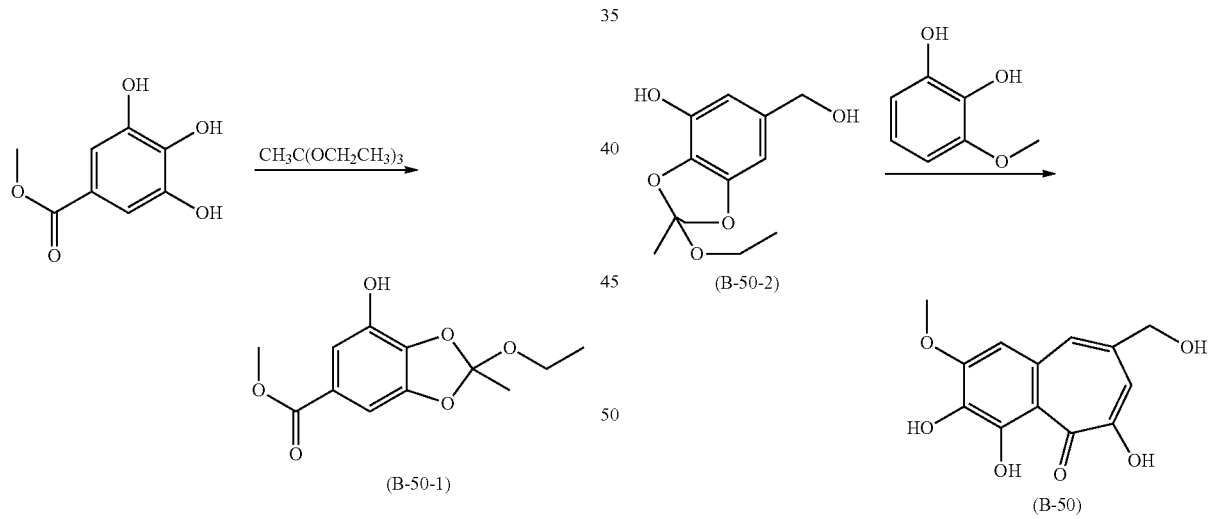

According to the protocol given in B-7-2, 43.8 g of triethyl orthoacetate and 53.2 g of gallic acid methyl ester (both commercial from FLUKA) in 180 ml xylene and heated at about 120° C.

After filtration over Celite and removal of the xylene 69.22 g of B-50-1 remain, which is used in the ensuing steps.

$^1$H-NMR (CDCl$_3$, 300 MHz): 7.39 (d, 1H); 7.12 (d, 1H); 6.21 (OH); 3.60 (dq, 2H); 1.82 (s, 3H); 1.20 (dt, 3H).

$^{13}$C-NMR (CDCl$_3$, 75 MHz): 15.13; 24.94; 52.60; 58.76; 102.56; 113.71; 123.79; 129.62; 137.89; 138.49; 147.74; 167.08.

0.85 g of lithium aluminium hydride are suspended at 0° C. in an argon atmosphere in 30 ml of dry tetrahydrofurane. Then 6.00 g of B-50-1, dissolved 40 ml of tetrahydrofurane, are added slowly during 1.5 h to this mixture under vigouress stirring, whereby the reaction warms up to room temperature. The mixture is then carefully quenched with water and 0.5 N hydrogen chloride until pH=7, filtered over Celite, evaporated, taken up in dichloromethane and dried over sodium sulphate. Usual work-up leaves 4.4 g of B-50-2 as yellow oil.

$^1$H-NMR (CDCl$_3$, 300 MHz): 7.52 (broad (OH), 6.45 (d, 1H); 6.39 (d, 1H); 4.48 (s, 2H); 3.55 (q, 2H); 3.10 (OH); 1.75 (s, 3H); 1.15 (q, 3H).

$^{13}$C-NMR (CDCl$_3$, 75 MHz): 15.17; 24.87; 58.49; 68.26; 99.98; 109.95; 123.54; 133.30; 134.52; 138.99; 147.96.

According to the protocol given for B-6, 0.74 g of 3-methoxycatechol (commercial from FLUKA) and 1.20 g of acetal B-50-2 are dissolved in a mixture of 130 ml phosphate buffer (pH=5, 0.05 M) and 25 ml acetone and are treated 6 mg of a laccase (T. versicolor, 26 U) at room temperature in an open beaker for 24 h.

The resulting solid is filtered off, washed with water and lyophilized from dioxane to give 0.25 g of B-50 as yellow powder.

$^1$H-NMR (DMSO$_6$, 300 MHz): 9.40 (OH); 9.25 (OH); 7.53 (d, 1H); 7.11 (d, 1H); 7.10 (s, 1H); 5.45 (OH); 4.42 (s, 2H); 3.95 (s, 3H).

$^{13}$C-NMR (DMSO$_6$, 75 MHz): 56.71; 66.46; 107.17; 116.40; 117.80; 131.62; 133.24; 135.47; 137.94; 151.34; 153.13; 154.67; 182.60.

Example A27—Synthesis of the Compound (B-51)

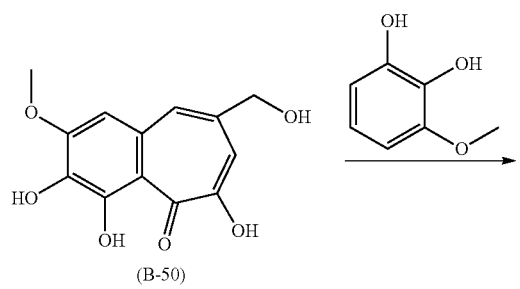

(B-50)

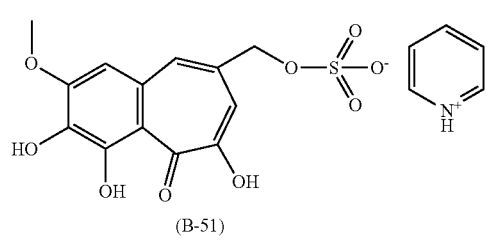

(B-51)

0.20 g of compound B-50 and 0.12 g of pyridine sulphur trioxide complex (Fluke) are dissolved in 5 ml of dry chloroform and 0.5 ml dry dimethyl formamide at room temperature. The resulting precipitate is filtered off and dried in vacuum to give 0.25 g of compound B-51.

$^1$H-NMR (DMSO$_6$, 300 MHz): 8.90 (d, 2H); 8.55 (tt, 1H); 8.03 (dt, 2H); 7.50 (d, 1H); 7.13 (d, 1H); 7.10 (s, 1H); 4.68 (s, 2H); 3.94 (s, 3H).

$^{13}$C-NMR (DMSO$_6$, 75 MHz): 56.72; 71.22; 107.52; 116.46; 117.80; 127.70; 132.79; 133.58; 135.79; 137.93; 143.29; 146.35; 151.42; 153.12; 154.66; 182.59.

Example A28—Laccase-Catalyzed Synthesis of the Compound (B-52)

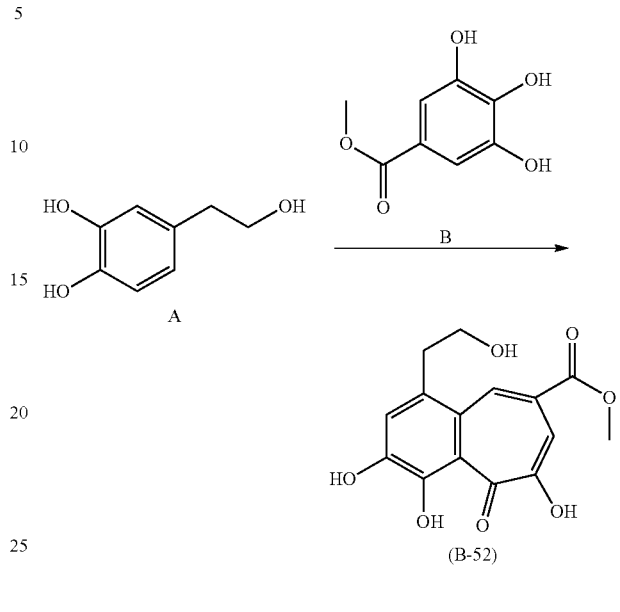

(B-52)

According to the protocol given for B-6, 1.00 g of 2-(3,4 dihydroxyphenyl)ethyl alcohol (Fluke) and 1.20 g of gallic acid methyl ester are dissolved in 150 ml phosphate buffer (pH=5, 0.05 M) and are treated 5 mg of a laccase (*T. versicolor*, 26 U) at room temperature in an open beaker for 1 d.

The resulting solid is filtered off, washed with water and lyophilized from dioxane to give 0.33 g of B-52 as yellow powder, which is contaminated with a reaction intermediate!

$^1$H-NMR (DMSO$_6$, 300 MHz) of the product: 10.0 (OH); 8.62 (d, 1H); 8.55 (OH); 7.55 (d, 1H); 6.84 (s, 1H); 3.55 (s, 3H); 3.64 (t, 2H); 3.10 (t, 2H).

$^{13}$C-NMR (DMSO$_6$, 75 MHz): 39.10; 53.83; 62.44; 111.75; 115.30; 121.91; 122.48; 127.00; 130.63; 134.83; 147.53; 150.60; 153.96; 167.29; 186.12.

Example A29—Laccase-Catalyzed Synthesis of the Compound (B-53)

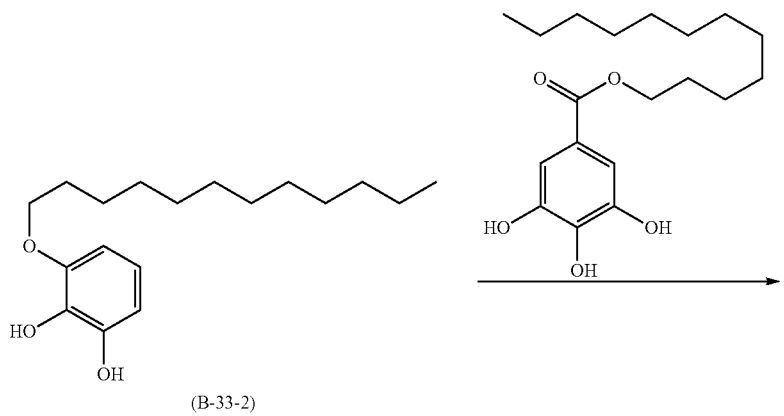

(B-33-2)

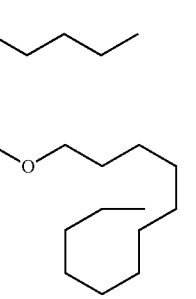

(B-53)

According to the protocol given for B-35, 2.00 g of the compound B-33-2 and 2.30 g of gallic acid dodecyl ester (FLUKA) are dissolved in 75 ml acetone and 50 ml phosphate buffer (0.05 M, pH=5). 7.0 mg of commercial (FLUKA) laccase from *T. versicolor* are added and the mixture is stirred for 24 h at room temperature.

The resulting precipitate is filtered off, extensively washed with water-acetone (1/1, vol/vol) and then lyophilized from dioxane to give 0.60 g of the compound B-53.

$^1$H-NMR (CDCl$_3$, 300 MHz): 8.27 (OH); 8.26 (d, 1H); 7.82 (d, 1H); 7.18 (OH); 6.96 (s, 1H); 6.20 (OH); 4.28 (t, 2H); 4.17 (t, 2H); 1.82 (quint. 2H); 1.72 (quint. 2H); 1.25-1.50 (m, 36H); 0.80 (dt, 6H).

$^{13}$C-NMR (CDCl$_3$, 75 MHz): 14.49; 23.05; 26.28; 26.37; 29.05; 29.37; 29.65; 29.70; (2×C); 29.89; 29.95; 29.99; 30.00; 32.27; 66.78; 69.80; 110.30; 114.81; 116.19; 125.51; 131.47; 137.09; 139.02; 150.93; 151.13; 153.52; 166.67; 182.46.

Example A30—Laccase-Catalyzed Synthesis of the Compound (B-54)

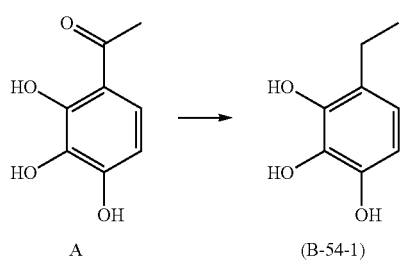

A      (B-54-1)

0.50 g of commercial (FLUKA) 2,3,4-trihydroxy acetophenone A are mixed with about 2.0 g of zinc powder and 5 ml of half-concentrated hydrogen chloride and are heated to reflux (according: E. Clemmensen, Ber. 1914, 51). More half-concentrated hydrogen chloride is added to the mixture during the course of the reaction to maintain a steady hydrogen evolution until all starting material is consumed for about 3-4 h. After cooling down the liquid phase is decanted. A brown sticky residue is removed by careful filtration and the filtrate saturated with brine. The aqueous phase is then extracted with diethyl ether, dried over sodium sulphate and evaporated to leave B-54-1 as a crystallizing syrupy mass, 0.30 g, which can be further purified e.g. via sublimation.

$^1$H-NMR (CD$_3$OD, 300 MHz): 6.40 (d, 1H); 6.26 (d, 1H); 2.50 (q, 2H); 1.13 (t, 3H).

$^{13}$C-NMR (CD$_3$OD, 75 MHz): 14.11; 22.76; 106.54; 118.69; 122.67; 133.01; 143.61; 143.66.

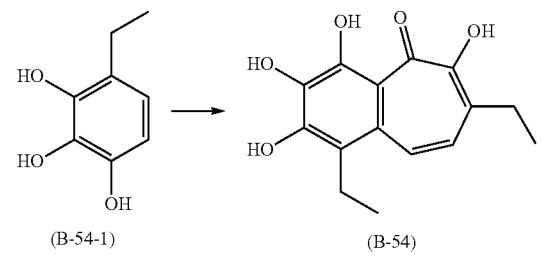

(B-54-1)      (B-54)

According to the standard protocol given in B-5 0.30 g of triol B-54-1 are dissolved in 20 ml of phosphate buffer containing 3 mg of laccase. Stirring over night yields a yellow precipitate which is removed via filtration and lyophilized from dioxane to give a yellow powder, 0.170 g.

$^1$H-NMR (CDCl$_3$, 300 MHz): 8.78 (OH); 7.53 (d, 1H); 6.79 (d, 1H); 6.15 (2×OH); 2.97 (q, 2H); 2.74 (q, 2H); 1.53 (OH); 1.21 (t, 3H); 1.14 (t, 3H).

$^{13}$C-NMR (CDCl$_3$, 75 MHz): 13.74; 14.58; 19.56; 28.11; 116.29; 120.55; 128.44; 128.57; 131.19; 132.42; 134.27; 147.12; 148.57; 152.08; 181.62.

Example A31—Laccase-Catalyzed Synthesis of the Compound (B-55)

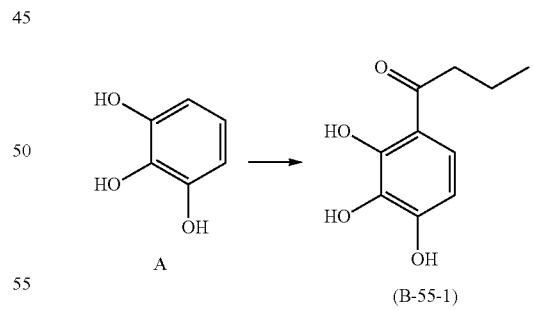

A      (B-55-1)

According to lit. (E. Clemmensen, Ber. 1914, 51) 2.82 g of commercial pyrogallol A (Fluke) and 4.00 g of butyric acid (Fluke) are heated in the presence of 3 g of an acid ion exchange resin (Amberlyst 15) to 120° C. over night. After cooling down the residue is extracted with ethyl acetate and washed with saturated sodium hydrogen carbonate and brine. The organic phase is evaporated and remaining unreacted pyrogallol removed via a short silica gel pad (eluent: hexane ethyl acetate vol/vol 1-1) to yield 2.28 g of solid colourless B-55-1.

¹H-NMR (CD₃OD, 300 MHz): 7.26 (d, 1H); 6.38 (d, 1H); 2.85 (t, 2H); 1.70 (hex, 2H); 0.92 (t, 3H).

¹³C-NMR (CD₃OD, 75 MHz): 13.16; 18.53; 39.62; 107.34; 113.27; 122.63; 132.39; 151.91; 152.17; 205.94.

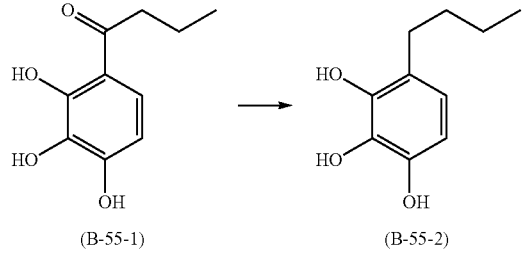

According to B-54-1, 1.60 g of compound B-55-1 are reacted with activated zinc to yield 0.74 g of compound B-55-2 as a colourless solid.

¹H-NMR (CD₃OD, 300 MHz): 6.36 (d, 1H); 6.24 (d, 1H); 2.40 (t, 2H); 1.36-1.47 (m, 2H); 1.16-1.28 (m, 2H); 1.12 (t, 3H).

¹³C-NMR (CD₃OD, 75 MHz): 14.47; 22.55; 29.44; 32.65; 106.61; 119.71; 121.32; 132.87; 143.58; 143.76.

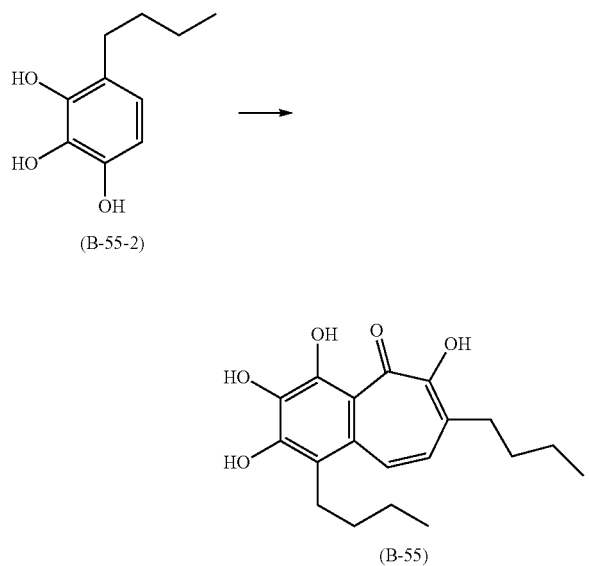

According to the standard protocol given in B-5 0.45 g of triol B-54-2 are dissolved in 100 ml of phosphate buffer and 5 ml acetone containing 7 mg of laccase. Stirring for 15 min yields a yellow precipitate which is removed via filtration and lyophilized from dioxane to give a yellow powder, 0.280 g.

¹H-NMR (CDCl₃, 300 MHz): 8.85 (OH); 7.58 (d, 1H); 6.85 (d, 1H); 6.21 (2×OH); 3.00 (t, 2H); 2.79 (t, 2H); 1.37-1.72 (m, 8H); 0.96 (dt, 6H).

¹³C-NMR (CDCl₃, 75 MHz): 14.37 (2×C); 23.17; 23.22; 25.97; 31.63; 32.45; 34.56; 116.31; 119.32; 128.32; 128.99; 131.40; 132.35; 133.16; 147.36; 148.55; 152.27; 181.55.

Example A32—Laccase-Catalyzed Synthesis of the Compound (B-56)

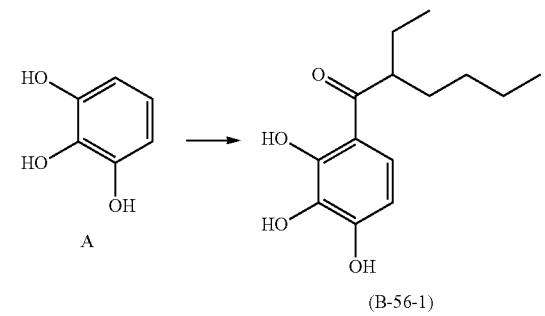

According to lit. (E. Clemmensen, Ber. 1914, 51) 3.96 g of commercial pyrogallol A (Fluke) and 4.53 g of 2-ethyl-hexanoic acid (Fluke) are heated in the presence of 3 g of an acid ion exchange resin (Amberlyst 15) to 120° C. over night. After cooling down the residue is extracted with ethyl acetate and washed with half-saturated sodium hydrogen carbonate and brine. The organic phase is evaporated and remaining unreacted pyrogallol removed via a short silica gel pad (eluent: hexane ethyl acetate vol/vol 1-1) to yield 4.14 g of brownish oil B-56-1.

¹H-NMR (CDCl₃, 300 MHz): 7.26 (d, 1H); 6.52 (d, 1H); 3.26 (m, 1H); 1.68-1.84 (m, 2H); 1.40-1.64 (m, 2H); 1.20-1.31 (m, 4H); 0.86 (dt, 6H).

¹³C-NMR (CDCl₃, 75 MHz): 12.34; 14.25; 22.99; 26.26; 30.11; 32.48; 107.53; 114.40; 122.86; 131.53; 150.30; 151.54; 210.17.

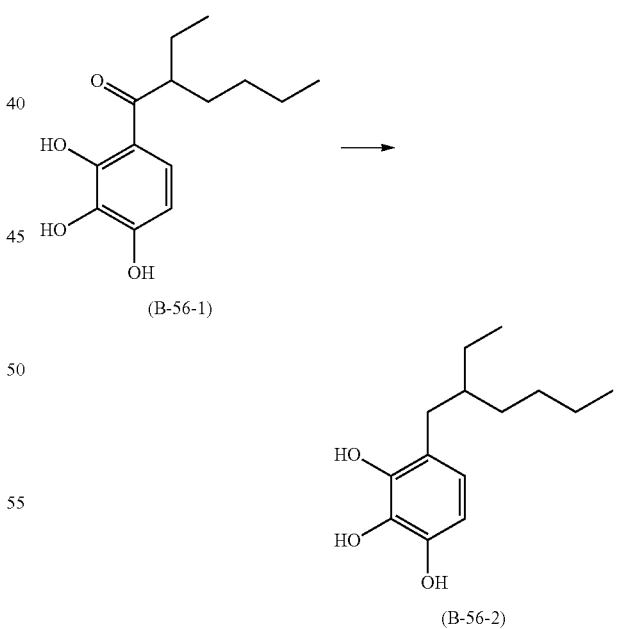

According to B-54-1, 4.00 g of compound B-56-1 are reacted with activated zinc to yield 1.80 g of compound B-56-2 as a dark syrupy mass.

¹H-NMR (CDCl₃, 300 MHz): 6.51 (d, 1H); 6.39 (d, 1H); 2.45 (d, 2H); 1.49-1.64 (m, 2H); 1.24-1.35 (m, 7H); 0.87 (dt, 6H).

$^{13}$C-NMR (CDCl$_3$, 75 MHz): 11.16; 14.50; 23.45; 25.95; 29.21; 32.85; 34.18; 40.12; 107.35; 121.11; 121.72; 131.81; 141.74; 142.77.

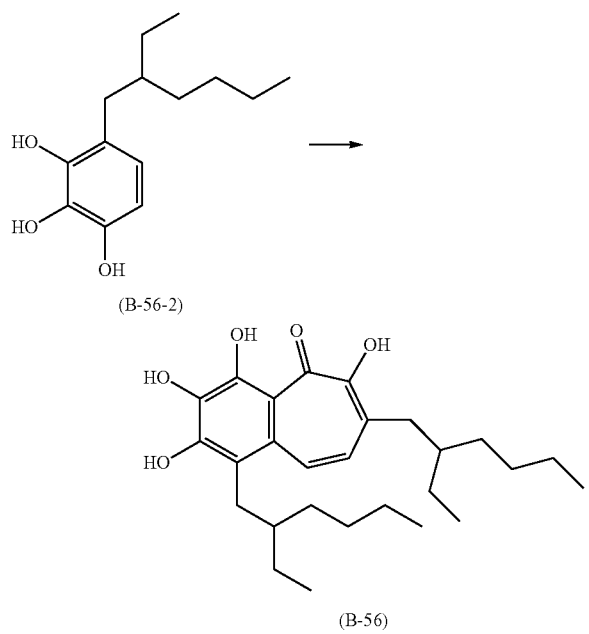

According to the standard protocol given in B-5 1.80 g of triol B-56-2 are dissolved in 50 ml of phosphate buffer and 20 ml acetone containing 7 mg of laccase. Stirring for over 29 h yields an oil which is worked-up in the usual way. A final purification on a silica gel column (eluent: dichloromethane methanol vol/vol 20-1) gives a dark red syrup B-56, 0.64 g, which is, however, still slightly contaminated with a reaction intermediate.

$^1$H-NMR (CDCl$_3$, 300 MHz): 8.86 (OH); 7.57 (d, 1H); 6.80 (d, 1H); 2.97 (d, 1H); 2.74 (d, 1H); 0.80-1.40 (m, 30H).

$^{13}$C-NMR (CDCl$_3$, 75 MHz): 11.20; 11.37; 14.47 (2×C); 23.39; 23.48; 25.72; 26.05; 29.15; 29.35; 32.89; 33.08; 33.28; 39.02; 39.94; 40.56; 116.50; 118.07; 128.32; 129.15; 131.03; 132.74; 134.32; 147.38; 149.03; 152.65; 181.11.

Example A33—Laccase-Catalyzed Synthesis of the Compound (B-57)

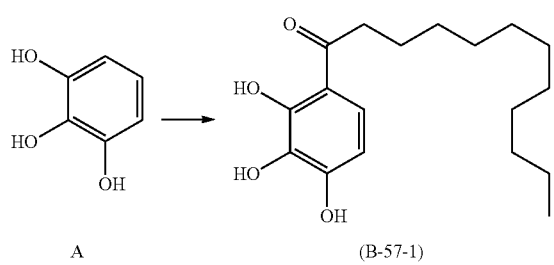

According to lit. (E. Clemmensen, Ber. 1914, 51) 3. g of commercial pyrogallol A (Fluka) and 4.77 g of laurinic acid (Fluka) are heated in the presence of 2.4 g of an acid ion exchange resin (Amberlyst 15) to 120° C. over night. After cooling down the residue is extracted with ethyl acetate and washed with saturated sodium hydrogen carbonate and brine. The organic phase is evaporated and remaining unreacted pyrogallol removed via a short silica gel pad (eluent: hexane ethyl acetate vol/vol 1-1) to yield 2.658 g of syrupy B-57-1.

$^1$H-NMR (CDCl$_3$, 300 MHz): 7.15 (d, 1H); 6.35 (d, 1H); 2.85 (t, 2H); 1.63 (quint., 2H); 1.17-1.29 (m, 16H); 0.80 (t, 3H).

$^{13}$C-NMR (CDCl$_3$, 75 MHz): 13.65; 22.35; 24.86; 29.02; 29.07; 29.13; 29.18; 29.30 (2×C); 31.59; 37.65; 107.04; 112.85; 121.95; 131.64; 150.83; 151.29; 205.47.

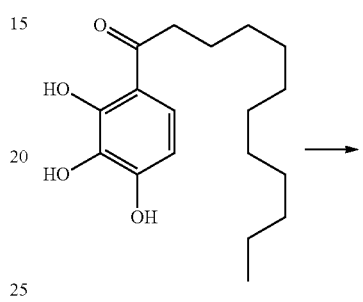

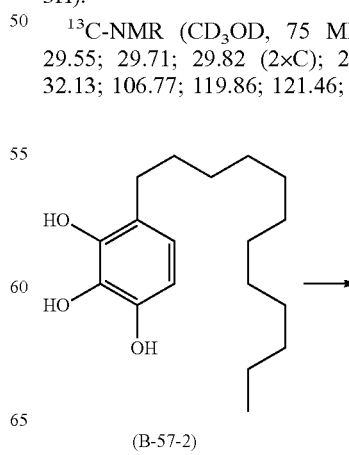

According to B-54-1, 1.95 g of compound B-57-1 are reacted with activated zinc to yield 1.21 g of compound B-57-2 as a waxy solid which can be crystallized from dichloromethane.

$^1$H-NMR (CD$_3$OD, 300 MHz): 6.42 (d, 1H); 6.28 (d, 1H); 2.49 (t, 2H); 1.53 (quint., 2H); 1.24-1.34 (m, 18H); 0.87 (t, 3H).

$^{13}$C-NMR (CD$_3$OD, 75 MHz): 13.85; 22.83; 24.59; 29.55; 29.71; 29.82 (2×C); 29.84; 29.89 (2×C); 30.42; 32.13; 106.77; 119.86; 121.46; 132.75; 143.48; 143.70.

-continued

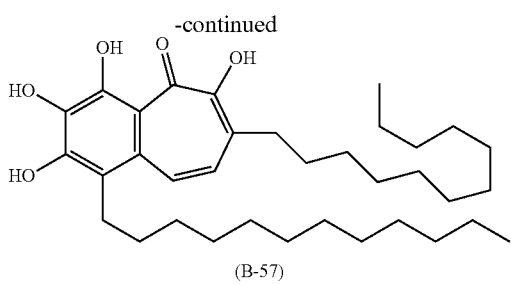

(B-57)

According to the standard protocol given in B-5 0.59 g of triol B-57-2 are dissolved in 250 ml of phosphate buffer and 10 ml acetone containing 12 mg of laccase. Stirring for 3.5 h yields a brown syrup after extraction with ethyl acetate and usual work-up, 0.17 g.

$^1$H-NMR (CDCl$_3$, 300 MHz): 8.82 (OH); 7.58 (d, 1H); 6.82 (d, 1H); 2.96 (t, 2H); 2.89 (t, 2H); 1.20-1.52 (m, 40H); 0.88 (t, 6H).

Example A34—Laccase-Catalyzed Synthesis of the Compound (B-58)

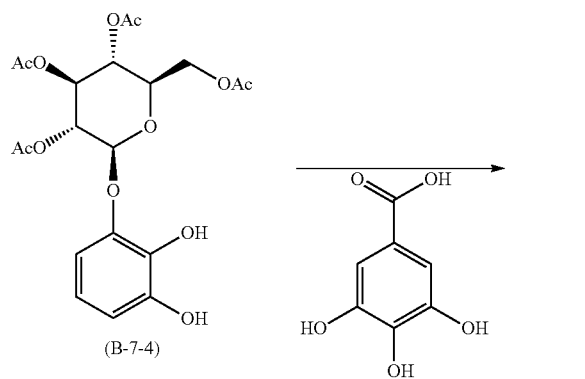

(B-58)

According to the standard protocol given in B-7 3.50 g of triol B-7-4 and 1.44 g gallic acid (Fluka) are dissolved in 230 ml and 46 ml acetone. 7 mg of laccase are added and the mixture incubated for 2 d. Usual work-up yields 1.80 g of compound B-58.

$^1$H-NMR (DMSO-D$_6$, 300 MHz): 9.95 (OH); 9.72 (OH); 8.28 (d, 1H); 7.62 (d, 1H); 7.40 (s, 1H); 5.79 (d, 1H); 5.35 (t, 1H); 5.15 (dd, 1H); 5.02 (t, 1H); 4.36 (dt, 1H); 4.10-4.16 (m, 2H); 2.01 (s, 3H); 1.99 (s, 3H); 1.98 (s, 3H); 1.96 (s, 3H).

Example A35—Laccase-Catalyzed Synthesis of the Compound (B-59)

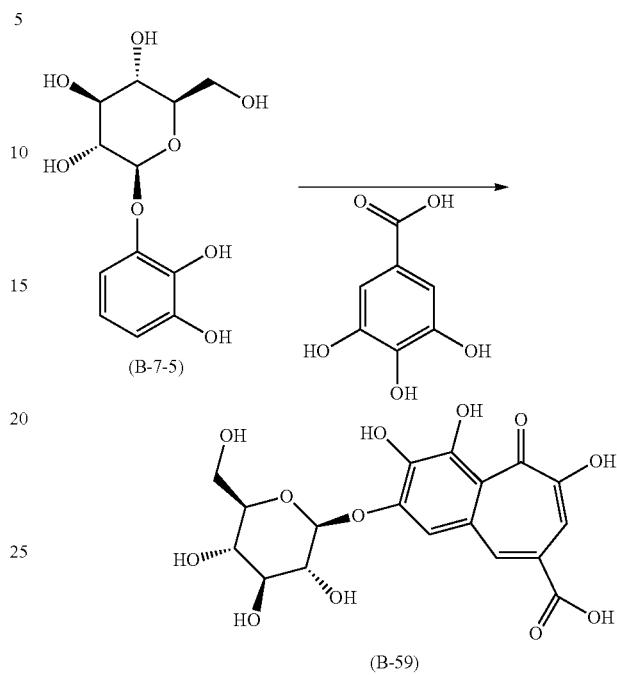

(B-59)

According to the standard protocol given in B-7 1.50 g of triol B-7-5 and 2.60 g gallic acid (Fluka) are dissolved in 30 ml and 7 ml acetone. 10 mg of horse radish peroxidase and 3 ml of a 3% hydrogen peroxide solution are added and the mixture incubated for 4 d. Over that time periodically further enzyme (overall 20 mg) and peroxide solution are added (overall 4 ml). The mixture is then lyophilized and the resulting residue taken up in methanol and centrifuged. The methanol solution is finally evaporated to yield and the residue purified by column chromatography (eluent: acetone-water vol/vol 10-1) to give 0.27 g of compound B-59.

$^1$H-NMR (CD$_3$$_6$OD, 300 MHz): 8.31 (d, 1H); 7.91 (d, 1H); 7.35 (s, 1); 5.19 (d, 1H); 3.95 (dd, 1H); 3.75 (dd, 1H); 3.42-3.62 (4H).

Example A36—Laccase-Catalyzed Synthesis of the Compound (B-60)

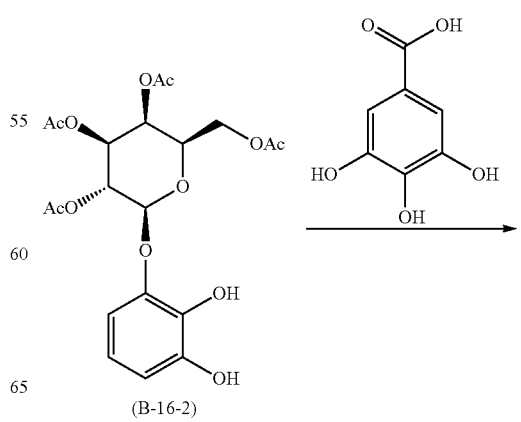

(B-16-2)

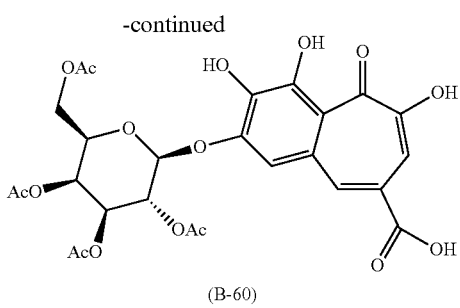

(B-60)

According to the protocol given in B-16, 0.05 g of protected sugar B-16-2, 0.025 g of gallic acid and 2 mg of laccase are incubated in 10 ml buffer and 2 ml acetone to give 20 mg of product B-60.

$^1$H-NMR (CD$_3$OD, 300 MHz): 8.23 (d, 1H); 7.71 (d, 1H); 7.30 (s, 1H); 5.42-5.54 (m, 2H); 5.31 (dd, 1H); 4.42 (dd, 1H); 4.15-4.30 (m, 3H); 2.19 (s, 3H); 2.11 (s, 3H); 2.08 (s 3H); 1.99 (s, 3H).

Example A37—Laccase-Catalyzed Synthesis of the Compound (B-61)

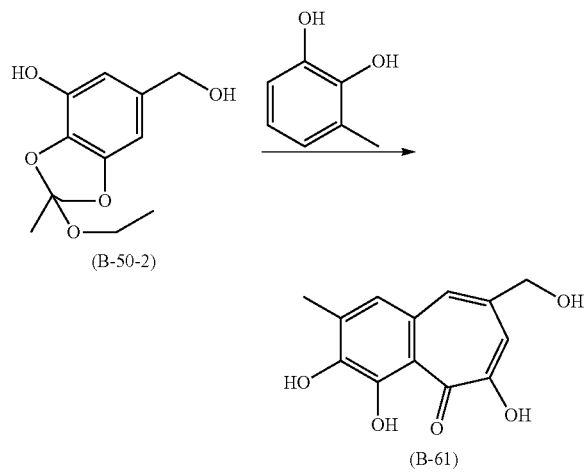

According to the protocol given for B-50, 0.39 g of 3-methylcatechol (commercial from FLUKA) and 0.70 g of acetal B-50-2 are dissolved in a mixture of 80 ml phosphate buffer (pH=5, 0.05 M) and 15 ml acetone and are treated 3 mg of a laccase (*T. versicolor*, 26 U) at room temperature in an open beaker for 24 h.

The resulting solid is filtered off, washed with water and lyophilized from dioxane to give 0.26 g of B-61 as deep yellow powder.

$^1$H-NMR (DMSO$_6$, 300 MHz): 9.40 (2×OH); 7.44 (d, 1H); 7.27 (s, 1H); 7.16 (d, 1H); 5.45 (OH); 4.40 (s, 2H); 2.33 (s, 3H).

$^{13}$C-NMR (DMSO$_6$, 75 MHz): 17.34; 66.45; 118.92; 118.99; 126.45; 131.33; 133.13; 133.44; 137.00; 145.45; 149.98; 154.30; 183.78.

B. APPLICATION EXAMPLES

Example B1: Measurement of Photostability

The method used for assessment of photostability is based on the irradiation of a highly diluted solution of the UV-filter.

The analysis after certain doses of irradiation is performed by UV-spectroscopy. The concentration of the UV-absorber in ethanol is adjusted to values between $1 \cdot 10^{-5}$ and $1 \cdot 10^{-6}$ mol/l, such that the absorbance of the solution in cuvette of 1 cm optical path length is ≤than 0.2. The mutual protection of filter molecules can be excluded under such conditions.

FIG. 1 shows the experimental set-up for the irradiation of the samples.

Prior to irradiation of a sample the UVB-intensity at the sample position is measured with a UV-radiometer (RM-12, Dr. Gröbel Electronic GmbH).

This radiometer is calibrated by comparison with a measurement of the spectral output of the metal halide lamp (including light guide and cut-off filter) using a wavelength-resolved radiometer (Gamma C11).

Therefore the relationship of the reading of the RM-12 radiometer and the corresponding spectral output of the lamp is known, and one is able to determine the wavelength-resolved intensities by measuring the UVB-intensity. By changing the distance between the end of the light guide and the cuvette, the UVB-intensity can be varied in the range of 100 µW/cm$^2$ and 4500 µW/cm$^2$.

For sample irradiation the highest possible intensity was used (4.5 mW/cm$^2$ UVB-intensity measured with the Macam 103 radiometer).

The irradiation time is varied from 0 to 180 min.

The dose the sample has received after 180 min corresponds to 60 MED.

During irradiation the sample was stirred. After certain intervals of irradiation, the samples were analyzed in a UV-spectrometer (Perkin Elmer, Lambda 16).

From the absorbance values at each dose of irradiation the concentration may be calculated using Lambert-Beer's law.

In order to get the half-life of the substance, a first order kinetic model was fitted to the experimental data. Since the UV-spectrum of the lamp and the UV-spectrum of the COLIPA standard sun are known, one can calculate the respective half-life of the UV-absorber under conditions of COLIPA standard sun irradiation [Bernd Herzog, Stefan Müller, Myriam Sohn, Uli Osterwalder, "New Insight and Prediction of Photostability of Sunscreens", SÖFW Journal 133, 26-36 (2007)].

The investigated half-time values and recovery after irradiation (10 MED) of some specific benzotropolones are listed in the table below:

| Comp. No. | Half time [h] | Recovery after 10MED [%] |
| --- | --- | --- |
| (B-1) | 31.5 | 94.6 |
| (B-2) | 33.6 | 95.0 |
| (B-3) | 61.9 | 97.2 |
| (B-4) | 16.6 | 90.1 |
| (B-5) | 116.5 | 98.5 |
| (B-13) | 51.3 | 96.7 |
| (B-19) | 40.1 | 95.8 |
| (B-32) | 16.6 | 90.1 |
| (B-36) | 22.8 | 92.7 |

The compounds Nos. B-1, B-2, B-3, B-4, B-5, B-13, B-19, B-32 and B-36 according to the present invention have high photostability and in all cases more than 90% of the benzotropolones are recovered after irradiation of 10 MED.

While many compounds derived from natural sources suffer from insufficient and low photostability particularly the compounds Nos. B-3 and B-5 exhibit an extraordinary high inherent photostability.

Example B2: UV Shielding Properties

The UV shielding properties of the benzotropolone derivatives were investigated by measuring their UV spectra in ethanol.

In the following table the investigated absorption maxima ($\lambda_{max}$) together with the corresponding $A^{1\%}_{1cm}$ values are listed.

| Comp. No. | Absorption maximum 1 | | Absorption maximum 2 | |
| --- | --- | --- | --- | --- |
| | $\lambda_{max}$ | $A^{1\%}_{1cm}$ | $\lambda_{max}$ | $A^{1\%}_{1cm}$ |
| (B-1) | 281 | 935 | 305 | 1179 |
| (B-2) | 276 | 966 | 400 | 460 |
| (B-3) | 277 | 1007 | 395 | 516 |
| (B-4) | 307 | 864 | 396 | 305 |
| (B-5) | 308 | 1008 | 403 | 399 |
| (B-6) | 280 | 997 | 396 | 447 |
| (B-7) | 287 | 593 | 399 | 246 |
| (B-13) | 310 | 573 | 404 | 208 |
| (B-15) | 310 | 754 | 398 | 269 |
| (B-16) | 288 | 550 | 397 | 204 |
| (B-59) | 300 | 497 | 388 | 174 |
| (B-19) | 308 | 726 | 397 | 236 |
| (B-33) | 310 | 575 | 403 | 210 |
| (B-31) | 281 | 1065 | 393 | 477 |
| (B-32) | 310 | 574 | 404 | 203 |
| (B-34) | 282 | 748 | 398 | 333 |
| (B-35) | 310 | 611 | 404 | 231 |
| (B-36) | 309 | 750 | 398 | 250 |
| (B-37) | 285 | 394 | 393 | 88 |
| (B-45) | 306 | 804 | 401 | 302 |
| (B-49) | 278 | 601 | 381 | 270 |
| (B-50) | 305 | 1027 | | |
| (B-52) | 280 | 437 | 399 | 176 |
| (B-53) | 309 | 533 | 402 | 193 |
| (B-54) | 309 | 1142 | | |
| (B-55) | 311 | 788 | | |
| (B-61) | 295 | 711 | | |
| (B-62) | 281 | 799 | 406 | 383 |

The benzotropolone compounds Nos. (B-1), (B-2), (B-3), (B-4); (B-5) and (B-6) according to the present invention have high shielding properties in the UV region as indicated by high $A^{1\%}_{1cm}$ values.

The benzotropolone compound (B-1 shows high absorption in the UV-C and UV-B region while the compounds Nos. (B-2), (B-3), (B-4); (B-5) and (B-6) have UV-C/UV-B shielding properties as well as UV-A shielding properties with a second absorption maximum at about 390 nm to 400 nm.

Example B3: The DPPH Assay

For tests of antioxidative activity, the DPPH assay is used. DPPH (2,2-Diphenyl-1-picryl-hydrazyl) is a stable radical, which absorbs in its radical form at 515 nm. Upon reduction by an antioxidant (AH), the absorption disappears:

$$DPPH.+AH \rightarrow DPPH-H+A. \tag{1}$$

Fig. 1: The DPPH radical

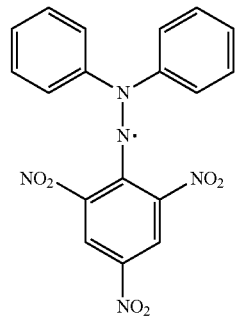

The rate of reaction (1) can be rather different for different antioxidants. In the case of the vitamins C and E, the equilibrium is reached in several minutes, however for other antioxidants it may also take hours.

In the test, the ratio of the molar concentrations of the antioxidant and DPPH is varied (this ratio is named "EC"=efficient concentration), and the concentration of DPPH in the equilibrium state is measured for each ratio. Antiradical activity is defined as the amount of antioxidant necessary to decrease the initial DPPH-concentration by 50%, and is characterized by the so-called $EC_{50}$ value. The smaller the $EC_{50}$ value, the more efficient is the antioxidant. Thus, the inverse, $1/EC_{50}$, can be used to quantify the antiradical power.

Solutions of DPPH and the antioxidants in ethanol are prepared separately and added together for starting the reaction (0.5 cm³ of a 250 µM antioxidant solution is added to 2.5 cm³ of a 100 µM DPPH solution). The absorption is measured using a Perkin Elmer Lambda 20 spectrophotometer.

The investigated $EC_{50}$ values and the inverse, $1/EC_{50}$ values, are listed in the table below:

| Comp. No. | $EC_{50}$ values | $1/EC_{50}$ values |
| --- | --- | --- |
| (B-2) | 0.0756 | 13.23 |
| (B-3) | 0.0937 | 10.67 |
| (B-4) | 0.1233 | 8.11 |
| (B-5) | 0.1502 | 6.66 |
| (B-6) | 0.1131 | 8.84 |
| (B-7) | 0.1335 | 7.49 |
| (B-13) | 0.341 | 2.93 |
| (B-15) | 0.1026 | 9.75 |
| (B-19) | 0.1132 | 8.83 |
| (B-17) | 0.3136 | 3.19 |
| (B-33) | 0.1575 | 6.35 |
| (B-37) | 0.1119 | 8.94 |
| (B-31) | 0.0980 | 10.20 |
| (B-34) | 0.1040 | 9.62 |
| (B-35) | 0.1235 | 8.10 |
| (B-36) | 0.1099 | 9.10 |
| (B-45) | 0.1456 | 6.87 |
| (B-52) | 0.2027 | 4.93 |
| (B-53) | 0.1125 | 8.88 |
| (B-54) | 0.1986 | 5.03 |
| (B-49) | 0.9142 | 1.09 |
| (B-50) | 0.2173 | 4.60 |
| (B-61) | 0.1662 | 6.02 |
| (B-62) | 0.0817 | 12.23 |

| Comp. No. | EC$_{50}$ values | 1/EC$_{50}$ values |
|---|---|---|
| Vitamin C | 0.243 | 4.11 |
| Vitamin E | 0.247 | 4.05 |
| resveratrol | 0.529 | 1.89 |

Most benzotropolone compounds according to the present invention have significantly higher antioxidant/radical scavenging power measured in EC$_{50}$ values and the 1/EC$_{50}$ values compared to the state-of-the-art antioxidants vitamin C and vitamin E.

The benzotropolone derivative (B-13) is still more effective in the DPPH assay than the state-of-the-art antioxidant resveratrol.

C. FORMULATION EXAMPLES

Example C1: Composition according to the invention in the form of a lotion (water/oil emulsion)

| | weight-% |
|---|---|
| Cyclomethicone | 25.00 |
| Polyglyceryl-sesquiisostearate/Beeswax/Mineral Oil/ Magnesium Stearate/Aluminum Stearate | 12.00 |
| Phenyl Dimethicone | 6.00 |
| Dimethicone | 3.00 |
| Isopropyl Myristate | 3.50 |
| BHT | 0.05 |
| Water | q.s.p. |
| C12-15 Alkyl Benzoate | 3.00 |
| Methyl 4-hydroxybenzoate | 0.16 |
| Propyl 4-hydroxybenzoate | 0.05 |
| 2-Phenoxyethanol | 0.58 |
| β-Sitosterol | 0.50 |
| Disodium EDTA | 0.10 |
| Compound according to this invention (B-2) | 0.05 |
| Total | 100.00% |

Equivalent formulations are obtained using the same amount of compound B-3, B-4, B-5, B-6, B-7, B-8, B-9, B-10, B-11, B-12, B-13, B-14, B-15, B-16, B-17, B-18, B-20, B-21, B-22, B-23, B-24, B-26, B-27, B-28, B-31, B-32, B-33, B-34, B-35, B-36, B-37, B-38, B-39 and B-44 instead of compound B-2.

Example C2: Composition according to the invention in the form of a lotion (water/oil emulsion)

| W/O-Creme | Weight-% |
|---|---|
| Paraffin DAB 9 | 13.00 |
| Glycerin | 6.30 |
| Aqua | 34.40 |
| Paraffinum Liquidum | 43.20 |
| Cetearyl Alcohol/PEG-40 Castor Oil/ Sodium Cetearyl Sulfate | 2.50 |
| Compound B-32 | 0.60 |

0.6 parts of compound B-32 dissolved in 3 parts of petrolatum are added to the warm oil phase at 75° C. The oil phase is then added to the warm water phase at 75° C., stirred and homogenized until a homogenous, pale yellow crème is obtained.

Examples C3-C7

| W/O-Crème | C3 [w-%] | C4 [w-%] | C5 [w-%] | C6 [w-%] | C7 [w-%] |
|---|---|---|---|---|---|
| Glyceryl Stearate/Malate | 2 | | | 2 | |
| Glyceryl Stearate | | 5 | 3 | | 2 |
| PEG-40-stearate | | | 1 | | 1 |
| Myristyl Myristate | 1 | | | | 1 |
| Stearyl Alcohol | 2 | 1 | | | |
| Cetearyl Alcohol | | | | 4 | 2 |
| Cetyl Alcohol | 1 | | 3 | | |
| Hydrogenated Coco Glycerides | 2 | | | | |
| C12-15 Benzoate | | 3 | 2 | | 3 |
| Butylene Glycol Dicaprylate/Dicaprate | 1 | | | 1 | |
| Caprylic/Capric Triglycerides | | 1 | 1 | 2 | 2 |
| Ethylhexyl Cocoate | 3 | | | | 1 |
| Octyldodecanol | | | 1 | | |
| Mineral oil | | 1 | | | |
| Petrolatum | 2 | | 1 | | 2 |
| Cyclomethicone | 4 | 1 | 4 | 3 | 5 |
| Dimethicone | | | | 1 | 1 |
| Dicaprylyl Ether | 1 | 4 | 2 | | |
| Dicaprylyl Carbonate | | | | 3 | |
| Titanium Dioxide | | | 1 | 0.5 | 1 |
| Ethylhexyl methoxycinnamate | 3 | 3 | 5 | | 2 |
| ethylhexyl triazone | | 2 | | | |
| Ethylhexylcyanodiphenylacrylate (Octocrylene) | | | | 5 | |
| Butylmethoxydibenzoylmethane (Avobenzone) | | | | 1 | |
| Bis-ethylhexyloxyphenolmethoxyphenyl-triazine | 1 | 0.5 | | | |
| Ethylhexylsalicylate | | | | 1 | |

-continued

Examples C3-C7

| W/O-Crème | C3 [w-%] | C4 [w-%] | C5 [w-%] | C6 [w-%] | C7 [w-%] |
|---|---|---|---|---|---|
| Ubiquinone (Q10) | 0.05 | 0.1 | | 0.01 | |
| Compound B-2 | 0.05 | 0.1 | 0.02 | 0.01 | 0.03 |
| Biotin | 0.2 | 0.05 | 0.04 | 0.01 | 0.04 |
| Retinol | 0.05 | | 0.03 | | |
| Retinyl Palmitate | | 0.2 | | 0.1 | 0.3 |
| Acetyl Carnitine | | | | 0.3 | |
| Tocopheryl Acetate | | | 1 | | |
| Sodium Citrate | | 0.1 | | | |
| Ascorbyl Palmitate, sodium salt | 0.1 | | | | 0.1 |
| γ-Cyclodextrin | 2.0 | | 0.5 | 1.0 | 0.8 |
| Trisodium EDTA | | 0.1 | | 0.2 | |
| Tetrasodium Iminodisuccinate | 0.2 | | 0.1 | | 0.1 |
| Phenoxyethanol | 0.3 | | 0.3 | 0.2 | 0.2 |
| 4-Hydroxybenzoic acid and its salts and esters (Parabens) | 0.6 | 0.3 | 0.2 | 0.3 | 0.3 |
| Hexamidin Diisethionate | | 0.04 | | | |
| Diazolidinyl Urea | 0.25 | | 0.1 | 0.2 | 0.1 |
| 1,3-Bis(hydroxymethyl)-5,5-dimethylhydantoin (DMDM Hydantoin) | | 0.2 | | | |
| Iodopropynyl Butylcarbamate | | 0.1 | | | |
| Alcohol denat. | | 2 | | | |
| Xanthan gum | 0.1 | | | | |
| Polyacrylic Acid (Carbomer) | 0.05 | | 0.1 | | 0.1 |
| Polyacrylamide | | 0.2 | | | |
| Glycerin | 10 | 6 | 6 | 7.5 | 8 |
| Butyleneglycol | 2 | 1 | | | |
| Water- and/or oilsoluble colouring agents | 0.05 | | | | |
| Bulking, anticaking materials/additives (Di-starch phosphate, Silica, BHT, talc, aluminum stearates) | 0.1 | 1 | 0.2 | 0.5 | 0.05 |
| Perfume | q.s. | q.s. | q.s. | q.s. | q.s. |
| Aqua | Ad 100 | Ad 100 | Ad 100 | Ad 100 | Ad 100 |

Equivalent formulations are obtained using the same amount of compound B-3, B-4, B-5, B-6, B-7, B-8, B-9, B-10, B-11, B-12, B-13, B-14, B-15, B-16, B-17, B-18, B-20, B-21, B-22, B-23, B-24, B-26, B-27, B-28, B-31, B-32, B-33, B-34, B-35, B-36, B-37, B-38, B-39 and B-44 instead of compound No. B-2.

Examples C8-C16

| | Emulsion high Protection / INCI-Name | C8 % w/w | C9 % w/w | C10 % w/w | C11 % w/w | C12 % w/w | C13 % w/w | C14 % w/w | C15 % w/w | C16 % w/w |
|---|---|---|---|---|---|---|---|---|---|---|
| Part A | Cyclomethicone | 7.0 | 7.0 | 7.0 | 7.0 | 7.0 | 7.0 | 7.0 | 7.0 | 7.0 |
| | Ethylhexyl Palmitate | 5.0 | 0.0 | 0.0 | 0.0 | 0.0 | 0.0 | 0.0 | 0.0 | 0.0 |
| | New UV filter (B-01-B-20) | 0.5 | 0.3 | 0.4 | 0.8 | 0.5 | 1.0 | 0.5 | 1.0 | 3.0 |
| | Glyceryl Stearate | 1.50 | 1.50 | 1.50 | 1.50 | 1.50 | 1.50 | 1.50 | 1.50 | 1.50 |
| | Potassium Cetyl Phosphate | 1.80 | 1.80 | 1.80 | 1.80 | 1.80 | 1.80 | 1.80 | 1.80 | 1.80 |
| | VP/Eicosene Copolymer | 0.60 | 0.60 | 0.60 | 0.60 | 0.60 | 0.60 | 0.60 | 0.60 | 0.60 |
| | Butyl Methoxydibenzoyl-methane | 0.0 | 3.0 | 5.0 | 0.0 | 0.0 | 3.0 | 5.0 | 0.0 | 0.0 |
| | Bis-Ethylhexyloxyphenol Methoxyphenyl Triazine | 0.4 | 1.0 | 1.0 | 0.0 | 0.5 | 0.0 | 0.0 | 0.8 | 1.0 |
| | Ethylhexyl Triazone | 0.4 | 0.5 | 0.5 | 0.0 | 0.0 | 0.0 | 2.0 | 1.0 | 1.0 |
| | 4-Methylbenzylidene Camphor | 0.0 | 0.0 | 0.0 | 0.5 | 0.0 | 2.0 | 0.0 | 0.0 | 0.0 |
| | Benzophenone-4 | 0.0 | 0.5 | 0.0 | 0.0 | 0.0 | 0.0 | 0.0 | 0.4 | 0.0 |
| | Octocrylene | 5.0 | 3.0 | 5.0 | 2.0 | 2.0 | 10.0 | 5.0 | 6.0 | 0.0 |
| | Ethylhexyl Methoxycinnamate | 3.0 | 2.0 | 0.0 | 5.0 | 2.0 | 0.0 | 0.0 | 6.0 | 6.0 |
| | Isoamyl p-Methoxycinnamate | 0.0 | 0.0 | 2.0 | 0.0 | 3.0 | 0.0 | 3.0 | 0.0 | 0.0 |
| | Homosalate | 0.0 | 0.0 | 5.0 | 0.0 | 0.0 | 0.0 | 2.0 | 0.0 | 0.0 |
| | Ethylhexyl Salicylate | 2.0 | 0.0 | 0.0 | 0.0 | 2.0 | 5.0 | 0.0 | 0.0 | 0.0 |
| | Diethylamino Hydroxy Benzoyl Hexyl Benzoate | 3.0 | 0.0 | 0.0 | 5.0 | 3.0 | 0.0 | 0.0 | 6.0 | 6.0 |
| | Polysilicone-15 | 0.0 | 0.0 | 0.0 | 0.0 | 0.0 | 0.0 | 10.0 | 0.0 | 0.0 |

| | Examples C8-C16 | | | | | | | | | |
|---|---|---|---|---|---|---|---|---|---|---|
| | Emulsion high Protection | C8 % | C9 % | C10 % | C11 % | C12 % | C13 % | C14 % | C15 % | C16 % |
| | INCI-Name | w/w | w/w | w/w | w/w | w/w | w/w | w/w | w/w | w/w |
| Part B | Aqua | Qs to 100 | Qs to 100 | Qs to 100 | Qs to 100 | Qs to 100 | Qs to 100 | Qs to 100 | Qs to 100 | Qs to 100 |
| | Acrylates/Palmeth-25 Acrylate Copolymer | 0.25 | 0.25 | 0.25 | 0.25 | 0.25 | 0.25 | 0.25 | 0.25 | 0.25 |
| | Glycerin | 6.0 | 6.0 | 6.0 | 6.0 | 6.0 | 6.0 | 6.0 | 6.0 | 6.0 |
| | Disodium EDTA | 0.20 | 0.20 | 0.20 | 0.20 | 0.20 | 0.20 | 0.20 | 0.20 | 0.20 |
| | Benzophenone-5 | | 5.0 | 0.0 | 0.0 | 0.0 | 0.0 | 0.0 | 0.0 | 2.0 |
| | Benzylidene Camphor Sulfonic Acid | | 1.0 | | | | | | | |
| | Camphor Benzalkonium Methosulfate | | | 1.0 | | | | | | |
| | Disodium Phenyl Dibenzylimidazole Tetrasulfonate | | | | 1.0 | | | | | |
| | Micronized Methylene Bis-Benzotriazolyl Tetramethyl-butylphenol | | | | | | 2.0 | 2.0 | 2.0 | 4.0 |
| | PABA | | | 1.0 | | | | | | |
| | PEG-25 PABA | | | | 1.0 | | | | | |
| | Phenylbenzimidazole Sulfonic Acid | | | | | 1.0 | | | | |
| | Terephthalylidene Dicamphor Sulfonic Acid | | | | | | 1.0 | | | |
| | Titanium Dioxide | | | | | | | 1.0 | | 2.0 |
| | Zinc Oxide | | | | | | | | 1.0 | |
| | Micronized Tris-Biphenyl Triazine | | 2.0 | | | | | | | |
| | Micronized (2-{4-[2-(4-Di-ethylamino-2-hydroxy-benzoyl)-benzoyl]-piperazine-1-carbonyl}-phenyl)-(4-di-ethylamino-2-hydroxy-phenyl)-methanone | | 2.0 | | | | | | | 1.0 |
| Part C | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.30 | 0.30 | 0.30 | 0.30 | 0.30 | 0.30 | 0.30 | 0.30 | 0.30 |

| | Examples C17-C25 | | | | | | | | | |
|---|---|---|---|---|---|---|---|---|---|---|
| | Sun Cream | C17 % | C18 % | C19 % | C20 % | C21 % | C22 % | C23 % | C24 % | C25 % |
| | INCI-Name | w/w | w/w | w/w | w/w | w/w | w/w | w/w | w/w | w/w |
| Part A | Cetearyl glucoside | 4.0 | 4.0 | 4.0 | 4.0 | 4.0 | 4.0 | 4.0 | 4.0 | 4.0 |
| | Dicaprylyl Carbonate | 8.0 | 0.0 | 0.0 | 0.0 | 0.0 | 0.0 | 0.0 | 0.0 | 0.0 |
| | New UV filter (B-01-B-20) | 0.2 | 0.5 | 2.5 | 1.0 | 3.0 | 1.5 | 0.4 | 1.0 | 2.0 |
| | Butyl Methoxydibenzoyl-methane | 0.0 | 3.0 | 5.0 | 0.0 | 0.0 | 3.0 | 5.0 | 0.0 | 0.0 |
| | Bis-Ethylhexyloxyphenol Methoxyphenyl Triazine | 0.4 | 1.0 | 1.0 | 0.5 | 0.5 | 0.5 | 0.5 | 0.8 | 0.8 |
| | Ethylhexyl Triazone | 0.0 | 0.5 | 0.5 | 0.0 | 0.0 | 0.0 | 2.0 | 1.0 | 0.0 |
| | 4-Methylbenzylidene Camphor | 0.0 | 0.0 | 0.0 | 0.0 | 0.0 | 2.0 | 0.0 | 0.0 | 0.0 |
| | Benzophenone-4 | 0.0 | 1.0 | 0.0 | 0.0 | 0.0 | 0.0 | 0.0 | 1.0 | 0.0 |
| | Octocrylene | 0.0 | 3.0 | 5.0 | 2.0 | 2.0 | 10.0 | 5.0 | 6.0 | 0.0 |
| | Ethylhexyl Methoxycinnamate | 8.0 | 2.0 | 0.0 | 5.0 | 2.0 | 0.0 | 0.0 | 6.0 | 5.0 |
| | Isoamyl p-Methoxycinnamate | 0.0 | 0.0 | 0.0 | 0.0 | 3.0 | 0.0 | 3.0 | 0.0 | 0.0 |
| | Homosalate | 0.0 | 0.0 | 5.0 | 0.0 | 0.0 | 0.0 | 0.0 | 0.0 | 0.0 |
| | Ethylhexyl Salicylate | 2.0 | 4.0 | 3.0 | 5.0 | 2.0 | 5.0 | 6.0 | 5.0 | 5.0 |
| | Diethylamino Hydroxy Benzoyl Hexyl Benzoate | 5.0 | 0.0 | 0.0 | 5.0 | 3.0 | 0.0 | 0.0 | 6.0 | 2.0 |
| Part B | Water | Qs to 100 | Qs to 100 | Qs to 100 | Qs to 100 | Qs to 100 | Qs to 100 | Qs to 100 | Qs to 100 | Qs to 100 |
| | Disodium EDTA | 0.20 | 0.20 | 0.20 | 0.20 | 0.20 | 0.20 | 0.20 | 0.20 | 0.20 |
| | Glycerin | 6.0 | 6.0 | 6.0 | 6.0 | 6.0 | 6.0 | 6.0 | 6.0 | 6.0 |

-continued

Examples C17-C25

| | Sun Cream INCI-Name | C17 % w/w | C18 % w/w | C19 % w/w | C20 % w/w | C21 % w/w | C22 % w/w | C23 % w/w | C24 % w/w | C25 % w/w |
|---|---|---|---|---|---|---|---|---|---|---|
| | PVP/dimethylconylacrylate/ polycarbamyl/polyglycol ester | 3.0 | 3.0 | 3.0 | 3.0 | 3.0 | 3.0 | 3.0 | 3.0 | 3.0 |
| | Benzylidene Camphor Sulfonic Acid | 0.0 | 1.0 | 0.0 | 1.0 | 1.0 | 0.0 | 0.0 | 0.0 | 0.0 |
| | Camphor Benzalkonium Methosulfate | 0.0 | 0.0 | 0.0 | 0.0 | 0.0 | 1.0 | 0.0 | 0.0 | 1.0 |
| | Disodium Phenyl Dibenzyl- imidazole Tetrasulfonate | 1.0 | 0.0 | 0.0 | 0.0 | 2.0 | 0.0 | 0.0 | 2.0 | 0.0 |
| | Micronized Methylene Bis- Benzotriazolyl Tetramethyl- butylphenol | 2.0 | 2.0 | 0.0 | 0.8 | 1.0 | 1.0 | 2.0 | 0.0 | 2.0 |
| | Phenylbenzimidazole Sulfonic Acid | 0.0 | 0.0 | 0.0 | 0.0 | 1.0 | 0.0 | 0.0 | 0.0 | 0.0 |
| | Terephthalylidene Dicamphor Sulfonic Acid | 1.0 | 0.0 | 1.0 | 0.0 | 0.0 | 0.0 | 1.0 | 0.0 | 0.0 |
| | Titanium Dioxide | 1.0 | 1.0 | 1.0 | 1.0 | 1.0 | 1.0 | 1.0 | 1.0 | 1.0 |
| | Zinc Oxide | 1.0 | 1.0 | 0.0 | 0.0 | 0.0 | 0.8 | 1.0 | 2.0 | 0.0 |
| | Sodium polyacrylate | 0.70 | 0.70 | 0.70 | 0.70 | 0.70 | 0.70 | 0.70 | 0.70 | 0.70 |
| Part C | Dimethicone | 3.0 | 3.0 | 3.0 | 3.0 | 3.0 | 3.0 | 3.0 | 3.0 | 3.0 |
| | Corn Starch modified | 3.0 | 3.0 | 3.0 | 3.0 | 3.0 | 3.0 | 3.0 | 3.0 | 3.0 |
| Part E | Phenoxyethanol (and) Methylparaben (and) Ethylparaben (and) Butylparaben (and) Propylparaben (and) Isobutylparaben | 1.0 | 1.0 | 1.0 | 1.0 | 1.0 | 1.0 | 1.0 | 1.0 | 1.0 |

Examples C26-C34

| Sunscreen Gel INCI-Name | C26 % w/w | C27 % w/w | C28 % w/w | C29 % w/w | C30 % w/w | C31 % w/w | C32 % w/w | C33 % w/w | C34 % w/w |
|---|---|---|---|---|---|---|---|---|---|
| Alcohol Denatured | Qs to 100 | Qs to 100 | Qs to 100 | Qs to 100 | Qs to 100 | Qs to 100 | Qs to 100 | Qs to 100 | Qs to 100 |
| Hydroxypropyl Cellulose | 1.0 | 1.0 | 1.0 | 1.0 | 1.0 | 1.0 | 1.0 | 1.0 | 1.0 |
| Acrylates/Octylacrylamide Copolymer | 1.0 | 1.0 | 1.0 | 1.0 | 1.0 | 1.0 | 1.0 | 1.0 | 1.0 |
| C12-15 Alkyl Benzoate | 10.0 | 0.0 | 0.0 | 0.0 | 0.0 | 0.0 | 0.0 | 0.0 | 0.0 |
| New UV filter (B-01-B-62) | 0.5 | 3.0 | 2.0 | 1.0 | 1.0 | 0.5 | 0.8 | 0.5 | 0.15 |
| Cyclotetrasiloxane (and) Cyclopentasiloxane | 3.0 | 3.0 | 3.0 | 3.0 | 3.0 | 3.0 | 3.0 | 3.0 | 3.0 |
| PEG/PPG-4/12 Dimethicone | 1.0 | 1.0 | 1.0 | 1.0 | 1.0 | 1.0 | 1.0 | 1.0 | 1.0 |
| New UV filter (B 01-20) | 0.2 | 0.5 | 2.5 | 1.0 | 2.0 | 1.5 | 0.4 | 1.0 | 3.0 |
| Butyl Methoxydibenzoyl- methane | 0.0 | 3.0 | 5.0 | 0.0 | 3.0 | 5.0 | 0.0 | 0.0 | 0.0 |
| Bis-Ethylhexyloxyphenol Methoxyphenyl Triazine | 4.0 | 1.0 | 1.0 | | 0.5 | | | 0.8 | 0.8 |
| Ethylhexyl Triazone | 0.5 | 0.5 | 0.5 | | | | 2.0 | 1.0 | 1.0 |
| Benzophenone-4 | 0.0 | 0.5 | | | | | | 0.4 | |
| Octocrylene | | 3.0 | 5.0 | 2.0 | 2.0 | 10.0 | 5.0 | 6.0 | 0.0 |
| Ethylhexyl Methoxycinnamate | 0.0 | 2.0 | | 5.0 | 2.0 | | | 6.0 | 6.0 |
| Homosalate | 0.0 | 0.0 | 5.0 | 0.0 | 0.0 | 0.0 | 0.0 | 0.0 | 10.0 |
| Ethylhexyl Salicylate | 8.0 | 4.0 | 5.0 | 8.0 | 2.0 | 5.0 | 6.0 | 4.0 | 0.0 |
| Diethylamino Hydroxy Benzoyl Hexyl Benzoate | 1.0 | 0.0 | 0.0 | 5.0 | 3.0 | 0.0 | 0.0 | 6.0 | 2.0 |
| Disodium Phenyl Dibenzylimidazole Tetrasulfonate | 2.0 | 0.0 | 0.0 | 1.0 | 0.0 | 0.0 | 0.0 | 2.0 | 0.0 |
| Micronized Methylene Bis-Benzotriazolyl Tetramethylbutyl- phenol | 2.0 | 2.0 | 4.0 | 0.8 | 1.0 | 1.0 | 2.0 | 1.5 | 0.0 |
| Titanium Dioxide | 1.0 | 1.0 | 1.0 | 1.0 | 1.0 | 1.0 | 1.0 | 4.0 | 2.0 |
| Zinc Oxide | 1.0 | 2.0 | 0.0 | 0.0 | 0.0 | 0.8 | 1.0 | 0.0 | 6.0 |
| Sodium polyacrylate | 0.70 | 0.70 | 0.70 | 0.70 | 0.70 | 0.70 | 0.70 | 0.70 | 0.70 |
| Benzylidene Camphor Sulfonic Acid | 0.0 | 1.0 | 0.0 | 0.0 | 1.0 | 0.0 | 0.0 | 0.0 | 0.0 |

Examples C35-C43

| Gel Cream INCI-Name | C35 % w/w | C36 % w/w | C37 % w/w | C38 % w/w | C39 % w/w | C40 % w/w | C41 % w/w | C42 % w/w | C43 % w/w |
| --- | --- | --- | --- | --- | --- | --- | --- | --- | --- |
| Sodium Carbomer | 0.50 | 0.50 | 0.50 | 0.50 | 0.50 | 0.50 | 0.50 | 0.50 | 0.50 |
| Acrylates/C10-C30 Alkyl Acrylate | 1.0 | 1.0 | 1.0 | 1.0 | 1.0 | 1.0 | 1.0 | 1.0 | 1.0 |
| Butyl Methoxydibenzoyl-methane | 0.0 | 0.0 | 0.0 | 0.0 | 0.0 | 3.0 | 5.0 | 4.0 | 1.0 |
| Bis-Ethylhexyloxyphenol Methoxyphenyl Triazine | 2.0 | 2.0 | 2.0 | 2.0 | 1.5 | 0.5 | 0.5 | 0.8 | 0.8 |
| Ethylhexyl Triazone | 0.0 | 0.0 | 0.5 | 0.0 | 0.0 | 0.0 | 0.0 | 0.5 | 0.0 |
| 4-Methylbenzylidene Camphor | 0.0 | 0.0 | 0.0 | 0.0 | 0.0 | 0.0 | 0.0 | 2.0 | 0.0 |
| Octocrylene | 8.0 | 3.0 | 5.0 | 8.0 | 5.0 | 8.0 | 10.0 | 8.0 | 8.0 |
| Ethylhexyl Methoxycinnamate | 8.0 | 8.0 | 10.0 | 8.0 | 5.0 | 0.0 | 0.0 | 0.0 | 0.0 |
| Homosalate | 0.0 | 0.0 | 5.0 | 0.0 | 0.0 | 0.0 | 0.0 | 6.0 | 5.0 |
| Ethylhexyl Salicylate | 10.0 | 4.0 | 8.0 | 5.0 | 8.0 | 5.0 | 6.0 | 0.0 | 0.0 |
| Diethylamino Hydroxy Benzoyl Hexyl Benzoate | 2.0 | 3.0 | 2.5 | 2.0 | 3.0 | 0.0 | 0.0 | 0.0 | 0.8 |
| Disodium Phenyl Dibenzyl-imidazole Tetrasulfonate | 0.0 | 0.0 | 1.0 | 0.0 | 0.0 | 2.0 | 0.0 | 2.0 | 1.0 |
| Micronized Methylene Bis-Benzotriazolyl Tetramethylbutyl-phenol | 2.0 | 2.0 | 0.0 | 0.8 | 1.0 | 1.0 | 2.0 | 0.0 | 4.0 |
| Titanium Dioxide | 1.0 | 1.0 | 1.0 | 1.0 | 1.0 | 1.0 | 1.0 | 1.0 | 0.0 |
| Zinc Oxide | 1.0 | 1.0 | 0.0 | 0.0 | 0.0 | 0.8 | 1.0 | 2.0 | 0.0 |
| C12-15 Alkyl Benzoate | 2.0 | 0.0 | 0.0 | 0.0 | 0.0 | 0.0 | 0.0 | 0.0 | 0.0 |
| New UV filter (B-01-B-62) | 2.0 | 3.0 | 5.0 | 1.0 | 1.0 | 1.0 | 1.0 | 0.5 | 0.5 |
| Butylenglycol | 4.0 | 0.0 | 0.0 | 0.0 | 0.0 | 0.0 | 0.0 | 0.0 | 0.0 |
| Dicaprylat/Dicaprate | 2.0 | 2.0 | 2.0 | 2.0 | 2.0 | 2.0 | 2.0 | 2.0 | 2.0 |
| Cetyl Dimethicone | 0.50 | 0.50 | 0.50 | 0.50 | 0.50 | 0.50 | 0.50 | 0.50 | 0.50 |
| Glycerine | 3.0 | 3.0 | 3.0 | 3.0 | 3.0 | 3.0 | 3.0 | 3.0 | 3.0 |
| Tocopherol | 1.0 | 1.0 | 1.0 | 1.0 | 1.0 | 1.0 | 1.0 | 1.0 | 1.0 |
| Methylparabene | 1.0 | 1.0 | 1.0 | 1.0 | 1.0 | 1.0 | 1.0 | 1.0 | 1.0 |
| Phenoxyethanol | 1.0 | 1.0 | 1.0 | 1.0 | 1.0 | 1.0 | 1.0 | 1.0 | 1.0 |
| Water | ad 100 | ad 100 | ad 100 | ad 100 | ad 100 | ad 100 | ad 100 | ad 100 | ad 100 |

Examples C44-C52

| Emulsifier Free INCI-Name | C44 % w/w | C45 % w/w | C46 % w/w | C47 % w/w | C48 % w/w | C49 % w/w | C50 % w/w | C51 % w/w | C52 % w/w |
| --- | --- | --- | --- | --- | --- | --- | --- | --- | --- |
| Acrylates/C10-30 Alkyl Acrylate Crosspolymer | 0.40 | 0.40 | 0.40 | 0.40 | 0.40 | 0.40 | 0.40 | 0.40 | 0.40 |
| Xanthan Gum | 0.10 | 0.10 | 0.10 | 0.10 | 0.10 | 0.10 | 0.10 | 0.10 | 0.10 |
| Butyl Methoxydibenzoyl-methane | 0.0 | 0.0 | 0.0 | 0.0 | 4.0 | 3.0 | 5.0 | 0.0 | 02.0 |
| Bis-Ethylhexyloxyphenol Methoxyphenyl Triazine | 2.0 | 2.0 | 2.0 | 2.0 | 1.5 | 0.5 | 0.5 | 0.8 | 0.8 |
| Ethylhexyl Triazone | 0.0 | 0.5 | 0.5 | 0.5 | 0.0 | 0.0 | 0.0 | 0.5 | 1.0 |
| Octocrylene | 4.0 | 3.0 | 0.0 | 8.0 | 5.0 | 8.0 | 10.0 | 8.0 | 8.0 |
| Ethylhexyl Methoxycinnamate | 4.0 | 8.0 | 10.0 | 8.0 | 5.0 | 0.0 | 0.0 | 0.0 | 0.0 |
| Homosalate | 0.0 | 0.0 | 5.0 | 0.0 | 0.0 | 0.0 | 0.0 | 6.0 | 5.0 |
| Ethylhexyl Salicylate | 4.0 | 4.0 | 8.0 | 5.0 | 8.0 | 5.0 | 6.0 | 0.0 | 0.0 |
| Diethylamino Hydroxy Benzoyl Hexyl Benzoate | 2.0 | 3.0 | 2.5 | 2.0 | 3.0 | 0.0 | 0.0 | 0.0 | 2.0 |
| Disodium Phenyl Dibenzylimidazole Tetrasulfonate | 0.0 | 0.0 | 1.0 | 0.0 | 0.0 | 2.0 | 0.0 | 2.0 | 2.0 |
| Micronized Methylene Bis-Benzotriazolyl Tetramethylbutyl-phenol | 2.0 | 2.0 | 0.0 | 0.8 | 1.0 | 1.0 | 2.0 | 0.0 | 4.0 |
| Titanium Dioxide | 1.0 | 1.0 | 1.0 | 1.0 | 1.0 | 1.0 | 1.0 | 1.0 | 0.0 |
| Zinc Oxide | 1.0 | 1.0 | 0.0 | 0.0 | 0.0 | 0.8 | 1.0 | 2.0 | 0.0 |
| New UV filter (B-01-B-62) | 0.8 | 1.0 | 1.0 | 1.0 | 1.0 | 1.0 | 1.0 | 0.0 | 1.0 |
| C12-15 Alkyl Benzoate | 6.0 | 0.0 | 0.0 | 0.0 | 0.0 | 0.0 | 0.0 | 0.0 | 0.0 |
| Octyldodecanol | 7.0 | 0.0 | 0.0 | 0.0 | 0.0 | 0.0 | 0.0 | 0.0 | 0.0 |
| Cetyl Dimethicone | 6.0 | 6.0 | 6.0 | 6.0 | 6.0 | 6.0 | 6.0 | 6.0 | 6.0 |
| Ethylhexyloxyglycerine | 1.0 | 1.0 | 1.0 | 1.0 | 1.0 | 1.0 | 1.0 | 1.0 | 1.0 |
| Butylen Glycol | 10.0 | 10.0 | 10.0 | 10.0 | 10.0 | 10.0 | 10.0 | 10.0 | 10.0 |
| *Glycine Soja* | 1.0 | 1.0 | 1.0 | 1.0 | 1.0 | 1.0 | 1.0 | 1.0 | 1.0 |
| Vitamin E Acetate | 0.25 | 0.25 | 0.25 | 0.25 | 0.25 | 0.25 | 0.25 | 0.25 | 0.25 |
| Trisodium EDTA | 0.10 | 0.10 | 0.10 | 0.10 | 0.10 | 0.10 | 0.10 | 0.10 | 0.10 |
| Ethanol | 3.50 | 3.50 | 3.50 | 3.50 | 3.50 | 3.50 | 3.50 | 3.50 | 3.50 |
| Parfume | 0.20 | 0.20 | 0.20 | 0.20 | 0.20 | 0.20 | 0.20 | 0.20 | 0.20 |

-continued

Examples C44-C52

| Emulsifier Free<br>INCI-Name | C44<br>%<br>w/w | C45<br>%<br>w/w | C46<br>%<br>w/w | C47<br>%<br>w/w | C48<br>%<br>w/w | C49<br>%<br>w/w | C50<br>%<br>w/w | C51<br>%<br>w/w | C52<br>%<br>w/w |
|---|---|---|---|---|---|---|---|---|---|
| Water soluble Dyes | 0.02 | 0.02 | 0.02 | 0.02 | 0.02 | 0.02 | 0.02 | 0.02 | 0.02 |
| Water | ad 100 | ad 100 | ad 100 | ad 100 | ad 100 | ad 100 | ad 100 | ad 100 | ad 100 |

Examples C53-C61

| | Sun Spray<br>INCI-Name | C53<br>%<br>w/w | C54<br>%<br>w/w | C55<br>%<br>w/w | C56<br>%<br>w/w | C57<br>%<br>w/w | C58<br>%<br>w/w | C59<br>%<br>w/w | C60<br>%<br>w/w | C61<br>%<br>w/w |
|---|---|---|---|---|---|---|---|---|---|---|
| Part A | Ethyl Trisiloxane | 2.50 | 2.50 | 2.50 | 2.50 | 2.50 | 2.50 | 2.50 | 2.50 | 2.50 |
| | Hydrogenated Coco-glycerides | 1.50 | 1.50 | 1.50 | 1.50 | 1.50 | 1.50 | 1.50 | 1.50 | 1.50 |
| | C12-15 Alkyl Benzoate | 3.60 | 3.60 | 3.60 | 3.60 | 3.60 | 3.60 | 3.60 | 3.60 | 3.60 |
| | New UV filter (B-01-B-62) | 0.5 | 1.0 | 1.0 | 1.0 | 1.0 | 1.0 | 1.0 | 0.8 | 1.0 |
| | Butyl Methoxydibenzoylmethane | 0.0 | 0.0 | 0.0 | 0.0 | 4.0 | 3.0 | 5.0 | 0.0 | 02.0 |
| | Bis-Ethylhexyloxyphenol Methoxyphenyl Triazine | 2.0 | 2.0 | 2.0 | 2.0 | 1.5 | 0.5 | 0.5 | 0.8 | 0.8 |
| | Ethylhexyl Triazone | 0.5 | 0.5 | 0.5 | 0.5 | 0.0 | 0.0 | 0.0 | 0.5 | 1.0 |
| | Octocrylene | 8.0 | 3.0 | 0.0 | 8.0 | 5.0 | 8.0 | 10.0 | 8.0 | 8.0 |
| | Ethylhexyl Methoxycinnamate | 8.0 | 8.0 | 10.0 | 8.0 | 5.0 | 0.0 | 0.0 | 0.0 | 0.0 |
| | Homosalate | 0.0 | 0.0 | 5.0 | 0.0 | 0.0 | 0.0 | 0.0 | 6.0 | 5.0 |
| | Ethylhexyl Salicylate | 10.0 | 4.0 | 8.0 | 5.0 | 8.0 | 5.0 | 6.0 | 0.0 | 0.0 |
| | Diethylamino Hydroxy Benzoyl Hexyl Benzoate | 4.0 | 3.0 | 2.5 | 2.0 | 3.0 | 0.0 | 0.0 | 0.0 | 2.0 |
| Part B | Water (and) Caprylic/Capric Triglyceride (and) Glycerin (and) Ceteareth-25 (and) Disodium Ethylene Di(Coc-amide PEG-15 Disulfate) (and) Sodium Lauroyl Lactylate (and) Behenyl Alcohol (and) Glyceryl Stearate (and) Glyceryl Stearate Citrate (and) Xanthan Gum | 10.0 | 10.0 | 10.0 | 10.0 | 10.0 | 10.0 | 10.0 | 10.0 | 10.0 |
| | PVP/Hexadecene Copolymer | 0.50 | 0.50 | 0.50 | 0.50 | 0.50 | 0.50 | 0.50 | 0.50 | 0.50 |
| | Aqua | Qs to 10 | Qs to 10 | Qs to 10 | Qs to 10 | Qs to 10 | Qs to 10 | Qs to 10 | Qs to 10 | Qs to 10 |
| | Glycerin | 3.0 | 3.0 | 3.0 | 3.0 | 3.0 | 3.0 | 3.0 | 3.0 | 3.0 |
| | Disodium Phenyl Dibenzyl-imidazole Tetrasulfonate | 0.0 | 0.0 | 1.0 | 0.0 | 0.0 | 2.0 | 0.0 | 2.0 | 0.0 |
| | Micronized Methylene Bis-Benzotriazolyl Tetramethyl-butylphenol | 0.0 | 2.0 | 0.0 | 0.8 | 1.0 | 1.0 | 2.0 | 0.0 | 0.0 |
| | Titanium Dioxide | 0.0 | 1.0 | 1.0 | 1.0 | 1.0 | 1.0 | 1.0 | 1.0 | 0.0 |
| | Zinc Oxide | 0.0 | 1.0 | 0.0 | 0.0 | 0.0 | 0.8 | 1.0 | 2.0 | 0.0 |
| | Disodium Phenyl Dibenzyl-imidazole Tetrasulfonate | 0.0 | 0.0 | 1.0 | 0.0 | 0.0 | 2.0 | 0.0 | 2.0 | 2.0 |
| Part C | Alcohol Denatured | 7.0 | 7.0 | 7.0 | 7.0 | 7.0 | 7.0 | 7.0 | 7.0 | 7.0 |
| Part D | Phenoxyethanol (and) Methylparaben (and) Ethylparaben (and) Butylparaben (and) Propylparaben (and) Isobutyl-paraben | 0.70 | 0.70 | 0.70 | 0.70 | 0.70 | 0.70 | 0.70 | 0.70 | 0.70 |
| | Tocopheryl Acetate | 0.60 | 0.60 | 0.60 | 0.60 | 0.60 | 0.60 | 0.60 | 0.60 | 0.60 |

Examples C62-C70

| Sun spray foaming | INCI-Name | C62 % w/w | C63 % w/w | C64 % w/w | C65 % w/w | C66 % w/w | C67 % w/w | C68 % w/w | C69 % w/w | C70 % w/w |
|---|---|---|---|---|---|---|---|---|---|---|
| Part A | Behenyl Alcohol (and) Glyceryl Stearate (and) Glyceryl Stearate Citrate (and) Disodium Ethylene Di(Cocamide PEG-15 Disulfate) | 0.50 | 0.50 | 0.50 | 0.50 | 0.50 | 0.50 | 0.50 | 0.50 | 0.50 |
| | Isotrideceth-12 | 0.50 | 0.50 | 0.50 | 0.50 | 0.50 | 0.50 | 0.50 | 0.50 | 0.50 |
| | Hydrogenated Coco-glycerides | 1.50 | 0.0 | 0.0 | 0.0 | 0.0 | 0.0 | 0.0 | 0.0 | 0.0 |
| | C12-15 Alkyl Benzoate | 8.0 | 0.0 | 0.0 | 0.0 | 0.0 | 0.0 | 0.0 | 0.0 | 0.0 |
| | New UV filter (B-01-B-62) | 0.5 | 1.0 | 1.0 | 1.0 | 1.0 | 1.0 | 1.0 | 0.8 | 1.0 |
| | Butyl Methoxydibenzoyl-methane | 0.0 | 0.0 | 0.0 | 0.0 | 4.0 | 3.0 | 5.0 | 0.0 | 02.0 |
| | Bis-Ethylhexyloxyphenol Methoxyphenyl Triazine | 2.0 | 2.0 | 2.0 | 2.0 | 1.5 | 0.5 | 0.5 | 0.8 | 0.8 |
| | Ethylhexyl Triazone | 0.5 | 0.5 | 0.5 | 0.5 | 0.0 | 0.0 | 0.0 | 0.5 | 1.0 |
| | Octocrylene | 0.0 | 3.0 | 0.0 | 8.0 | 5.0 | 8.0 | 10.0 | 8.0 | 8.0 |
| | Ethylhexyl Methoxycinnamate | 6.0 | 8.0 | 10.0 | 8.0 | 5.0 | 0.0 | 0.0 | 0.0 | 0.0 |
| | Homosalate | 0.0 | 0.0 | 5.0 | 0.0 | 0.0 | 0.0 | 0.0 | 6.0 | 5.0 |
| | Ethylhexyl Salicylate | 10.0 | 4.0 | 8.0 | 5.0 | 8.0 | 5.0 | 6.0 | 0.0 | 0.0 |
| | Diethylamino Hydroxy Benzoyl Hexyl Benzoate | 2.0 | 3.0 | 2.5 | 2.0 | 3.0 | 0.0 | 0.0 | 0.0 | 2.0 |
| Part B | Aqua | 5.0 | 5.0 | 5.0 | 5.0 | 5.0 | 5.0 | 5.0 | 5.0 | 5.0 |
| | Glycerin | 4.0 | 4.0 | 4.0 | 4.0 | 4.0 | 4.0 | 4.0 | 4.0 | 4.0 |
| | Galactoarabinan | 0.25 | 0.25 | 0.25 | 0.25 | 0.25 | 0.25 | 0.25 | 0.25 | 0.25 |
| | Disodium Phenyl Dibenzyl-imidazole Tetrasulfonate | 0.0 | 0.0 | 1.0 | 0.0 | 0.0 | 2.0 | 0.0 | 2.0 | 0.0 |
| | Micronized Methylene Bis-Benzotriazolyl Tetramethyl-butylphenol | 0.0 | 2.0 | 0.0 | 0.8 | 1.0 | 1.0 | 2.0 | 2.0 | 0.0 |
| | Titanium Dioxide | 0.0 | 1.0 | 1.0 | 1.0 | 1.0 | 1.0 | 1.0 | 1.0 | 0.0 |
| | Zinc Oxide | 0.0 | 1.0 | 0.0 | 0.0 | 0.0 | 0.8 | 1.0 | 2.0 | 0.0 |
| Part C | Disodium Ethylene Di(Cocamide PEG-15 Disulfate) (and) Sodium Lauroyl Lactylate | 1.0 | 1.0 | 1.0 | 1.0 | 1.0 | 1.0 | 1.0 | 1.0 | 1.0 |
| | Water | Qs to 100 | Qs to 100 | Qs to 100 | Qs to 100 | Qs to 100 | Qs to 100 | Qs to 100 | Qs to 100 | Qs to 100 |
| Part D | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.60 | 0.60 | 0.60 | 0.60 | 0.60 | 0.60 | 0.60 | 0.60 | 0.60 |

Examples C71-C79

| Active Naturals Continuous Spray INCI-Name | C71 % w/w | C72 % w/w | C73 % w/w | C74 % w/w | C75 % w/w | C76 % w/w | C77 % w/w | C78 % w/w | C79 % w/w |
|---|---|---|---|---|---|---|---|---|---|
| Acrylates/Octylacrylamide Copolymer | 3.0 | 3.01 | 3.02 | 3.03 | 3.04 | 3.05 | 3.06 | 3.07 | 3.08 |
| Ascorbyl Palmitate | 0.30 | 0.31 | 0.32 | 0.33 | 0.34 | 0.35 | 0.36 | 0.37 | 0.38 |
| Diisopropyl Adipate | 3.0 | 0.0 | 0.0 | 0.0 | 0.0 | 0.0 | 0.0 | 0.0 | 0.0 |
| Glycerine soja seed extract soybean | 3.0 | 0.0 | 0.0 | 0.0 | 0.0 | 0.0 | 0.0 | 0.0 | 0.0 |
| Isodecyl Neopentanoate | 2.50 | 0.0 | 0.0 | 0.0 | 0.0 | 0.0 | 0.0 | 0.0 | 0.0 |
| New UV filter (B-01-B-39) | 0.5 | 0.8 | 1.0 | 0.8 | 1.0 | 1.0 | 1.0 | 1.0 | 2.0 |
| Butyl Methoxydibenzoyl-methane | 0.0 | 0.0 | 0.0 | 0.0 | 4.0 | 3.0 | 0.0 | 0.0 | 02.0 |
| Bis-Ethylhexyloxyphenol Methoxyphenyl Triazine | 2.0 | 2.0 | 2.0 | 2.0 | 1.5 | 0.5 | 0.5 | 0.8 | 0.8 |
| Ethylhexyl Triazone | 0.5 | 0.5 | 0.5 | 0.5 | 0.0 | 0.0 | 0.0 | 0.5 | 1.0 |
| Octocrylene | 0.0 | 3.0 | 0.0 | 8.0 | 5.0 | 8.0 | 00.0 | 8.0 | 8.0 |
| Ethylhexyl Methoxycinnamate | 8.0 | 8.0 | 10.0 | 8.0 | 5.0 | 0.0 | 0.0 | 0.0 | 0.0 |
| Homosalate | 0.0 | 0.0 | 5.0 | 0.0 | 0.0 | 0.0 | 0.0 | 6.0 | 5.0 |
| Ethylhexyl Salicylate | 10.0 | 4.0 | 8.0 | 5.0 | 8.0 | 5.0 | 0.0 | 0.0 | 0.0 |
| Diethylamino Hydroxy Benzoyl Hexyl Benzoate | 2.0 | 3.0 | 2.5 | 2.0 | 3.0 | 0.0 | 0.0 | 0.0 | 2.0 |

Examples C71-C79

| Active Naturals Continuous Spray<br>INCI-Name | C71<br>% w/w | C72<br>% w/w | C73<br>% w/w | C74<br>% w/w | C75<br>% w/w | C76<br>% w/w | C77<br>% w/w | C78<br>% w/w | C79<br>% w/w |
|---|---|---|---|---|---|---|---|---|---|
| Disodium Phenyl Dibenzylimidazole Tetrasulfonate | 0.0 | 0.0 | 1.0 | 0.0 | 0.0 | 2.0 | 0.0 | 2.0 | 0.0 |
| Micronized Methylene Bis-Benzotriazolyl Tetramethyl-butylphenol | 0.0 | 2.0 | 0.0 | 0.8 | 1.0 | 1.0 | 4.0 | 0.0 | 0.0 |
| Titanium Dioxide | 0.0 | 1.0 | 1.0 | 1.0 | 1.0 | 1.0 | 4.0 | 1.0 | 0.0 |
| Zinc Oxide | 0.0 | 1.0 | 0.0 | 0.0 | 0.0 | 0.8 | 1.0 | 2.0 | 0.0 |
| Disodium Phenyl Dibenzyl-imidazole Tetrasulfonate | 0.0 | 0.0 | 1.0 | 0.0 | 0.0 | 2.0 | 0.0 | 2.0 | 0.0 |
| Lauryl Lactate | 1.50 | 1.50 | 1.50 | 1.50 | 1.50 | 1.50 | 1.50 | 1.50 | 1.50 |
| PPG-12/SMDI Copolymer | 1.0 | 1.0 | 1.0 | 1.0 | 1.0 | 1.0 | 1.0 | 1.0 | 1.0 |
| Retinyl Palmitate | 0.30 | 0.30 | 0.30 | 0.30 | 0.30 | 0.30 | 0.30 | 0.30 | 0.30 |
| SD Alcohol 40 | 80% v/v | 80% v/v | 80% v/v | 80% v/v | 80% v/v | 80% v/v | 80% v/v | 80% v/v | 80% v/v |
| Tocopherol Acetate | 1.0 | 1.0 | 1.0 | 1.0 | 1.0 | 1.0 | 1.0 | 1.0 | 1.0 |
| Parfume | q.s. | q.s. | q.s. | q.s. | q.s. | q.s. | q.s. | q.s. | q.s. |
| Aqua | ad 100 | ad 100 | ad 100 | ad 100 | ad 100 | ad 100 | ad 100 | ad 100 | ad 100 |
| Propellent | Qs | Qs | Qs | Qs | Qs | Qs | Qs | Qs | Qs |

Examples C80-C88

| | W/O Sunscreen Lotion<br>INCI-Name | C80<br>% w/w | C81<br>% w/w | C82<br>% w/w | C83<br>% w/w | C84<br>% w/w | C85<br>% w/w | C86<br>% w/w | C87<br>% w/w | C88<br>% w/w |
|---|---|---|---|---|---|---|---|---|---|---|
| Part A | PEG-7 Hydrogenated Castor Oil | 3.0 | 3.0 | 3.0 | 3.0 | 3.0 | 3.0 | 3.0 | 3.0 | 3.0 |
| | Polyglyceryl-3 Diisostearate | 4.0 | 4.0 | 4.0 | 4.0 | 4.0 | 4.0 | 4.0 | 4.0 | 4.0 |
| | Microcrystalline Wax | 1.0 | 1.0 | 1.0 | 1.0 | 1.0 | 1.0 | 1.0 | 1.0 | 1.0 |
| | Magnesium Stearate | 1.50 | 1.50 | 1.50 | 1.50 | 1.50 | 1.50 | 1.50 | 1.50 | 1.50 |
| | Propylparaben | 0.10 | 0.10 | 0.10 | 0.10 | 0.10 | 0.10 | 0.10 | 0.10 | 0.10 |
| | Mineral Oil | 15.0 | 5.0 | 0.0 | 10.0 | 0.0 | 5.0 | 0.0 | 5.0 | 10.0 |
| | New UV filter (B-01-B-62) | 0.5 | 1.0 | 2.5 | 1.0 | 1.0 | 1.0 | 1.0 | 1.0 | 10.0 |
| | Octyldodecanol | 8.0 | 0.0 | 0.0 | 0.0 | 0.0 | 0.0 | 0.0 | 0.0 | 0.0 |
| | Butyl Methoxydibenzoyl-methane | 0.0 | 0.0 | 0.0 | 0.0 | 4.0 | 3.0 | 5.0 | 0.0 | 02.0 |
| | Bis-Ethylhexyloxyphenol Methoxyphenyl Triazine | 2.0 | 2.0 | 2.0 | 2.0 | 1.5 | 0.5 | 0.5 | 0.8 | 0.8 |
| | Ethylhexyl Triazone | 0.5 | 0.5 | 0.5 | 0.5 | 0.0 | 0.0 | 0.0 | 0.5 | 1.0 |
| | Octocrylene | 8.0 | 3.0 | 0.0 | 8.0 | 5.0 | 8.0 | 10.0 | 8.0 | 8.0 |
| | Ethylhexyl Methoxycinnamate | 8.0 | 8.0 | 10.0 | 8.0 | 5.0 | 0.0 | 0.0 | 0.0 | 0.0 |
| | Homosalate | 0.0 | 0.0 | 5.0 | 0.0 | 0.0 | 0.0 | 0.0 | 6.0 | 5.0 |
| | Ethylhexyl Salicylate | 10.0 | 4.0 | 8.0 | 5.0 | 8.0 | 5.0 | 6.0 | 0.0 | 0.0 |
| Part B | Water | qs to 100 | qs to 100 | qs to 100 | qs to 100 | qs to 100 | qs to 100 | qs to 100 | qs to 100 | qs to 100 |
| | Disodium Phenyl Dibenzyl-imidazole Tetrasulfonate | 0.0 | 0.0 | 1.0 | 0.0 | 0.0 | 2.0 | 0.0 | 2.0 | 0.0 |
| | Micronized Methylene Bis-Benzotriazolyl Tetramethyl-butylphenol | 0.0 | 2.0 | 0.0 | 0.8 | 1.0 | 1.0 | 2.0 | 0.0 | 0.0 |
| | Titanium Dioxide | 0.0 | 1.0 | 1.0 | 1.0 | 1.0 | 1.0 | 1.0 | 1.0 | 0.0 |
| | Zinc Oxide | 0.0 | 1.0 | 0.0 | 0.0 | 0.0 | 0.8 | 1.0 | 2.0 | 0.0 |
| Part C | Water (and) Citric Acid | 0.05 | 0.05 | 0.05 | 0.05 | 0.05 | 0.05 | 0.05 | 0.05 | 0.05 |
| | Methylparaben | 0.15 | 0.15 | 0.15 | 0.15 | 0.15 | 0.15 | 0.15 | 0.15 | 0.15 |
| | Magnesium Sulfate | 0.50 | 0.50 | 0.50 | 0.50 | 0.50 | 0.50 | 0.50 | 0.50 | 0.50 |
| | Fragrance | qs | qs | qs | qs | qs | qs | qs | qs | qs |

Examples C89-C97

| | W/Si sun cream INCI-Name | C89 % w/w | C90 % w/w | C91 % w/w | C92 % w/w | C93 % w/w | C94 % w/w | C95 % w/w | C96 % w/w | C97 % w/w |
|---|---|---|---|---|---|---|---|---|---|---|
| Part A | Cyclopentasiloxane (and) Dimethicone/Vinyl Dimethicone Crosspolymer | 3.0 | 3.0 | 3.0 | 3.0 | 3.0 | 3.0 | 3.0 | 3.0 | 3.0 |
| | PEG-10 Dimethicone | 0.30 | 0.30 | 0.30 | 0.30 | 0.30 | 0.30 | 0.30 | 0.30 | 0.30 |
| | Polyglyceryl-3 Polydimethylsiloxyethyl Dimethicone | 4.0 | 4.0 | 4.0 | 4.0 | 4.0 | 4.0 | 4.0 | 4.0 | 4.0 |
| | Dimethicone | 5.0 | 5.0 | 5.0 | 5.0 | 5.0 | 5.0 | 5.0 | 5.0 | 5.0 |
| | Cyclomethicone | 15.0 | 15.0 | 15.0 | 15.0 | 15.0 | 15.0 | 15.0 | 15.0 | 15.0 |
| | New UV filter (B-01-B-62) | 0.5 | 1.0 | 2.0 | 1.0 | 1.5 | 1.0 | 1.0 | 1.0 | 3.0 |
| | Butyl Methoxydibenzoyl-methane | 0.0 | 0.0 | 0.0 | 0.0 | 4.0 | 3.0 | 5.0 | 0.0 | 02.0 |
| | Bis-Ethylhexyloxyphenol Methoxyphenyl Triazine | 2.0 | 2.0 | 2.0 | 2.0 | 1.5 | 0.5 | 0.5 | 0.8 | 0.8 |
| | Ethylhexyl Triazone | 0.5 | 0.5 | 0.5 | 0.5 | 0.0 | 0.0 | 0.0 | 0.5 | 1.0 |
| | Octocrylene | 8.0 | 3.0 | 0.0 | 8.0 | 5.0 | 8.0 | 10.0 | 8.0 | 8.0 |
| | Ethylhexyl Methoxycinnamate | 8.0 | 8.0 | 10.0 | 8.0 | 5.0 | 0.0 | 0.0 | 0.0 | 0.0 |
| | Homosalate | 0.0 | 0.0 | 5.0 | 0.0 | 0.0 | 0.0 | 0.0 | 6.0 | 5.0 |
| | Ethylhexyl Salicylate | 10.0 | 4.0 | 8.0 | 5.0 | 8.0 | 5.0 | 6.0 | 0.0 | 0.0 |
| | Diethylamino Hydroxy Benzoyl Hexyl Benzoate | 2.0 | 3.0 | 2.5 | 2.0 | 3.0 | 0.0 | 0.0 | 0.0 | 2.0 |
| Part C | 1.3-Butylen Glycol | 8.0 | 8.0 | 8.0 | 8.0 | 8.0 | 8.0 | 8.0 | 8.0 | 8.0 |
| | Sodium Citrate | 0.20 | 0.20 | 0.20 | 0.20 | 0.20 | 0.20 | 0.20 | 0.20 | 0.20 |
| | Ethyl Alcohol | 5.0 | 5.0 | 5.0 | 5.0 | 5.0 | 5.0 | 5.0 | 5.0 | 5.0 |
| | Sodium Chloride | 0.50 | 0.50 | 0.50 | 0.50 | 0.50 | 0.50 | 0.50 | 0.50 | 0.50 |
| | Disodium Phenyl Dibenzylimidazole Tetrasulfonate | 0.0 | 0.0 | 1.0 | 0.0 | 0.0 | 2.0 | 0.0 | 2.0 | 0.0 |
| | Micronized Methylene Bis-Benzotriazolyl Tetra-methylbutylphenol | 0.0 | 2.0 | 0.0 | 0.8 | 1.0 | 1.0 | 2.0 | 0.0 | 0.0 |
| | Titanium Dioxide | 0.0 | 1.0 | 1.0 | 1.0 | 1.0 | 1.0 | 1.0 | 1.0 | 0.0 |
| | Zinc Oxide | 0.0 | 1.0 | 0.0 | 0.0 | 0.0 | 0.8 | 1.0 | 2.0 | 0.0 |
| | Aqua | Qs to 100 | Qs to 100 | Qs to 100 | Qs to 100 | Qs to 100 | Qs to 100 | Qs to 100 | Qs to 100 | Qs to 100 |

Examples C98-C106

| Lipstick INCI-Name | C98 % w/w | C99 % w/w | C100 % w/w | C101 % w/w | C102 % w/w | C103 % w/w | C104 % w/w | C105 % w/w | C106 % w/w |
|---|---|---|---|---|---|---|---|---|---|
| Caprylic/Capric Triglyceride | 12.00 | 0.0 | 0.0 | 0.0 | 0.0 | 0.0 | 0.0 | 0.0 | 0.0 |
| New UV filter (B-01-B-62) | 0.5 | 1.0 | 2.0 | 1.0 | 2.0 | 1.0 | 1.0 | 1.0 | 4.0 |
| Octyldodecanol | 7.0 | 7.0 | 7.0 | 7.0 | 7.0 | 7.0 | 7.0 | 7.0 | 7.0 |
| Pentaerythrityl Tetraisostearate | 10.0 | 5.0 | 0.0 | 5.0 | 0.0 | 0.0 | 0.0 | 0.0 | 5.0 |
| Polyglyceryl-3 Diisostearate | 2.50 | 2.50 | 2.50 | 2.50 | 2.50 | 2.50 | 2.50 | 2.50 | 2.50 |
| Bis-Diglyceryl Polyacyl-adipate-2 | 9.0 | 9.0 | 9.0 | 9.0 | 9.0 | 9.0 | 9.0 | 9.0 | 9.0 |
| Cetearyl Alcohol | 8.0 | 8.0 | 8.0 | 8.0 | 8.0 | 8.0 | 8.0 | 8.0 | 8.0 |
| Myristyl Myristate | 3.50 | 3.50 | 3.50 | 3.50 | 3.50 | 3.50 | 3.50 | 3.50 | 3.50 |
| Beeswax | 5.0 | 5.0 | 5.0 | 5.0 | 5.0 | 5.0 | 5.0 | 5.0 | 5.0 |
| *Copernicia Cerifera* (Carnauba) Wax | 1.50 | 1.50 | 1.50 | 1.50 | 1.50 | 1.50 | 1.50 | 1.50 | 1.50 |
| *Cera Alba* | 0.50 | 0.50 | 0.50 | 0.50 | 0.50 | 0.50 | 0.50 | 0.50 | 0.50 |
| Butyl Methoxydibenzoyl-methane | 0.0 | 0.0 | 0.0 | 0.0 | 4.0 | 3.0 | 5.0 | 0.0 | 02.0 |
| Bis-Ethylhexyloxyphenol Methoxyphenyl Triazine | 2.0 | 2.0 | 2.0 | 2.0 | 1.5 | 0.5 | 0.5 | 0.8 | 0.8 |
| Ethylhexyl Triazone | 0.5 | 0.5 | 0.5 | 0.5 | 0.0 | 0.0 | 0.0 | 0.5 | 1.0 |
| Octocrylene | 8.0 | 3.0 | 0.0 | 8.0 | 5.0 | 8.0 | 10.0 | 8.0 | 8.0 |
| Ethylhexyl Methoxycinnamate | 8.0 | 8.0 | 10.0 | 8.0 | 5.0 | 0.0 | 0.0 | 0.0 | 0.0 |
| Homosalate | 0.0 | 0.0 | 5.0 | 0.0 | 0.0 | 0.0 | 0.0 | 6.0 | 5.0 |
| Ethylhexyl Salicylate | 10.0 | 4.0 | 8.0 | 5.0 | 8.0 | 5.0 | 6.0 | 0.0 | 0.0 |
| Diethylamino Hydroxy Benzoyl Hexyl Benzoate | 2.0 | 3.0 | 2.5 | 2.0 | 3.0 | 0.0 | 0.0 | 0.0 | 2.0 |
| Tocopheryl Acetate | 0.50 | 0.50 | 0.50 | 0.50 | 0.50 | 0.50 | 0.50 | 0.50 | 0.50 |
| Tocopherol; Ascorbyl Palmitate | 0.05 | 0.05 | 0.05 | 0.05 | 0.05 | 0.05 | 0.05 | 0.05 | 0.05 |

-continued

| Examples C98-C106 | | | | | | | | | |
|---|---|---|---|---|---|---|---|---|---|
| Lipstick<br>INCI-Name | C98<br>%<br>w/w | C99<br>%<br>w/w | C100<br>%<br>w/w | C101<br>%<br>w/w | C102<br>%<br>w/w | C103<br>%<br>w/w | C104<br>%<br>w/w | C105<br>%<br>w/w | C106<br>%<br>w/w |
| *Simmondsia Chinensis* (*Jojoba*) Seed Extract | 2.0 | 2.0 | 2.0 | 2.0 | 2.0 | 2.0 | 2.0 | 2.0 | 2.0 |
| Parfum. BHT | q.s | q.s | q.s | q.s | q.s | q.s | q.s | q.s | q.s |
| *Ricinus Communis* | QS to 100 | QS to 100 | QS to 100 | QS to 100 | QS to 100 | QS to 100 | QS to 100 | QS to 100 | QS to 100 |

| Examples C107-C115 | | | | | | | | | |
|---|---|---|---|---|---|---|---|---|---|
| Waterproof Gel<br>INCI-Name | C107<br>%<br>w/w | C108<br>%<br>w/w | C109<br>%<br>w/w | C110<br>%<br>w/w | C111<br>%<br>w/w | C112<br>%<br>w/w | C113<br>%<br>w/w | C114<br>%<br>w/w | C115<br>%<br>w/w |
| Anhydrous Ethanol | Qsp 100 | Qsp 100 | Qsp 100 | Qsp 100 | Qsp 100 | Qsp 100 | Qsp 100 | Qsp 100 | Qsp 100 |
| Hydroxypropyl Cellulose | 1.0 | 1.0 | 1.0 | 1.0 | 1.0 | 1.0 | 1.0 | 1.0 | 1.0 |
| Acrylates/Octylacrylamide Copolymer | 1.0 | 1.0 | 1.0 | 1.0 | 1.0 | 1.0 | 1.0 | 1.0 | 1.0 |
| New UV filter (B-01-B-62) | 0.3 | 1.0 | 1.6 | 2.0 | 2.0 | 0.8 | 1.0 | 0.6 | 6.0 |
| C12-15 Alkyl Benzoate | 10.0 | 10.0 | 10.0 | 10.0 | 10.0 | 10.0 | 10.0 | 10.0 | 10.0 |
| Butyl Methoxydibenzoylmethane | 0.0 | 0.0 | 0.0 | 0.0 | 4.0 | 3.0 | 5.0 | 0.0 | 02.0 |
| Bis-Ethylhexyloxyphenol Methoxyphenyl Triazine | 2.0 | 2.0 | 2.0 | 2.0 | 1.5 | 0.5 | 0.5 | 0.8 | 0.8 |
| Ethylhexyl Triazone | 0.5 | 0.5 | 0.5 | 0.5 | 0.0 | 0.0 | 0.0 | 0.5 | 1.0 |
| Octocrylene | 8.0 | 3.0 | 0.0 | 8.0 | 5.0 | 8.0 | 10.0 | 8.0 | 8.0 |
| Ethylhexyl Methoxycinnamate | 8.0 | 8.0 | 10.0 | 8.0 | 5.0 | 0.0 | 0.0 | 0.0 | 0.0 |
| Homosalate | 0.0 | 0.0 | 5.0 | 0.0 | 0.0 | 0.0 | 0.0 | 6.0 | 5.0 |
| Ethylhexyl Salicylate | 10.0 | 4.0 | 8.0 | 5.0 | 8.0 | 5.0 | 6.0 | 0.0 | 0.0 |
| Diethylamino Hydroxy Benzoyl Hexyl Benzoate | 2.0 | 3.0 | 2.5 | 2.0 | 3.0 | 0.0 | 0.0 | 0.0 | 2.0 |
| Cyclomethicone | 3.0 | 3.0 | 3.0 | 3.0 | 3.0 | 3.0 | 3.0 | 3.0 | 3.0 |
| PEG/PPG-4/12 Dimethicone | 1.0 | 1.0 | 1.0 | 1.0 | 1.0 | 1.0 | 1.0 | 1.0 | 1.0 |

| Examples C116-C124 | | | | | | | | | |
|---|---|---|---|---|---|---|---|---|---|
| SUNSCREEN Oleogel<br>INCI-Name | C116<br>%<br>w/w | C117<br>%<br>w/w | C118<br>%<br>w/w | C119<br>%<br>w/w | C120<br>%<br>w/w | C121<br>%<br>w/w | C122<br>%<br>w/w | C123<br>%<br>w/w | C124<br>%<br>w/w |
| Isopropyl Myristate | 38.0 | qs. 100 | qs. 100 | qs. 100 | qs. 100 | qs. 100 | qs. 100 | qs. 100 | qs. 100 |
| C12-15 Alkyl Benzoate | 10.0 | 5.0 | 5.0 | 5.0 | 5.0 | 5.0 | 5.0 | 5.0 | 5.0 |
| New UV filter (B-01-B-62) | 0.5 | 1.5 | 3.0 | 2.0 | 4.0 | 1.0 | 1.0 | 1.0 | 8.0 |
| Caprylic/Capric Triglyceride | 39.0 | 15.0 | 15.0 | 15.0 | 15.0 | 15.0 | 15.0 | 15.0 | 15.0 |
| Perfume | q.s. | q.s. | q.s. | q.s. | q.s. | q.s. | q.s. | q.s. | q.s. |
| Disteardimonium Hectorite | 15.0 | 15.0 | 15.0 | 15.0 | 15.0 | 15.0 | 15.0 | 15.0 | 15.0 |
| Butyl Methoxydibenzoyl-methane | 0.0 | 0.0 | 0.0 | 0.0 | 4.0 | 3.0 | 5.0 | 0.0 | 02.0 |
| Bis-Ethylhexyloxyphenol Methoxyphenyl Triazine | 2.0 | 2.0 | 2.0 | 2.0 | 1.5 | 0.5 | 0.5 | 0.8 | 0.8 |
| Ethylhexyl Triazone | 0.5 | 0.5 | 0.5 | 0.5 | 0.0 | 0.0 | 0.0 | 0.5 | 1.0 |
| Octocrylene | 8.0 | 3.0 | 0.0 | 8.0 | 5.0 | 8.0 | 10.0 | 8.0 | 8.0 |
| Ethylhexyl Methoxycinnamate | 8.0 | 8.0 | 10.0 | 8.0 | 5.0 | 0.0 | 0.0 | 0.0 | 0.0 |
| Homosalate | 0.0 | 0.0 | 5.0 | 0.0 | 0.0 | 0.0 | 0.0 | 6.0 | 5.0 |
| Ethylhexyl Salicylate | 10.0 | 4.0 | 8.0 | 5.0 | 8.0 | 5.0 | 6.0 | 0.0 | 0.0 |
| Diethylamino Hydroxy Benzoyl Hexyl Benzoate | 2.0 | 3.0 | 2.5 | 2.0 | 3.0 | 0.0 | 0.0 | 0.0 | 2.0 |
| Propylene Carbonate | 5.0 | 5.0 | 5.0 | 5.0 | 5.0 | 5.0 | 5.0 | 5.0 | 5.0 |

Examples C125-C133

| O/W/O Soft Cream | INCI-Name | C125 % w/w | C126 % w/w | C127 % w/w | C128 % w/w | C129 % w/w | C130 % w/w | C131 % w/w | C132 % w/w | C133 % w/w |
|---|---|---|---|---|---|---|---|---|---|---|
| Part A | PEG-60 Hydrogenated Castor Oil | 0.40 | 0.40 | 0.40 | 0.40 | 0.40 | 0.40 | 0.40 | 0.40 | 0.40 |
| | Water | 0.90 | 0.90 | 0.90 | 0.90 | 0.90 | 0.90 | 0.90 | 0.90 | 0.90 |
| Part B | Tocopheryl Acetate | 2.0 | 2.0 | 2.0 | 2.0 | 2.0 | 2.0 | 2.0 | 2.0 | 2.0 |
| | Retinyl Palmitate | 0.50 | 0.50 | 0.50 | 0.50 | 0.50 | 0.50 | 0.50 | 0.50 | 0.50 |
| | Caprylic/Capric Triglyceride | 2.50 | 2.50 | 2.50 | 2.50 | 2.50 | 2.50 | 2.50 | 2.50 | 2.50 |
| Part C | Water | Qs to 100 | Qs to 100 | Qs to 100 | Qs to 100 | Qs to 100 | Qs to 100 | Qs to 100 | Qs to 100 | Qs to 100 |
| | Sodium Chloride | 0.40 | 0.40 | 0.40 | 0.40 | 0.40 | 0.40 | 0.40 | 0.40 | 0.40 |
| | Disodium Phenyl Dibenzylimidazole Tetrasulfonate | 0.0 | 0.0 | 1.0 | 0.0 | 0.0 | 2.0 | 0.0 | 2.0 | 0.0 |
| | Micronized Methylene Bis-Benzotriazolyl Tetra-methylbutylphenol | 0.0 | 2.0 | 0.0 | 0.8 | 1.0 | 1.0 | 2.0 | 0.0 | 0.0 |
| | Titanium Dioxide | 0.0 | 1.0 | 1.0 | 1.0 | 1.0 | 1.0 | 1.0 | 1.0 | 0.0 |
| | Zinc Oxide | 0.0 | 1.0 | 0.0 | 0.0 | 0.0 | 0.8 | 1.0 | 2.0 | 0.0 |
| Part D | Cetyl PEG/PPG-10/1 Dimethicone | 2.0 | 2.0 | 2.0 | 2.0 | 2.0 | 2.0 | 2.0 | 2.0 | 2.0 |
| | Microcrystalline Wax | 0.90 | 0.90 | 0.90 | 0.90 | 0.90 | 0.90 | 0.90 | 0.90 | 0.90 |
| | Hydrogenated Castor Oil | 0.60 | 0.60 | 0.60 | 0.60 | 0.60 | 0.60 | 0.60 | 0.60 | 0.60 |
| | Decyl Oleate | 10.5 | 5.0 | 5.0 | 5.0 | 5.0 | 5.0 | 5.0 | 5.0 | 5.0 |
| | Caprylic/Capric Triglyceride | 10.0 | 0.0 | 0.0 | 0.0 | 0.0 | 0.0 | 0.0 | 0.0 | 0.0 |
| | *Jojoba* (*Buxus Chinensis*) Oil | 2.0 | 2.0 | 2.0 | 2.0 | 2.0 | 2.0 | 2.0 | 2.0 | 2.0 |
| | Butyl Methoxydibenzoyl-methane | 0.0 | 0.0 | 0.0 | 0.0 | 4.0 | 3.0 | 5.0 | 0.0 | 02.0 |
| | Bis-Ethylhexyloxyphenol Methoxyphenyl Triazine | 2.0 | 2.0 | 2.0 | 2.0 | 1.5 | 0.5 | 0.5 | 0.8 | 0.8 |
| | Ethylhexyl Triazone | 0.5 | 0.5 | 0.5 | 0.5 | 0.0 | 0.0 | 0.0 | 0.5 | 1.0 |
| | Octocrylene | 8.0 | 3.0 | 0.0 | 8.0 | 5.0 | 8.0 | 10.0 | 8.0 | 8.0 |
| | Ethylhexyl Methoxycinnamate | 8.0 | 8.0 | 10.0 | 8.0 | 5.0 | 0.0 | 0.0 | 0.0 | 0.0 |
| | Homosalate | 0.0 | 0.0 | 5.0 | 0.0 | 0.0 | 0.0 | 0.0 | 6.0 | 5.0 |
| | Ethylhexyl Salicylate | 10.0 | 4.0 | 8.0 | 5.0 | 8.0 | 5.0 | 6.0 | 0.0 | 0.0 |
| | Diethylamino Hydroxy Benzoyl Hexyl Benzoate | 2.0 | 3.0 | 2.5 | 2.0 | 3.0 | 0.0 | 0.0 | 0.0 | 2.0 |
| | New UV filter (B-01-B-62) | 0.05 | 1.0 | 2.0 | 1.0 | 1.5 | 1.0 | 2.0 | 5.0 | 8.0 |
| | Preservative, Parfum | q.s. | q.s. | q.s. | q.s. | q.s. | q.s. | q.s. | q.s. | q.s. |

Examples C134-C142

| W/O/W Emulsion INCI-Name | C134 % w/w | C135 % w/w | C136 % w/w | C137 % w/w | C138 % w/w | C139 % w/w | C140 % w/w | C141 % w/w | C142 % w/w |
|---|---|---|---|---|---|---|---|---|---|
| Glycerylstearate | 3.0 | 3.0 | 3.0 | 3.0 | 3.0 | 3.0 | 3.0 | 3.0 | 3.0 |
| PEG-100-Stearate | 0.75 | 0.75 | 0.75 | 0.75 | 0.75 | 0.75 | 0.75 | 0.75 | 0.75 |
| Behenylalcohol | 2.0 | 2.0 | 2.0 | 2.0 | 2.0 | 2.0 | 2.0 | 2.0 | 2.0 |
| Caprylic-/Capric-Triglyceride | 8.0 | 0.0 | 0.0 | 0.0 | 0.0 | 0.0 | 0.0 | 0.0 | 0.0 |
| Octyldodecanol | 5.0 | 0.0 | 0.0 | 0.0 | 0.0 | 0.0 | 0.0 | 0.0 | 0.0 |
| C12-15 Alkylbenzoate | 3.0 | 0.0 | 0.0 | 0.0 | 0.0 | 0.0 | 0.0 | 0.0 | 0.0 |
| New UV filter (B-01-B-62) | 0.1 | 0.8.0 | 2.0 | 1.0 | 1.5 | 0.8 | 0.5 | 0.6 | 1.0 |
| Butyl Methoxydibenzoyl-methane | 0.0 | 0.0 | 0.0 | 0.0 | 4.0 | 3.0 | 5.0 | 0.0 | 02.0 |
| Bis-Ethylhexyloxyphenol Methoxyphenyl Triazine | 2.0 | 2.0 | 2.0 | 2.0 | 1.5 | 0.5 | 0.5 | 0.8 | 0.8 |
| Ethylhexyl Triazone | 0.5 | 0.5 | 0.5 | 0.5 | 0.0 | 0.0 | 0.0 | 0.5 | 1.0 |
| Octocrylene | 8.0 | 3.0 | 0.0 | 8.0 | 5.0 | 8.0 | 10.0 | 8.0 | 8.0 |
| Ethylhexyl Methoxycinnamate | 8.0 | 8.0 | 10.0 | 8.0 | 5.0 | 0.0 | 0.0 | 0.0 | 0.0 |
| Homosalate | 0.0 | 0.0 | 5.0 | 0.0 | 0.0 | 0.0 | 0.0 | 6.0 | 5.0 |
| Ethylhexyl Salicylate | 10.0 | 4.0 | 8.0 | 5.0 | 8.0 | 5.0 | 6.0 | 0.0 | 0.0 |
| Diethylamino Hydroxy Benzoyl Hexyl Benzoate | 2.0 | 3.0 | 2.5 | 2.0 | 3.0 | 0.0 | 0.0 | 0.0 | 2.0 |
| Disodium Phenyl Dibenzyl-imidazole Tetrasulfonate | 0.0 | 0.0 | 1.0 | 0.0 | 0.0 | 2.0 | 0.0 | 2.0 | 0.0 |

-continued

Examples C134-C142

| W/O/W Emulsion INCI-Name | C134 % w/w | C135 % w/w | C136 % w/w | C137 % w/w | C138 % w/w | C139 % w/w | C140 % w/w | C141 % w/w | C142 % w/w |
|---|---|---|---|---|---|---|---|---|---|
| Micronized Methylene Bis-Benzotriazolyl Tetramethyl-butylphenol | 0.0 | 2.0 | 0.0 | 0.8 | 1.0 | 1.0 | 2.0 | 0.0 | 0.0 |
| Titanium Dioxide | 0.0 | 1.0 | 1.0 | 1.0 | 1.0 | 1.0 | 1.0 | 1.0 | 0.0 |
| Zinc Oxide | 0.0 | 1.0 | 0.0 | 0.0 | 0.0 | 0.8 | 1.0 | 2.0 | 0.0 |
| Dodecanedioic Acid | 1.0 | 1.0 | 1.0 | 1.0 | 1.0 | 1.0 | 1.0 | 1.0 | 1.0 |
| Magnesium Sulfate | 0.80 | 0.80 | 0.80 | 0.80 | 0.80 | 0.80 | 0.80 | 0.80 | 0.80 |
| EDTA | 0.10 | 0.10 | 0.10 | 0.10 | 0.10 | 0.10 | 0.10 | 0.10 | 0.10 |
| Phenoxyethanol | q.s. | q.s. | q.s. | q.s. | q.s. | q.s. | q.s. | q.s. | q.s. |
| Parfume | q.s. | q.s. | q.s. | q.s. | q.s. | q.s. | q.s. | q.s. | q.s. |
| Water | ad 100 | ad 10.0 | ad 100 | ad 100 | ad 100 | ad 100 | ad 100 | ad 100 | ad 100 |

PH-value adjusted to 6.0

Examples C143-C151

| Cream-to-powder INCI-Name | C143 % w/w | C144 % w/w | C145 % w/w | C146 % w/w | C147 % w/w | C148 % w/w | C149 % w/w | C150 % w/w | C151 % w/w |
|---|---|---|---|---|---|---|---|---|---|
| Isoeicosane | 10.0 | 5.0 | 5.0 | 5.0 | 5.0 | 5.0 | 5.0 | 5.0 | 5.0 |
| Polyisobutene | 2.0 | 2.0 | 2.0 | 2.0 | 2.0 | 2.0 | 2.0 | 2.0 | 2.0 |
| New UV filter (B-01-B-62) | 0.5 | 3.0 | 8.0 | 2.0 | 5.0 | 1.0 | 1.0 | 1.0 | 2.0 |
| Cetearyl Octanoate | 20.5 | 10.0 | 5.0 | 10.0 | 5.0 | 5.0 | 5.0 | 5.0 | 10.0 |
| Oleyl alcohol | 5.0 | 5.0 | 5.0 | 5.0 | 5.0 | 5.0 | 5.0 | 5.0 | 5.0 |
| Ceresin | 4.50 | 4.50 | 4.50 | 4.50 | 4.50 | 4.50 | 4.50 | 4.50 | 4.50 |
| Talc | 11.60 | 11.60 | 11.60 | 11.60 | 11.60 | 11.60 | 11.60 | 11.60 | 11.60 |
| Polyethylene | 4.0 | 4.0 | 4.0 | 4.0 | 4.0 | 4.0 | 4.0 | 4.0 | 4.0 |
| Butyl Methoxydibenzoyl-methane | 0.0 | 0.0 | 0.0 | 0.0 | 4.0 | 3.0 | 5.0 | 0.0 | 02.0 |
| Bis-Ethylhexyloxyphenol Methoxyphenyl Triazine | 2.0 | 2.0 | 2.0 | 2.0 | 1.5 | 0.5 | 0.5 | 0.8 | 0.8 |
| Ethylhexyl Triazone | 0.5 | 0.5 | 0.5 | 0.5 | 0.0 | 0.0 | 0.0 | 0.5 | 1.0 |
| Octocrylene | 8.0 | 3.0 | 0.0 | 8.0 | 5.0 | 8.0 | 10.0 | 8.0 | 8.0 |
| Ethylhexyl Methoxycinnamate | 8.0 | 8.0 | 10.0 | 8.0 | 5.0 | 0.0 | 0.0 | 0.0 | 0.0 |
| Homosalate | 0.0 | 0.0 | 5.0 | 0.0 | 0.0 | 0.0 | 0.0 | 6.0 | 5.0 |
| Ethylhexyl Salicylate | 10.0 | 4.0 | 8.0 | 5.0 | 8.0 | 5.0 | 6.0 | 0.0 | 0.0 |
| Diethylamino Hydroxy Benzoyl Hexyl Benzoate | 2.0 | 3.0 | 2.5 | 2.0 | 3.0 | 0.0 | 0.0 | 0.0 | 2.0 |
| Silica | 17.75 | 17.75 | 17.75 | 17.75 | 17.75 | 17.75 | 17.75 | 17.75 | 17.75 |
| Calcium Aluminum Boro-silicate (and) Bismuth oxychloride | 1.0 | 1.0 | 1.0 | 1.0 | 1.0 | 1.0 | 1.0 | 1.0 | 1.0 |
| Iron Oxides | 3.40 | 3.40 | 3.40 | 3.40 | 3.40 | 3.40 | 3.40 | 3.40 | 3.40 |
| Tocopherol Acetate | 0.25 | 0.25 | 0.25 | 0.25 | 0.25 | 0.25 | 0.25 | 0.25 | 0.25 |

Examples C152-C160

| Foundations: Anhydrous forms INCI-Name | C152 % w/w | C153 % w/w | C154 % w/w | C155 % w/w | C156 % w/w | C157 % w/w | C158 % w/w | C159 % w/w | C160 % w/w |
|---|---|---|---|---|---|---|---|---|---|
| Isononyl Isononanoate | qsp | qsp | qsp | qsp | qsp | qsp | qsp | qsp | qsp |
| New UV filter (B-01-B-62) | 1.0 | 3.0 | 5.0 | 2.0 | 5.0 | 2.0 | 2.0 | 3.0 | 5.0 |
| Sorbitan Sesquioleate | 0.50 | 0.50 | 0.50 | 0.50 | 0.50 | 0.50 | 0.50 | 0.50 | 0.50 |
| Cyclopentasiloxane | 15.0 | 15.0 | 15.0 | 15.0 | 15.0 | 15.0 | 15.0 | 15.0 | 15.0 |
| Cylopentasiloxane (and) Quaternium-18 Hectorite | 15.0 | 15.0 | 15.0 | 15.0 | 15.0 | 15.0 | 15.0 | 15.0 | 15.0 |
| Talc | 5.0 | 5.0 | 5.0 | 5.0 | 5.0 | 5.0 | 5.0 | 5.0 | 5.0 |
| Butyl Methoxydibenzoyl-methane | 0.0 | 0.0 | 0.0 | 0.0 | 4.0 | 3.0 | 5.0 | 0.0 | 02.0 |
| Bis-Ethylhexyloxyphenol Methoxyphenyl Triazine | 2.0 | 2.0 | 2.0 | 2.0 | 1.5 | 0.5 | 0.5 | 0.8 | 0.8 |
| Ethylhexyl Triazone | 0.5 | 0.5 | 0.5 | 0.5 | 0.0 | 0.0 | 0.0 | 0.5 | 1.0 |
| Octocrylene | 8.0 | 3.0 | 0.0 | 8.0 | 5.0 | 8.0 | 10.0 | 8.0 | 8.0 |

-continued

Examples C152-C160

| Foundations: Anhydrous forms INCI-Name | C152 % w/w | C153 % w/w | C154 % w/w | C155 % w/w | C156 % w/w | C157 % w/w | C158 % w/w | C159 % w/w | C160 % w/w |
|---|---|---|---|---|---|---|---|---|---|
| Ethylhexyl Methoxycinnamate | 8.0 | 8.0 | 10.0 | 8.0 | 5.0 | 0.0 | 0.0 | 0.0 | 0.0 |
| Homosalate | 0.0 | 0.0 | 5.0 | 0.0 | 0.0 | 0.0 | 0.0 | 6.0 | 5.0 |
| Ethylhexyl Salicylate | 10.0 | 4.0 | 8.0 | 5.0 | 8.0 | 5.0 | 6.0 | 0.0 | 0.0 |
| Diethylamino Hydroxy Benzoyl Hexyl Benzoate | 2.0 | 3.0 | 2.5 | 2.0 | 3.0 | 0.0 | 0.0 | 0.0 | 2.0 |
| Iron oxides | 2.50 | 2.50 | 2.50 | 2.50 | 2.50 | 2.50 | 2.50 | 2.50 | 2.50 |
| PVP/eicosane copolymer | 1.0 | 1.0 | 1.0 | 1.0 | 1.0 | 1.0 | 1.0 | 1.0 | 1.0 |
| Tocopherol Acetate | 0.50 | 0.50 | 0.50 | 0.50 | 0.50 | 0.50 | 0.50 | 0.50 | 0.50 |

While there have been shown, described and pointed out the features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention.

The invention claimed is:

1. A method of improving the UV absorbing and UV screening capacity for protecting human and animal hair and skin against UV radiation comprising applying thereto to a subject in need thereof a benzotropolone and their derivatives, wherein the benzotropolone derivatives correspond to the formula

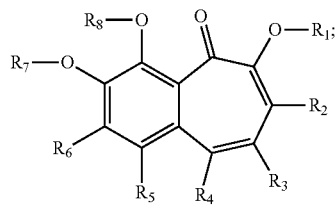

(1)

wherein $R_2$, $R_3$, $R_4$, $R_5$ and $R_6$ independently of one another are hydrogen; OH; $C_1$-$C_{30}$alkyl, $C_2$-$C_{30}$alkenyl, $C_1$-$C_{30}$alkoxy, $C_3$-$C_{12}$cycloalkyl or $C_1$-$C_{30}$hydroxyalkyl, which may be substituted by one or more E and/or interrupted by one or more D; $C_6$-$C_{20}$aryl, which may be substituted by one or more G; $C_4$-$C_{20}$heteroaryl, which may be substituted by one or more G, $C_2$-$C_{18}$alkenyl, $C_2$-$C_{18}$alkynyl, $C_7$-$C_{25}$aralkyl, CN, or —CO—$R_{17}$; $C_1$-$C_{30}$mono- or dialkylamino; $COR_9$; $COOR_9$; $CONR_9R_{10}$; CN; $SO_2R_9$; $OCOOR_9$; $OCOR_9$; NHCOOR_9$; $NR_9COR_{10}$; $NH_2$; *—(CO)—NH—$(CH_2)_{n1}$—(PO)—$(OR_{11})_2$; —(CO)—O—$(CH_2)_{n1}$—(PO)—$(OR_{11})_2$; sulphate; sulphonate; phosphate; phosphonate; —$(CH_2)_{n2}$—[O—$(SO_2)]_{n3}$—$OR_{11}$; —O—$(CH_2)_{n4}(CO)_{n5}$—$R_{11}$; —$(O)_{n6}$—$(CH_2)_{n7}$—(PO)—$(OR_9)_2$; —$(O)_{n6}$—$(CH_2)_{n7}$—$SO_2$—$OR_9$; halogen; organosilanyl; organosiloxanyl; or a sugar residue linked directly in an α- or β-mode via the anomeric oxygen to the benzotropolone system or via a linear or branched alkylene, alkenylene, alkadiene or alkatriene spacer (sugar-$(CH_2)_n$—$(X_1)_{1\ or\ 0}$-benzotropolone system, wherein n=1-10 and $X_1$=—O—; —(CO)—; —O—CO—; —COO—, —NH—; —S—; —$SO_2$—);

$R_1$, $R_7$ and $R_8$ are hydrogen;

$R_9$ and $R_{10}$ independently from each other are hydrogen; $C_1$-$C_{18}$alkyl or $C_3$-$C_{12}$-cycloalkyl which may be substituted by one or more E and/or interrupted by one or more D; $C_6$-$C_{20}$aryl, which may be substituted by one or more G; $C_4$-$C_{20}$heteroaryl, which may be substituted by one or more G; organosilanyl; organosiloxanyl; or a sugar residue linked directly in an α- or β-mode via the anomeric oxygen or via a linear or branched alkylene, alkenylene, alkadiene or alkatriene spacer (sugar-$(CH_2)_n$-*, wherein n=1-10); or $R_9$ and $R_{10}$ together form a five or six membered ring, $R_{11}$ is hydrogen; or $C_1$-$C_5$alkyl;

$n_1$, $n_2$, $n_4$ and $n_7$ independently from each other are a number from 1 to 5;

$n_3$, $n_5$ and $n_6$ independently from each other are a 0; or 1;

D is —CO—; —COO—; —S—; —SO—; —$SO_2$—; —O—; —$NR_{14}$—; —$SiR_{19}R_{20}$—; —$POR_{11}$—; —$CR_{12}$=$CR_{13}$—; or —C≡C—; and E is —$OR_{18}$; —$SR_{18}$; —$NR_{14}R_{15}$; —$NR_{14}COR_{15}$; —$COR_{17}$; —$COOR_{16}$; —$CONR_{14}R_{15}$; —CN; halogen; or $SO_3R_{18}$; $SO_2R_{18}$; $PO_3(R_{18})_2$; $PO_2(R_{18})_2$; organosilanyl; organosiloxanyl; or a sugar residue linked directly in an α- or β-mode via the anomeric oxygen or via a linear or branched alkylene, alkenylene, alkadiene or alkatriene spacer (sugar-$(CH_2)_n$—$(X_1)_{1\ or\ 0}$-*, wherein n=1-10 and $X_1$=—O—; —C(=O)—; —O—CO—; —COO—; —NH—; —S—; —$SO_2$—);

G is E; $C_1$-$C_{18}$alkyl, which is optionally interrupted by D; $C_1$-$C_{18}$perfluoroalkyl; $C_1$-$C_{18}$alkoxy, which is optionally substituted by E and/or interrupted by D; wherein $R_{12}$, $R_{13}$, $R_{14}$ and $R_{15}$ independently of each other are hydrogen; $C_6$-$C_{18}$aryl which is optionally substituted by OH, $C_1$-$C_{18}$alkyl or $C_1$-$C_{18}$alkoxy; $C_1$-$C_{18}$alkyl, which is optionally interrupted by —O—; or $R_{14}$ and $R_{15}$ together form a five or six membered ring, $R_{16}$ is hydrogen; $C_6$-$C_{18}$aryl which is optionally substituted by OH, $C_1$-$C_{18}$alkyl or $C_1$-$C_{18}$alkoxy; $C_1$-$C_{18}$alkyl which is optionally interrupted by —O—;

$R_{17}$ is H; $C_6$-$C_{18}$aryl which is optionally substituted by OH, $C_1$-$C_{18}$alkyl or $C_1$-$C_{18}$alkoxy; or $C_1$-$C_{18}$alkyl which is optionally interrupted by —O—;

$R_{18}$ is hydrogen; $C_6$-$C_{18}$aryl, which is optionally substituted by OH, $C_1$-$C_{18}$alkyl or $C_1$-$C_{18}$alkoxy; $C_1$-$C_{18}$alkyl, which is optionally interrupted by —O—;

$R_{19}$ and $R_{20}$ independently of each other are hydrogen; $C_1$-$C_{18}$alkyl; $C_6$-$C_{18}$aryl which is optionally substituted by $C_1$-$C_{18}$alkyl; and

* means, that this radical is directed to the benzotropolone moiety.

2. The method according to claim 1; wherein in formula (1)

$R_2$, $R_3$, $R_4$, $R_5$ and $R_6$ independently of one another are hydrogen; OH; $C_1$-$C_{30}$alkyl, $C_2$-$C_{30}$alkenyl, $C_1$-$C_{30}$alkoxy, $C_3$-$C_{12}$cycloalkyl or $C_1$-$C_{30}$hydroxyalkyl, which may be substituted by one or more E and/or interrupted by one or more D; $C_6$-$C_{20}$aryl, which may be substituted by one or more G; $C_6$-$C_{20}$heteroaryl, which may be substituted by one or more G, $C_2$-$C_{18}$alkenyl, $C_2$-$C_{18}$alkynyl, $C_7$-$C_{25}$aralkyl, CN, or —CO—$R_{17}$; $C_1$-$C_{30}$mono- or dialkylamino; COR$_9$; COOR$_9$; CONR$_9$R$_{10}$; CN; SO$_2$R$_9$; OCOOR$_9$; NHCOOR$_9$; NR$_9$COR$_{10}$; NH$_2$; *—(CO)—NH—(CH$_2$)$_{n1}$—(PO)—(OR$_{11}$)$_2$; —(CO)—O—(CH$_2$)$_{n1}$—(PO)—(OR$_{11}$)$_2$; sulphate; sulphonate; phosphate; phosphonate; —(CH$_2$)$_{n2}$—[O—(SO$_2$)]$_{n3}$—OR$_{11}$; —O—(CH$_2$)$_{n4}$(CO)$_{n5}$—R$_{11}$; —(O)$_{n6}$—(CH$_2$)$_{n7}$—(PO)—(OR$_9$)$_2$; —(O)$_{n6}$—(CH$_2$)$_{n7}$—SO$_2$—OR$_9$; halogen; organosilanyl; organosiloxanyl; or a sugar residue linked directly in an α- or β-mode via the anomeric oxygen to the benzotropolone system or via a linear or branched alkylene, alkenylene, alkadiene or alkatriene spacer (sugar-(CH$_2$)$_n$—(X$_1$)$_{1\ or\ 0}$-benzotropolone system, wherein n=1-10 and X$_1$=—O—; —(CO)—; —O—CO—; —COO—, —NH—; —S—; —SO$_2$—);

$R_9$ and $R_{10}$ independently from each other are hydrogen; $C_1$-$C_{18}$alkyl or $C_3$-$C_{12}$-cycloalkyl which may be substituted by one or more E and/or interrupted by one or more D; $C_6$-$C_{20}$aryl, which may be substituted by one or more G; organosilanyl; organosiloxanyl; or a sugar residue linked directly in an α- or β-mode via the anomeric oxygen or via a linear or branched alkylene, alkenylene, alkadiene or alkatriene spacer (sugar-(CH$_2$)$_n$-*, wherein n=1-10); or $R_9$ and $R_{10}$ together form a five or six membered ring, $R_{11}$ is hydrogen; or $C_1$-$C_5$alkyl;

$n_1$, $n_2$, $n_4$ and $n_7$ independently from each other are a number from 1 to 5;

$n_3$ and $n_5$ independently from each other are a 0; or 1;

D is —CO—; —COO—; —S—; —SO—; —SO$_2$—; —O—; —NR$_{14}$—; —SiR$_{19}$R$_{20}$—; —POR$_{11}$—; —CR$_{12}$=CR$_{13}$—; or —C≡C—; and E is —OR$_{18}$; —SR$_{18}$; —NR$_{14}$R$_{15}$; —NR$_{14}$COR$_{15}$; —COR$_{17}$; —COOR$_{16}$; —CONR$_{14}$R$_{15}$; —CN; halogen; or SO$_3$R$_{18}$; SO$_2$R$_{18}$; PO$_3$(R$_{18}$)$_2$; PO$_2$(R$_{18}$)$_2$; organosilanyl; organosiloxanyl; or a sugar residue linked directly in an α- or β-mode via the anomeric oxygen or via a linear or branched alkylene, alkenylene, alkadiene or alkatriene spacer (sugar-(CH$_2$)$_n$—(X$_1$)$_{1\ or\ 0}$-*, wherein n=1-10 and X$_1$=—O—; —C(=O)—; —O—CO—; —NH—; —S—; —SO$_2$—);

G is E; $C_1$-$C_{18}$alkyl, which is optionally interrupted by D; $C_1$-$C_{18}$perfluoroalkyl; $C_1$-$C_{18}$alkoxy, which is optionally substituted by E and/or interrupted by D; wherein $R_{12}$, $R_{13}$, $R_{14}$ and $R_{15}$ independently of each other are hydrogen; $C_6$-$C_{18}$aryl which is optionally substituted by $C_1$-$C_{18}$alkyl or $C_1$-$C_{18}$alkoxy; $C_1$-$C_{18}$alkyl, which is optionally interrupted by —O—; or $R_{14}$ and $R_{15}$ together form a five or six membered ring, $R_{16}$ is hydrogen; $C_6$-$C_{18}$aryl which is optionally substituted by $C_1$-$C_{18}$alkyl or $C_1$-$C_{18}$alkoxy; $C_1$-$C_{18}$alkyl which is optionally interrupted by —O—;

$R_{17}$ is H; $C_6$-$C_{18}$aryl which is optionally substituted by $C_1$-$C_{18}$alkyl or $C_1$-$C_{18}$alkoxy; or $C_1$-$C_{18}$alkyl which is optionally interrupted by —O—;

$R_{18}$ is hydrogen; $C_6$-$C_{18}$aryl, which is optionally substituted by $C_1$-$C_{18}$alkyl or $C_1$-$C_{18}$alkoxy; $C_1$-$C_{18}$alkyl, which is optionally interrupted by —O—;

$R_{19}$ and $R_{20}$ independently of each other are hydrogen; $C_1$-$C_{18}$alkyl; $C_6$-$C_{18}$aryl which is optionally substituted by $C_1$-$C_{18}$alkyl; and

* means, that this radical is directed to the benzotropolone moiety.

3. The method according to claim 1, wherein $R_2$, $R_3$, $R_4$, $R_5$ and $R_6$, independently of one another are hydrogen; hydroxy; $C_1$-$C_{12}$alkyl, $C_1$-$C_{30}$alkoxy; or $C_1$-$C_{12}$alkenyl substituted by E; and E is carboxylate; OCOR$_9$; sulphate; sulphonate; phosphonate; or phosphate.

4. The method according to claim 1, wherein $R_3$ is a radical of formula

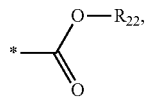

wherein $R_{22}$ is hydrogen; $C_1$-$C_{12}$alkyl, which may be substituted by one or more E and/or interrupted by one or more D; $C_6$-$C_{20}$aryl, which may be substituted by one or more G; $C_4$-$C_{20}$heteroaryl, which may be substituted by one or more G, $C_2$-$C_{18}$alkenyl, $C_2$-$C_{18}$alkynyl, $C_7$-$C_{25}$aralkyl, or —CO—$R_{17}$; organosilanyl; organosiloxanyl; or a sugar residue linked directly in an α- or β-mode via the anomeric oxygen to the carboxylic group or via a linear or branched alkylene, alkenylene, alkadiene or alkatriene spacer (sugar-(CH$_2$)$_n$-carboxylic group, wherein n=1-10);

$R_{17}$ is H; $C_6$-$C_{18}$aryl which is optionally substituted by $C_1$-$C_{18}$alkyl or $C_1$-$C_{18}$alkoxy; or $C_1$-$C_{18}$alkyl which is optionally interrupted by —O—.

5. The method according to claim 1, wherein the benzotropolones and their derivatives according to claim 1 are UV absorbers.

6. The method according to claim 1, wherein the benzotropolone derivatives of formula (1) simultaneously protect human and animal hair and skin against UV radiation and oxidative damage.

7. The method according to claim 1, wherein the benzotropolone derivative is in a cosmetic composition and the concentration is from 1 ppm to 100000 ppm, based on the total weight of the cosmetic composition.

8. The method according to claim 7, wherein the composition further comprises one or more further antioxidants.

9. The method according to claim 8, wherein the additional antioxidant is selected from vitamin C, vitamin C-palmitate, vitamin C-phosphate, vitamin E, vitamin E-acetate and vitamin E-phosphate.

10. The method according to claim 1, wherein the benzotropolone is in a cosmetic composition.

* * * * *